(12) United States Patent
Buchine et al.

(10) Patent No.: US 12,239,822 B2
(45) Date of Patent: Mar. 4, 2025

(54) PORTABLE DRUG MIXING AND DELIVERY DEVICE AND ASSOCIATED METHODS

(71) Applicant: Windgap Medical, Inc., Watertown, MA (US)

(72) Inventors: Brent Buchine, Austin, TX (US); Adam R. Standley, Cambridge, MA (US); Christopher J. Stepanian, Somerville, MA (US); Kaliappanadar Nellaiappan, Watertown, MA (US); Cole Constantineau, Cambridge, MA (US); Michel Bruehwiler, Newton, MA (US); Jeffrey Thomas Chagnon, Bow, NH (US); Robert Brik, Cambridge, MA (US)

(*) Notice: Subject to any disclaimer, the term of this patent is extended or adjusted under 35 U.S.C. 154(b) by 232 days.

(21) Appl. No.: 16/675,219

(22) Filed: Nov. 5, 2019

(65) Prior Publication Data
US 2020/0139048 A1    May 7, 2020

Related U.S. Application Data

(63) Continuation-in-part of application No. 16/423,344, filed on May 28, 2019, which is a continuation-in-part
(Continued)

(51) Int. Cl.
*A61M 5/24* (2006.01)
*A61K 9/00* (2006.01)
(Continued)

(52) U.S. Cl.
CPC ......... *A61M 5/2448* (2013.01); *A61K 9/0019* (2013.01); *A61K 31/137* (2013.01);
(Continued)

(58) Field of Classification Search
CPC .. A61M 5/2448; A61M 5/1409; A61M 5/284; A61M 5/3294; A61M 5/31596;
(Continued)

(56) References Cited

U.S. PATENT DOCUMENTS 1,506,429 A * 8/1924 Kahn ..................... A61M 5/00
                                                        206/229
3,164,303 A * 1/1965 Trautmann ............ A61M 5/284
                                                        222/386
(Continued)

FOREIGN PATENT DOCUMENTS

CN    1634002 A    7/2005
CN    1827109 A    9/2006
(Continued)

OTHER PUBLICATIONS

English translation of Gabriel et al. EP 0112574 A1 (Year: 1984).*
(Continued)

*Primary Examiner* — Nilay J Shah
(74) *Attorney, Agent, or Firm* — Stephen J. Kenny; Foley Hoag LLP

(57) ABSTRACT

A portable dual chamber auto-injector configured to store a dry opioid antagonist medicament separately from a liquid component, wherein a user actuated mixing system comprising a movable component to create a fluidic pathway between the first and second chambers and release a portion of energy from a pre-stored energy to drive a displacement mechanism into the first chamber and displace the liquid component into the second chamber and solubilize the opioid antagonist. A needle assembly in fluid communication with the second chamber can be used to transfer the solubilized opioid antagonist.

17 Claims, 68 Drawing Sheets

Related U.S. Application Data of application No. 15/832,346, filed on Dec. 5, 2017, now Pat. No. 10,300,198, which is a continuation-in-part of application No. 15/034,967, filed as application No. PCT/US2015/045761 on Aug. 18, 2015, now Pat. No. 9,907,911, application No. 16/675,219 is a continuation-in-part of application No. 16/266,341, filed on Feb. 4, 2019, now abandoned, which is a continuation-in-part of application No. 14/255,909, filed on Apr. 17, 2014, now Pat. No. 10,195,361, which is a continuation-in-part of application No. 14/218,355, filed on Mar. 18, 2014, now Pat. No. 9,199,037, application No. 16/675,219 is a continuation-in-part of application No. 14/975,695, filed on Dec. 18, 2015, now Pat. No. 11,246,842, and a continuation-in-part of application No. 14/576,179, filed on Dec. 18, 2014, now abandoned.

(60) Provisional application No. 62/204,940, filed on Aug. 13, 2015, provisional application No. 62/126,011, filed on Feb. 27, 2015, provisional application No. 62/120,792, filed on Feb. 25, 2015, provisional application No. 62/061,664, filed on Oct. 8, 2014, provisional application No. 62/038,386, filed on Aug. 18, 2014, provisional application No. 61/917,943, filed on Dec. 19, 2013, provisional application No. 61/800,014, filed on Mar. 15, 2013, provisional application No. 62/094,063, filed on Dec. 18, 2014, provisional application No. 62/016,260, filed on Jun. 24, 2014, provisional application No. 62/756,056, filed on Nov. 5, 2018, provisional application No. 61/917,925, filed on Dec. 18, 2013.

(51) Int. Cl.

| | |
|---|---|
| *A61K 31/137* | (2006.01) |
| *A61K 31/4045* | (2006.01) |
| *A61K 38/26* | (2006.01) |
| *A61K 45/06* | (2006.01) |
| *A61M 5/14* | (2006.01) |
| *A61M 5/19* | (2006.01) |
| *A61M 5/20* | (2006.01) |
| *A61M 5/28* | (2006.01) |
| *A61M 5/32* | (2006.01) |
| *A61M 5/44* | (2006.01) |
| *A61K 38/00* | (2006.01) |

(52) U.S. Cl.
CPC .......... *A61K 31/4045* (2013.01); *A61K 38/26* (2013.01); *A61K 45/06* (2013.01); *A61M 5/1409* (2013.01); *A61M 5/19* (2013.01); *A61M 5/2046* (2013.01); *A61M 5/284* (2013.01); *A61M 5/3294* (2013.01); *A61M 5/44* (2013.01); *A61K 38/00* (2013.01); *A61M 2205/364* (2013.01); *A61M 2205/366* (2013.01)

(58) Field of Classification Search
CPC .......... A61M 3/005; A61M 2005/2451; A61M 2005/31598; A61M 5/19; A61M 5/16827
See application file for complete search history.

(56) References Cited

U.S. PATENT DOCUMENTS

| | | | |
|---|---|---|---|
| 3,342,180 A * | 9/1967 | Sandhage | A61M 5/284 604/89 |
| 3,785,379 A * | 1/1974 | Cohen | A61M 5/31596 604/88 |
| 3,946,732 A * | 3/1976 | Hurscham | A61J 1/2093 604/88 |
| 4,059,109 A * | 11/1977 | Tischlinger | A61M 5/284 604/88 |
| 4,147,767 A | 4/1979 | Yapel, Jr. | |
| 4,479,794 A | 10/1984 | Urquhart et al. | |
| 4,511,351 A | 4/1985 | Theeuwes | |
| 4,689,042 A * | 8/1987 | Sarnoff | A61M 5/2066 604/191 |
| 4,755,169 A | 7/1988 | Sarnoff et al. | |
| 4,820,286 A | 4/1989 | van der Wal | |
| 5,281,198 A * | 1/1994 | Haber | A61J 1/2093 604/209 |
| 5,569,193 A * | 10/1996 | Hofstetter | A61M 5/31596 604/91 |
| 5,637,087 A * | 6/1997 | O'Neil | A61M 5/284 604/82 |
| 5,704,918 A * | 1/1998 | Higashikawa | A61M 5/19 604/191 |
| 5,899,881 A * | 5/1999 | Grimard | A61M 5/31596 604/82 |
| 6,641,561 B1 | 11/2003 | Hill et al. | |
| 6,656,150 B2 | 12/2003 | Hill et al. | |
| 6,770,052 B2 | 8/2004 | Hill et al. | |
| 6,793,646 B1 | 9/2004 | Giambattista et al. | |
| 6,953,455 B2 | 10/2005 | Cho et al. | |
| 7,323,477 B2 | 1/2008 | Chow et al. | |
| 7,449,012 B2 | 11/2008 | Young et al. | |
| 7,544,189 B2 | 6/2009 | Griffiths | |
| 7,556,614 B2 | 7/2009 | Griffiths et al. | |
| 7,608,055 B2 | 10/2009 | Griffiths et al. | |
| 7,621,887 B2 | 11/2009 | Griffiths et al. | |
| 7,678,073 B2 | 3/2010 | Griffiths et al. | |
| 7,749,190 B2 | 7/2010 | Griffiths et al. | |
| 7,757,370 B2 | 7/2010 | Griffiths | |
| 7,776,015 B2 | 8/2010 | Sadowski et al. | |
| 7,794,432 B2 | 9/2010 | Young et al. | |
| 7,947,742 B2 | 5/2011 | Batycky et al. | |
| 8,048,035 B2 | 11/2011 | Mesa et al. | |
| 8,057,427 B2 | 11/2011 | Griffiths et al. | |
| 8,092,420 B2 | 1/2012 | Bendek et al. | |
| 8,123,719 B2 | 2/2012 | Edwards et al. | |
| 8,177,758 B2 | 5/2012 | Brooks, Jr. et al. | |
| 8,187,220 B2 | 5/2012 | Griffiths et al. | |
| 8,251,947 B2 | 8/2012 | KraMer et al. | |
| 8,313,466 B2 | 11/2012 | Edwards et al. | |
| 8,496,619 B2 | 7/2013 | Kramer et al. | |
| 8,506,526 B2 | 8/2013 | Griffiths et al. | |
| 8,568,367 B2 | 10/2013 | Griffiths et al. | |
| 8,613,720 B2 | 12/2013 | Bendek et al. | |
| 8,632,504 B2 | 1/2014 | Young | |
| 8,696,618 B2 | 4/2014 | Kramer et al. | |
| 8,770,827 B2 | 7/2014 | Steinmuller et al. | |
| 8,870,827 B2 | 10/2014 | Young et al. | |
| 8,945,053 B2 | 2/2015 | Vogt et al. | |
| 9,364,610 B2 | 6/2016 | KraMer et al. | |
| 9,364,611 B2 | 6/2016 | KraMer et al. | |
| 9,586,010 B2 | 3/2017 | Mesa et al. | |
| 2003/0187388 A1 | 10/2003 | Sharon et al. | |
| 2004/0076588 A1 | 4/2004 | Batycky et al. | |
| 2004/0110781 A1 | 6/2004 | Harmon et al. | |
| 2004/0122359 A1* | 6/2004 | Wenz | B01F 35/713 604/82 |
| 2005/0281883 A1 | 12/2005 | Daniloff et al. | |
| 2006/0257488 A1 | 11/2006 | Hubbard | |
| 2007/0203247 A1 | 8/2007 | Phillips et al. | |
| 2008/0026934 A1 | 1/2008 | Jensen et al. | |
| 2008/0269347 A1 | 10/2008 | Bruss et al. | |
| 2010/0179090 A1 | 7/2010 | Havelund et al. | |
| 2011/0092906 A1 | 4/2011 | Bottger et al. | |
| 2011/0092917 A1 | 4/2011 | Wei et al. | |
| 2012/0016296 A1 | 1/2012 | Charles | |
| 2012/0046225 A1 | 2/2012 | Prestrelski et al. | |
| 2012/0101325 A1* | 4/2012 | Lee | A61K 47/34 604/20 |
| 2012/0130318 A1 | 5/2012 | Young | |
| 2013/0018313 A1 | 1/2013 | Kramer et al. | |
| 2013/0178823 A1 | 7/2013 | Buchine et al. | |

(56) References Cited

U.S. PATENT DOCUMENTS

| | | | |
|---|---|---|---|
| 2013/0274707 A1* | 10/2013 | Wilmot | A61M 5/2066 604/506 |
| 2014/0088512 A1 | 3/2014 | Quinn | |
| 2014/0276385 A1 | 9/2014 | Buchine et al. | |
| 2014/0276430 A1 | 9/2014 | Baker et al. | |
| 2015/0011975 A1 | 1/2015 | Anderson et al. | |
| 2015/0231334 A1 | 8/2015 | Buchine et al. | |
| 2016/0243060 A1 | 8/2016 | Standley et al. | |
| 2023/0088439 A1 | 3/2023 | Buchine et al. | |

FOREIGN PATENT DOCUMENTS

| | | |
|---|---|---|
| CN | 101674812 A | 3/2010 |
| CN | 102497882 A | 6/2012 |
| CN | 102389403 B | 11/2012 |
| CN | 102802668 A | 11/2012 |
| CN | 103442695 A | 12/2013 |
| CN | 106061253 A | 10/2016 |
| EP | 0112574 A1 * | 7/1984 |
| FR | 2082128 A5 * | 12/1971 |
| FR | 2741810 A1 | 6/1997 |
| JP | 2010-526039 A | 7/2010 |
| JP | 2012-528830 A | 11/2012 |
| JP | 2013-500952 A | 1/2013 |
| JP | 55-31075 B2 | 6/2014 |
| JP | 2014-523296 A | 9/2014 |
| WO | WO-00/48662 A1 | 8/2000 |
| WO | WO-00/66214 A1 | 11/2000 |
| WO | WO-02/41830 A3 | 8/2002 |
| WO | WO-03/047663 A2 | 6/2003 |
| WO | WO-2007/057717 A3 | 9/2007 |
| WO | WO-2008/132224 A2 | 11/2008 |
| WO | WO-2010/139751 A2 | 12/2010 |
| WO | WO-2010/139752 A2 | 12/2010 |
| WO | WO-2011/012719 A1 | 2/2011 |
| WO | WO-2012/122535 A2 | 9/2012 |
| WO | WO-2012/177948 A2 | 12/2012 |
| WO | WO-2014/005463 A1 | 1/2014 |
| WO | WO-2014/026694 A1 | 2/2014 |
| WO | WO-2014/066731 A1 | 5/2014 |
| WO | WO-2014/060563 A3 | 7/2014 |
| WO | WO-2014/059444 A3 | 8/2014 |
| WO | WO-2014/146060 A1 | 9/2014 |
| WO | WO-2015/095624 A3 | 10/2015 |
| WO | WO-2019/011069 A1 | 1/2019 |

OTHER PUBLICATIONS

[No Author Listed], Addrenalin (epinephrine injection) 1 mg/mL (1:1000). JHP Pharmaceuticals, LLC. Dec. 2012. <URL: https://www.accessdata.fda.gov/drugsatfda_docs/label/2012/204200s0001b1.pdf> [retrieved from internet on Feb. 11, 2021] 10 pages.

[No Author Listed], Epinephrine Injection USP, Material Data Sheet. Luitpold Pharmaceuticals, Inc. Jan. 10, 2009. <URL: https://marketing.msdsonline.com/library/iojhoj708.pdf > retrieved from internet on Feb. 11, 2021] 8 pages.

Bansal, Product Development Issues of Powders for Injection. Mar. 2002. Last accessed on Feb. 27, 2017 from https://www.researchgate.net/profile/Arvind_Bansal/publication/228912123_Product_development_issues_of_powder_for_injection/links/55e43bc808aecb1a7cc8fa.pdf. 12 pages.

International Preliminary Report on Patentability for International application No. PCT/US14/71324 mailed Jun. 30, 2016.

International Preliminary Report on Patentability for International Application No. PCT/US2015/066940 mailed on Jun. 29, 2017.

International Search Report and Written opinion for International application No. PCT/US14/71324 mailed Sep. 2, 2015.

International Search Report and Written Opinion for International Application No. PCT/US2015/066940 mailed Feb. 25, 2016.

Kerddonfak et al., The stability and sterility of epinephrine prefilled syringe. Asian Pac J Allergy Immunol. Mar. 2010;28(1):53-7.

Landy et al., An open-label trial of a sumatriptan auto-injector for migraine in patients currently treated with subcutaneous sumatriptan. Headache. Jan. 2013;53(1):118-125. doi: 10.1111/j.1526-4610.2012.02295.x. Epub Nov. 13, 2012.

Supplementary European Search Report for Application No. EP 15 871 257.0 mailed Jul. 11, 2018.

Supplementary European Search Report for European Application No. EP 14 872 735.7 mailed on Aug. 23, 2017.

* cited by examiner

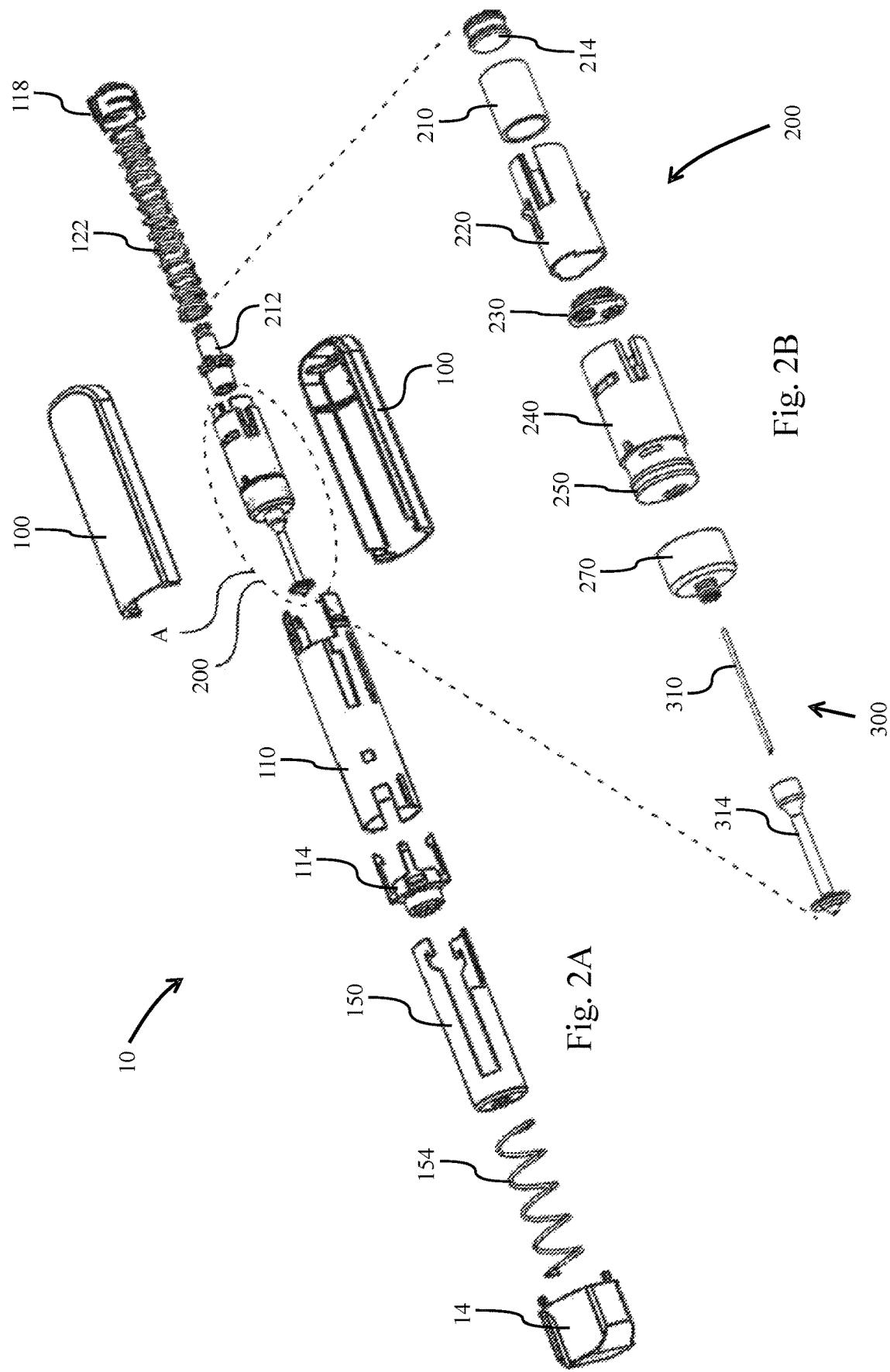

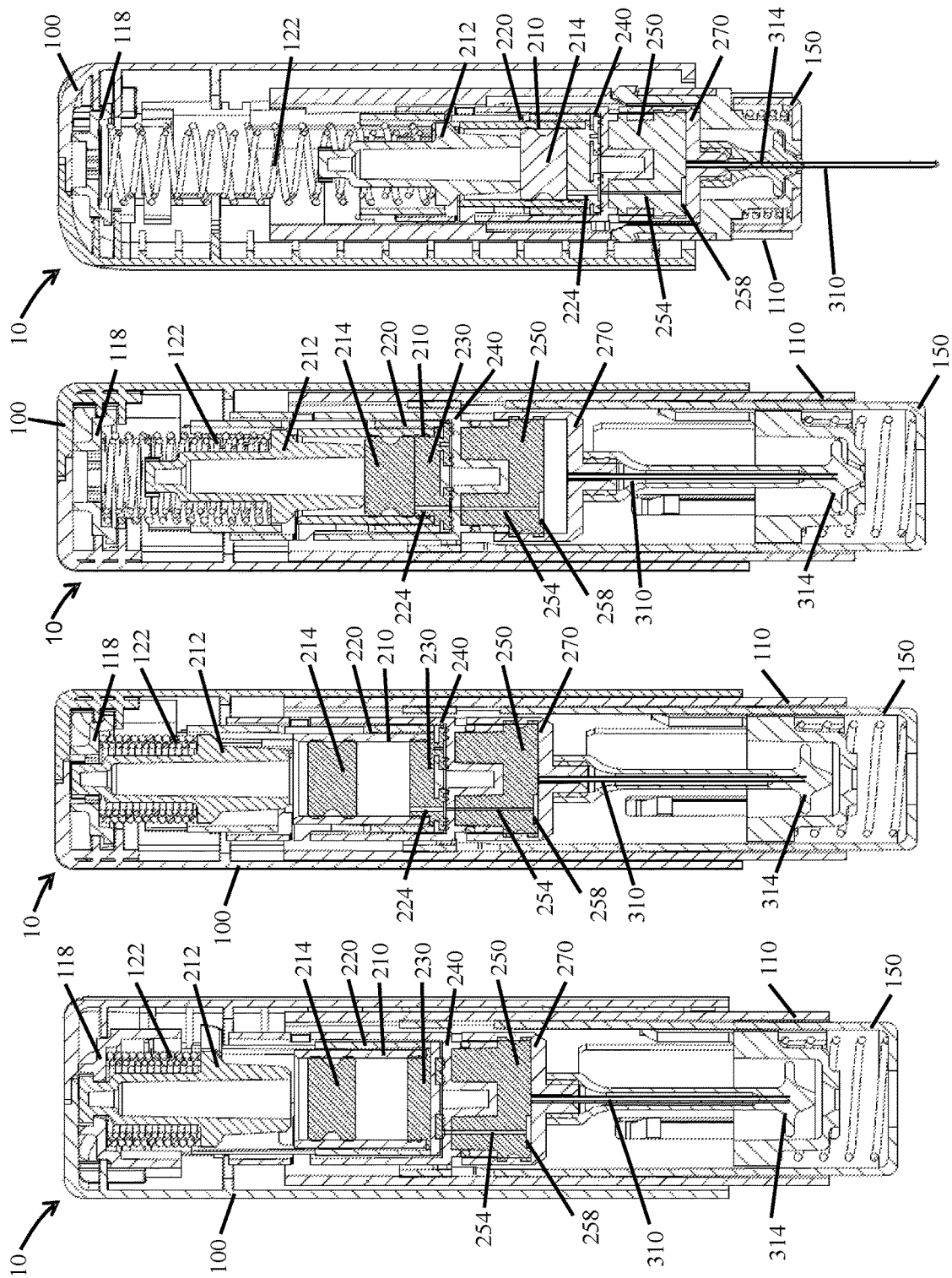

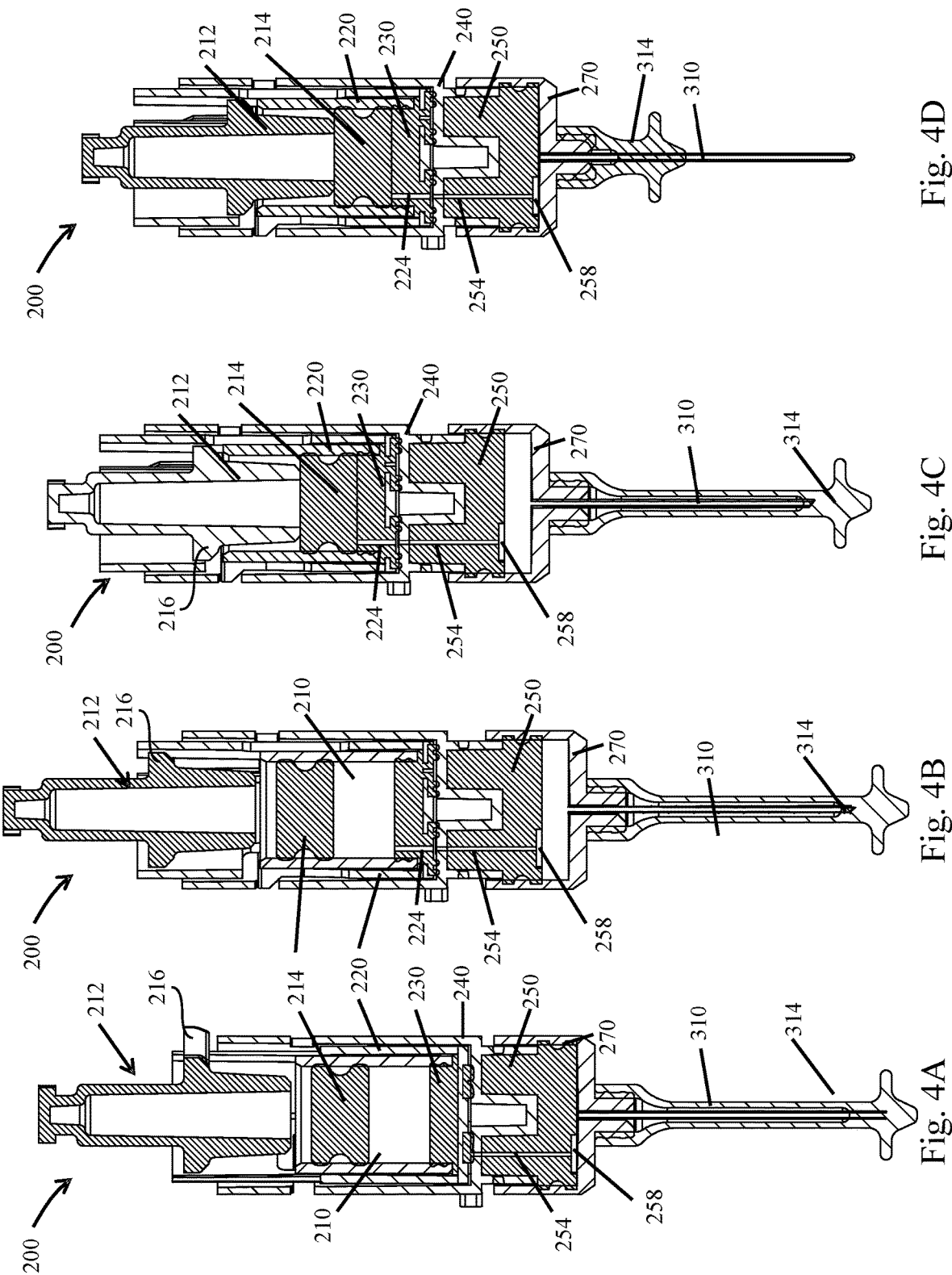

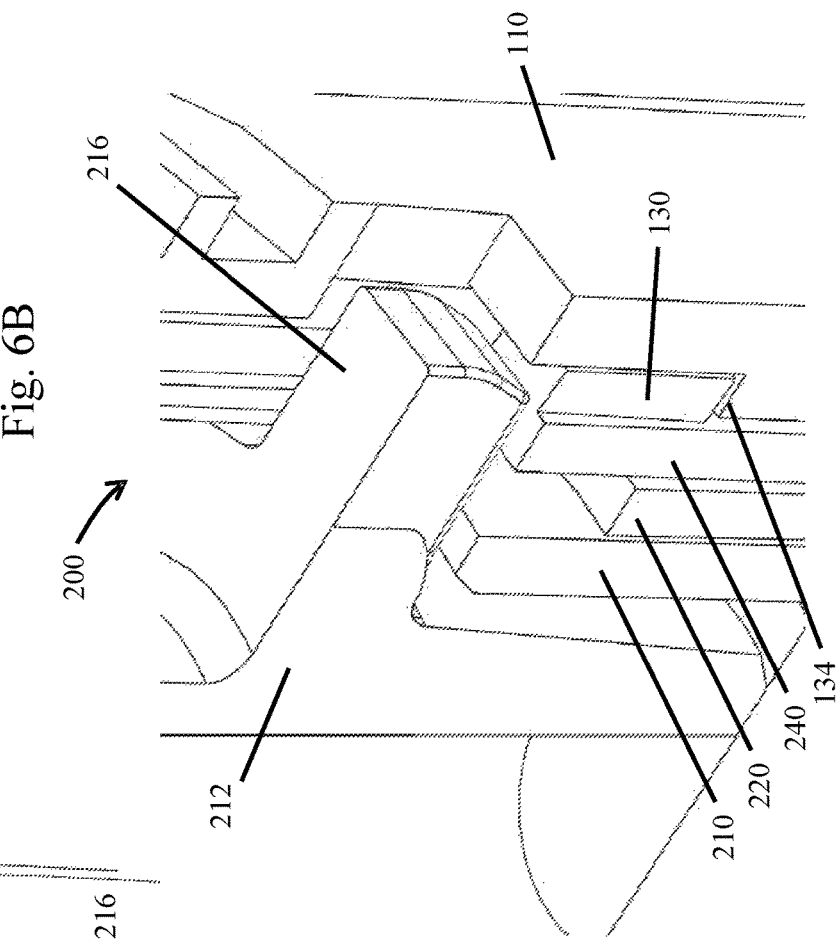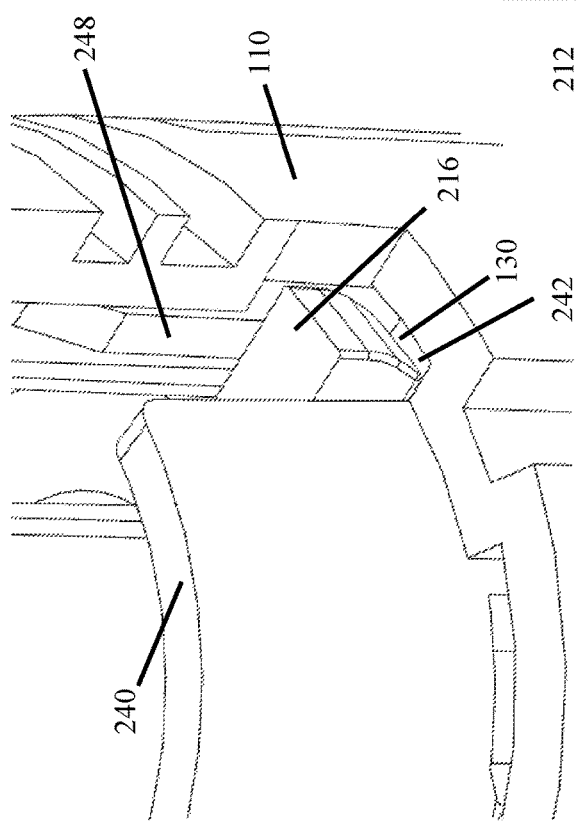
Fig. 6B
Fig. 6A

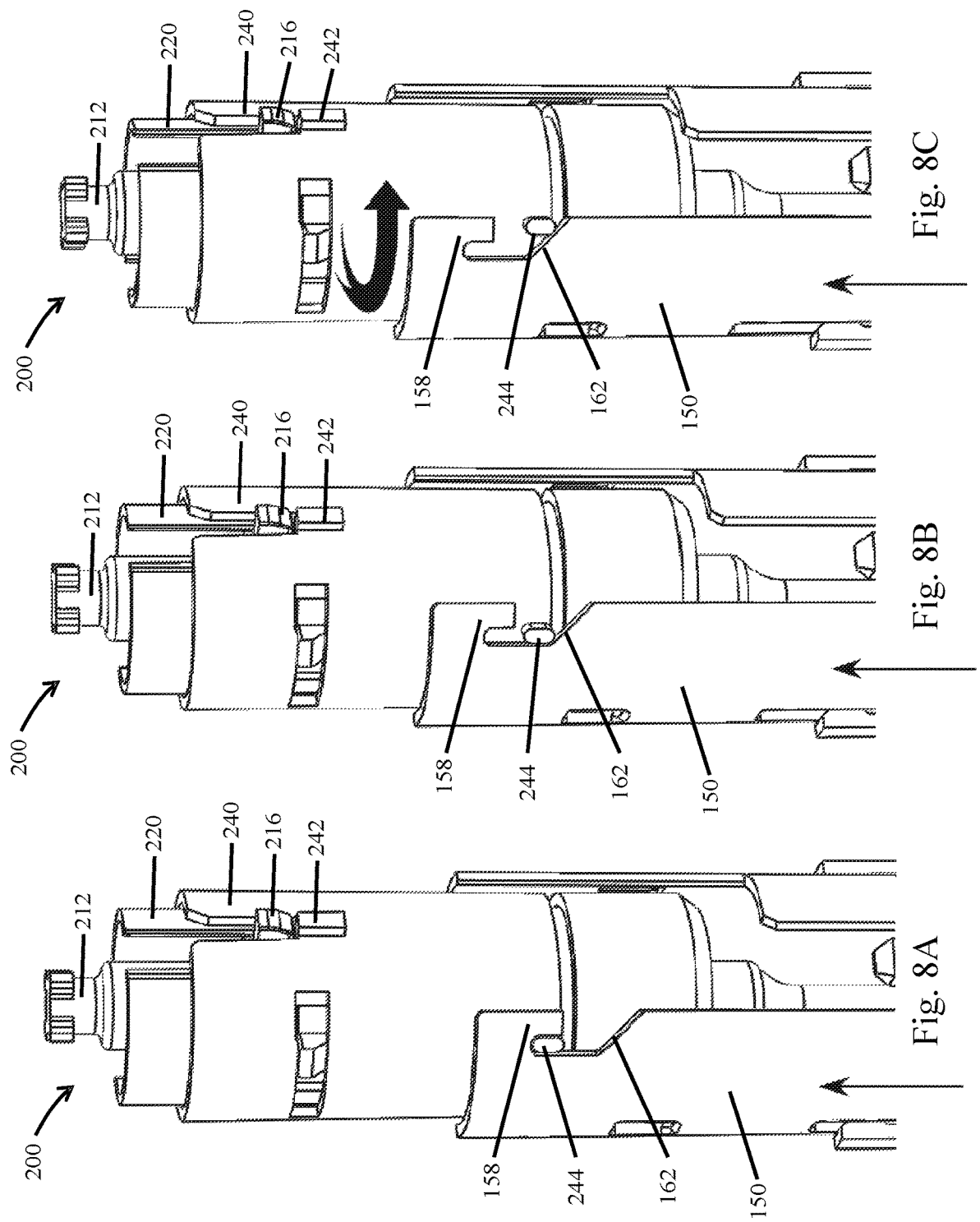

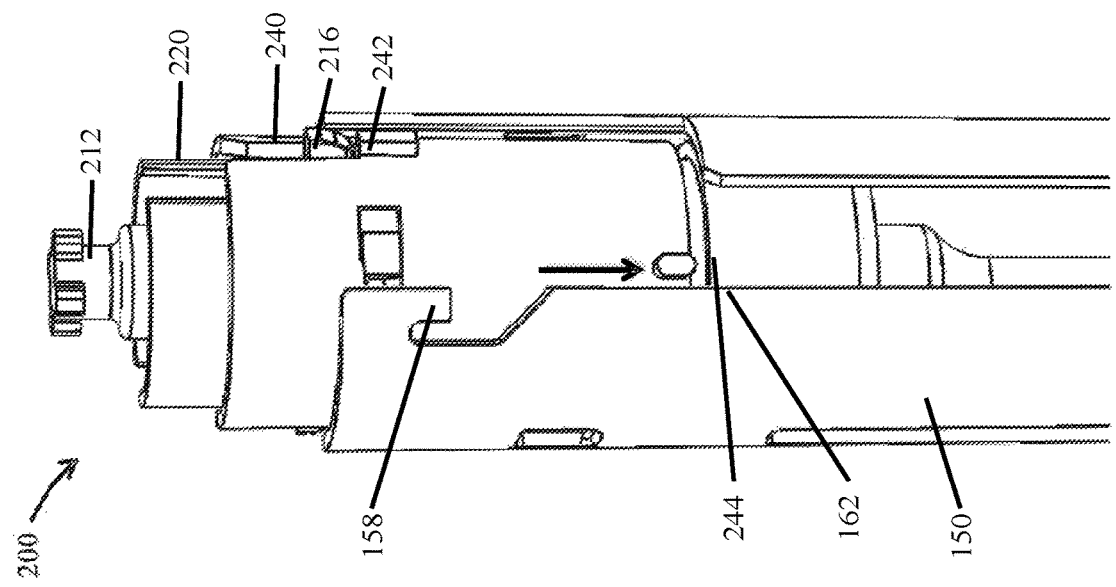
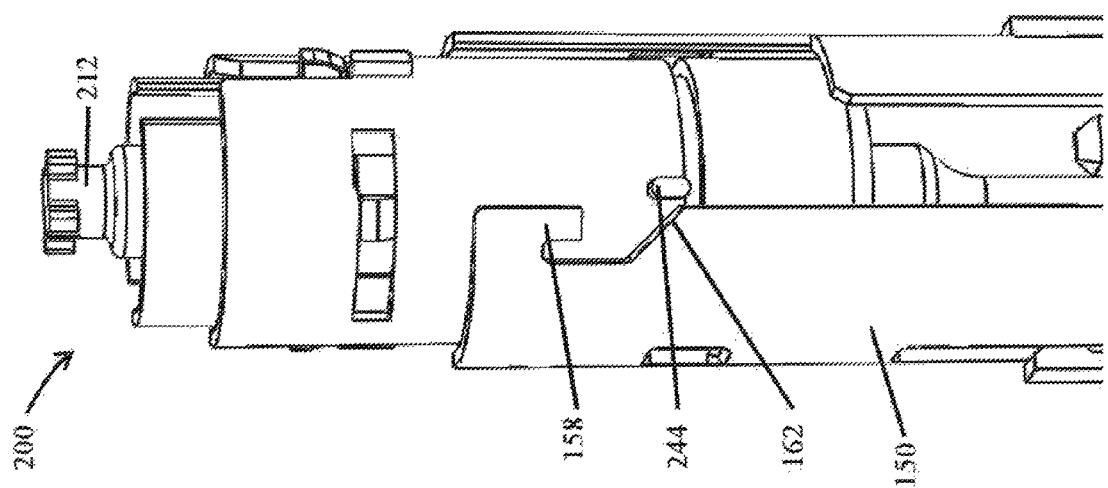

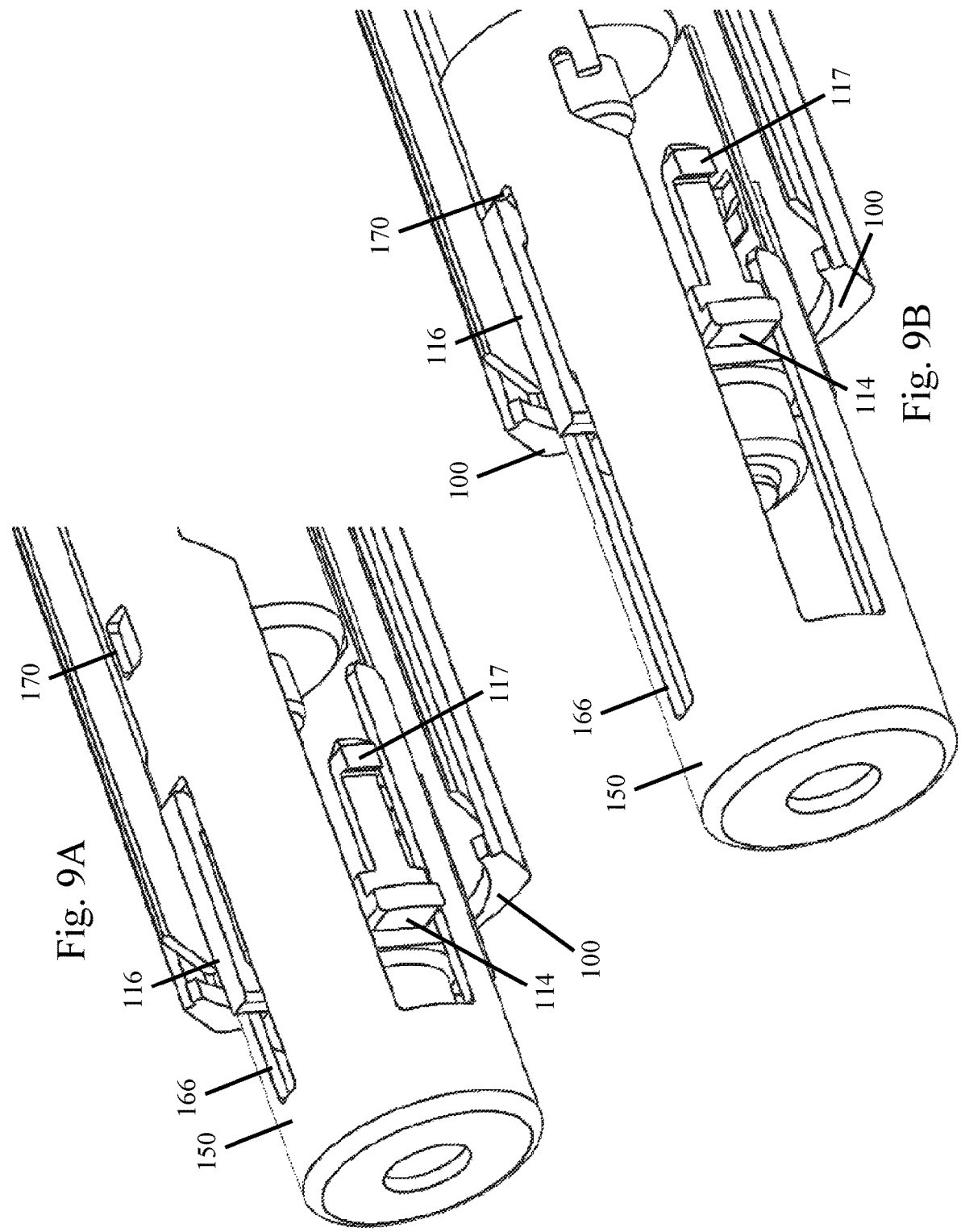

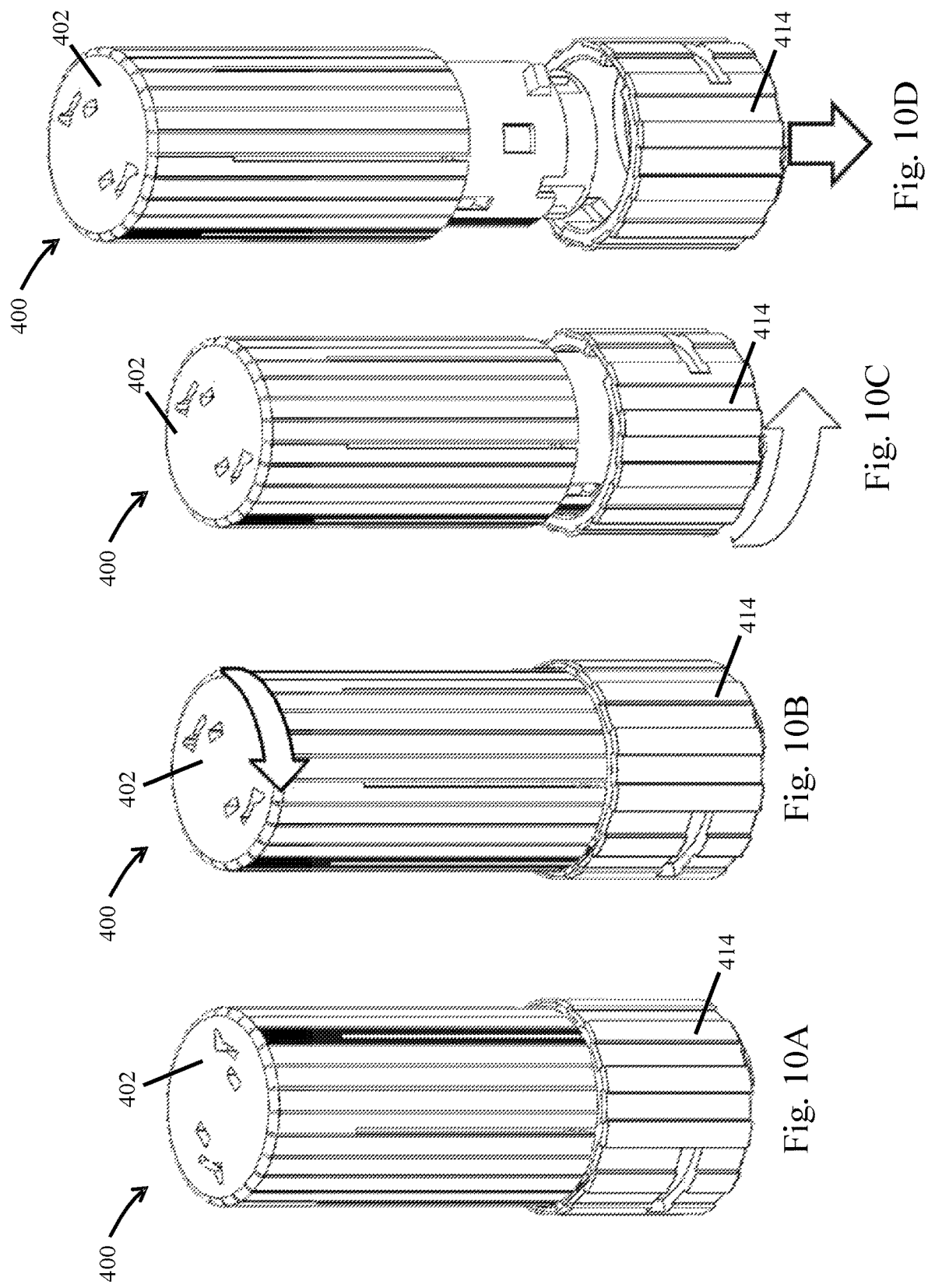

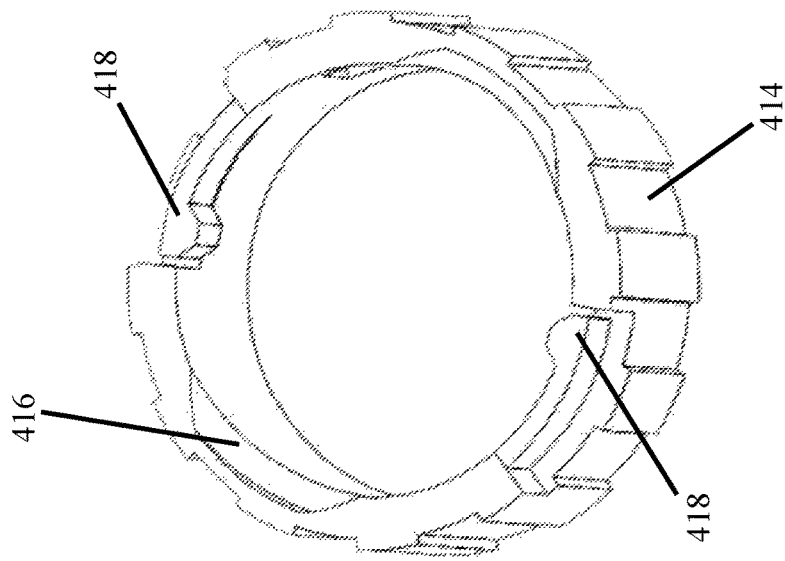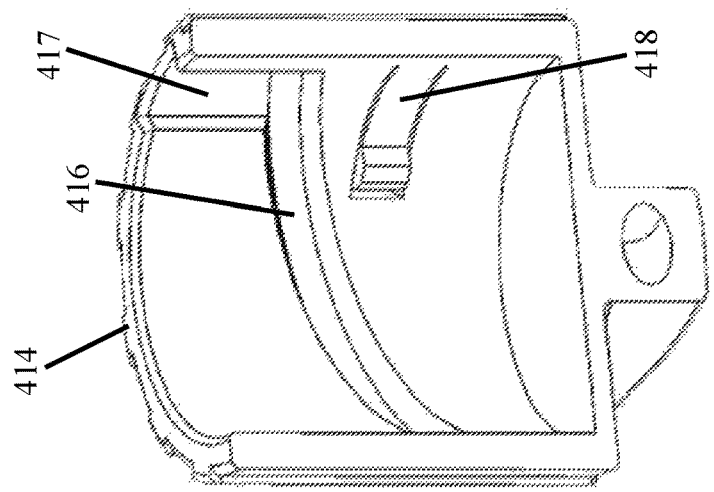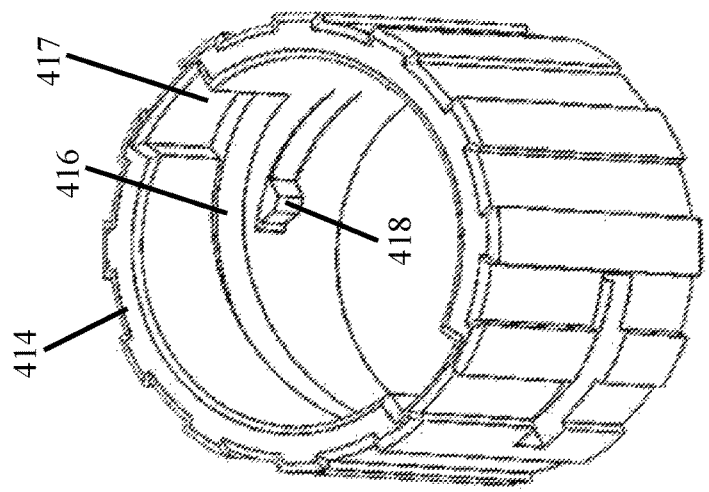

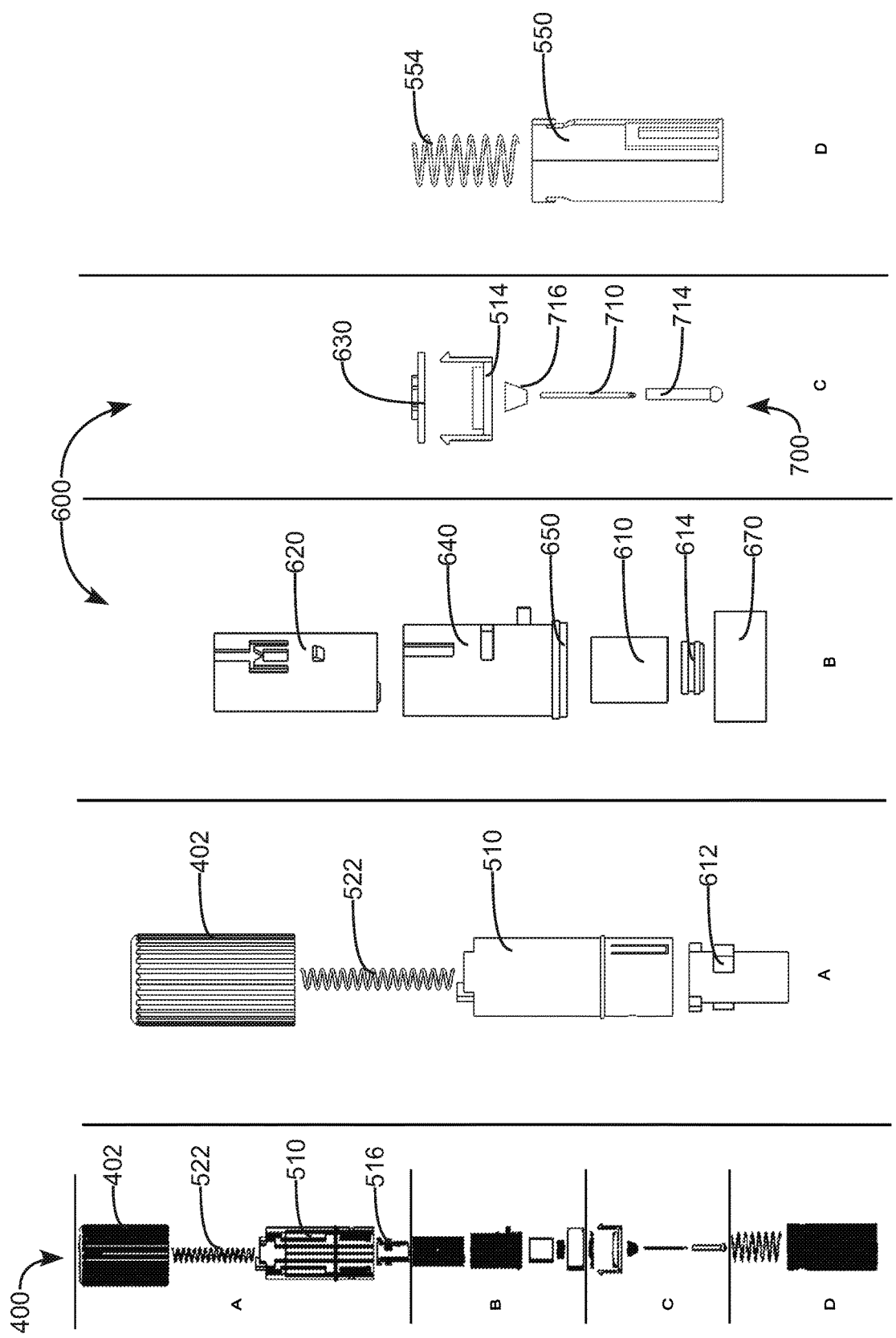

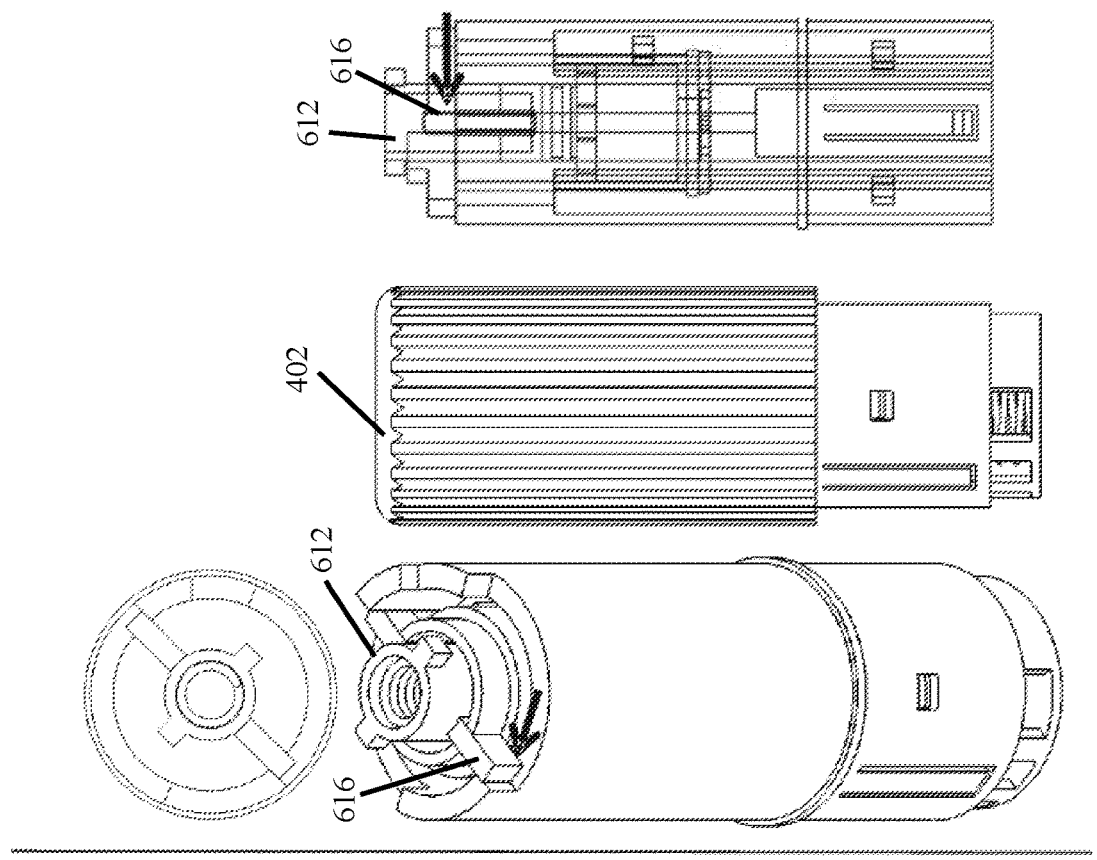
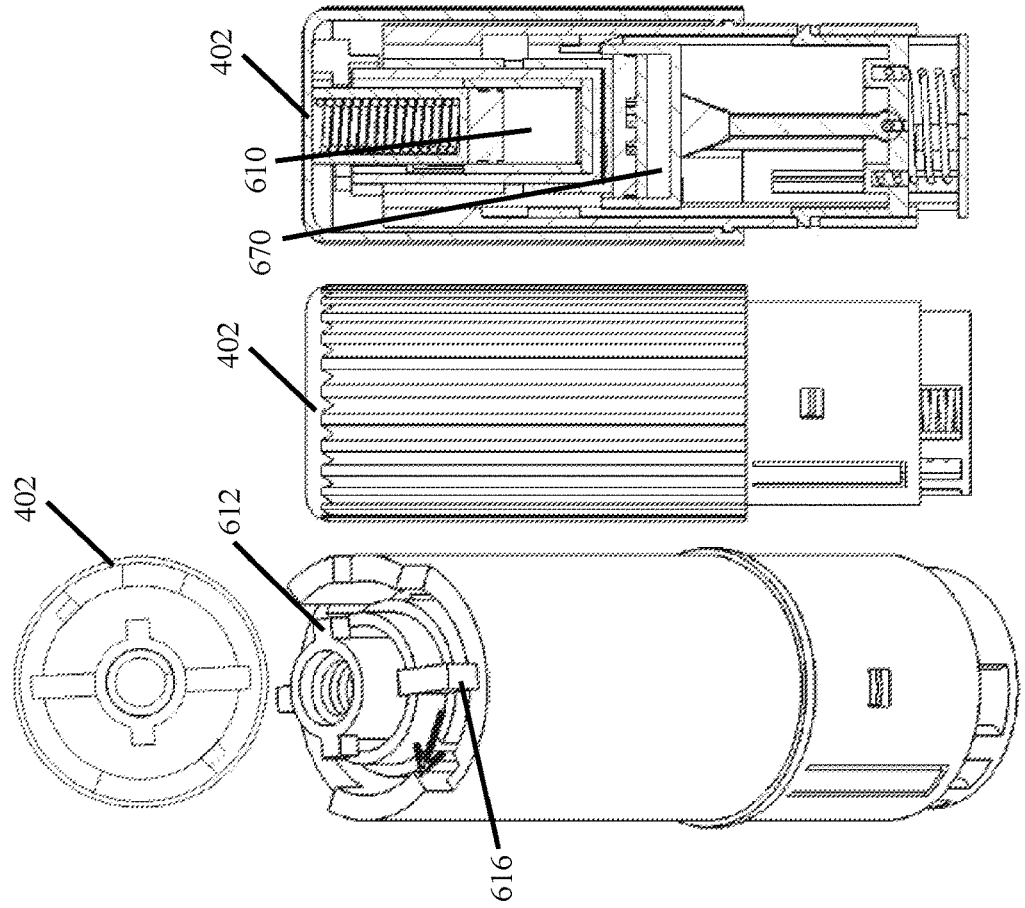

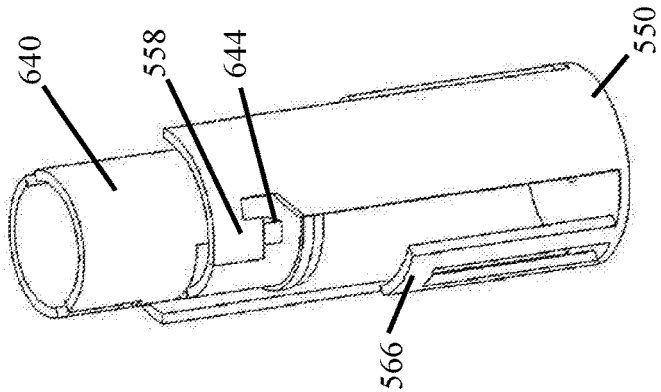
FIG. 20D
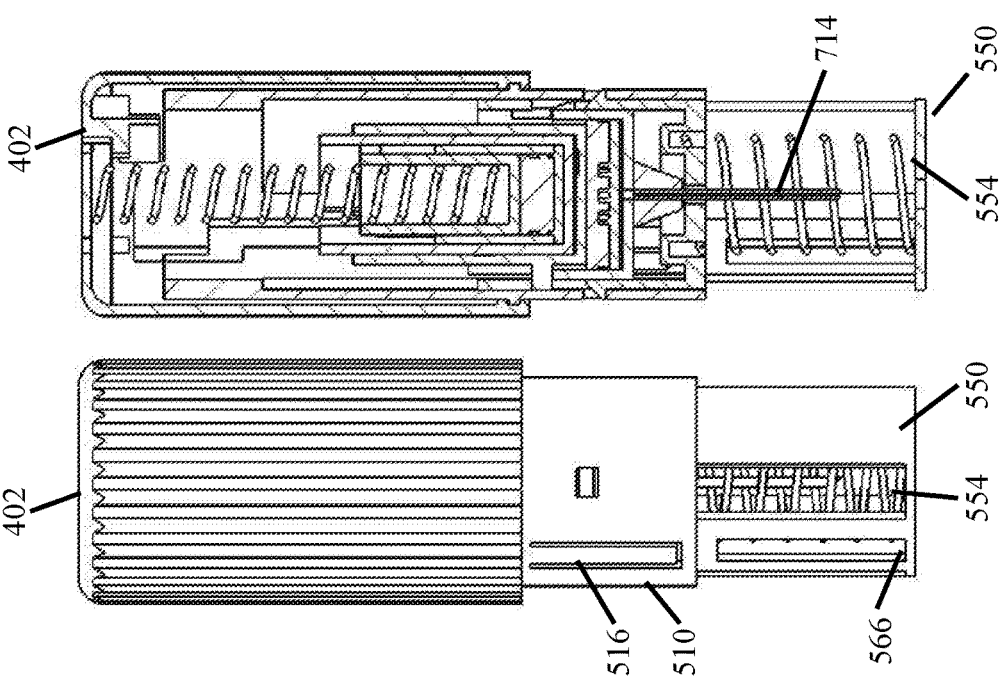
FIG. 20C
FIG. 20B
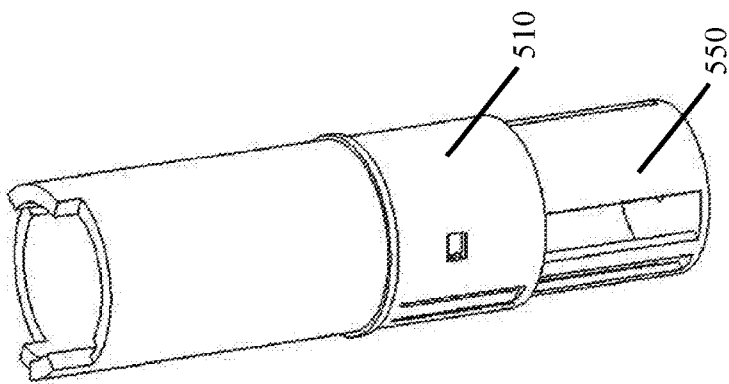
FIG. 20A

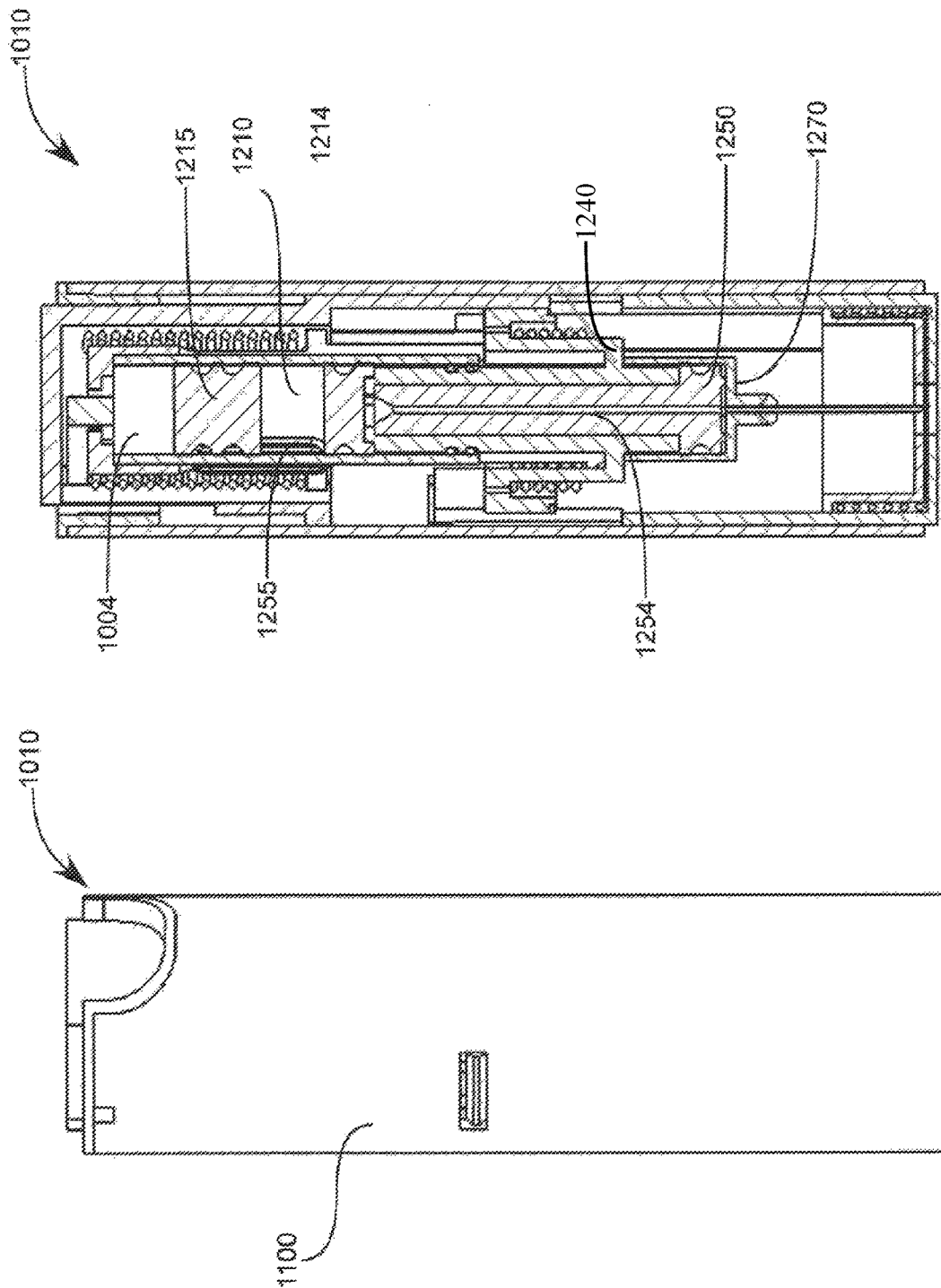

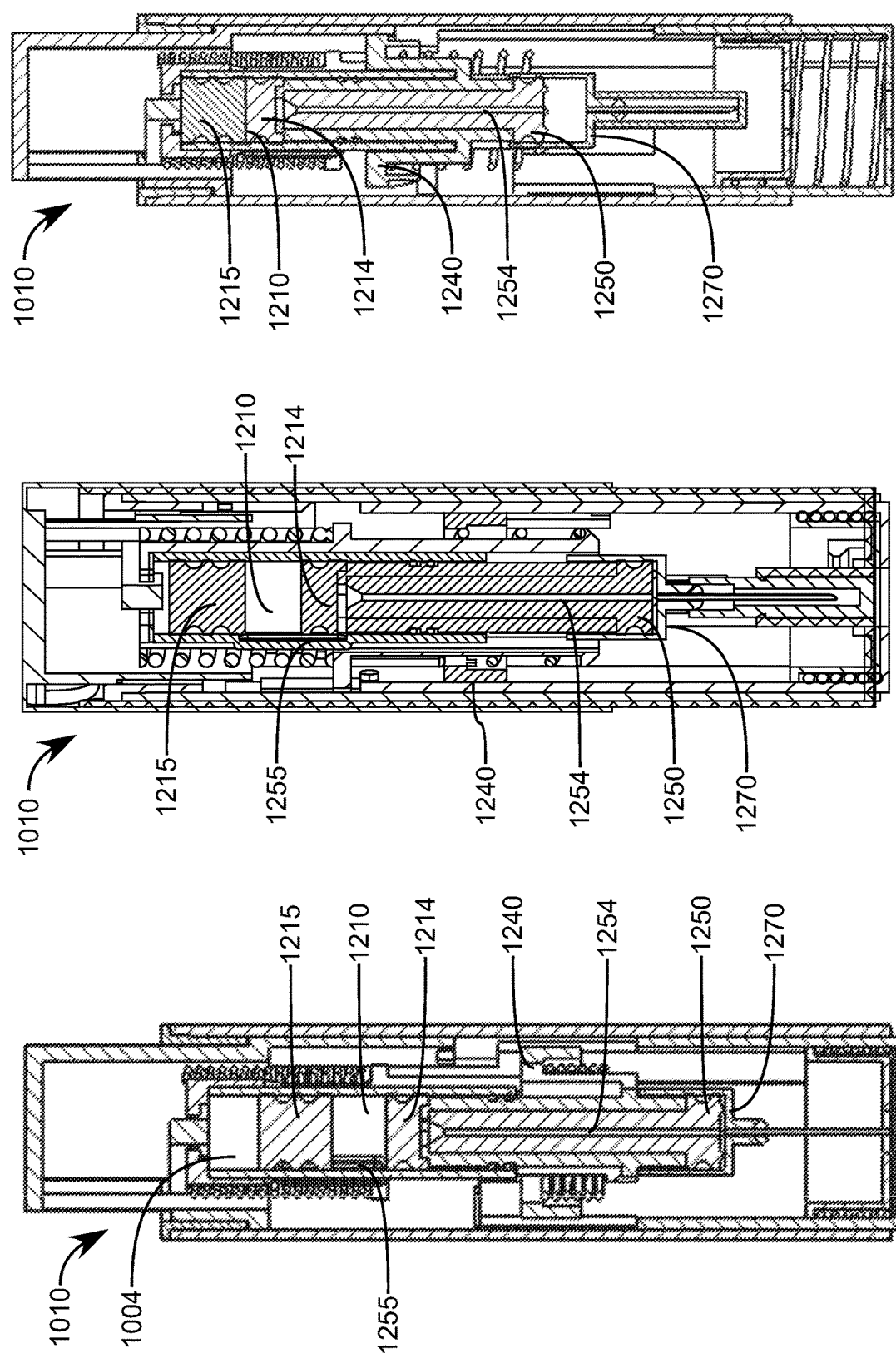

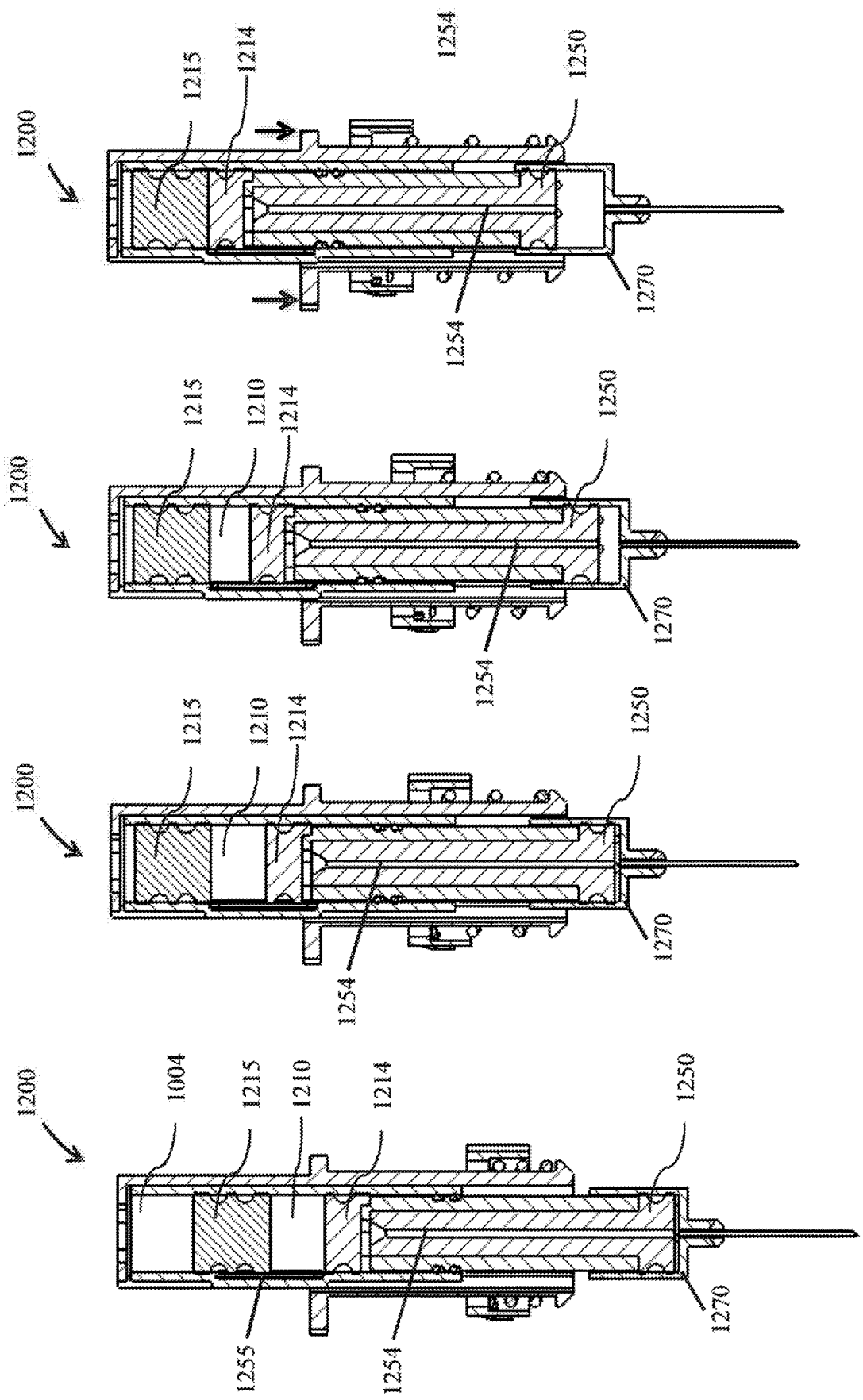

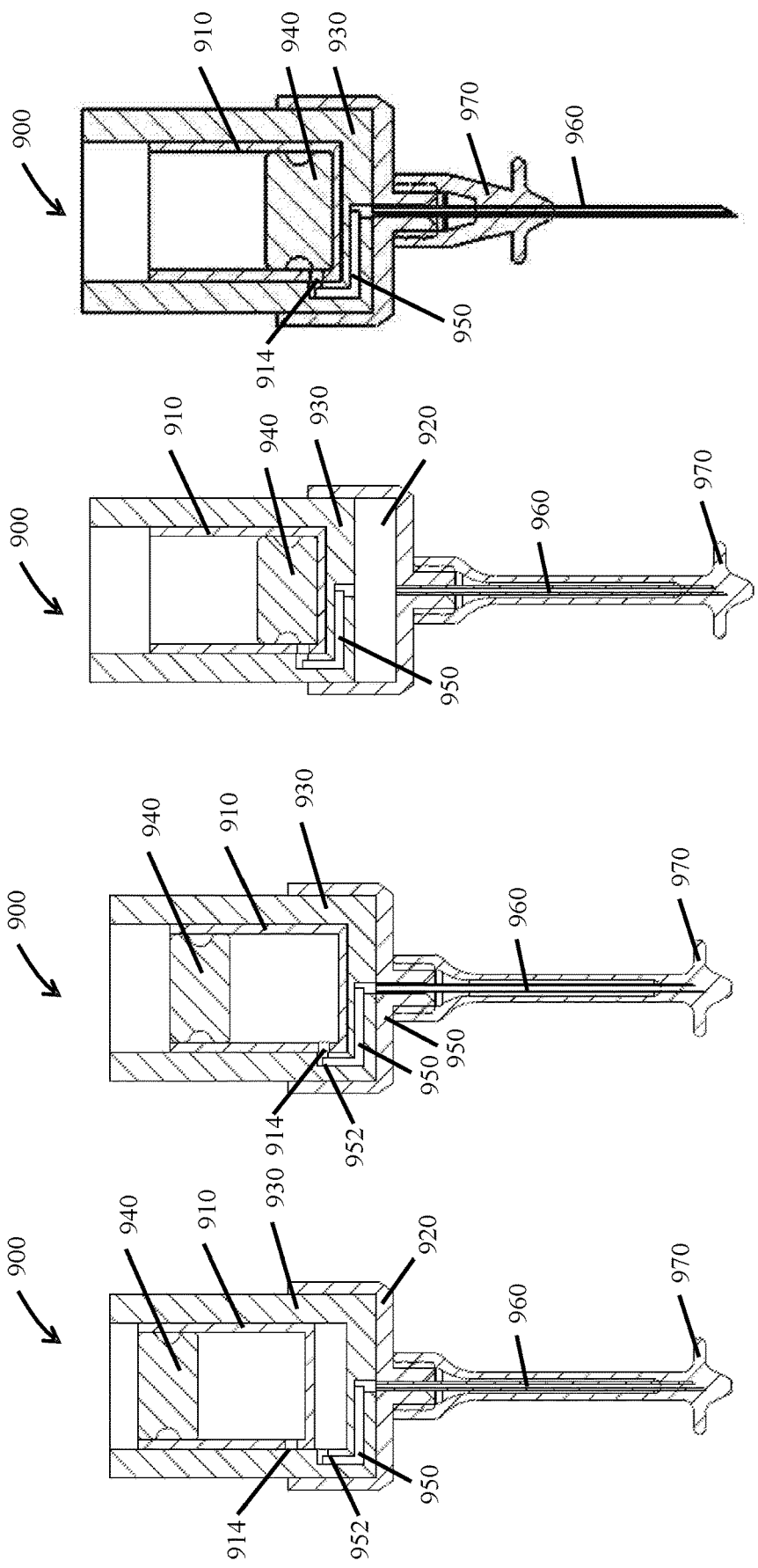

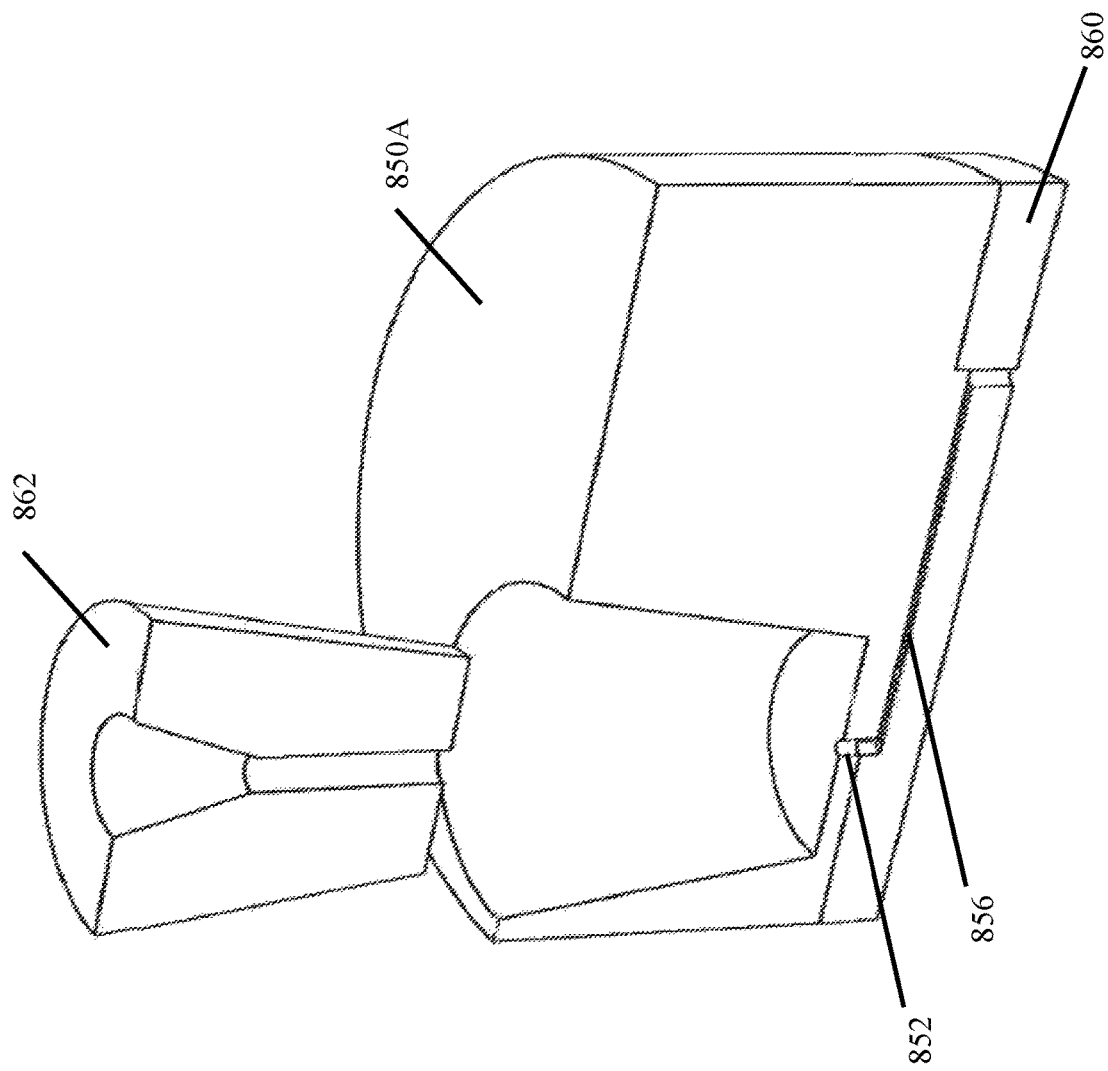

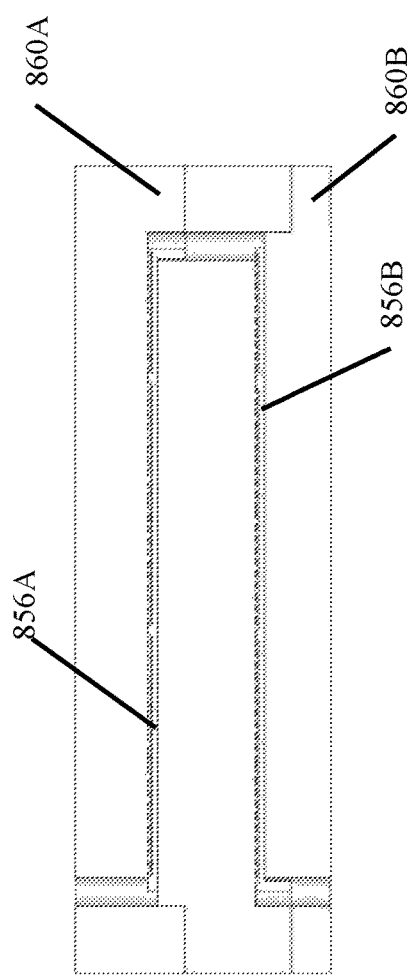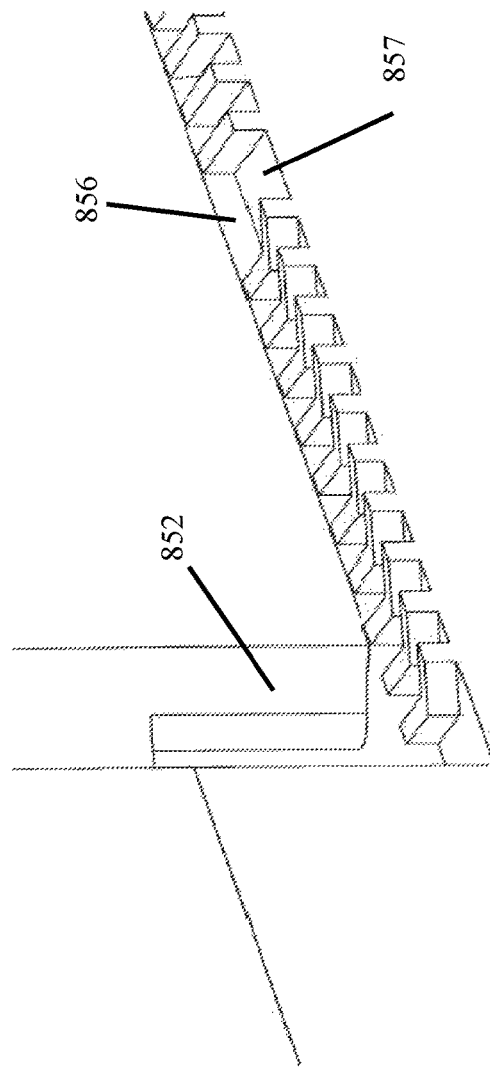
Fig. 31A
Fig. 31B

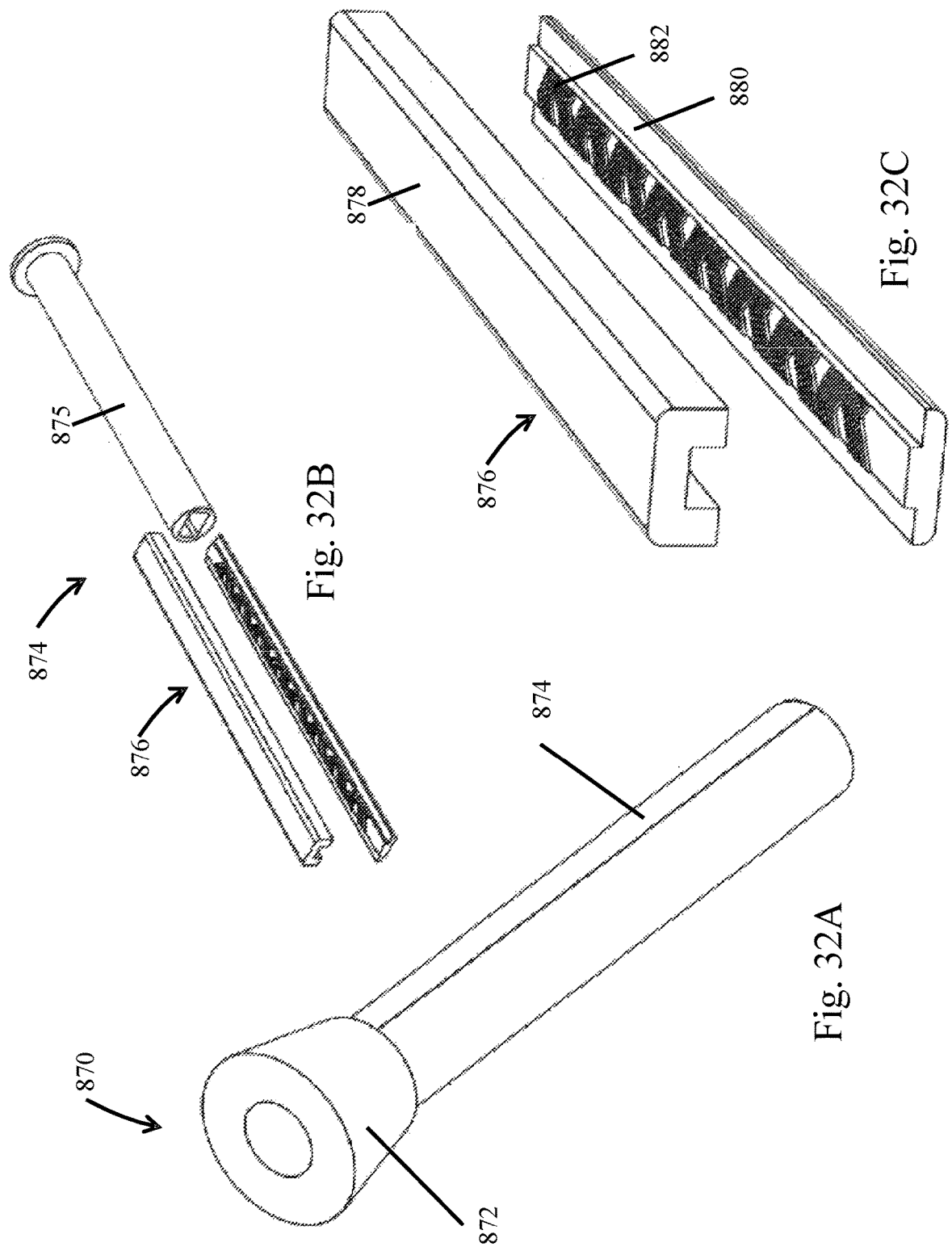

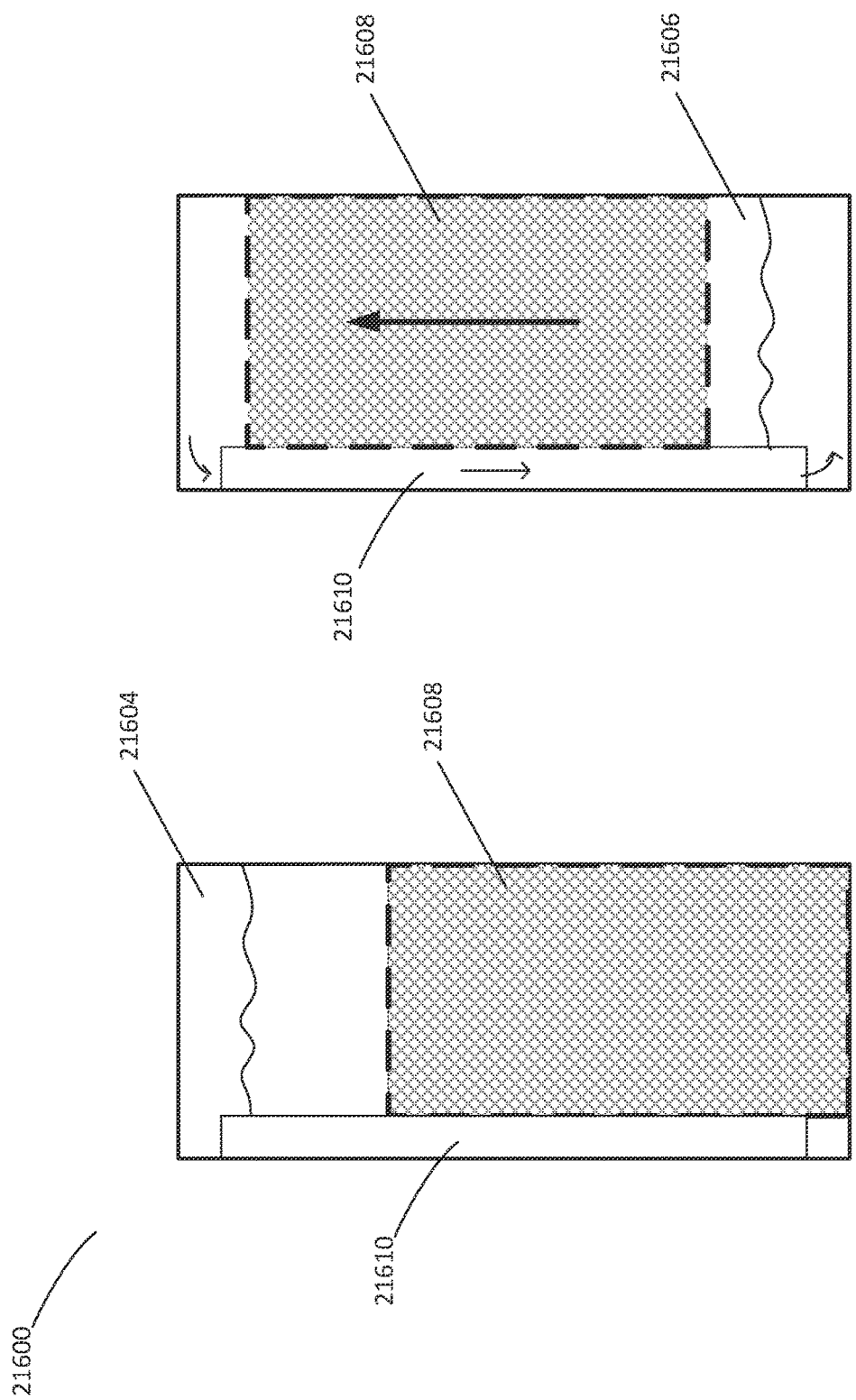

PORTABLE DRUG MIXING AND DELIVERY DEVICE AND ASSOCIATED METHODS

CROSS-REFERENCE TO RELATED APPLICATIONS

This application claims the benefit of U.S. Patent Application 62/756,056, filed on Nov. 5, 2018; this application is also a continuation-in-part of U.S. patent application Ser. No. 16/423,344 filed on May 28, 2019, which claims the benefit of the following: U.S. Pat. No. 10,300,198, issued on May 28, 2019, U.S. Pat. No. 9,907,911, issued on Mar. 6, 2018, PCT application number PCT/US15/45761 filed on Aug. 18, 2015; U.S. Patent Application 62/204,940, filed on Aug. 13, 2015; U.S. Patent Application 62/126,011, filed on Feb. 27, 2015; U.S. Patent Application 62/120,792, filed on Feb. 25, 2015; U.S. Patent Application 62/061,664, filed on Oct. 8, 2014; U.S. Patent Application 62/038,386, filed on Aug. 14, 2014; this application is also a continuation-in-part of U.S. patent application Ser. No. 16/266,341, filed on Feb. 4, 2019 which claims the benefit of the following: U.S. Pat. No. 10,195,361, issued on Feb. 5, 2019; U.S. Pat. No. 9,199,037 issued on Dec. 1, 2015; U.S. Patent Application 61/917,943, filed on Dec. 19, 2013; U.S. Patent Application 61/800,014, filed on Mar. 15, 2013, this application is also a continuation-in-part of U.S. patent application Ser. No. 14/975,695, filed on Dec. 18, 2015 which claims the benefit of U.S. Application 62/094,063 filed on Dec. 18, 2014; this application is also a continuation-in-part of U.S. patent application Ser. No. 14/576,179, filed on Dec. 18, 2014, which claims the benefit of U.S. Patent Application 62/016,260, filed on Jun. 24, 2014; U.S. Patent Application 61/917,925, filed on Dec. 18, 2013; all of which are herein incorporated by reference in their entirety.

FIELD OF THE INVENTION

The present invention relates generally to auto-injectors and prefilled syringes and more particularly to auto-injectors that store in a compact state and allow for formation or reconstitution of a therapeutic agent for injection.

BACKGROUND OF THE INVENTION

Individuals who suffer from certain medical conditions are often required to keep an auto-injector or prefilled syringe nearby in order to address a medical need. A few examples of this are insulin pens for people with diabetes, epinephrine for those with food and insect stings allergies, antidotes for soldiers at risk of exposure to chemical and/or biological toxins in the field and opioid antagonists to combat the opioid and other drug overdose and addiction issues. For example, an allergic reaction may occur in a location which is physically distant from the nearest hospital or medical facility. Overdosing also occurs in various places. Food containing peanuts are more likely to be supplied to the individual away from a controlled home environment like at a baseball park. Having a portable dual chamber auto-injector with the appropriate medicament nearby enables emergency intervention after an exposure to an allergen or overdose can save lives.

Size is an issue when it comes to auto-injectors. Many owners of the devices are hesitant to carry their injector with them if it represents a burden, by providing injectors in more compact sizes it will make it more likely that they will.

Consistency is import, where traditional mixing during emergency situations can be compromised or result in error.

Shelf-life is also a large issue with respect to auto-injectors, which can be expensive and used fairly infrequently. For example, a user who has intense allergic reactions to shellfish can go years between exposures and subsequent injections. In such a case it can be easy to forget to replace the auto-injector after expiration, whereupon in an emergency, the drugs contained therein have expired and are either ineffective or have a greatly reduced effectiveness due to decomposition of the drugs contained therein. As will be appreciated by those having skill in the art, the shelf life can be increased by storing the desired medication in an unmixed and dry state and dissolved just prior to injection. This ability to store the wet and dry components separately within the device can increase the shelf life and thus increase the likelihood that the user will have an injector with effective dosages when an emergency arises.

In such devices it is required that the mixing and reconstitution processes are consistent and complete prior to injection.

SUMMARY OF THE INVENTION

It has been recognized that if a drug can be kept out of the liquid phase and stored as a dry medication, the shelf-life can be substantially increased and temperature susceptibility can be decreased substantially thus allowing the efficacy and potency of the drug to endure longer and through harsher environments.

It has been recognized that a smaller drug delivery device than a conventional epinephrine auto-injector, which could be attached to a key chain and/or easily fit in a person's pocket, would make the device easier to carry and more likely that the user will have it on their person when needed. Various structures are contemplated herein which address many of the problems discussed above through the use of mixing structures, and actuation devices which ensure proper storage integrity, and full mixing prior to injection.

A portable auto-injector is capable of moving from a compact state where the auto-injector is in a shape easier to transport than in an activation state wherein the auto-injector has been extended and/or made larger and/or longer and/or easier to handle in some way. In some embodiments a safety limits movement of the needle assembly and prevents premature needle sticks. The drug is stored in one or more dry and/or wet medicament states until needed.

Contemplated herein is a medication mixing and delivery device which can include a housing, a first chamber located within the housing, wherein the first chamber can be defined by an annular side wall and a bottom, the first chamber having an outlet, and a second chamber located within the housing, the second chamber having an inlet. A sliding valve can be located within the housing between the first and second chambers, the sliding valve can be configured to selectively open or close by aligning or misaligning the outlet of the first chamber with the inlet of the second chamber so as to cause or prevent fluid communication between the outlet of the first chamber and the inlet of the second chamber. An actuation device can also be provided within the housing which can include a pre-loaded energy source, such as a spring, or compressed gas. The actuation device can also be in mechanical communication with the sliding valve and be configured to allow the sliding valve to alternate between a closed state and an open state. A displacement mechanism can also be provided within the housing and be configured so as to reduce the effective volume of the first chamber upon actuation, as well as a second displacement mechanism configured to reduce the effective volume of the second chamber.

A fluidic channel can be disposed between the outlet of the first chamber and the inlet of the second chamber in order to provide fluid communication between the outlet of the first chamber and an inlet of the second chamber. In some embodiments the dry medicament can be stored within this fluidic channel, or alternatively within the second chamber itself.

A delivery assembly configured to be in fluid communication with the second chamber. The delivery assembly can include a needle subassembly which is partially disposed within a septum, wherein the septum that is disposed between the needle subassembly and the second chamber, wherein the second actuation device can cause the needle assembly to pierce the septum and allow the needle assembly to establish fluid communication with the second chamber. Alternatively, the delivery assembly can include a blocking mechanism which is disposed between the second chamber and the delivery assembly, and wherein the blocking mechanism prevents fluid communication prior to activating the second actuation device.

In some embodiments, the actuation device can be activated by a triggering device, which activation causes the actuation device to generate an alignment force, which alignment force causes the sliding valve to be placed into the open state and wherein the alignment force causes a first portion of energy stored within the pre-stored energy source to be released, causing the displacement mechanism to force a liquid stored in the first chamber to pass through outlet and inlet to be received by the second chamber.

In some embodiments, a dry medicament is stored within the housing and outside the first chamber, such as in the second chamber, or within a fluidic channel connecting the outlet of the first chamber to the inlet of the second chamber.

In yet additional embodiments, a second actuation device can be provided which is configured to release a second portion of energy from the pre-loaded energy source, which upon release, forces the liquid, which is now located in the second liquid chamber, to be displaced out of the second chamber through the delivery assembly.

In some embodiments the first actuation device can be formed in part by the housing and a rotatable cap which can receive an actuation force and counter force, wherein the rotatable cap can be removably attached to the housing.

In some embodiments the first chamber can be rotatable disposed with respect to, and within the housing.

Additionally, in yet additional embodiments the second chamber can be configured such that it becomes rotationally fixed with the first chamber upon releasing the first portion of stored energy, and wherein the first and second chamber can be further configures so as to rotate together upon activating the second actuation device.

In yet additional embodiments the second chamber can be configured such that it is independently expandable and contractible with respect to the first chamber.

In some embodiments the medication mixing and delivery device can include a removable ferrule disposed within the second chamber about the inlet thereof which can be configured to contain the dry medicament.

In some embodiments the fluidic channel, which can be provided between the outlet of the first chamber and the inlet of the second chamber can be formed by providing a plurality of stacked disks, wherein each disk has a channel formed therethrough which forms the fluidic channel.

Some embodiments contemplated herein can further include a needle shield assembly, the needle shield assembly can further include a needle shield and secondary spring, the secondary spring can further be configured to bias the needle shield in an extended position. In some such embodiments the needle shield can form a part of a second actuation assembly, the second actuation device being configurable so as to release a second portion of energy from the pre-loaded energy source which upon release forces the liquid, which is now located in the second liquid chamber, to be displaced out of the second chamber through the delivery assembly, and whereupon depressing the needle shield toward the housing triggers the release of the second portion of energy stored within the pre-stored energy source which release causes both an extension of the delivery assembly and the displacement of the liquid from the second chamber through the delivery assembly. Some such embodiments can additionally include a locking mechanism, which is triggered after a first needle shield depression, the locking mechanism being configurable so as to lock in an extended position after being removed from an injection site.

In some alternative embodiments the sliding valve can be positioned so as to align cross-axially, or alternatively the sliding valve can be configured to be positioned in an aligned state by sliding axially. In some embodiments, the sliding valve can be configured to be positioned in an aligned state by rotational movement, and may be referred to as a rotary valve.

In yet additional embodiments the first actuation device can be provided in mechanical communication with an external trigger, the external trigger being coupled to the housing in a manner such that the external trigger can be rotated, slid, depressed, or detached.

Also contemplated herein is a method of mixing and delivering a medication, the method including various steps, such steps including but not limited to: coupling a pre-stored energy source to a first actuation mechanism, wherein actuation releases a first portion of stored energy from the pre-stored energy source to activate a first displacement mechanism which forces a fluid stored in a first chamber to be displaced into a second chamber; coupling a sliding valve to the first actuation mechanism, whereupon actuating the first actuation mechanism generates an alignment force to convert the sliding valve from a closed state to an open state which slidingly aligns an outlet of the first chamber such that it becomes aligned and in fluid communication with an inlet of the second chamber; triggering a triggering device mechanically coupled to the first actuation mechanism, wherein said triggering causes the first actuation device to release a first portion of stored energy; and activating a second actuation mechanism, whereupon actuation releases a second portion of stored energy from the pre-stored energy source so as to activate a second displacement mechanism which forces the fluid from the second chamber through a delivery mechanism.

The method can further include the steps of: placing a dry medicament within the second chamber, wherein activating the first actuation mechanism causes a fluid to mix with the dry medicament; and extending the delivery mechanism in response to activating the second actuation mechanism.

The various steps can be effectuated by various means, for example, the activation of the second actuation mechanism can be effectuated by depressing a needle guard.

In some embodiments, after delivery of the fluid through the delivery mechanism, the needle guard can be extended and locked into an extended state which covers a needle of the delivery assembly.

In some embodiments, a dry medicament in accordance with the application comprises an opioid antagonist (e.g., a dry opioid antagonist). In some embodiments, the dry medicament comprises nalmefene, naloxone (e.g., naloxone hydrochloride), and/or naltrexone. In some embodiments, the dry medicament comprises an opioid antagonist in the form of a dry salt or a dry free base. For example, in some embodiments, the dry medicament comprises nalmefene in the form of a hydrochloride salt (e.g., nalmefene HCl).

In some embodiments, a dry medicament comprises a dry pharmaceutical composition (e.g., dry powder composition) that can be rapidly reconstituted into solution for delivery to a subject, for example a human subject (e.g., by injection). In some embodiments, a dry pharmaceutical composition comprises a combination of a dry opioid antagonist and one or more dry excipients (e.g., one or more of a dry pH adjusting agent, a salt, an antioxidant, and a pharmaceutically acceptable carrier).

In some aspects, the application provides an injection device (e.g., an autoinjector) comprising a dry opioid antagonist and a liquid. In some embodiments, the liquid is located in a first chamber of the injection device, and the dry opioid antagonist is located in a second chamber of the injection device. In some embodiments, the dry opioid antagonist is in the form of a dry salt or a dry free base. In some embodiments, the liquid comprises a pH optimizing agent. In some embodiments, the liquid is a solution that is pH optimized for reconstituting the dry salt or the dry free base form of the opioid antagonist.

For example, in some embodiments, the injection device comprises an opioid antagonist in the form of a dry salt, and a liquid comprising a pH optimized solution having an approximately neutral pH (e.g., between about 6.0 and about 8.0). In some embodiments, the injection device comprises an opioid antagonist in the form of a dry free base, and a liquid comprising a pH optimized solution having an acidic pH (e.g., below about 6.0) or a basic pH (e.g., above about 8.0). In some embodiments, the injection device further comprises a dry pH adjusting agent. In some embodiments, the dry pH adjusting agent adjusts the pH of a reconstituted opioid antagonist to a physiologically acceptable range.

In at least one embodiment, a mixing system is a dual chamber drug mixing system that includes a housing, a first chamber, a second chamber, and a user operable mixing system. The first chamber and the second chamber are disposed at least partially within the housing. The first chamber has an outlet and a first medicament component provided therein. The second chamber has an inlet, an outlet, and a second medicament component provided therein. The second medicament component includes an opioid antagonist compound. The user operable mixing system has a movable component associated with the first chamber and a pre-loaded energy source. When the user operable system is activated the movable component creates a fluidic pathway between the outlet of the first chamber and the inlet of the second chamber; and releases a portion of energy from the pre-loaded energy source to drive the displacement mechanism within the first chamber, thus causing the first medicament component to transfer through the outlet of the first chamber into the second chamber and mix with the second medicament component.

In some embodiments, a valve is disposed between the outlet of the first chamber and the inlet of the second chamber and the valve is configured to open or close a fluidic pathway between the first chamber and the second chamber. The movable component is mechanically coupled to the valve. The movable component may cause the valve to rotate or slide to open or close the valve. The movable component may cause the valve to align the outlet of the first chamber with the inlet of the second chamber, with the alignment occurring prior to causing the pre-loaded energy source to release a portion of energy. This alignment and release of a portion of the energy may be caused by a continuous action of motion of the movable.

In at least one embodiment the first chamber has a first sidewall and the second chamber has a second sidewall separate and distinct from the first sidewall.

In at least one embodiment, the movable component interfaces with a removable cap that is user operated and removing the removable cap causes the movable body to perform the aligning and releasing steps.

The moveable component may be rotatable or axially translated, and may encapsulate the first chamber. The movable component may be a frame.

A needle assembly can be provided in fluidic communication with the outlet of the second chamber.

The second chamber may be configured to axially move and expand a volume of the second chamber formed therein. In at least one embodiment, the second chamber has an outlet that is in fluid communication with the needle assembly. During a mixing phase, the second chamber moves axially and the volume of the second chamber expands during the axial movement. During axial movement in a delivery phase, when a fluid is delivered to the needle, the volume of the second chamber contracts.

The second chamber may be a cartridge having a seal disposed between the second chamber and the needle assembly. Alternatively, the second chamber may be a syringe component having a staked needle on one end, with the staked needle forming an outlet to the second chamber.

The first chamber and the second chamber are configured to move with the housing independently from each other.

In at least one embodiment, a medication mixing device includes a housing having a first chamber and a second chamber, a valve assembly, and a first displacement mechanism. A first medicament component, in a liquid form, is provided in the first chamber. A second medicament component, which is dry and includes an opioid antagonist compound, is provided in the second chamber. The valve assembly is disposed between the first chamber and the second chamber and is configured to selectively allow fluid communication between the first chamber and the second chamber. The valve assembly may extend partially into the second chamber. The first displacement mechanism is configured to cause a movement of the first medicant component from the first chamber into the second chamber, thus causing the first medicament component and the second medicament components to mix resulting in a mixed medicament compound.

The medication mixing device may include a pre-loaded energy source configured to drive the first displacement mechanism.

The first chamber and the second chamber may be structurally independent from each other.

In at least one embodiment, the medication mixing device includes a second displacement mechanism provided in association with the second chamber. The second displacement mechanism is configured to displace the mixed medicament compound from the second chamber and the pre-loaded energy source also contains energy configured to drive the second displacement mechanism. The second displacement mechanism is provided on a lower portion of the valve assembly. The first actuation assembly is provided in communication with the first displacement mechanism, whereupon actuation of the first actuation assembly releases a first portion of energy from the pre-loaded energy source so as to cause the first displacement mechanism to displace the first medicament component from the first chamber into the second chamber.

In at least one embodiment, a delivery assembly is provided in fluid communication with the second chamber and a second actuation assembly. The second actuation assembly is configured to release a second portion of energy, from pre-loaded energy source, when the second actuation assembly is actuated. The release of the second portion of energy causes the second displacement mechanism to force the mixed medicament compound out of the second chamber through the delivery assembly.

In at least one embodiment, a frame is provided between the housing and the first chamber. The first actuation assembly is formed in part by the housing the frame, and a rotatable cap. The rotatable cap is removably attached to the housing. The frame includes a channel disposed on inner surface.

In at least one embodiment, the medication mixing device also includes a needle shield assembly. The needle shield assembly further includes a needle shield and a secondary spring, the secondary spring biases the needle shield in an extended position. The needle shield assembly forms part of the second actuation assembly and is configured so that depression of the needle shield into the housing initiates actuation of the second actuation assembly.

In another embodiment, a medication mixing and delivery system is disclosed. The system includes a housing having a first chamber and a second chamber, a valve assembly, a first displacement mechanism, a second displacement mechanism, a first actuation assembly, and a needle assembly. A first medicament component is provided in the first chamber and a second medicament component is provided in the second chamber. The first medicament component is a liquid. The second medicament component is dry and includes an opioid antagonist compound. The valve assembly is disposed between the first chamber and the second chamber. The first displacement mechanism is provided in association with the first chamber and the second displacement mechanism is provided in association with the second chamber. The first actuation assembly is coupled to a pre-stored energy source provided within the housing and associated with the first displacement mechanism. Actuation of the first actuation assembly causes the pre-stored energy source to release a first portion of energy and the first displacement mechanism to displace the first medicament component from the first chamber into the second chamber so as to mix with the second medicament component thus resulting in a mixed medicament compound. The needle assembly is in fluid communication with the second chamber.

In at least one embodiment, the system also includes a second actuation assembly associated with the second displacement mechanism. The second actuation assembly is configured to be actuated so as to allow the second displacement mechanism to displace the mixed medicament compound from the second chamber and through the needle assembly, and the pre-stored energy source is also associated with the second displacement mechanism.

In at least one embodiment, the first actuation assembly is formed in part by the housing, a frame, and a rotatable cap that is removably attached to the housing.

In another embodiment a drug mixing system is disclosed. The system includes a housing having a fluid channel between a first chamber and a second chamber, a movable body disposed between the first chamber and the second chamber, a first displacement mechanism, and an actuation assembly. A wet component is provided in the first chamber and dry component is provided outside the first chamber. The dry component includes at least one of following compounds: nalmefene, naloxone, or naltrexone. The movable body includes a valve. The first displacement mechanism is provided in association with the first chamber and is configured to displace the wet component from the first chamber. Actuating the actuation assembly causes the first displacement mechanism to displace the wet component from the first chamber into the second chamber so as to mix with the dry component thus resulting in a mixed medicament compound.

The system may also include a pre-stored energy source, a needle assembly in fluid communication with the second chamber, a trigger, and a second displacement mechanism associated with the second chamber. The second displacement mechanism is configured to displace the mixed medicament compound from the second chamber through the needle assembly. The first chamber is structurally independent from the second chamber. The trigger is configured so that when the trigger is actuated it releases energy from the stored energy storage to displace the second displacement mechanism into the second chamber so as to displace the mixed medicament compound from the second chamber and through the needle assembly.

The movable body may extend partially into the first chamber and also extends partially into the second chamber.

In at least one embodiment, the actuation assembly includes an intra-housing that is configured to displace the movable body into the first chamber in response to a manual input thus displacing the wet component into the second chamber. The movable body extends partially into the first chamber and partially into the second chamber. The first displacement mechanism is provided about a first end of the movable body, and the second displacement mechanism is provided about a second end of the movable body.

In some aspects, the application provides an autoinjector comprising a first liquid located in a first chamber of the autoinjector. In some embodiments, the first liquid is an acid or a base. In some embodiments, the autoinjector further comprises a dry pharmaceutical composition located in a second chamber of the autoinjector. In some embodiments, the dry pharmaceutical composition comprises a mixture of a therapeutically effective amount of a dry opioid antagonist and one or more dry pH adjusting agents.

In some embodiments, the dry opioid antagonist is more soluble in the acid or the base than the one or more dry pH adjusting agents. In some embodiments, the dry opioid antagonist and the one or more dry pH adjusting agents are in different particles. In some embodiments, the dry opioid antagonist is in particles that are smaller than the one or more dry pH adjusting agents. In some embodiments, the dry opioid antagonist particles dissolve faster than the one or more dry pH adjusting agent particles. In some embodiments, the dry opioid antagonist particles have a size between about 1 μm and about 30 μm. In some embodiments, the one or more dry pH adjusting agent particles have a size between about 35 μm and about 100 μm.

In some embodiments, the one or more dry pH adjusting agents are coated with one or more layers of a pharmaceutically acceptable carrier or one or more layers of a pharmaceutically acceptable polymer. In some embodiments, the dry opioid antagonist is associated with the one or more dry pH adjusting agents. In some embodiments, the one or more dry pH adjusting agents are coated with one or more layers of the dry opioid antagonist. In some embodiments, the one or more dry pH adjusting agents are selected from the group consisting of sodium and potassium buffering agents (e.g., sodium citrate, sodium phosphate, potassium citrate, potassium phosphate).

In some embodiments, the first liquid is an acid, and the acid is hydrochloric acid, phosphoric acid, or sulfuric acid. In some embodiments, the first liquid is an acid, and the first liquid has a pH of below about 6.0. In some embodiments, the first liquid has a pH of between about 0.1 and about 5.0. In some embodiments, the first liquid is a base, and the base is sodium hydroxide or potassium hydroxide. In some embodiments, the first liquid is a base, and the first liquid has a pH of above about 8.0. In some embodiments, the first liquid has a pH of between about 9.0 and about 13.5.

In some embodiments, the dry opioid antagonist is an opioid antagonist in the form of a dry free base. In some embodiments, the opioid antagonist is nalmefene, naloxone, naltrexone, or a combination thereof. In some embodiments, the opioid antagonist is nalmefene. In some embodiments, the opioid antagonist is nalmefene in the form of a dry free base.

In some aspects, the application provides a method of preparing an opioid antagonist solution in an injection device (e.g., an autoinjector). In some embodiments, the method comprises mixing a dry opioid antagonist and a liquid to reconstitute (e.g., solubilize, rehydrate, dissolve) the opioid antagonist within the injection device. In some embodiments, the liquid is located in a first chamber of the injection device, and the dry opioid antagonist is located in a second chamber of the injection device.

In some aspects, the application provides a method of preparing an opioid antagonist solution in a dual chamber autoinjector. In some embodiments, the method comprises mixing a dry opioid antagonist and a first liquid. In some embodiments, the dry opioid antagonist is located in a second chamber of an autoinjector, and the first liquid is located in a first chamber of the autoinjector. In some embodiments, the dry opioid antagonist is solubilized within the autoinjector upon opening a valve disposed between the first chamber and the second chamber and causing the first liquid disposed in the first chamber to be displaced through a fluid pathway formed by the valve in an open position to mix with the dry opioid antagonist located in the second chamber, thus forming an opioid antagonist solution.

In some embodiments, the dry opioid antagonist is an opioid antagonist in the form of a dry salt or a dry free base. In some embodiments, the dry salt is a maleate, malate, fumarate, tartrate, bitartrate, sulfate, hydrochloride, or borate salt of the opioid antagonist.

In some embodiments, the first liquid includes a pH optimizing agent. For example, in some embodiments, the first liquid is a pH optimized solution. In some embodiments, the first liquid is an aqueous solution comprising a pH optimizing agent. In some embodiments, the pH optimizing agent is an acid or a base. In some embodiments, the acid is hydrochloric acid, phosphoric acid, or sulfuric acid. In some embodiments, the base is sodium hydroxide, potassium hydroxide, or lithium hydroxide. In some embodiments, the first liquid is water.

In some embodiments, the dry opioid antagonist particles have a size between about 1 micrometer and 30 micrometers. In some embodiments, the dry opioid antagonist is an opioid antagonist in the form of a dry salt, and the first liquid has a pH of between about 6.0 and about 8.0. In some embodiments, the first liquid has a pH of between about 6.5 and about 7.5. In some embodiments, the dry opioid antagonist is an opioid antagonist in the form of a dry free base, and the first liquid has a pH of below about 6.0 or above about 8.0. In some embodiments, the first liquid has a pH of between about 0.1 and about 5.0. In some embodiments, the first liquid has a pH of between about 9.0 and about 13.5.

In some embodiments, the opioid antagonist solution is formed within about 5 minutes of mixing the dry opioid antagonist and the first liquid. In some embodiments, the opioid antagonist solution is formed within about 1 minute, within about 30 seconds, within about 10 seconds, within about 5 seconds, within about 3 seconds, or within about 1 second of mixing the dry opioid antagonist and the first liquid.

In some embodiments, the opioid antagonist is nalmefene, naloxone, naltrexone, or a combination thereof. In some embodiments, the opioid antagonist is nalmefene. In some embodiments, the opioid antagonist is nalmefene in the form of a dry salt. In some embodiments, the opioid antagonist is nalmefene hydrochloride.

In some embodiments, the methods further comprise administering the opioid antagonist solution to a subject through the autoinjector. In some embodiments, the subject is suspected of being at risk of death or injury due to overdose caused by an addictive agent. In some embodiments, the addictive agent is an opioid agonist. In some embodiments, the opioid agonist is morphine, methadone, fentanyl, sufentanil, heroin, or a combination thereof.

In some embodiments, the dry opioid antagonist is reconstituted within the injection device upon mixing with the liquid. In some embodiments, the reconstitution process is generally completed within less than 5 minutes (e.g., within less than about 1 minute, within less than about 30 seconds, within less than about 10 seconds, within less than about 5 seconds, within less than about 1 second). In some embodiments, the reconstituted opioid antagonist is administered through the injection device to a subject. In some embodiments, the reconstitution process is generally completed when at least about 80% of the dry opioid antagonist is solubilized.

Accordingly, in some aspects, the application provides methods of treating an opioid exposure (e.g., an opioid overdose) in a subject in need thereof. In some embodiments, the methods comprise administering to the subject a reconstituted opioid antagonist as described herein. In some embodiments, the methods comprise reconstituting a dry opioid antagonist in an injection device, and administering the reconstituted opioid antagonist to the subject. In some embodiments, the reconstitution and administration processes are generally completed within less than 10 minutes (e.g., within less than 5 minutes, within less than 1 minute, within less than 30 seconds, within less than 10 seconds).

In some embodiments, a subject to be treated in accordance with the invention is addicted to an addictive agent, at risk for relapse use of an addictive agent, or at immediate risk of death or injury due to overdose caused by an addictive agent. In some embodiments, the addictive agent is alcohol, nicotine, marijuana, a marijuana derivative, an opioid agonist, a benzodiazepine, a barbiturate, or a psychostimulant. In some embodiments, the opioid agonist is selected from the group consisting of morphine, methadone, fentanyl, sufentanil, and heroin. In some embodiments, the psychostimulant is cocaine, amphetamine or an amphetamine derivative. In addition, the subject may be addicted to more than one addictive agent, and the pharmaceutical compositions, unit dosage forms, and kits may be useful for treating or preventing addiction or relapse use of more than one addictive agent.

These aspects of the invention are not meant to be exclusive and other features, aspects, and advantages of the present invention will be readily apparent to those of ordinary skill in the art when read in conjunction with the following description, appended claims, and accompanying drawings. Further, it will be appreciated that any of the various features, structures, steps, or other aspects discussed herein are for purposes of illustration only, any of which can be applied in any combination with any such features as discussed in alternative embodiments, as appropriate.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention, wherein:

FIGS. 2A-B illustrate perspective exploded views of the medication mixing and delivery device and a mixing subassembly in accordance with the embodiment of FIGS. 1 A-C;

FIGS. 3A-D illustrate side cross sectional views of a medication mixing and delivery device through various actuation steps in accordance with the embodiment of FIGS. 1 A-C;

FIGS. 4A-D illustrate side cross sectional views of the mixing subassembly through various actuation steps for use in conjunction within the embodiment of FIGS. 1 A-C;

FIGS. 6A-E illustrate various exterior perspective views and cross-sectional views of the enlarged area of the mixing subassembly as indicated by area A in FIG. 5E;

FIGS. 8A-E illustrate various exterior perspective views of the mixing subassembly and a secondary actuation mechanism through various actuation steps moving from the mixed state to an injected state as would be effectuated using the embodiment of FIGS. 1 A-C;

FIGS. 9A-B illustrate various exterior perspective views of a needle guard and associated subassembly through various actuation steps to shield an exposed needle after injection using the embodiment of FIGS. 1 A-C;

FIGS. 10A-D illustrate perspective exterior views of an alternative embodiment of a medication mixing and delivery device through various actuation steps;

FIGS. 11A-C illustrate various perspective and cross-sectional views of a cap for use in the medication mixing and delivery device of FIGS. 10A-D;

FIGS. 12A-E illustrate side exterior exploded views of the medication mixing and delivery device, a housing assembly, a mixing assembly, a delivery assembly and a needle guard assembly, respectively;

FIGS. 14A-C illustrate various exterior perspective, side, and cross-sectional views of the medication mixing and delivery device as embodied in FIGS. 10A-D illustrating a first actuation step so as to initiate mixing;

FIGS. 15A-C illustrate various exterior perspective, side, and cross-sectional views of the medication mixing and delivery device as embodied in FIGS. 10A-D illustrating an actuated state;

FIGS. 20A-D illustrate various perspective, side and cross-sectional views of the medication mixing and delivery device as embodied in FIGS. 10A-D illustrating a needle shield lockout mechanism;

FIGS. 21A-B illustrate a perspective and cross-sectional view, respectively, of yet another alternative embodiment of a medication mixing and delivery device in a stowed state;

FIGS. 22A-E illustrate various cross-sectional views of the medication mixing and delivery device of FIGS. 21A-B through various actuation steps;

FIGS. 23A-D illustrate various cross-sectional detailed views of a mixing assembly for use with the medication mixing and delivery device of FIGS. 21A-B through various actuation steps;

FIGS. 27A-D illustrate principles of a sliding valve adaptable for use in any of the embodiments discussed herein;

FIG. 30 illustrates an exemplary fluidic channel and removable ferrule arrangement adaptable for use in any of the embodiments discussed herein;

FIGS. 31A-B illustrate various features and embodiments of fluidic channel arrangements adaptable for use in any of the embodiments discussed herein;

FIGS. 32A-C illustrate various additional features of other alternative embodiments of a fluidic channel arrangement adaptable for use in any of the embodiments discussed herein;

DETAILED DESCRIPTION OF THE INVENTION

It will be appreciated by those having skill in the area of fabrication and storage of drugs, that the lifespan and effectiveness of the drug can be increased substantially by keeping the medication in a dry state. Storage in a dry state also decreases the rate of degeneration as well as the degenerative effects of temperature, for example heat exposure. By keeping the drug in a dry state the breadth of environments where the device can be stored is increased while decreasing the frequency of required replacement.

The present invention illustrates various principles and devices which allow for the storage of a device having two or more components contained therein but which can quickly and reliably reconstitute, dissolve, fluidize, and/or put into a suspension, the components, i.e. mix them, immediately prior to delivery.

As such a system and method for storing and/or mixing a dry medicament component with a wet component for delivery to a user is contemplated herein. The system can include an auto-injector having various chambers therein, wherein the components of the drug are stored separately within the various chambers in various states so as to increase longevity, i.e. a dry drug component in one chamber, and a liquid, such as a solvent, in another. When the auto-injector is needed, the system can be actuated so as to mix the components, thus reconstituting, dissolving, fluidizing, and/or suspending a deliverable mixed drug, wherein the mixed drug can then be properly delivered to a patient. Examples of delivery can include, but are not limited to nebulization for inhalation, injection through a needle or cannula, topical application, etc. A chamber is a cavity or space that is defined by walls and can be filled with drug components, medicaments, liquids, gases, or other substances. For example, a chamber can be a vial or any other container.

With reference to FIGS. 1-9, shown is an exemplary embodiment of an auto-injector 10 in accordance with a first embodiment. The auto-injector 10 illustrates various aspects of the present invention, each of which will be discussed in more detail below.

Figure 1C:
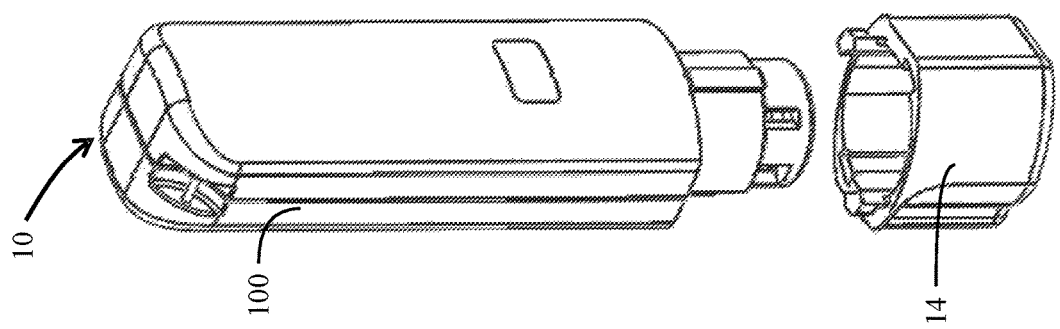
FIGS. 1A-C illustrate perspective exterior views of a medication mixing and delivery device through various actuation steps.
Figure 1B:
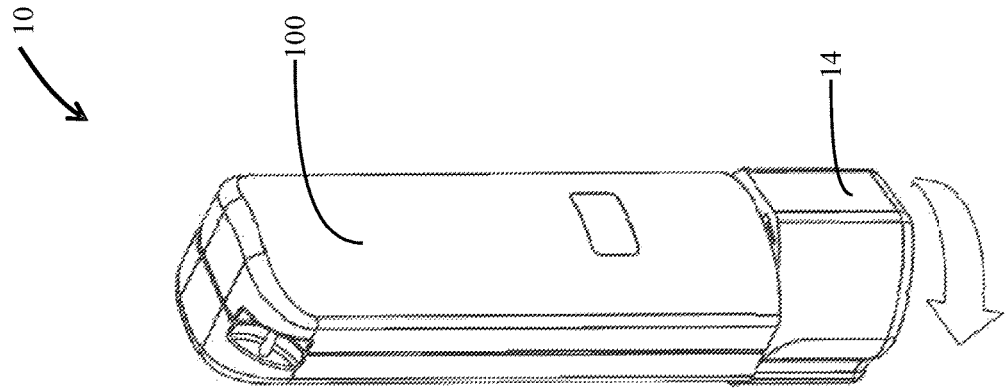
Figure 1A:
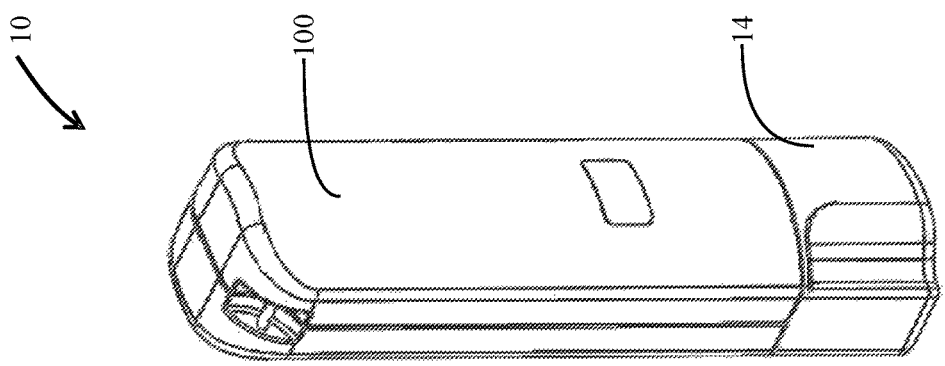

Referring to FIGS. 1A-C illustrate perspective views of an auto-injector which illustrates various aspects of the present invention. This embodiment illustrates an auto-injector 10 which has a housing 100 and a cap 14. The cap 14 can be in mechanical communication with a first actuation mechanism contained within the housing 100. By applying an axial torsional force between the cap 14 and the exterior housing, the actuator can cause certain components contained within the housing to initiate certain steps in the mixing process, for example open a valve between the various chambers, and move fluid contained in one chamber into the chamber containing the dry component of the medicament, which steps will be discussed in more detail below.

In certain embodiments, the cap 14 can be configured such that separation of the cap 14 from the housing 100 can be delayed until the device has moved completely from a stowed state to a completely mixed state. In this manner it can be ensured that the needle end of the auto-injector 10 is not exposed until the device is completely ready for delivery. Such mechanisms can include a threaded interface between the cap 14 and the housing 100, or the components can be keyed such that separation is not possible until a certain degree of rotation has been achieved, etc. Once the cap is removed, the injection end of the housing can then be exposed and a second actuation device triggered so as to inject or otherwise deliver the mixed medicament to a delivery or injection site, for example by depressing the housing up against the delivery site.

In other embodiments, the delivery of the mixed medicament to the injection site can be configured in such a way that the second actuation step cannot be activated until the device has moved completely from a stowed state to a completely mixed state. In this manner it can be ensured that the needle end of the auto-injector 10, while exposed after removal of cap 14, cannot be activated until the device is ready. Such embodiments are enabled by features internal to the device, which will be described below. Once mixing is complete, a second actuation device can be triggered so as to inject or otherwise deliver the mixed medicament to a delivery or injection site, for example by depressing the housing up against the delivery site.

FIGS. 2A-B illustrate an exploded view of an auto-injector 10 in accordance with one embodiment of the present invention. This exploded view illustrates the various internal components within the housing 100 and the cap 14. The housing can include a pre-loaded energy source 122 which is shown here as a spring, or which can be embodied as a compressed air chamber, which is not shown but could be adapted by those having skill in the art. The spring can be configured to provide a driving force and counter force between an inner plunger shaft 212, and transferred to various components of a mixing assembly 200 through various stages, as will be discussed below. The mixing assembly 200 can be contained within a frame 110 wherein individual components of the mixing assembly 200 can be configured to selectively rotate within the housing 100.

The mixing assembly 200 can be retained within the frame using a frame cap 114 which can be formed separately or unitarily with the frame 110. The frame cap 114 prevents the mixing assembly 200 from pushing through the frame 110 and exiting the housing 100 completely upon injection.

A needle shield 150 and needle shield spring 154 can be provide between the frame 110 and the housing 100 at an injection end of the housing 100. The needle shield spring 154 can be configured to bias the needle shield 150 axially downward so as to continuously restrict inappropriate exposure of the needle 310 prior to, during, and after injection.

The frame 110 and portions of the mixing assembly 200 can be configured to rotate together within the housing when an axially torsional force is applied between the cap 14 and the housing 100. The cap 14 can thus be coupled in a radially fixed manner to the frame 110 which is in turn coupled to certain components of the mixing assembly 200, and a driver interface 118 can also be provided which is rigidly coupled to the housing 100 as well as coupled in a radially fixed manner to alternative portions of the mixing assembly 200 such as to the inner plunger shaft 212. In this manner the axially torsional force and counter force applied between the cap and the housing can be transferred into and caused to actuate certain components of the mixing assembly 200.

The mixing assembly can include an inner plunger shaft 212 and an inner plunger 214 which together form a first displacement mechanism. The first displacement mechanism can be configured to reduce the effective volume of the first chamber, which will initially contain the wet solvent or other liquid component of the medicament.

The plunger is configured to interface with an inner vial 210 which forms the first chamber. The inner vial can be housed within a vial sleeve 220, or alternatively the vial sleeve 220 and the inner vial 210 can be formed unitarily of a single material.

The vial sleeve 220 can then interface with a rotational valve seal 230 which sits within an intermediate support 240. The intermediate support 240 can have a second displacement mechanism 250, i.e. a second plunger, which is coupled thereto, the second plunger being configured to reduce the effective volume of a second chamber located within a second vial 270.

The second vial 270 can then be provided with a delivery assembly 300 affixed thereto which can include a needle 310 or cannula as well as a needle guard 314 or other barrier configured to maintain sterility of the delivery assembly prior to use.

For purposes of this application, vial can mean any container suitable for holding liquids or dry particulates and is not limited to a circular cross-section and is not limited to being formed of a particular material, such as glass, plastic, or metal. For example, a vial may have a conical, square, rectangular, triangular, oval, or any other suitable cross-section.

FIGS. 3A-D and 4A-D illustrate cross sectional views of the auto-injector 10 and the mixing assembly 200 through various stages of mixing and delivery from a stowed state to a delivered state.

FIGS. 3A and 4A specifically illustrate a stowed configuration of the auto-injector 10 and the mixing assembly 200 contained therein. In this state the inner plunger shaft 212 is configured to rest on an upper edge of the inner frame 110 wherein the upper edge of the frame 110 is configured to prevent the pre-loaded energy source from releasing the energy stored therein and causing the plunger shaft 212 to depress and force the inner plunger 214 to move downward and reduce the effective volume of the interior of the inner vial, i.e. first chamber. Fluid communication between the first chamber and the second chamber, which is contained within the second vial 270, has not yet been established because an outlet of the inner or first vial (not shown here) is not aligned with the fluidic channel 254.

Dry medication can be kept in a recess 258 formed about an inlet of the second chamber within the second vial 270, such that fluid passing through the fluidic channel passes through or at least in close proximity to the dry medicament stored therein. It will be appreciated that in embodiments that do not include the recess 258, the dry medication can also be stored in the fluidic channel connecting the first and second chambers, or merely kept in any portion of the second.

In this stowed state the second chamber has its effective volume initially reduced to near zero by the second displacement device or plunger 250 so as to further decrease the space occupied by the auto-injector device 10, which decreased space occupation aides in allowing the device to be incrementally smaller, and thus easier to carry.

In this state the needle 310 and assembly, or other deliver mechanism, is retracted so as to prevent premature injection. The needle 310 is also still within the needle guard 314 so as to preserve sterility until the auto-injector is ready for injection.

It will be appreciated that the cap is not shown in these views for purposes of simplicity, however, the cap can, and will usually be, on for the stowed state.

FIGS. 3B and 4B illustrate a second intermediate state wherein the sliding valve is open and fluid communication is established between the first and second chambers just prior to depressing the plunger shaft 212 and the plunger 214. In this state a rotational force has been applied between the outer housing 100 which retains the driver interface 118 plunger shaft 212, vial sleeve 220, inner vial 210 and the valve seal 230 stationary with respect to the housing, then the counter force which is applied to the cap 14 can then be applied so as to twist the frame 110, and the intermediate support 240 which carries the fluidic channel. This opposing respective rotation between the plunger shaft 212, inner vial 210, and the rotational valve seal 230 causes two things to occur simultaneously: First, an outlet of the inner vial is caused to align with an inlet to the fluidic channel thus establishing fluidic communication between the inner vial 210 and the second chamber 270; second, a set of protrusions of the plunger shaft are brought into an axially aligned channel provided in the frame 110 which allows the plunger shaft to be partially driven downward and cause displacement of the fluid contained in the inner vial through the fluidic channel and into the second vial or chamber 270. The plunger shaft is not driven partially downward until after the fluidic communication is established between first chamber formed by the inner vial 210 and the second chamber formed by the second vial 270.

In this embodiment, the respective rotation causes the outlet 224 of the first chamber or inner vial 210 which outlet is formed in the rotational valve seal 230 rotate about a central axis until it is aligned with the inlet fluidic channel 254. In some embodiments the rotational valve seal 230 can be configured to form the bottom wall of the inner vial 210, or the inner vial 210 and rotational valve seal 230 can be formed separately and distinctly.

As seen in FIG. 2, the rotational valve seal 230 of this embodiment is keyed having protrusions and channels or apertures corresponding to protrusions and apertures in the vial sleeve such that it remains stationary with respect to the vial sleeve and does not rotate as the cap and intermediate support 240 are rotated so as to allow selective alignment and misalignment between the outlet 224 and the fluidic channel 254. Alternatively, in embodiments being devoid a specific fluidic channel, alignment between the outlet 224 and an inlet of the second chamber so as to selectively allow or prohibit fluid communication therebetween.

In this state the second chamber still has its effective volume near zero by the second displacement device or plunger 250. Additionally, in this state the needle 310 or other deliver mechanism and assembly is still retracted so as to prevent premature injection as mixing has not yet occurred. The needle 310 is also still within the needle guard 314 so as to preserve sterility until the auto-injector is ready for injection and the needle shield 150 is still extended to prevent premature injection.

FIGS. 3C and 4C illustrate a mixed state wherein the intermediate support 240 and frame 110 have been rotated with respect to the mixing assembly 200 such that plunger protrusions 216 of the plunger shaft 212 have been aligned with an axially aligned channel of the of the vial sleeve 220 as well as through a channel in a sidewall of the intermediate support 240.

The axial alignment between the plunger shaft protrusions allows axial translation of the plunger shaft 212 into the inner vial 210. Once this alignment has been achieved, the plunger shaft 212 is allowed to translate axially downward thus depressing the inner plunger 214 into the inner vial 210 which acts to displace the fluid contained therein through the outlet 224 through the fluidic channel 254 and into the second chamber contained within the second vial 270. The second vial 270 is permitted to expand its effective volume by being free to translate downward slightly within the frame and housing. As the second chamber expands to receive the fluid being displaced from the first chamber, the fluid passes through or into the recess 258, which contains the dry medicament, the fluid dissolves the dry component and mixes with the fluid as it enters the second chamber. In another embodiment, the fluid passes into the second chamber 270, without a recess 258, and with the powder being located elsewhere in the second chamber 270. The expanding volume of the second chamber still allows for sufficient mixing with the dry medicament to achieve appropriate mixing.

In the embodiment shown the intermediate support 240 includes similar protrusions resting on an intermediate stop of the frame, and the plunger protrusions of the plunger shaft come to rest on the bottom of the intermediate support channel which indicates full depression of the first plunger into the inner vial, which also signifies that mixing is complete and that the device is ready for the injection step.

In this state the needle 310 or other deliver mechanism and assembly is still retracted so as to prevent premature injection as mixing has not yet occurred. The needle 310 is also still within the needle guard 314 so as to preserve sterility until the auto-injector is ready for injection and the needle shield 150 is still extended to prevent premature injection. However, the needle shield 150, which forms part of a second trigger, is ready to be depressed and thus trigger injection. The functionality of the needle shield 150 will be discussed in greater detail below.

Figure 7D:
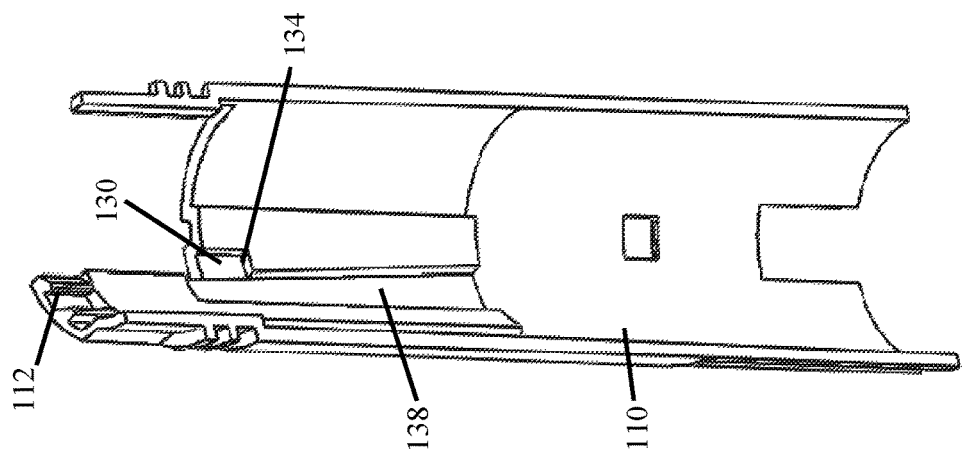
FIGS. 7A-D illustrate various perspective and cross-sectional views of a frame being used within the medication mixing and delivery device of FIGS. 1A-C.
Figure 7B:
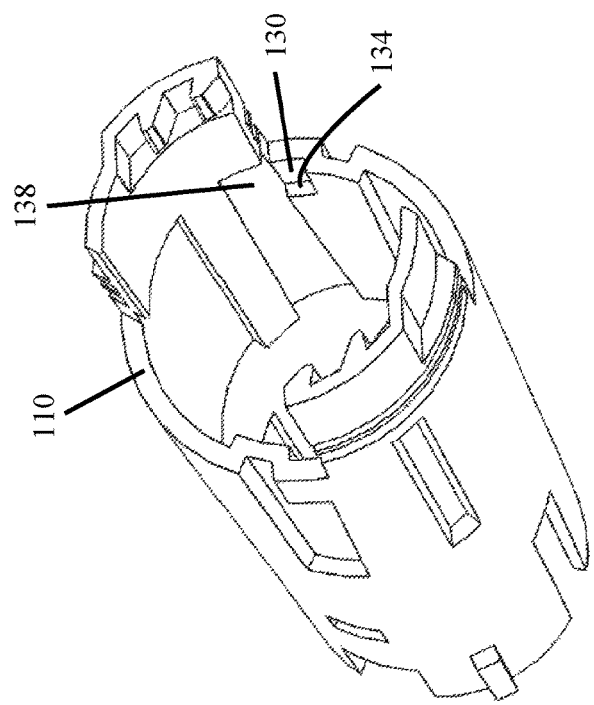
Figure 7C:
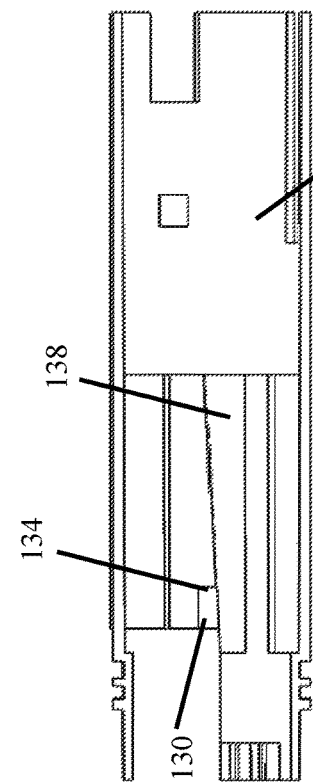
Figure 7A:
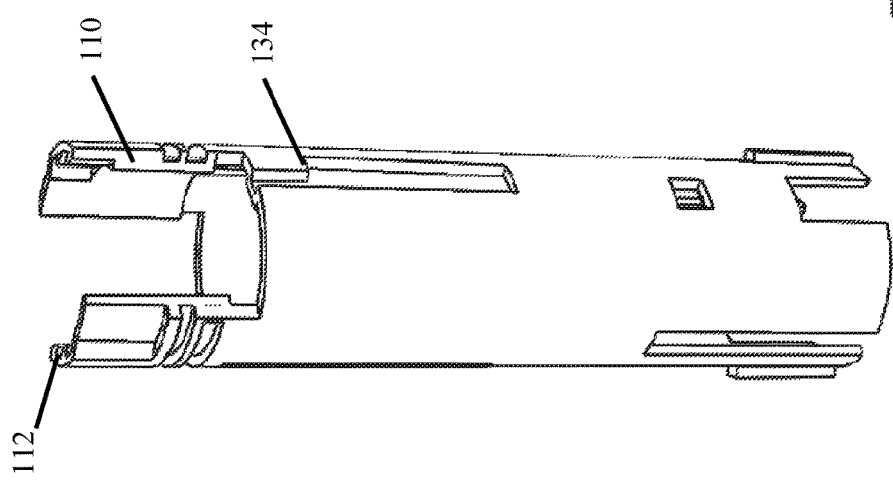
Figure 13D:
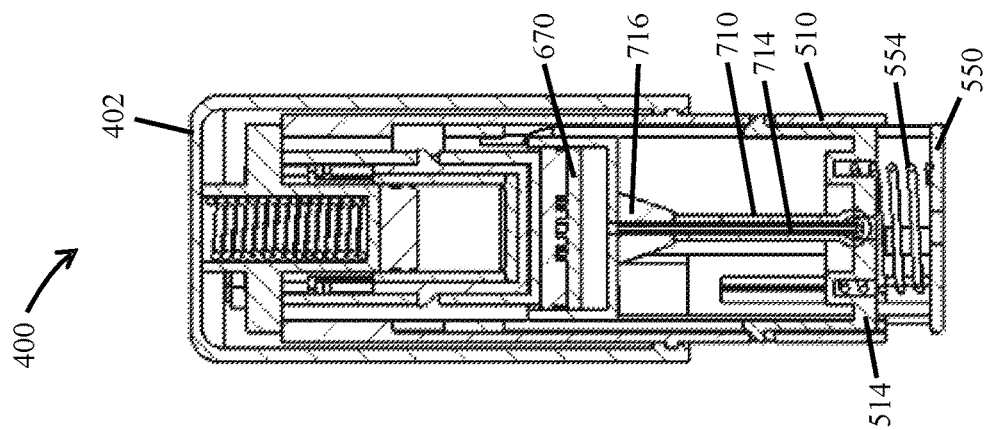
FIGS. 13A-D illustrate various exterior perspective, side, and cross-sectional views of the medication mixing and delivery device as illustrated in FIGS. 10A-D in a stowed state.
Figure 13C:
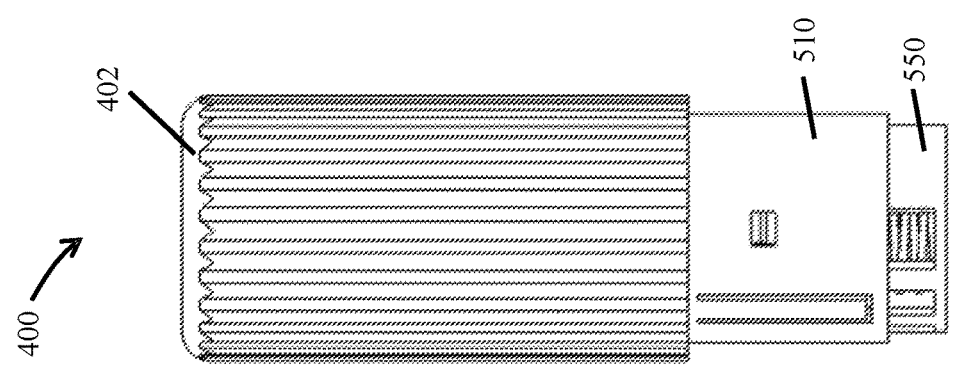
Figure 13B:
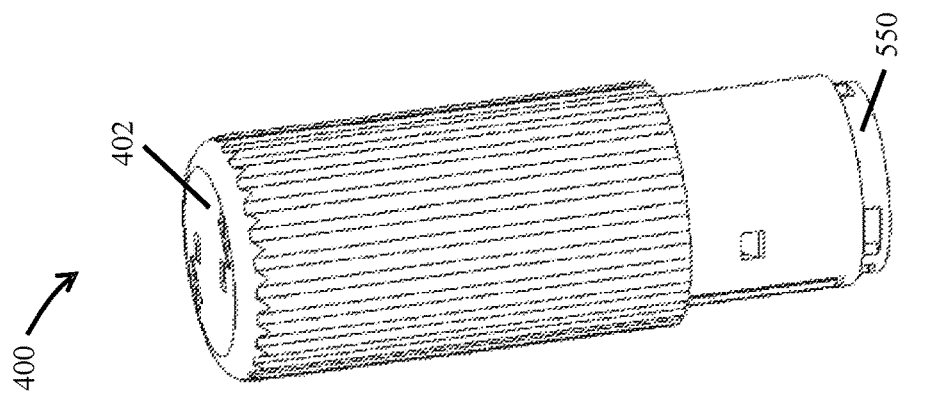
Figure 13A:
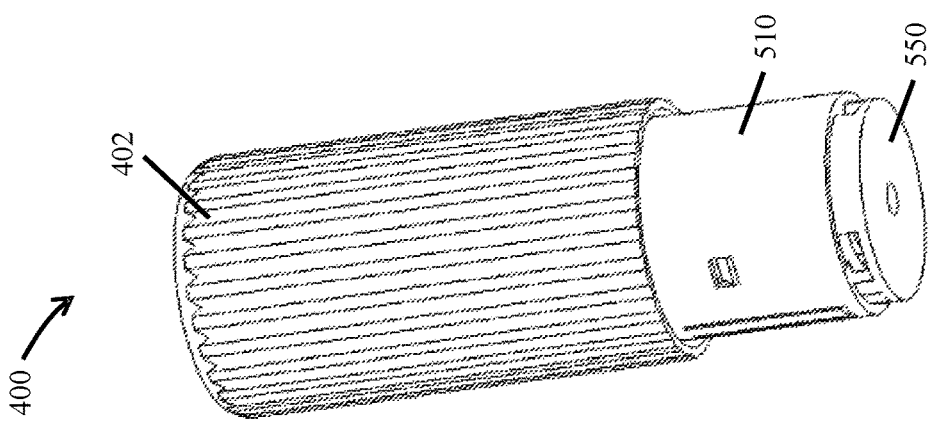
Figures 17A, 17B:
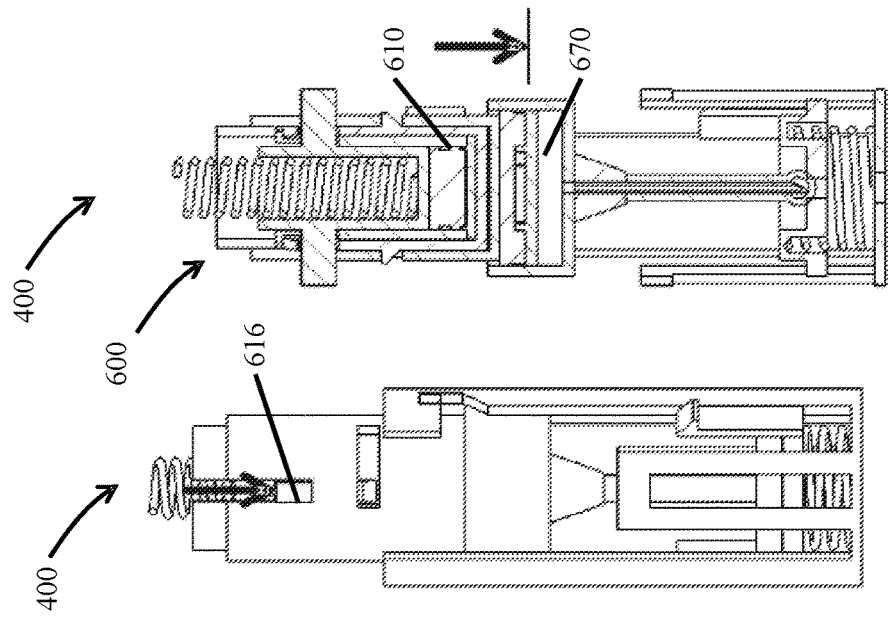
FIGS. 17A-B illustrate side and cross-sectional views of the medication mixing and delivery device as embodied in FIGS. 10A-D illustrating an injection ready state.
Figures 16A, 16B, 16C:
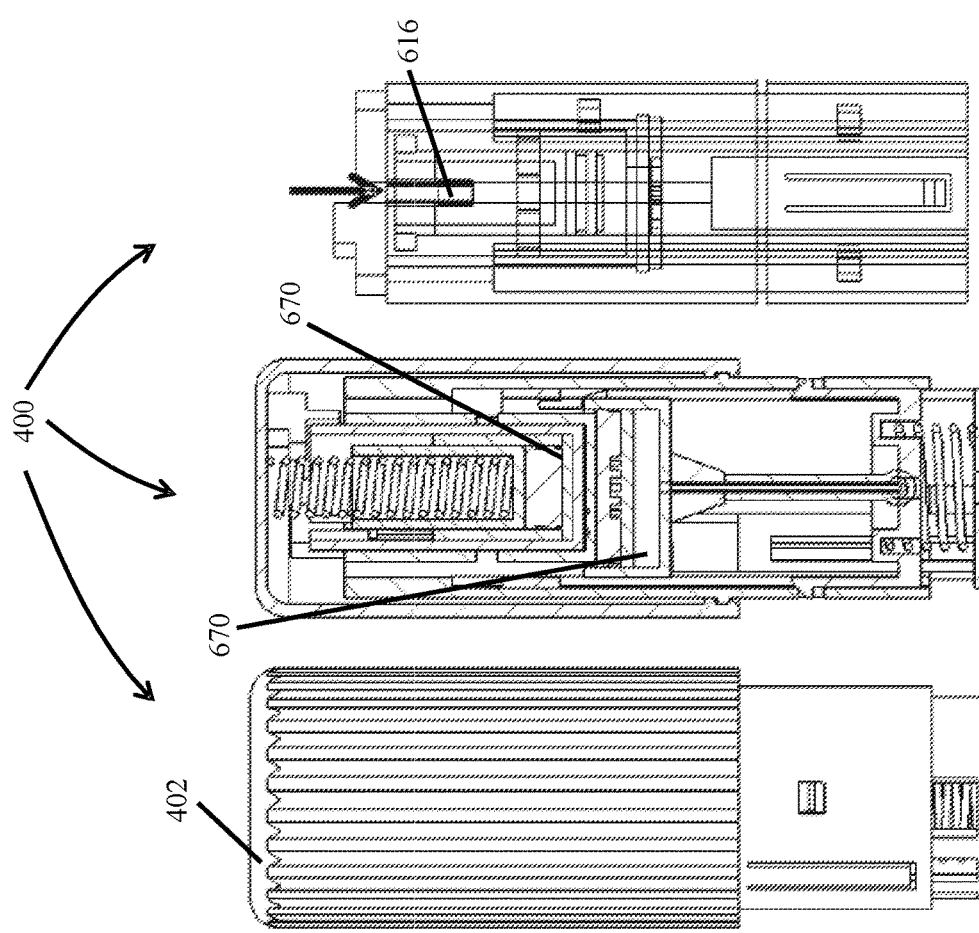
FIGS. 16A-C illustrate various side, cross sectional, and partially transparent views of the medication mixing and delivery device as embodied in FIGS. 10A-D illustrating a mixed state.
Figure 18B:
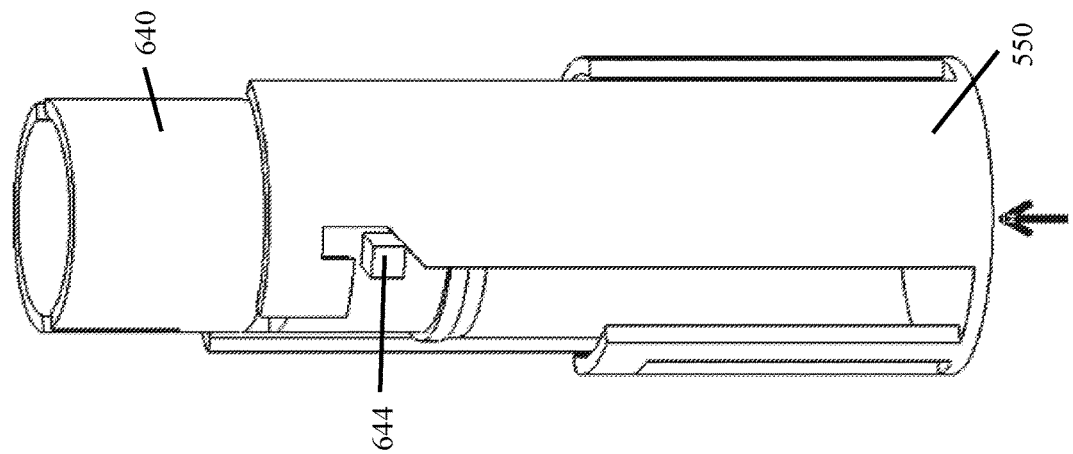
FIGS. 18A-D illustrate various perspective views of a second actuation mechanism of the medication mixing and delivery device as embodied in FIGS. 10A-D illustrating changing from the mixed state to an injected state.
Figure 18A:
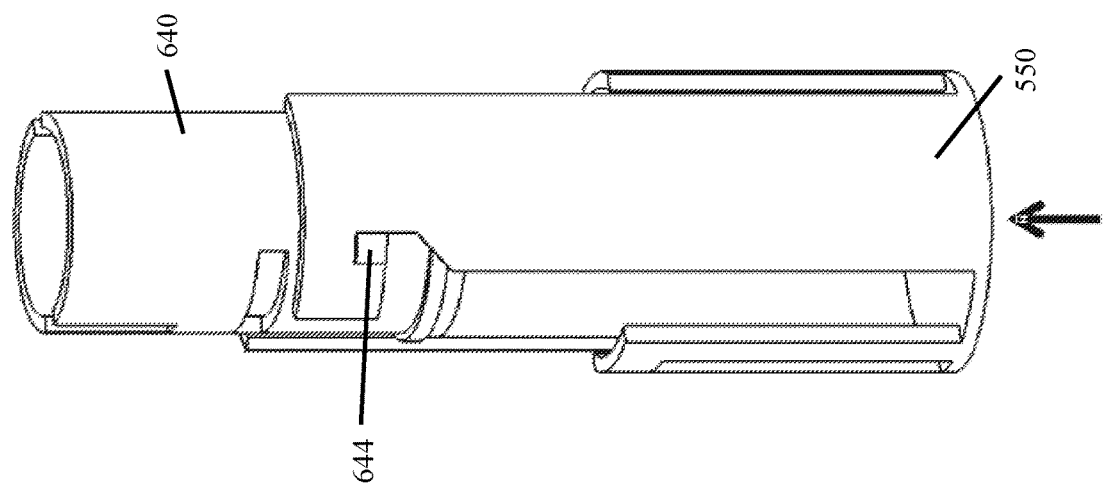
Figure 18D:
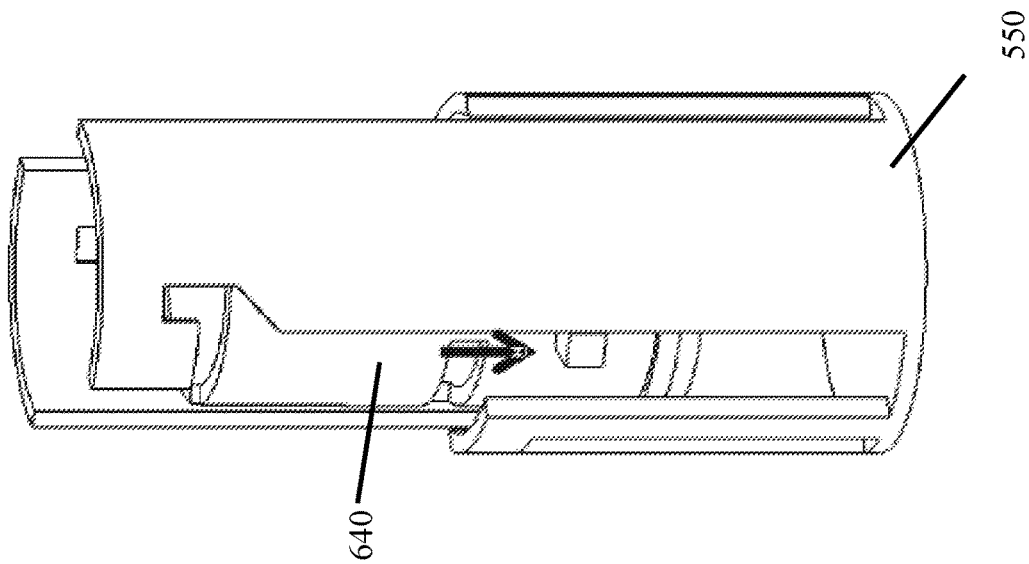
Figure 18C:
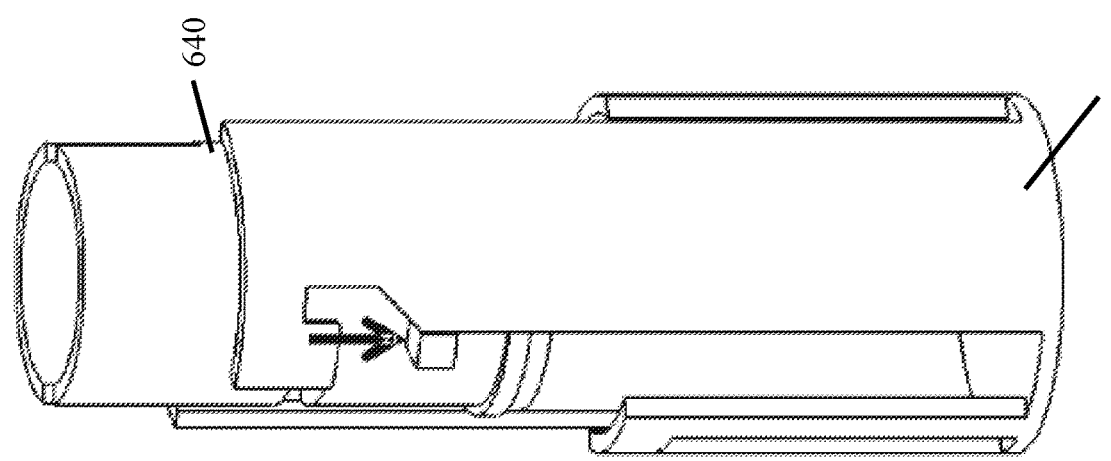

FIGS. 3D and 4D illustrate an injected state wherein the mixing assembly 200 has been rotated another small increment within the housing 100 of the auto-injector 10 such that that protrusions of the plunger shaft 212 as well as additional protrusions, lower intermediate support protrusions 244 as seen in FIGS. 8A-E which will be discussed in more detail below, which are provided on the intermediate support 240 have been rotated around sufficiently so as to align with a second axially aligned channel, 138 as seen in FIGS. 7B-D, of the frame 110.

Once this alignment has been achieved, a second portion of energy stored within the pre-stored energy source which causes the entire mixing assembly to be pushed downward such that the needle guard 314 comes into contact with the frame cap 114 to stop the needle guard 314 such that the needle 310 punctures needle guard 314 and is extended through the needle guard 314. The needle 310 then extends further past the needle shield 150, and the needle 310 is thus extended into or about a delivery site, further as the second vial or chamber 270 hits the bottom portion of the frame cap 114, the second plunger 250 is depressed into the second vial or chamber 270 reducing its effective volume and causes the fluid to be ejected through the delivery assembly and into the patient or onto the delivery site.

FIGS. 5A-E illustrate perspective views of the mixing assembly 200 within the frame 110 which illustrate various stages of actuation through the mixing and injection process.

Figure 5A:
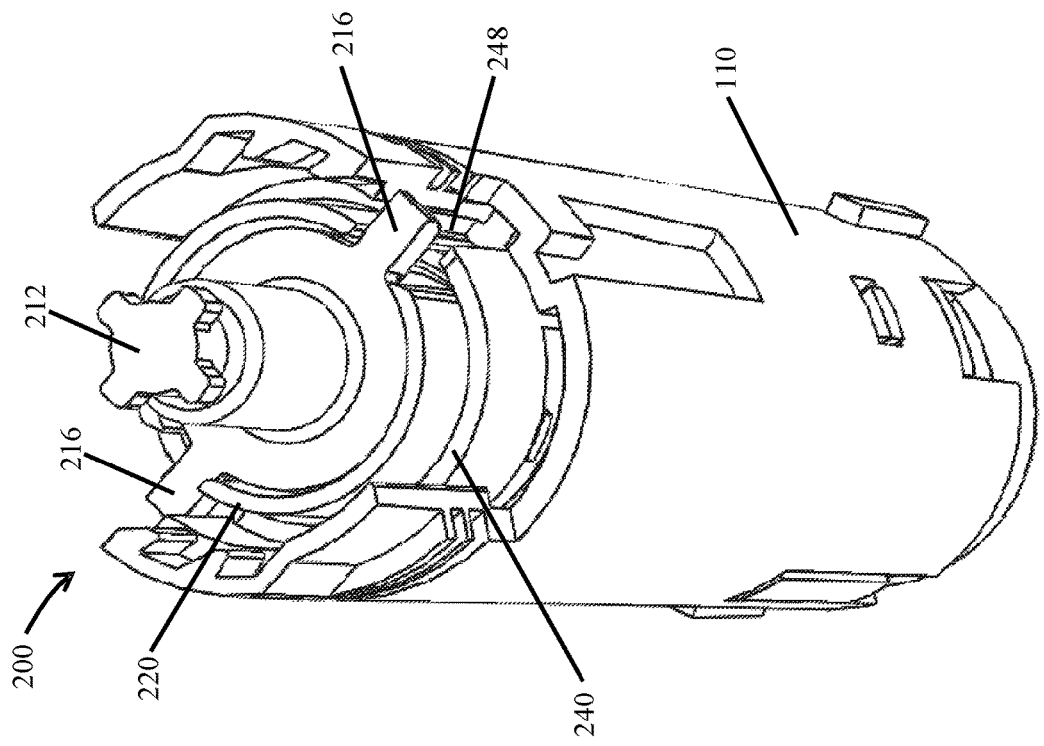
FIGS. 5A-E illustrate various exterior perspective views of the mixing subassembly through various actuation steps moving from a stowed state to a mixed state as would be effectuated using the embodiment of FIGS. 1 A-C.

In particular, FIG. 5A illustrates the relative position of the mixing assembly 200 with respect to the frame 110 in a stowed state. In this state the plunger shaft 212 is provided with a plurality of plunger protrusions 216 which extend radially outward and rest on an upper lip of the intermediate support 240. It will be appreciated that the vial sleeve 220 is also provided with a channel through which the plunger protrusions 216 extend and allow for axial translation in later steps of actuation. In this manner the plunger shaft is maintained in a non-depressed or stowed state wherein rotation of the plunger protrusions 216 into the middle support channel 248 must be effectuated before the plunger shaft 212 can translate axially and depress into the vial (not shown) contained within the vial sleeve 220.

Figure 5B:
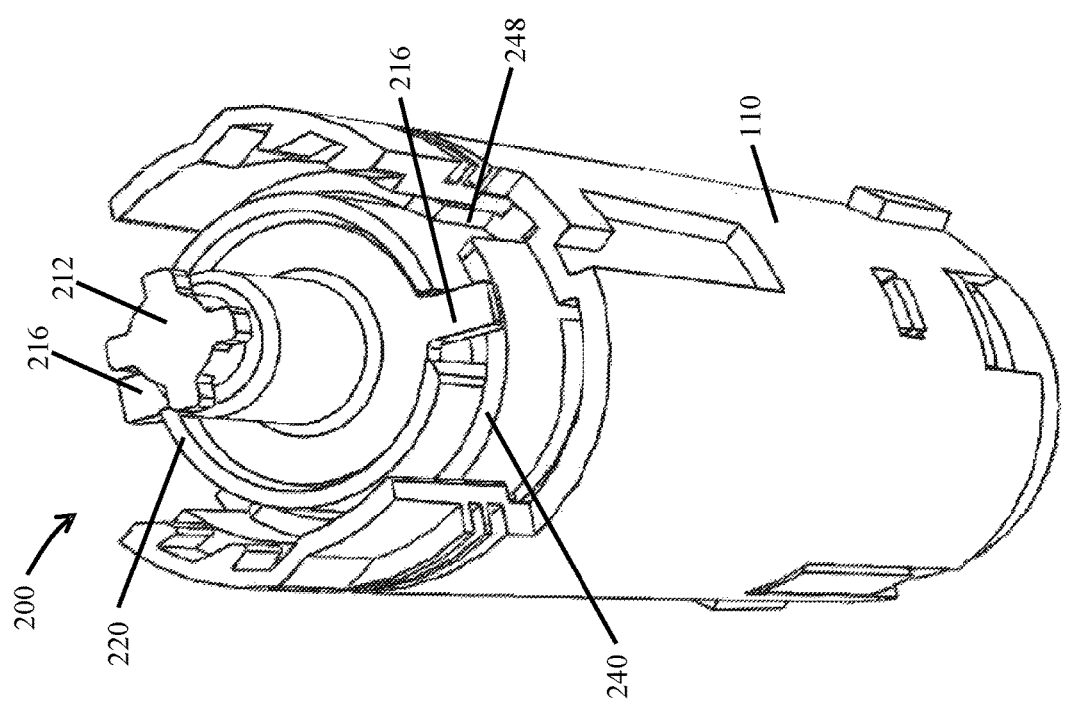
Figure 5D:
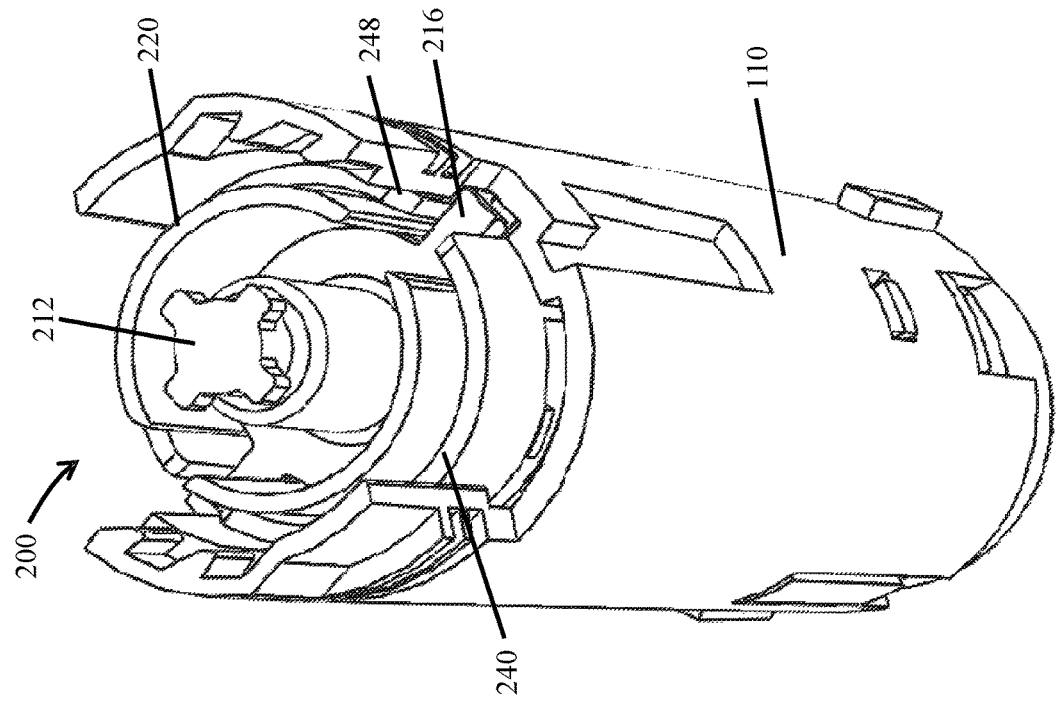
Figure 5C:
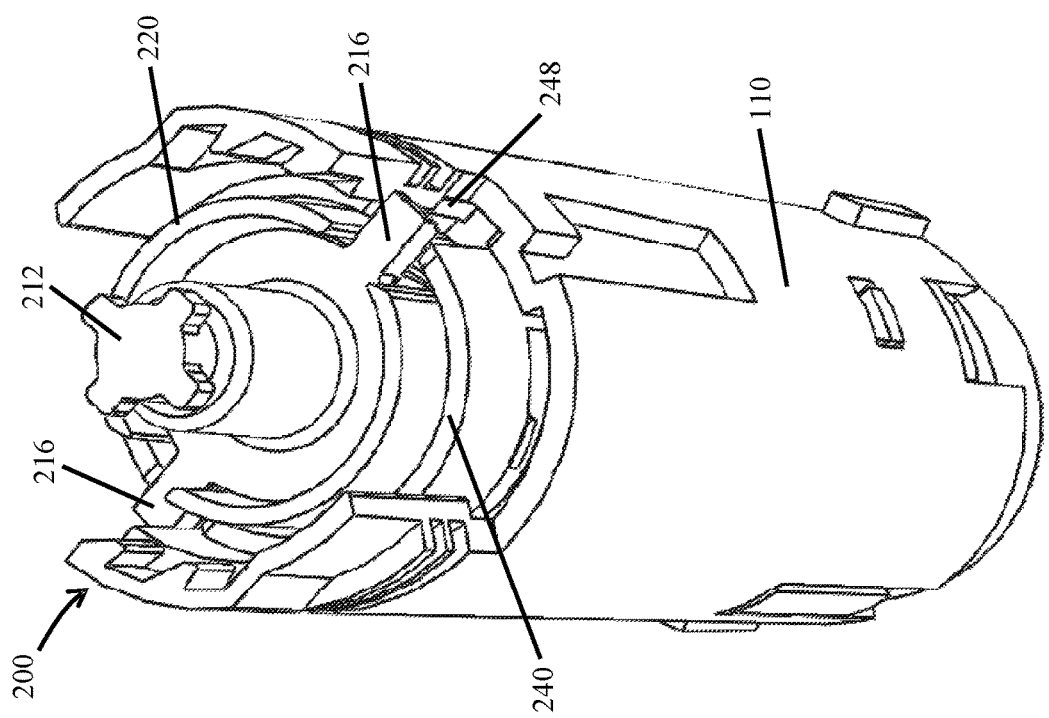

FIGS. 5B-D illustrate the travel of the rotated state of the plunger shaft 212 with respect to the vial sleeve 220 and intermediate support 240. The plunger protrusions 216 are aligned with the channel 248 and are thus ready for release of a portion of energy contained in the pre-loaded energy source to depress the plunger shaft 212 into the vial sleeve 220 and the vial contained therein (not shown) so as to displace the fluid contained therein. In this embodiment, the rotation of the plunger shaft also causes rotation of the vial sleeve 220, which rotation causes the outlet of the first chamber to align with the inlet of the fluidic channel leading to the second chamber. In this manner the alignment and thus opening of the fluidic channel occurs simultaneously with the alignment of the protrusions 216 with the intermediate support channel and allows the pre-loaded energy source to depress the plunger shaft 212.

FIG. 5C illustrates an intermediate partially depressed state and FIG. 5D illustrates a mixed configuration wherein the plunger shaft and plunger have been fully depressed into the first chamber displacing all of the liquid into the second chamber.

Figure 5E:
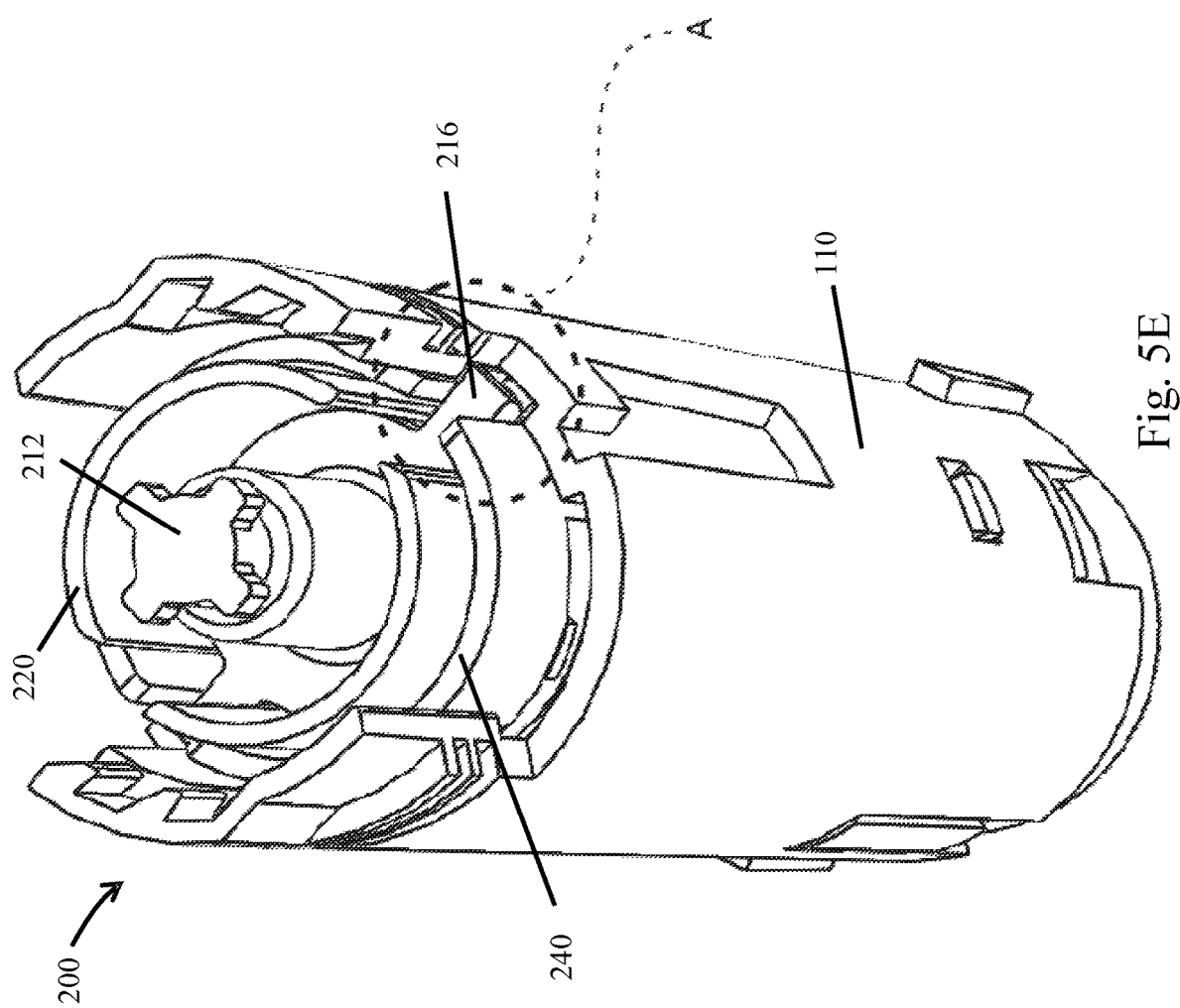

FIG. 5E illustrates a fully mixed state wherein the auto-injector is fully ready for injection. The area A as illustrated in FIG. 5E will be discussed in further detail wherein the mixing assembly 200, which includes the intermediate support 240 together with the vial sleeve 220 and plunger shaft 212 all need to rotate a small distance into the frame 110 so as to initiate the injection step.

FIGS. 6A-E illustrate various perspective detailed and cross sectional views of the area A as defined in FIG. 5E. As discussed above the frame is provided with a plurality of channels. The first frame channel 130 and the intermediate stop 134 have a pair of upper support protrusions 242 of the intermediate support supported therein. After the mixing stage is complete the protrusions 216 of the plunger shaft 212 are resting on the intermediate support 240 on top of the upper support protrusions 242.

In order to translate axially downward to eject the fluid through the delivery assembly the intermediate support 240, vial sleeve 220 and the inner plunger must rotate together so as to be aligned with a second frame channel so as to allow for a second portion of energy to be released from the pre-loaded energy source thus driving the mixing assembly downward, with the delivery assembly affixed to the bottom end thus effectuation injection or delivery. To move from the mixed state and begin injection the upper support protrusions 242 along with the plunger shaft protrusions 216 are rotated radially into a second frame channel 138 as seen best between the positions illustrated in FIG. 6D to FIG. 6E.

In particular, FIGS. 6A-B illustrate perspective exterior and cross sectional views of the interface shown by area A of FIG. 5E wherein the auto injector and mixing assembly is in a mixed state with the plunger protrusions 216 being depressed against the intermediate support 240 and associated upper support protrusions 242. All of which rests on the intermediate stop 134 within the first frame channel 130.

Figure 6D:
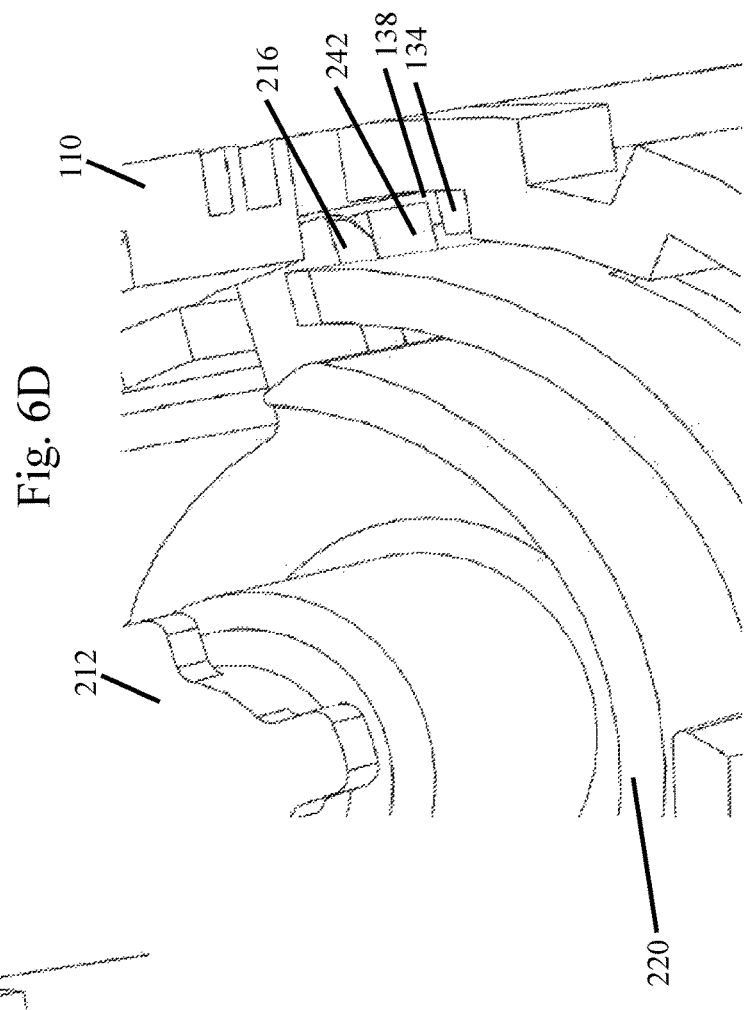
Figure 6C:
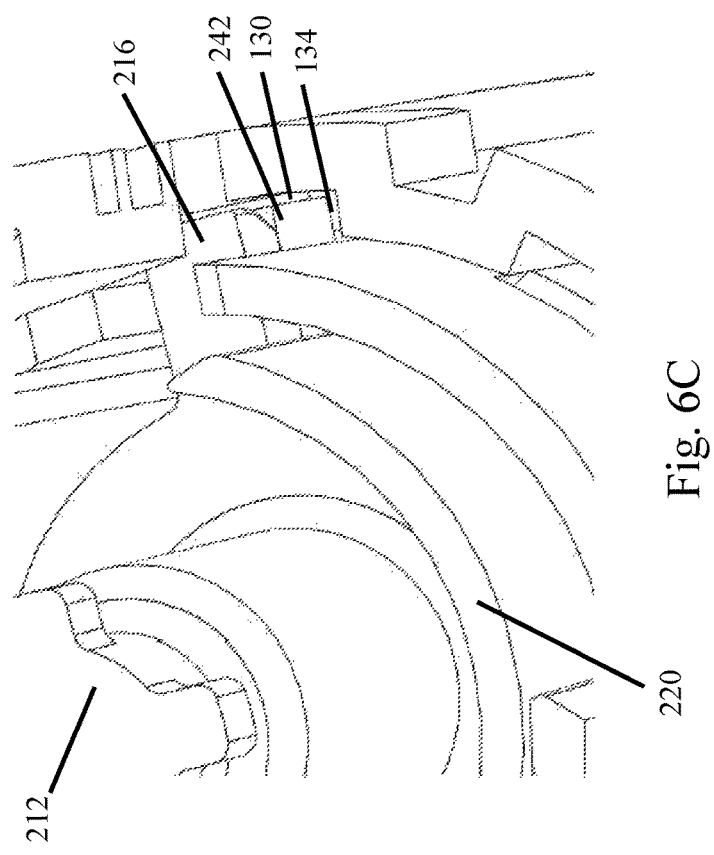

FIGS. 6C-D illustrate perspective exterior views of the interface shown by area A of FIG. 5E wherein the auto injector and mixing assembly is in a mixed state but more importantly illustrating an intermediate rotation of the plunger and upper support protrusions 216 and 242 respectively with respect to the frame 110 into an aligned configuration with the second frame channel 138 just prior to injection.

Figure 6E:
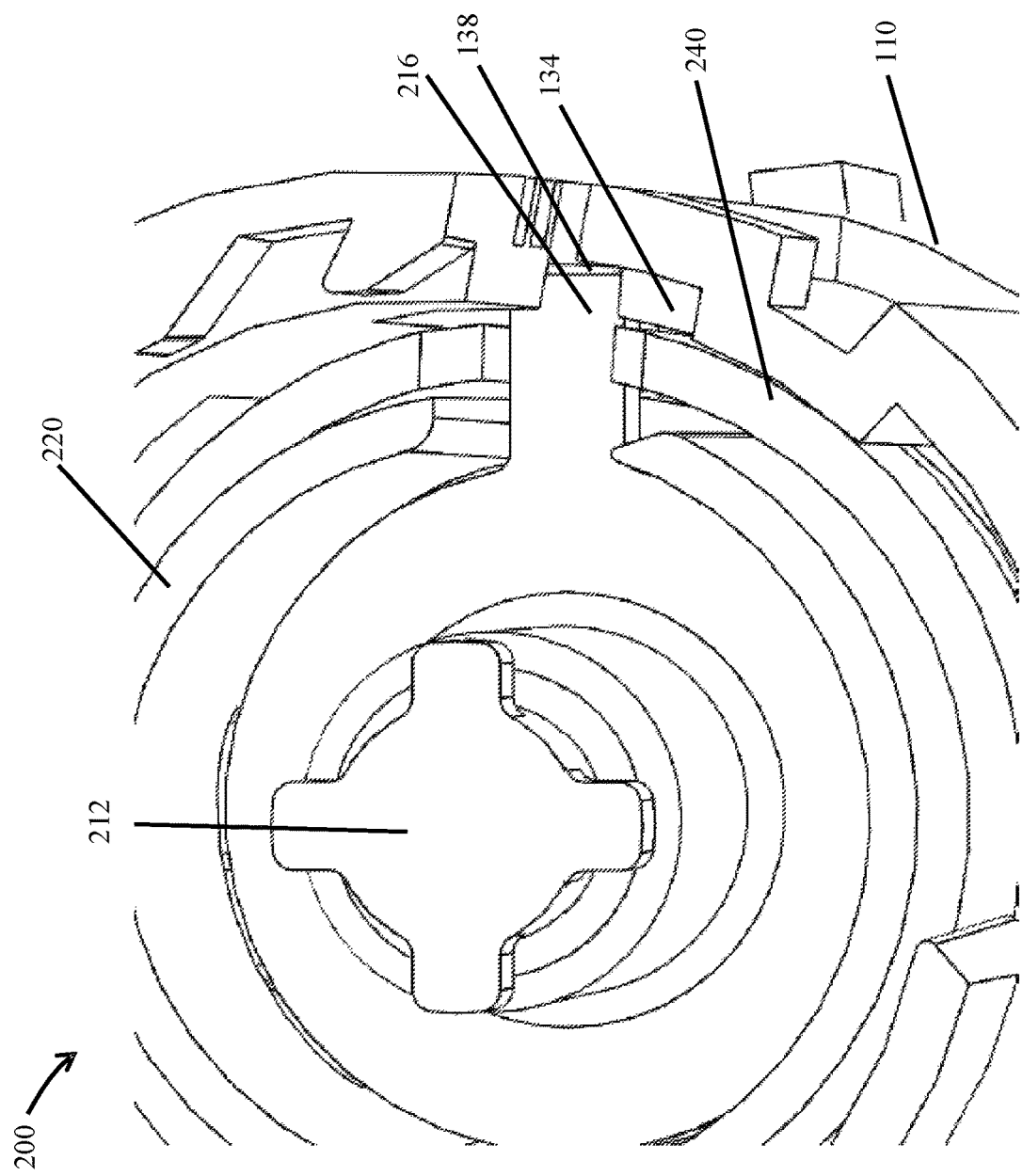

FIG. 6E illustrates the mixing assembly 200 as it is being further depressed into the frame 110 wherein the plunger shaft 212 and protrusions 216 along with the intermediate support 240 are depressed downward thus driving the delivery assembly (not shown) downward to inject the needle, until the second vial engages the lower end of the frame, stops, and the intermediate support (not shown) then drives the second plunger (not shown) into the second vial displacing the mixed drug out of the delivery assembly and into the delivery site. It is this reason, as described above, that the second actuation, which results in the translation of the mixing assembly downward, can not occur until mixing is complete. The plunger protrusions 216 can not rotate with the upper support protrusions 242 until they are able to rotate together, clear the frame and access the second frame channel 138. If the user attempts to actuate the second actuation mechanism prior to plunger protrusions 216 coming into contact with upper support protrusions 242, the mixing assembly will get stopped from entering the second frame channel 138 by the frame 110. This mechanism is helpful in preventing the second actuation step from occurring until all of the fluid from the first chamber has been transferred into the second chamber.

FIGS. 7A-D illustrate various perspective exterior and cross-sectional views of the frame 110. These views illustrate the interior first frame channel 130 and second frame channel 138 with more clarity. These views also illustrate the intermediate stop 134 upon which the upper support protrusions of the intermediate support rests (not shown). In some embodiments the second frame channel 138 can have a tapered channel when effectively increases the width of the second frame channel 138 as the various protrusions travel downward within the second frame channel 138. This tapering ensures that the various protrusions do not bind up during the injections step, and allow the protrusions to travel freely downward until the second vial hits the stops, signaling full needle extension and driving of the second plunger into the vial thus fully ejecting the mixed fluid and medication compound.

FIGS. 7A-D also illustrate a safety mechanism in the form of cap rotation locks 112 which interface with an upper portion of the plunger shaft as well as the driver interface such that once the cap is rotated a certain degree, a corresponding protrusion enters into and meshes with the teeth of the cap rotation lock 112 of the frame and prevents the cap from being twisted back. In this manner, if the cap is inadvertently twisted, and a risk of premature mixing is presented by such rotation, a user cannot simply twist the cap back and place the auto-injector back into storage believing that no mixing has occurred. It will be appreciated that, once mixed, even partially, the dry drug will typically begin to degrade at an increased rate. The purpose of the lock is to prevent accidental mixing, or at least signal to the user that the drugs inside might have been previously mixed, wherein instructions on whether or not to use in the case of premature mixing can be provided.

FIGS. 8A-E illustrate how the needle shield 150 can be configured in one embodiment to act as a bump switch and trigger the injection step by providing the slight rotation of the protrusions 216 and 242 off of the intermediate stop (not shown here) and into the second frame channel discussed above, (not shown). It will be appreciated that this view of the mixing assembly 200 and needle shield 150 are shown herein without the frame so as to better illustrate the interaction of the needle shield 150 with the mixing assembly 200. However, it will be appreciated that the slight rotation shown here provides the rotation as illustrated in FIGS. 6C-E.

In the embodiment shown in FIGS. 8A-E an upward force is applied to the needle shield 150 by depressing the injection end of the auto-injector against the delivery site. In response to this depression force, the needle shield 150 translates upward within the housing and frame such that a lower support protrusion 244 is released from a needle shield hook 158. The needle shield hook prevents premature rotation of the intermediate support off of the intermediate stop during the changing of states from the stowed state to the mixed state by rotation of the vial sleeve and inner plunger as discussed above, preventing the intermediate support from rotating with those components during mixing and thus preventing premature injection. Additionally, the shield hook can be configured so as to transfer the axially rotational force to be applied to the cap, through the frame, and into the intermediate support, which allows for relative rotation between the rotational valve seal, as discussed above, and the fluidic channel disposed within the intermediate support so as to allow initial opening of the sliding valve.

As the needle shield 150 translates upward, the lower support protrusions 244 of the intermediate support interface with a needle shield cam ramp 162. As the needle shield 150 continues to travel upward relative to the intermediate support, the lower support protrusions 244 slide on the needle shield cam ramps 162 and a rotation of the entire mixing assembly 200 is induced as shown in FIG. 8C. In this embodiment the width of the needle shield cam ramps 162 corresponds with a radial distance required to move the upper support protrusions 242 and the plunger protrusions 216 off of the intermediate stop and into the second frame channel which corresponds to the released configuration as illustrated in FIG. 8D. Whereupon, as shown by FIG. 8E the entire mixing assembly 200 can travel downward by force applied from the pre-stored energy source and result in injection or other delivery.

FIGS. 9A-B illustrate an extension and locking function of the needle shield 150. It will be understood that it is of general interest to reduce the potential for inadvertent contamination or sticks of other people prior to injection, during injection, and after injection. As such the needle shield 150 of the present embodiment serves both as a bump switch as well as a protective barrier between the user, and other people from inadvertent sticks, jabs, or cuts from an exposed needle. As such, after the bump switch is activated, the needle shield hook, as discussed above, is released and a needle shield spring 154, as shown in FIG. 2, or other biasing mechanism, is released so as to push the needle shield outward, or axially downward after activation. The delivery assembly and needle are not ejected until the bump switch is first activated, then after injection, as the user pulls the auto-injector away from the delivery site, the needle shield is simultaneously extended until it clears past the tip of the needle, essentially eliminating the risk of secondary pricks and cross contamination of bodily fluids to other people post injection.

In the embodiment shown the frame cap 114 can be provided with a plurality of protrusions, both lock protrusions 116 for interfacing with one or more needle shield guide channels 166 and needle shield extension lock aperture 170. Protrusions 117 alternatively interface with the interior of the frame 110. The guide channels can have space for allowing initial depression whereupon the extension lock protrusions can slide up and then interferingly engage with the lock tabs in a fully extended state after injection. The tabs can prevent pulling the needle shield 150 completely free from the housing as well as prevent a secondary depression of the needle shield 150 which would expose the extended needle.

With reference to FIGS. 10-20, shown is an alternative exemplary embodiment of an auto-injector 400 in accordance with a second embodiment. The auto-injector 20 illustrates additional aspects of the present invention, each of which will be discussed in more detail below.

Referring to FIGS. 10A-C illustrate perspective views of an auto-injector 400 which illustrates various aspects of the present invention. This embodiment illustrates an auto-injector 400 which has an exterior housing 402 and a cap 414. The cap 414 can be in mechanical communication with a first actuation mechanism contained within the exterior housing 402. Similar to the embodiment discussed previously, by applying an axial torsional force between the cap 414 and the exterior housing 402, the actuator can cause certain components contained within the housing to initiate certain steps in the mixing process, for example open a valve between the various chambers, and move fluid contained in one chamber into the chamber containing the dry component of the medicament, which steps will be discussed in more detail below. The relative motion of the various components can be provided through the use of various protrusions which engage with or otherwise interact with cams or channels within the housing.

In certain embodiments, the cap 414 can be configured such that separation of the cap 14 from the housing 402 can be delayed until the device has moved completely from a stowed state to a completely mixed state. In other embodiments the cap can act merely as a contaminant barrier and actuation is effectuated after removing the cap. The embodiment shown illustrates the first, wherein removal of the cap effectuates initiation of, and completion of, the mixing step. In this manner it can be ensured that the needle end of the auto-injector 400 is not exposed until the device is completely ready for delivery.

With regard to the cap 414 and in reference to FIGS. 11A-C, the Cap 414 can include cam protrusions on an internal portion of the housing or frame which interact with associated cam ramps 416, wherein the cam ramps 416 allow for release through the keyway 417 after a certain degree of rotation has been achieved. In alternative embodiments, threaded interfaces can be provided between the cap 414 and the housing 400 wherein the axial relative translation of the cap and the housing can effectuate an initiation of the mixing step is also contemplated. However, in each of these embodiments once the cap is removed, the injection end of the housing can then be exposed and a second actuation device triggered so as to inject or otherwise deliver the mixed medicament to a delivery or injection site, for example by depressing the housing up against the delivery site, which acts as a bump switch which in turn initiates injection.

The cap 414 can also include a pair of retaining clips 418 which can interface with a pair of indents on the frame of housing so as to prevent premature rotation of the cap and associated activation of the auto injector.

FIGS. 12A-E illustrate various exploded views of various internal assemblies within the auto-injector 400 in accordance with one embodiment of the present invention. These exploded views illustrate the various internal components within the housing 402 and the cap 14. The housing 402 can include a pre-loaded energy source 522 which is shown here as a spring, or which can be embodied as a compressed air chamber, which is not shown but could be adapted by those having skill in the art. The spring can be configured to provide a driving force and counter force between an inner plunger shaft 612, the driving force being transferred to various components of a mixing assembly 600 through various stages, as will be discussed below. The mixing assembly 600 can be contained within a frame 510 which is can be configured to rotate within the housing 402.

A needle shield 550 and needle shield spring 554 can be provide between the frame 510 and the housing 402 at an injection end of the housing. The needle shield spring 554 can be configured to bias the needle shield axially downward so as to continuously restrict open and inappropriate exposure of the needle prior to, during, and after injection.

The frame 510 and portions of the mixing assembly 600 can be configured to rotate together within the housing when an axially torsional force is applied between the cap 414 and the housing 402. The cap 414 can thus be coupled in a radially fixed manner to the frame 510 which is in turn coupled to certain components of the mixing assembly 600. In this manner the axially torsional force applied between the cap 414 and the housing 402 can be transferred into and caused to actuate certain components of the mixing assembly 600 using actuation means which will be discussed in more detail below.

The mixing assembly 600 can include an inner plunger shaft 612 and an inner plunger 614 which together form a first displacement mechanism which can be configured to reduce the effective volume of the first chamber, which will initially contain the wet solvent or component of the end injectable medicament.

The plunger 614 is configured to interface with an inner vial 610 which forms the first chamber. The inner vial can be housed within a vial sleeve 620, or alternatively, the vial sleeve 620 and the inner vial 610 can be formed unitarily of a single material.

The intermediate support 640 can have a second displacement mechanism 650, i.e. a second plunger, which is coupled thereto, the second plunger being configured to reduce the effective volume of a second chamber located within a second vial 670.

The second vial 670 can have a delivery assembly 700 affixed thereto which can include a needle 710 or cannula as well as a needle guard 714 or other barrier configured to maintain sterility of the delivery assembly prior to use. The needle 710 can be affixed to the second vial 670 using a bonding interface 716, which can be provided as a crimp, adhesive, curing epoxy, or any other number of suitable interfaces.

FIGS. 13A-D illustrate various perspective, side and cross-sectional views of the auto-injector 400, with the cap removed, wherein the mixing assembly is maintained in a stowed state prior to initiation.

FIGS. 14A-C illustrate various perspective, side and cross sectional views of a various states of assembly of the auto-injector 400, with the cap or housing removed which illustrates actuation of the first mixing step, wherein rotational motion of the upper portion of the mixing assembly is illustrated prior to the valve being open and energy from the pre-loaded energy source is released. In this state the inner plunger shaft 612 is resting on an upper edge of the inner frame 510 wherein the upper edge of the frame 510 is preventing the pre-loaded energy source from releasing the energy stored therein and causing the plunger shaft from depressing and forcing the inner plunger from moving downward and reducing the effective volume of the interior of the inner vial, i.e. first chamber. Fluid communication between the first chamber and the second chamber within the second vial 670 has not yet been established because an outlet (not shown here) is not aligned with the fluidic channel (not shown).

Dry medication can be kept within the fluidic channel between the two chambers, or alternatively the dry medication can be stored within the second chamber within the second vial 470.

In this state the needle 710 or other deliver mechanism and assembly is retracted so as to prevent premature injection. The needle 710 is also still within the needle guard 714 so as to preserve sterility until the auto-injector is ready for injection.

It will be appreciated that the cap is not shown in these views for purposes of simplicity, however, the cap can and will usually be on for the stowed state.

FIGS. 15A-C specifically illustrate a mixing initiated step wherein a fluidic pathway has been established between the first and second chambers just prior to release of energy from the pre-loaded energy source to drive the fluid from the first chamber into the second chamber. In this state the sliding valve is open and fluid communication is established between the first and second chambers just prior to depressing the plunger shaft 612 and the plunger, 614 in FIG. 12C. In this state a rotational force has been applied to the outer housing 402 and the cap 414 wherein the force is applied to twist the plunger 614 and plunger shaft 612 inner vial 610 vial sleeve 620 with respect to the housing 100, the frame 510 and intermediate support 640.

This respective rotation causes an alignment of an outlet of the first chamber formed by the inner vial 610 with a fluidic channel extending into the second chamber formed by the second vial 670.

In this state the needle 710 or other deliver mechanism and assembly is still retracted so as to prevent premature injection as mixing has not yet occurred. The needle 710 is also still within the needle guard 714 so as to preserve sterility until the auto-injector is ready for injection and the needle shield 550 is still extended to prevent premature injection.

FIGS. 16A-C and 17A-B illustrate a mixed state wherein the mixing assembly 600 has been rotated sufficiently within the housing such that protrusions, 616 from FIGS. 14A and 15A, of the plunger shaft 612 have been rotated around sufficiently so as to align with an axially aligned channel of the of the vial sleeve 620 as well as through the intermediate support 640, and has translated axially so as to rest on an intermediate stop of the frame. This axial alignment allows axial translation of the plunger shaft 612 into the inner vial 610, which acts to displace the fluid contained therein through the outlet, through the fluidic channel, and into the second chamber contained within the second vial 670 to mix with the dry medicament in the fluidic path.

In this state the needle 710 or other deliver mechanism and assembly is still retracted so as to prevent premature injection as mixing has not yet occurred. The needle 710 is also still within the needle guard 714 so as to preserve sterility until the auto-injector is ready for injection and the needle shield 550 is still extended to prevent premature injection.

However, the needle shield 550, which forms part of a second trigger, is ready to be depressed and thus trigger injection. The functionality of the needle shield 550 will be discussed in greater detail below.

FIGS. 18A-D illustrate various perspective views of a second actuation mechanism of the medication mixing and delivery device as embodied in FIGS. 10A-D illustrating changing from the mixed state to an injected state. This actuator functions similarly to the embodiment discussed above wherein the intermediate support 640 is provided with a protrusion 644 which is rotated incrementally by depressing the needle shield 550. The incremental rotation of the intermediate support 640 causes the plunger protrusions, not shown here, to rotate with the intermediate support 640 and align with a second channel of the housing or frame, and allow for injection to be initiated.

FIGS. 18A-D illustrate a bump switch which operates similarly in function to the embodiments discussed above, however the protrusions of the intermediate support are located in a slightly different configuration, as seen. In particular, the intermediate support does not have an upper protrusion and instead has channels through which the protrusions of the inner plunger can travel through and interface with the intermediate stop, thus allowing the auto-injector to stop in a mixed but non-injected state.

It will be understood that this embodiment also works using a rotational style valve which utilizes selective alignment of an outlet 624 of the first chamber 610 with the inlet of the fluidic channel, wherein the selective alignment corresponds with an open configuration when aligned and a closed configuration when misaligned.

Figure 19B:
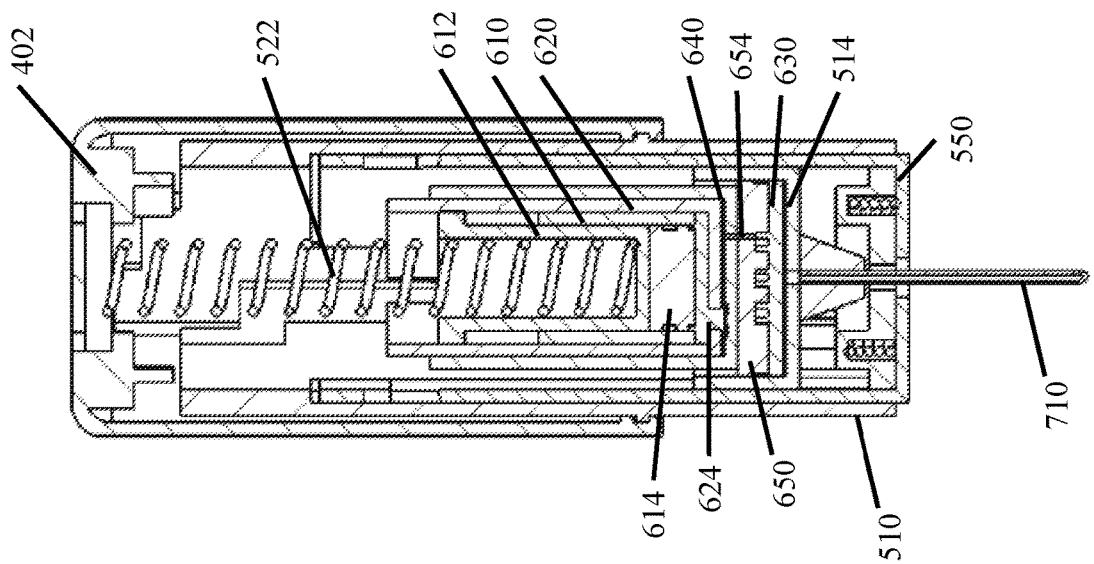
FIGS. 19A-B illustrate side and cross-sectional views of the medication mixing and delivery device as embodied in FIGS. 10A-D illustrating an injection complete state.
Figure 19A:
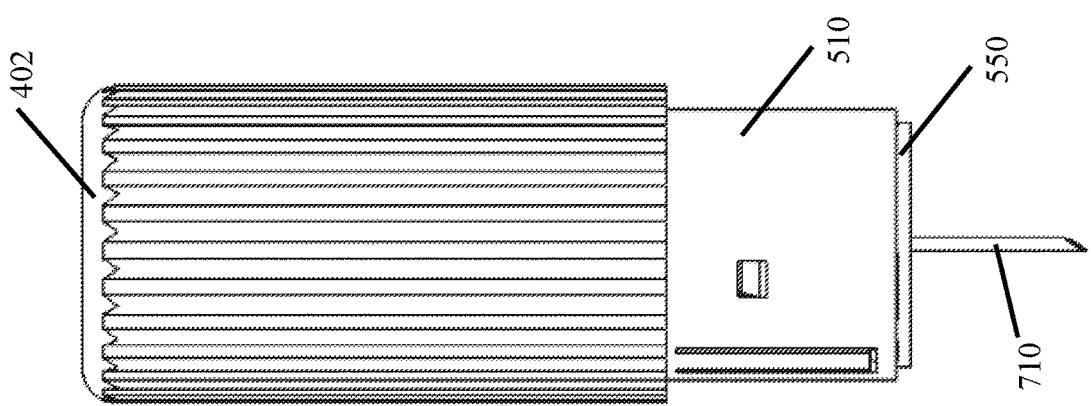

FIGS. 19A-B illustrate an injected state wherein the mixing assembly 600 has been rotated another small increment within the housing 402 of the auto-injector 400 such that that protrusions of the plunger shaft 612 have been rotated around sufficiently so as to align with a second axially aligned channel of the frame 510, the second channel is not shown herein, but is similar in arrangement to the embodiment previously discussed in particular with reference to FIG. 7A-D. Once this alignment has been achieved, a second portion of energy stored within the pre-stored energy source which causes the entire mixing assembly to be pushed downward wherein the second vial 670 hits a bottom portion of the frame 510 and frame cap 414 wherein the needle 710 is extended through the needle guard 714 past the needle shield 550 and extended into or about a delivery site, further as the second vial 670 hits the bottom portion of the frame 510 the second plunger 650 is depressed into the second vial 670 reducing its effective volume and causes the fluid to be ejected through the delivery assembly and into the patient or onto the delivery site.

In this state the needle 710 or other deliver mechanism and assembly are extended such that the needle 710 penetrates the needle guard 714 and is extended past the needle shield 750.

In order to translate axially downward to eject the fluid through the delivery assembly the intermediate support 640, vial sleeve 630 and the inner plunger 612 must rotate together so as to be aligned with a second frame channel so as to allow for a second portion of energy to be released from the pre-loaded energy source thus driving the mixing assembly downward, with the delivery assembly affixed to the bottom end thus effectuation injection or delivery. To move from the mixed state and begin injection, and as discussed above with reference to FIGS. 18A-D, the intermediate support can be provided with one or more protrusions 644, which can be caused to rotate similar to the previously discussed embodiment using cam ramps associated with a bump switch, which the needle shield 550 forms part.

FIGS. 20A-D illustrate an extension and locking function of the needle shield 550. It will be understood that it is of general interest to reduce the potential for inadvertent contamination or sticks of other people prior to injection, during injection, and after injection. As such the needle shield 550 of the present embodiment serves both as a bump switch as well as a protective barrier between the user, and other people from inadvertent sticks, jabs, or cuts from an exposed needle. As such, after the bump switch is activated, the needle shield hooks as discussed above are released and a needle shield spring 554 or other biasing mechanism which is configured to push the needle shield outward, or axially downward. The delivery assembly and needle are not ejected until the bump switch is first activated, then after injection, as the user pulls the auto-injector away from the delivery site, the needle shield is simultaneously extended until the needle clears past the tip of the needle, essentially eliminating the risk of secondary pricks and cross contamination of bodily fluids to other people post injection.

In the embodiment shown the housing 402 can be provided with a plurality of protrusions 516 for interfacing with an upper locking edge 566 of the needle shield. Once the needle shield 550 has been extended a certain degree the protrusions 516 engage with the upper locking edge 566 and prevent subsequent depression of the needle shield. The needle shield hook 558 which previously prevented the premature rotation of the intermediate support can now act as an extension prevention mechanism and can interface with the protrusion 644 of the intermediate support 640 so as to prevent complete removal of the needle shield 550 and thus expose the contaminated needle.

FIGS. 21-24 illustrate various aspects of yet another auto-injector 1010 in accordance with yet another embodiment of the present invention. The auto-injector 1010 can include a housing 1100 which houses a plurality of chambers. The chambers can include a first wet chamber 1210 which can initially contain a wet component for reconstituting, dissolving, and/or suspending a dry medicament. The dry medicament can be contained within a second chamber 1270 or within a fluidic channel 1254 which connects the two chambers, or within a recess formed at an opening or outlet thereof. The orientation of this embodiment includes an intermediate support 1240 which pushes a first plunger 1214 upwards into the first chamber 1210.

It will be appreciated that, with respect to gasses, most fluids are considered incompressible. In order to facilitate upward motion of the first plunger 1214 and the fluid contained within the first chamber 1210, a third plunger 1215 and a squeeze chamber 1004 can be provided wherein a compressible gas is provided within the squeeze chamber 1004 or the gas contained therein is permitted to exit the squeeze chamber 1004. The upward translation of the first plunger 1214 allows it to travel into a portion of the first chamber 1210 which is provided with a fluidic bypass 1255 in the sidewall. In this bypass portion, the fluidic bypass 1255 allows the first chamber 1210 to be compressed and the fluid to travel around the first plunger 1214 through the fluidic bypass 1255 and into and through a fluidic channel 1254 so as to enter into the second chamber 1270 so as to mix with the dry medicament provided within the fluidic channel 1254 or within the second chamber 1270. In the embodiment shown, the plunger 1214 can be provided with a radially disposed slot on its bottom surface so as to allow fluid to travel from the bypass channel 1255 which is located about the perimeter of the chamber, to the inlet of the fluidic channel 1254 which is located about a central portion.

In this embodiment the intermediate support 1240 can support the second plunger 1250 such that the upward translation of the first plunger 1214 also causes the second chamber 1270 to push away from the second plunger 1250 simultaneously as the first chamber 1210 is compressed so as to expand and accordingly receive the fluid as it travels through the bypass 1255, through a channel formed in the bottom of the first plunger 1214, through the fluidic channel 1254, and into the second chamber 1270.

FIGS. 21B, 22A-E, and 23A-D illustrate the various stages of the auto injector 1010 and the mixing assembly 1200 from a stowed through the various mixing stages and finally to an injected state.

FIG. 22A and FIG. 23A illustrate the auto-injector and mixing subassembly in a stowed state wherein the fluid is in the first chamber 1210, the first plunger 1214, intermediate support 1240 and the third plunger 1215 have not been translated upward.

FIG. 22B and FIG. 23B illustrate the auto-injector and mixing subassembly in an intermediate state wherein the intermediate support 1240 is beginning to move the first plunger 1214 and the third plunger 1215 upward so as to move the first plunger 1214 into the fluidic bypass portion along the length of the bypass fluidic channel 1255 and wherein the third plunger 1215 is beginning to compress the squeeze chamber 1004. This position allows the fluid contained in the first chamber formed by inner vial 1210 to bypass around the first plunger 1214 through the bypass channel 1255 and through 1214 into the fluidic channel 1254 and into the second chamber formed by the second vial 1270 which expands in effective volume as the intermediate support 1240 moves upwards.

Figure 22E:
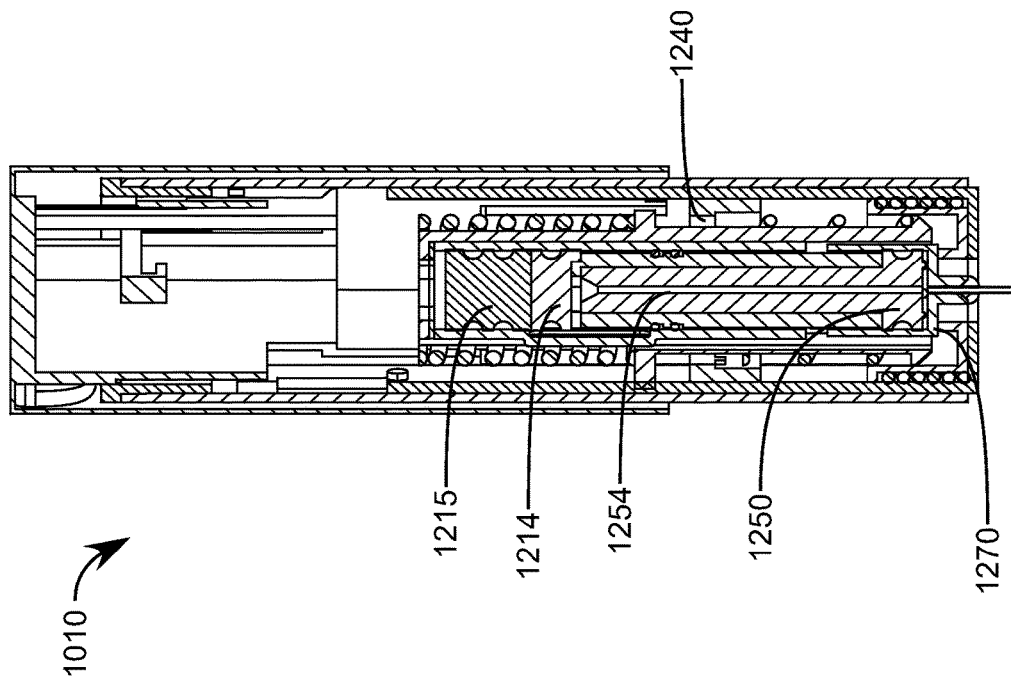
Figure 22D:
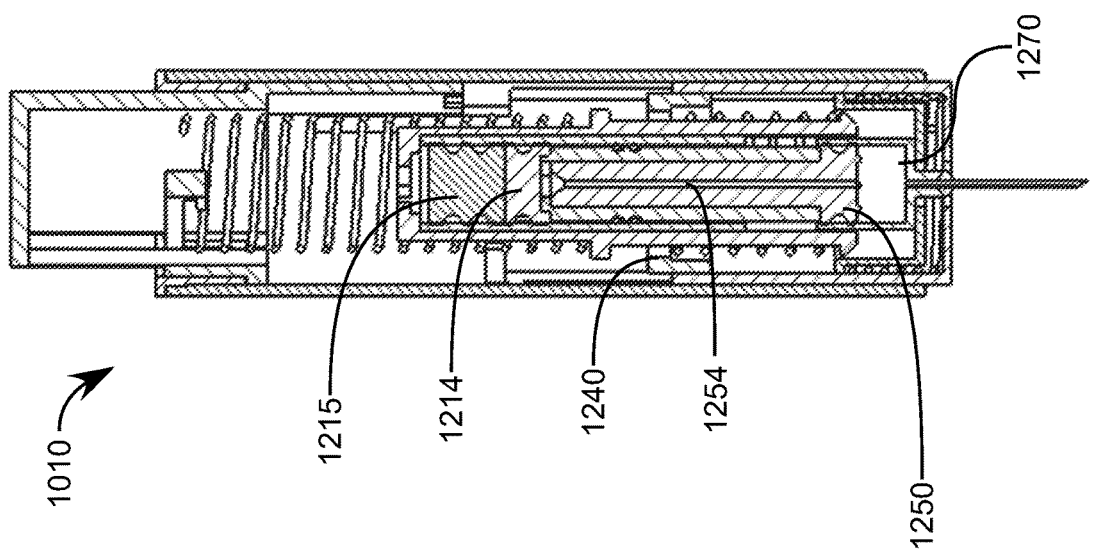

FIGS. 22C-D and FIG. 23C illustrate the auto-injector and mixing subassembly in a mixed state wherein the intermediate support 1240 is fully depressed upwards having moved the first plunger 1214 and the third plunger 1215 completely upward so as to fully displace all of the fluid out of the first chamber formed by inner vial 1210. In this position the fluid is completely contained in the second chamber formed by the second vial 1270 and ready for injection. In this fully injected state the needle is extended through the housing 1100 and into or about a delivery site.

FIG. 22E illustrates the auto-injector and mixing subassembly in a fully injected state wherein the entire mixing assembly is depressed downward and into the second chamber thus displacing the mixed medication and fluid out through the delivery assembly, i.e. the needle.

FIG. 25A-D illustrates yet another embodiment of an auto-injector 1300 which has a first chamber 1410 containing a fluid component therein and a second chamber 1470 containing a dry medicament component. The auto-injector 1300 can have a movable body 1450 which has a fluidic channel 1454 provided therethrough. In one embodiment the fluidic channel can contain the dry medicament component. In another embodiment the dry medicament component can be placed just upstream from the fluidic channel In order to displace the fluid within the first chamber 1410 into the second chamber 1470.

In one embodiment an initial tensile force can be applied at two ends of the housing so as to be pulled or telescoped axially apart thus causing a first telescoping effect which causes the movable body 1450 to be displace upwards into the first chamber 1410 and force the fluid from the first chamber 1410, through the fluidic channel 1454 and into the second chamber 1470. This motion of the movable body upwards causes the second chamber 1470 to simultaneously expand so as to facilitate in the receipt of the fluid being displaced and thus facilitate mixing of the fluid with a dry medicament stored either within the fluidic channel 1454 or within the second chamber 1470. Once the fluid and the dry medicament are fully mixed the device can be pulled or telescoped axially apart further, which telescoping causes a pin 1314 disposed within the housing 1310 to pull away from a lock mechanism 1304, wherein a trigger device causes protrusions of the locking mechanism to translate radially inward and release through a hole, wherein translation was previously restricted by the pin 1314, wherein the trigger also allows a pre-loaded energy source 1322, i.e. a spring to be released, and push the entire mixing assembly 1350 in an axial direction toward the needle assembly. This trigger device can also be provided as a bump switch or needle guard depression switch similar to those disclosed with reference to the embodiments disclosed above. Once the needle is extended from the housing a bottom portion of the second chamber 1470 will engage the housing 1310 and cause the movable body 1450 to displace the fluid in the second chamber 1470 out through the needle 1490 and into the delivery site.

Figure 24:
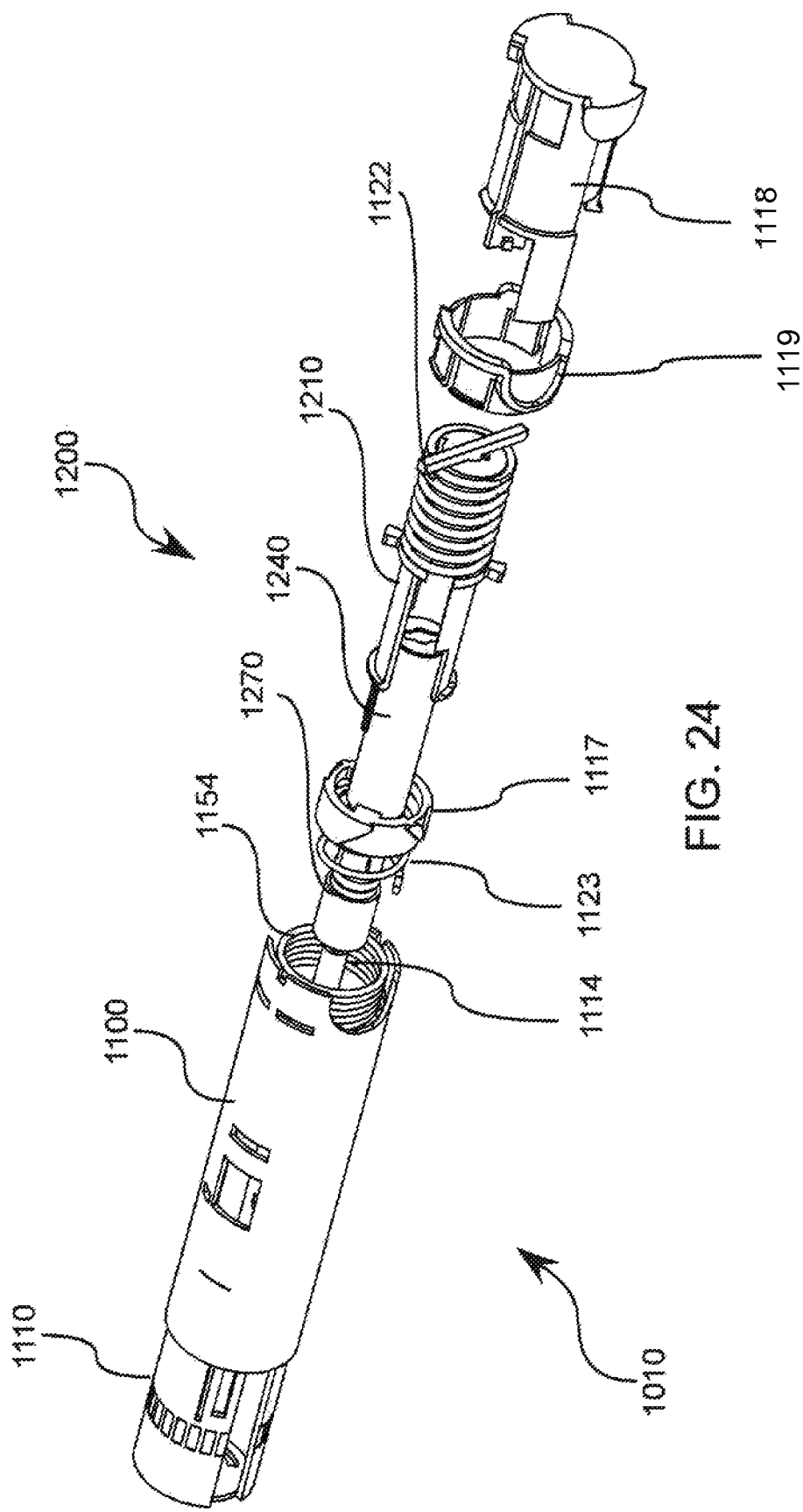
FIG. 24 illustrates a perspective exploded view of a mixing assembly for use with the medication mixing and delivery device of FIGS. 21A-B through various actuation steps.
Figure 25A:
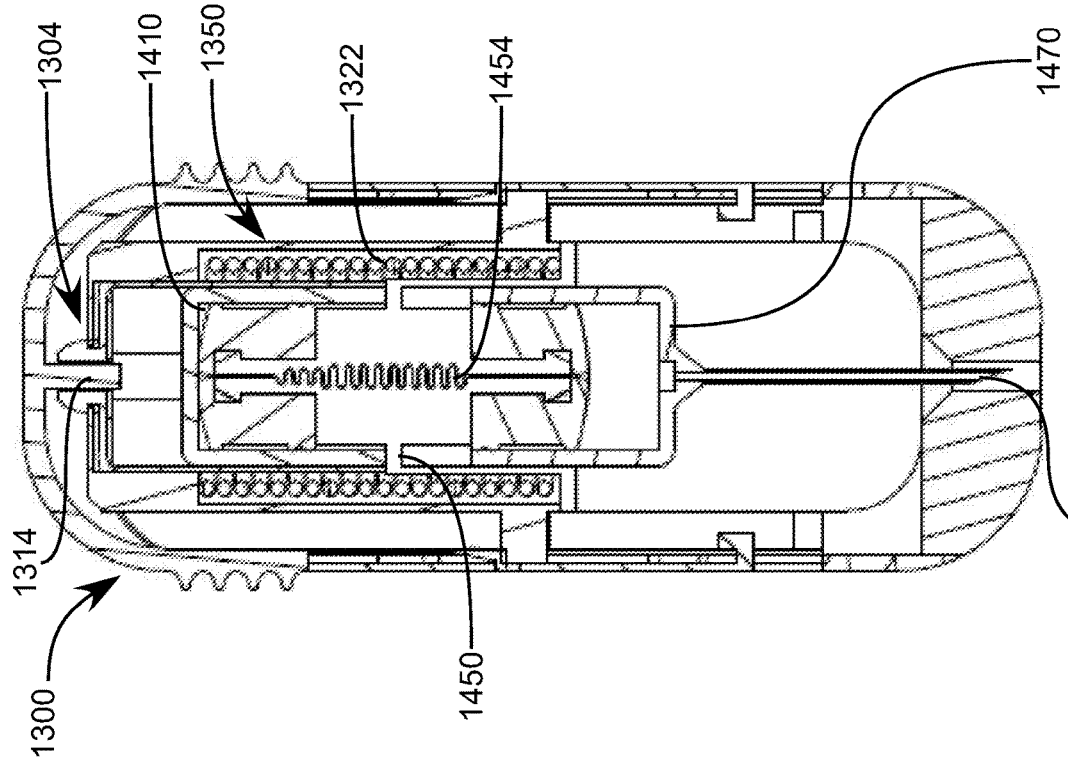
FIGS. 25A-D illustrate various cross-sectional views of yet another alternative embodiment of a medication mixing and delivery device in various actuated states.
Figure 25B:
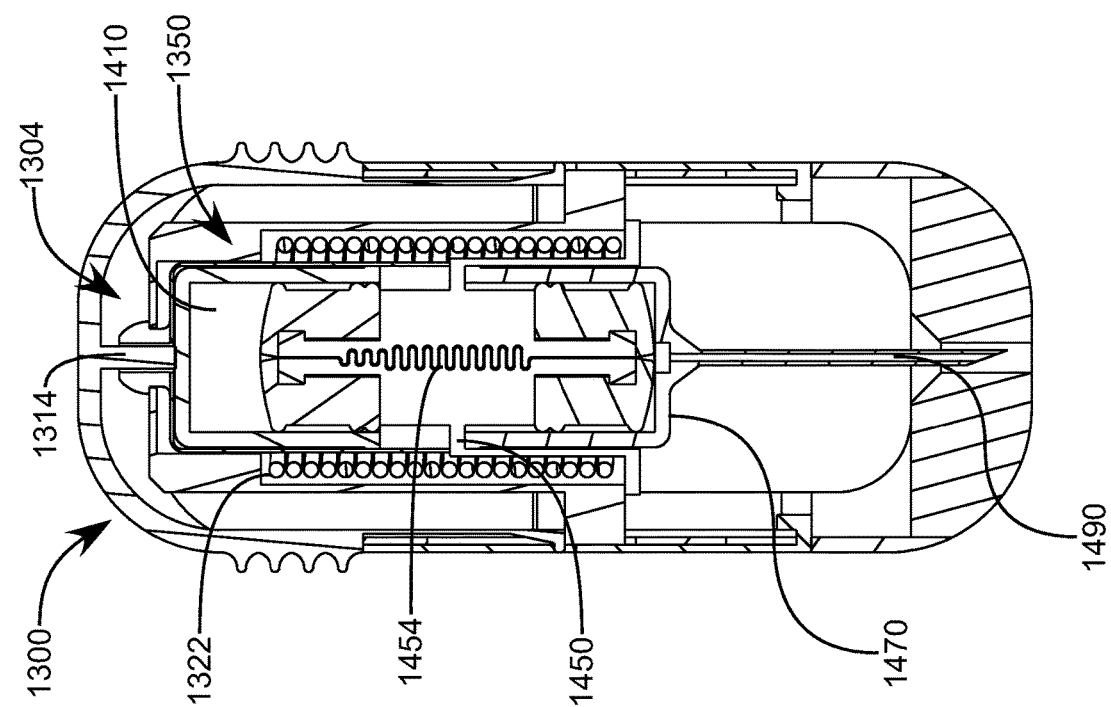
Figure 25D:
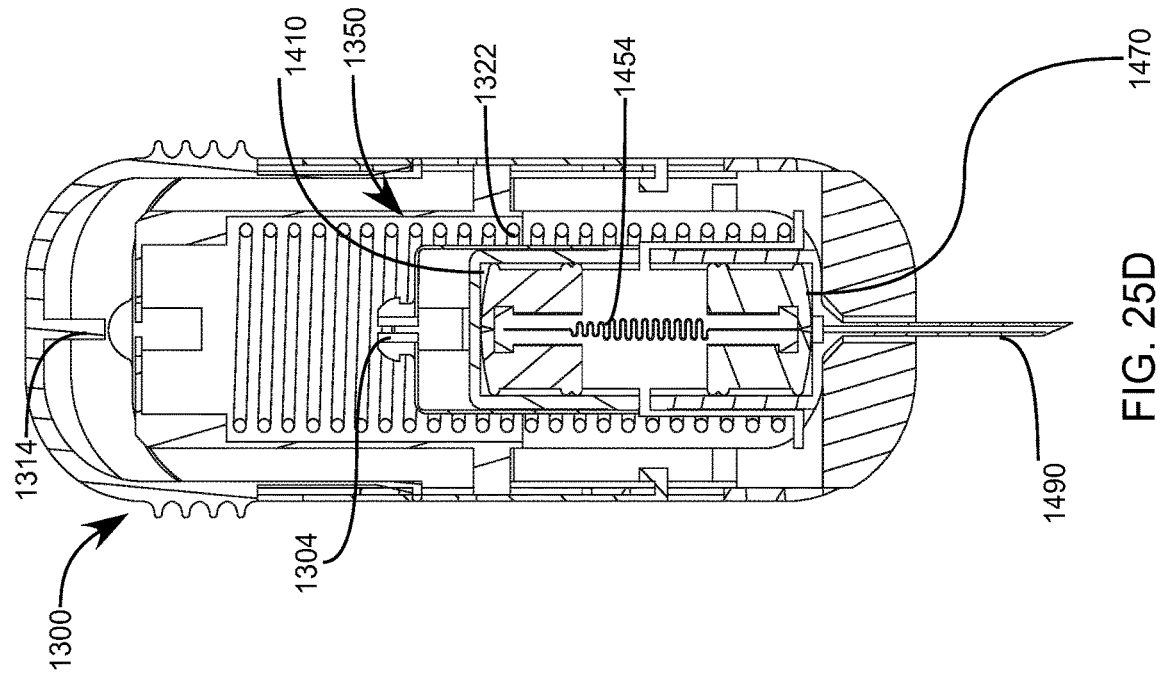
Figure 25C:
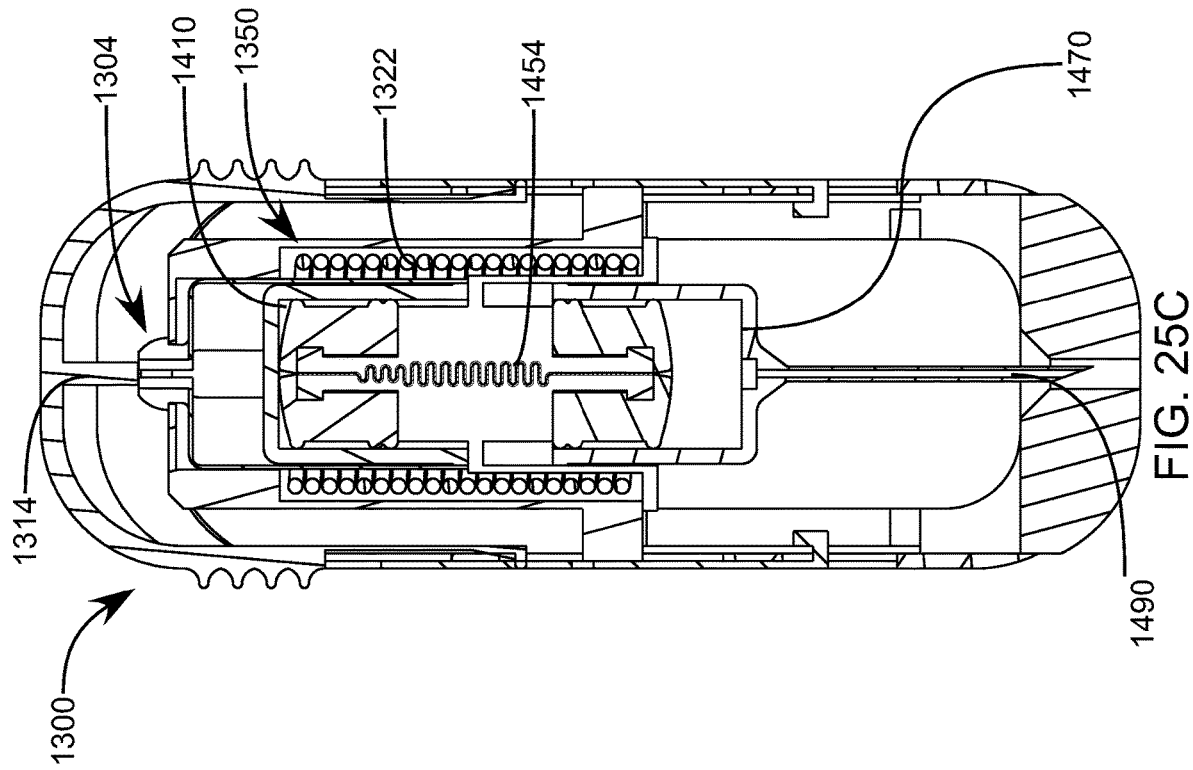

FIG. 24 illustrates a perspective exploded view of the embodiment of the auto-injector 1010 of FIGS. 21-23, which better illustrate the assembly and how many of the individual components interact with one another. A housing 1100 can contain the mixing assembly 1200, wherein the mixing assembly 1200 can be retained within the frame 1100 by the needle guard 1110 on an injection end and by a retention clip 1119 and pull trigger 1118 on an opposing distal end. The mixing assembly 1200 can include up inner vial 1210 and an intermediate support 1240 wherein the extension of the pull trigger 1118 causes the cam ring 1117 to rotate and allow the mixing spring 1123 to discharge a torsional and axial force stored therein so as to rotate the middle stopper 1117. Rotation of the cam ring 1117 is configured to cause the intermediate support 1240 to translate upward into the inner vial 1210, open fluidic communication, and displace the fluid contained therein into the second vial 1270. It will be appreciated that cam ring 1117 and intermediate support 1240 can be separate components for purposes of assembly, or alternatively they can be unitarily formed. Then upon depressing the needle guard 1110 into the housing the main spring 1122 is discharged and the entire mixing assembly 1200 is forced downward extending a needle (not shown) through the housing. The fluid, which is now contained in vial 1270, is then displaced through the needle contained in sterility barrier 1114. It will be appreciated that sterility barrier 1114 can be configured to be removed prior to use, or penetrated during injection just prior to delivery of the mixed fluid. Once injection is completed the needle guard spring 1154 can bias the needle guard 1110 outward into an extended and locked position so as to protect inadvertent sticks by the now extended needle.

Figure 26B:
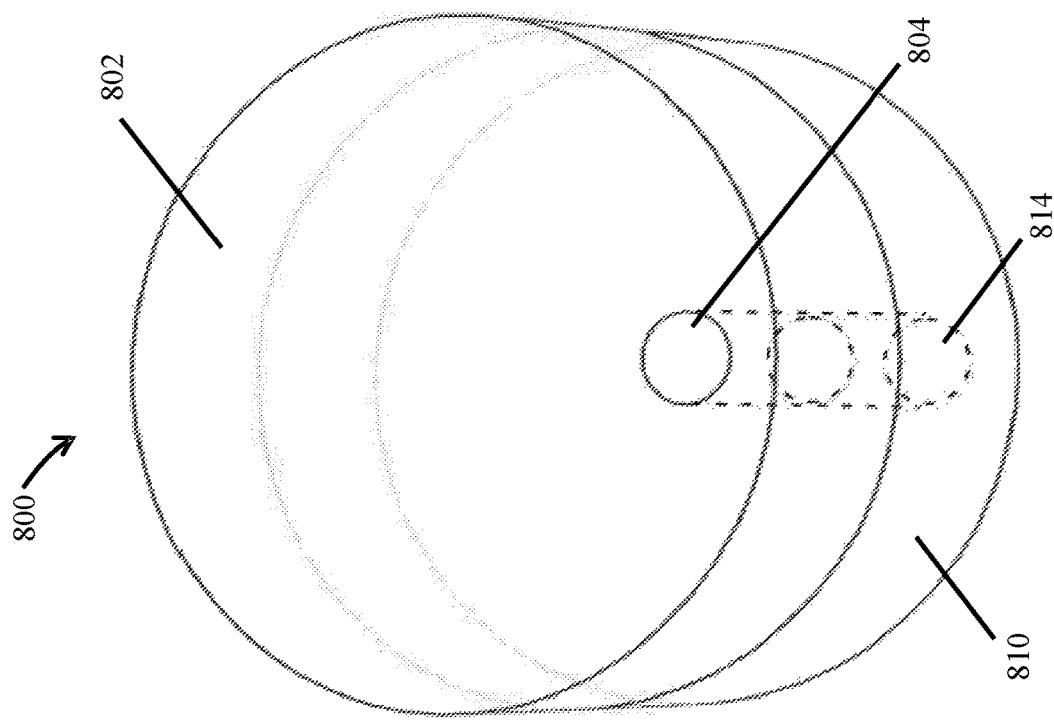
FIGS. 26A-B illustrate principles of a rotary valve adaptable for use in any of the embodiments discussed herein.
Figure 26A:
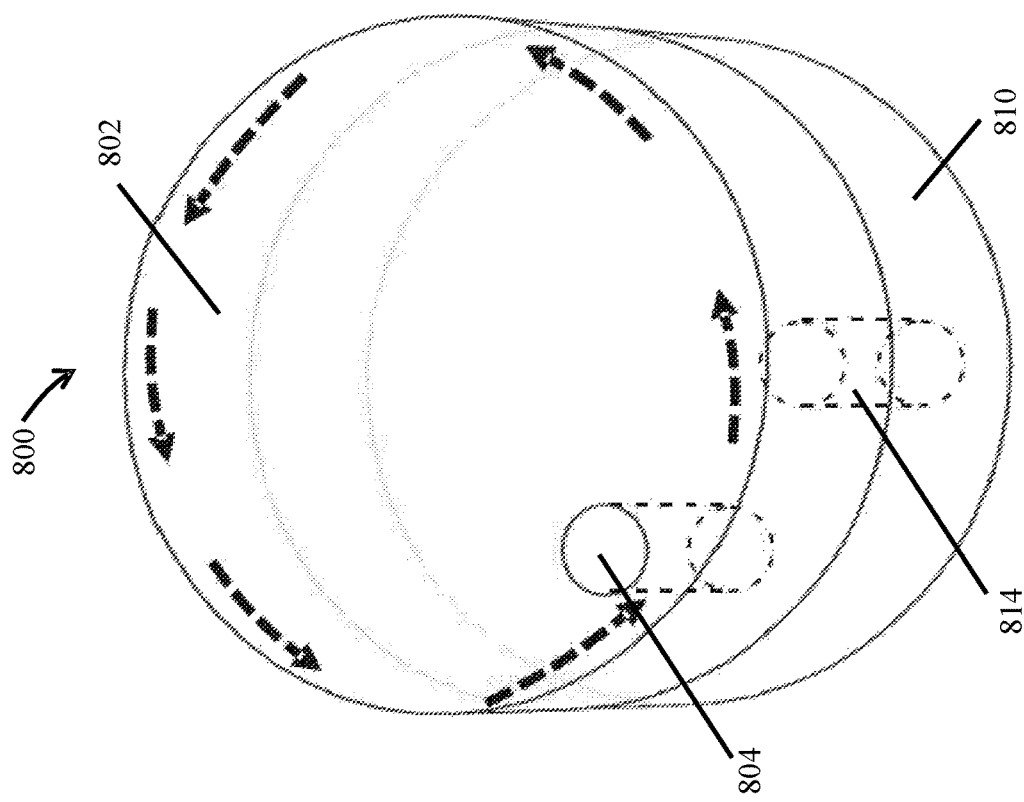

FIGS. 26A-B illustrate the principles of operation of a rotary valve 800 for use in the embodiments discussed above. A rotary valve can be formed wherein a fluidic pathway is established by rotating one aperture with another. In this exemplary illustration the aperture 804 can be provided in a bottom portion of a vial which forms a top interfacing portion 802 forming a chamber and the secondary aperture 814 provided through a bottom interfacing portion of the seal 810, which can be the inlet to the remaining portion of a fluidic channel leading to another chamber. FIG. 26A illustrates a closed configuration wherein the two apertures are misaligned and fluid communication does not exist. FIG. 26B illustrates an open configuration wherein the two apertures are aligned and fluid communication is established. It will be appreciated that in order to form a better seal, one or both of the components can be formed of a material having elastic properties such as rubber or silicone. In another embodiment, one of the components is rubber and another is hard plastic. In another embodiment each of the sealing surfaces are made up of a combination of hard plastic and elastomeric materials in one interface.

FIGS. 27A-D illustrate an alternative valve mixing assembly 900 which is effectuated by means of sliding two components axially with respect to one another so as to effectuate establishment of fluidic communication, rather than through rotation.

FIG. 27A illustrates a stowed state wherein fluid is contained in a first vial 910 by a first plunger 940, wherein the first vial 910 has an outlet 914 which is misaligned with the fluidic channel inlet 952 of the fluidic channel 950 in an axial direction, wherein the fluidic channel 950 provides fluidic communication with the second vial 920. The fluidic channel 950 is disposed in an intermediate support 930 which can double as a second plunger for the second vial. Mixing can be initiated through various cams or axially forces applied to the mixing system which cause a relative axial translation between the first vial 910 and the intermediate support 930 so as to align the outlet 914 with the fluidic channel inlet 952. The intermediate support can then be caused to translate axially with respect to the intermediate support simultaneously as the first plunger 940 is depressed into the first vial 910 until all of the fluid has been received in the second chamber 920 and completely displaced from the first chamber 910. Then both the first plunger and the intermediate support can be simultaneously depressed so as to displace the fluid out of the needle 960 which simultaneous depression can cause the needle to penetrate the needle guard 970. It will be appreciated that axial translation can be achieved by translating rotational motion using ramped cam systems and corresponding protrusions, various spring mechanisms in different configurations all of which will be within the scope of the present invention and will also be within the understanding of one of ordinary skill in the art having possession of this disclosure.

For purposes of the sliding valve of FIGS. 27A-D it will be appreciated that various effectuation means can be effectuated by various protrusions such as on the vial sleeve which can translate within channels provided in adjacent components so as to effectuate the axial translation of the first chamber, and its associated outlet, with the inlet of the fluidic channel.

Figure 28C:
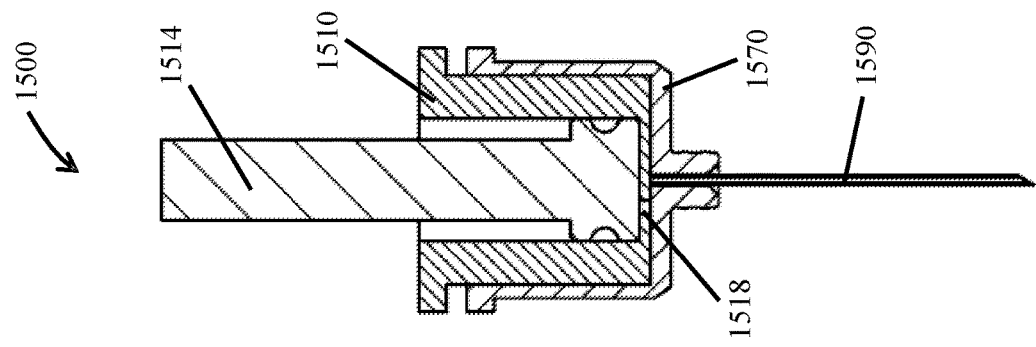
FIGS. 28A-C illustrate various cross-sectional views of yet another alternative embodiment of a medication mixing and delivery device in various actuated states which utilize chambers which are independently movable within a housing.
Figure 28B:
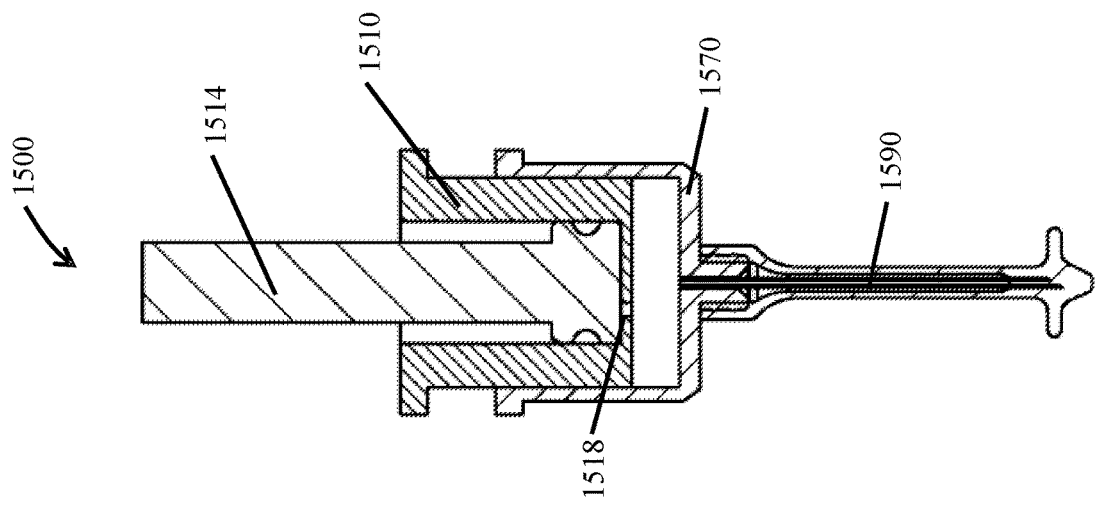
Figure 28A:
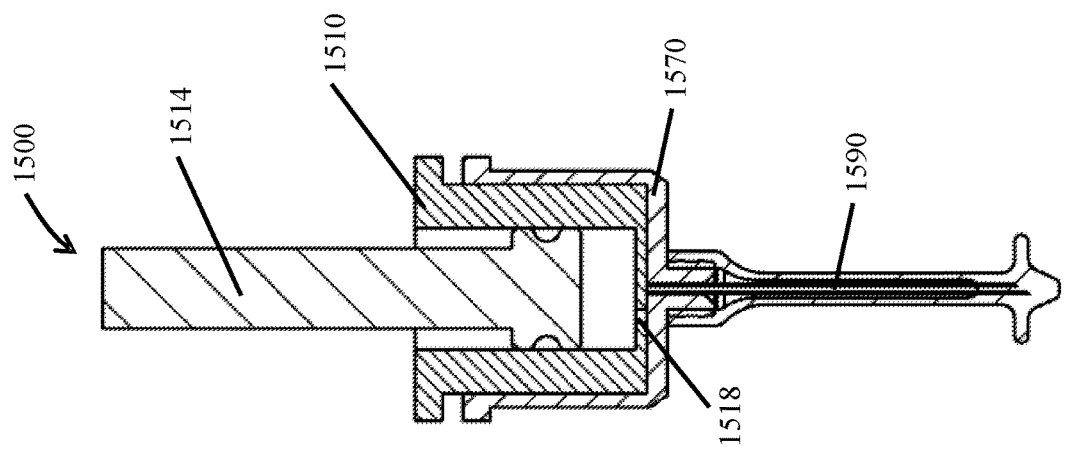

FIGS. 28A-C illustrate yet another mixing assembly 1500 adaptable for use in one or more of the auto-injectors above. This alternative valve mixing assembly 1500 is effectuated by displacing a first chamber 1510 with respect to an initially stationary plunger 1514, the outer surface of the first chamber 1510 can be provided with a seal and function as a plunger for a second chamber 1570. By displacing the first chamber 1510 upward, a fluid contained therein can travel through an aperture or valve 1518 so as to be displaced into the second chamber 1570, which can contain the dry medicament therein, or the dry medicament can be stored in the fluidic channel, wherein the upward motion of the first chamber automatically expands in response to the upward motion of the first chamber 1510. The second vial 1570 can be held stationary, or be provided with independent protrusions which cause it to not be drawn upward at all, or at least not be drawn upward at the same rate as the first chamber 1510 so as to facilitate proper expansion in response to the volume of fluid moving from the first chamber into the second chamber. Once mixing is complete the plunger 1514 as well as the rest of the assembly can be forced downward so as to facilitate injection. For purposes of illustration, a spring could be configured to act on the plunger after mixing is complete and provide a compressive force of the mixing assembly 1500 between the spring and an outer housing in which the mixing assembly resides so as to displace the fluid from the second chamber and out of the needle 1590.which is effectuated by means of sliding two components axially with respect to one another so as to effectuate establishment of fluidic communication, rather than through rotation.

Figure 29:
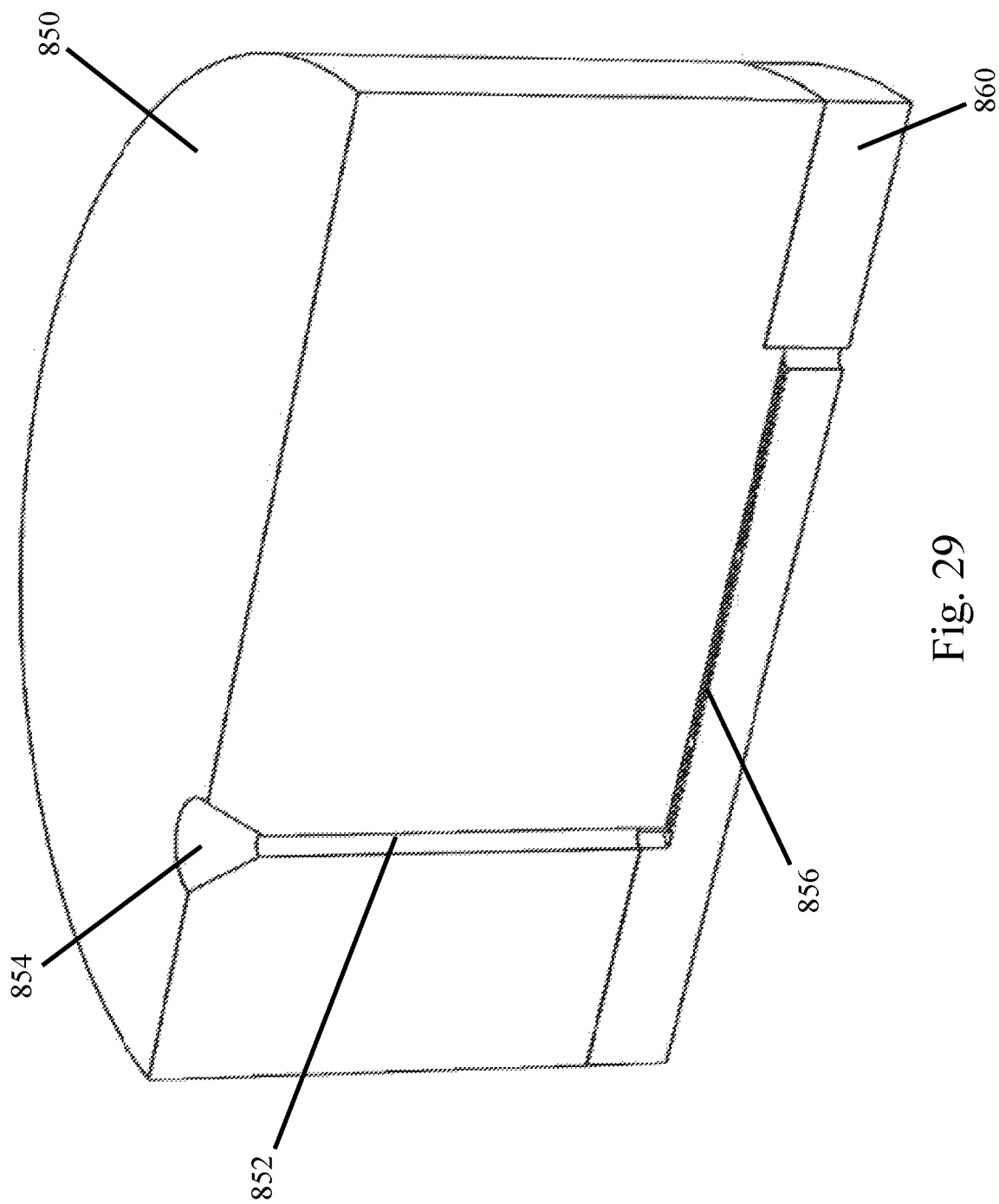
FIG. 29 illustrates an exemplary fluidic channel arrangement adaptable for use in any of the embodiments discussed herein.

FIGS. 29-30 illustrate various intermediate bodies 850 and 850A having fluidic channels 852 disposed therein. The fluidic channel 852 can have an inlet 854 for receiving a fluid and allowing the fluid to pass therethrough. In some embodiments a secondary fluidic body 860 having a secondary fluidic channel 856 can be provided which receives the fluid, the secondary fluidic body can introduce additional flow features so as to affect flow therethrough. In the embodiment shown the secondary body can be provided with a plurality of turbulence features which induce turbulent flow and increase flow speed, pressure differential, and can increase the effectiveness of mixing between the fluid and a dry medicament which can be stored therein. In another embodiment the dry medicament can be stored in 854.

FIG. 30 illustrates an alternative intermediate body 850A with a recess configured to receive a customizable ferrule 862. The ferrule can have an enlarged interior portion configured to receive an amount of dry medicament wherein a selection of ferrules can be provided having greater or smaller interior portions for adjusting the dosage of medicament for a particular end user. It will be appreciated that the intermediate bodies of these respective embodiments can be oriented in any fashion such that the inlets or outlets are switched or such that the ferrule is at either an inlet or outlet of its respective intermediate body.

FIG. 31A illustrates additional embodiments of secondary fluidic bodies 860A and 860B which can introduce additional bends and passes to the various fluidic pathways 856A-B.

FIG. 31B illustrates a detailed perspective cross sectional view of a fluidic channel 856 and respective turbulence inducing features 857.

FIGS. 32A-C illustrates a fluidic channel assembly 870 which can be adapted for use with any of the embodiments discussed above. The fluidic channel assembly 870 can include a dosage ferrule 872, which in one embodiment contains dry powder medicament, a channel sleeve 875 and a fluidic channel 876. A fluidic channel insert 874 for use in the fluidic channel assembly 870 can be formed by coupling two separate plates 878 and 880 which are machined to form a gap when pressed together thus forming the fluidic channel 876. By forming the fluidic channel between two separate plates, more complex internal features 882 can be formed prior to assembly. It will be appreciated that the two plates can be bonded in any suitable manner such as welding, adhesive, etc. The channel sleeve can then be provided so as to ensure a seal and reduce leakage. This fluidic channel assembly 870 can be adapted for use with any of the embodiments discussed above.

Figure 33B:
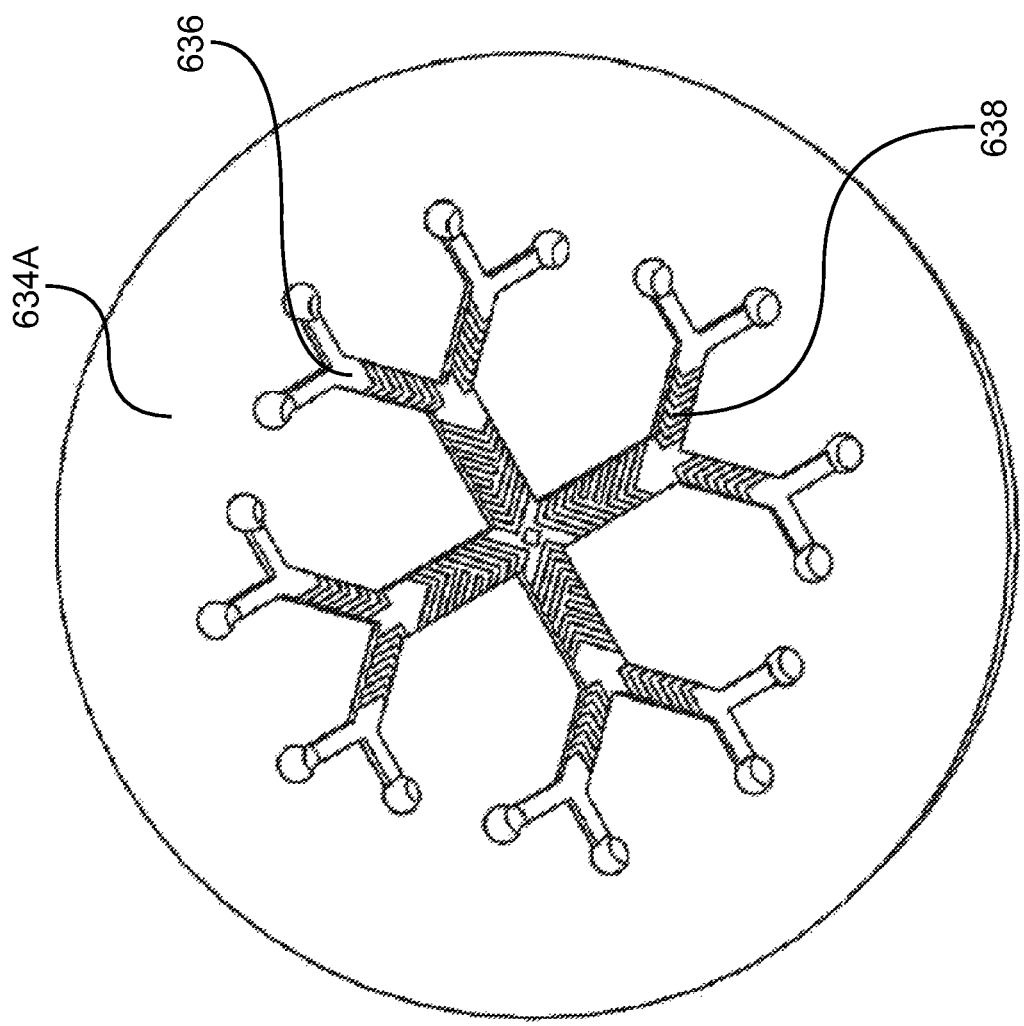
FIGS. 33A-B illustrates various additional features of yet another alternative embodiment of a fluidic channel arrangement adaptable for use in various embodiments discussed herein.
Figure 33A:
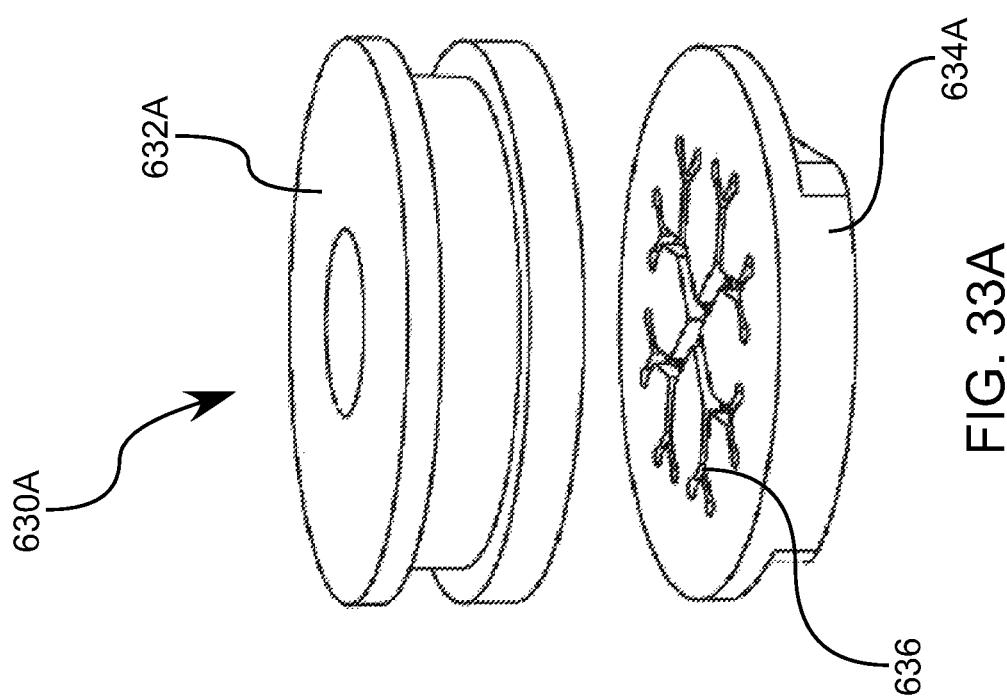

FIGS. 33A-B illustrate yet another embodiment of a proposed fluidic channel assembly 630A. This fluidic channel assembly 630A can be formed of a seal component 632A which directs fluid received from an upper portion into a desired entry point on a fluidic channel component 634A. In one embodiment, a dry powder medicament can be stored in the pocket recess in 632A. In another embodiment, a dry powder medicament can be stored in the fluidic channels 636 and 638. Various fluidic channel designs 636 and features 638 can be formed into an upper surface of the fluidic channel component 634A in virtually any suitable configuration through various machining means, laser, acid etching, injection molding, or embossing or any other suitable process so as to form a desired channel configuration 636 or features 638. The channels can ensure proper fluid dispersion, induce turbulence, or provide any other number of desired flow characteristics of the fluid passing therethrough.

It will be further understood by those in possession of this disclosure that the chambers and respective plungers can be movable with respect to one another. As such, in some cases, and as shown here, translating the plunger into the vial which forms the respective chamber can be one method of reducing the effective volume and displacing fluid contained therein. In other embodiments the vials themselves may be displaced onto, or with respect to, a stationary plunger so as to provide the displacement force. In yet other embodiments a combination of the two can be utilized so as to provide the displacement effect.

Figure 34B:
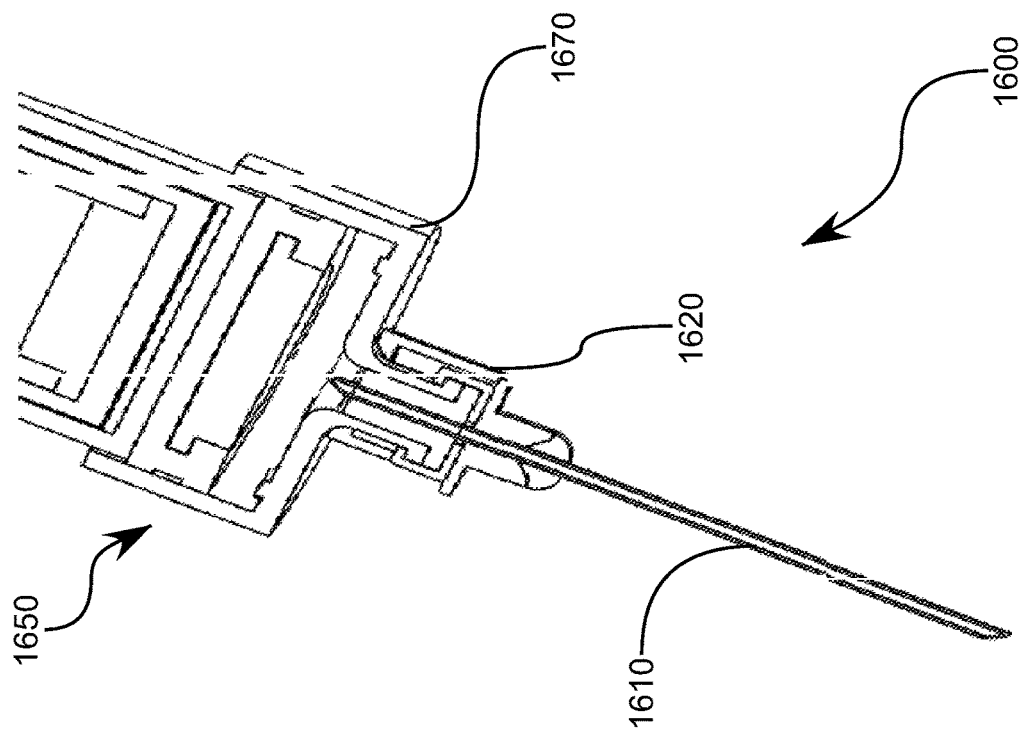
FIGS. 34A-B illustrate extended and retracted states of a delivery or injection assembly adaptable for use in any of the aforementioned embodiments.
Figure 34A:
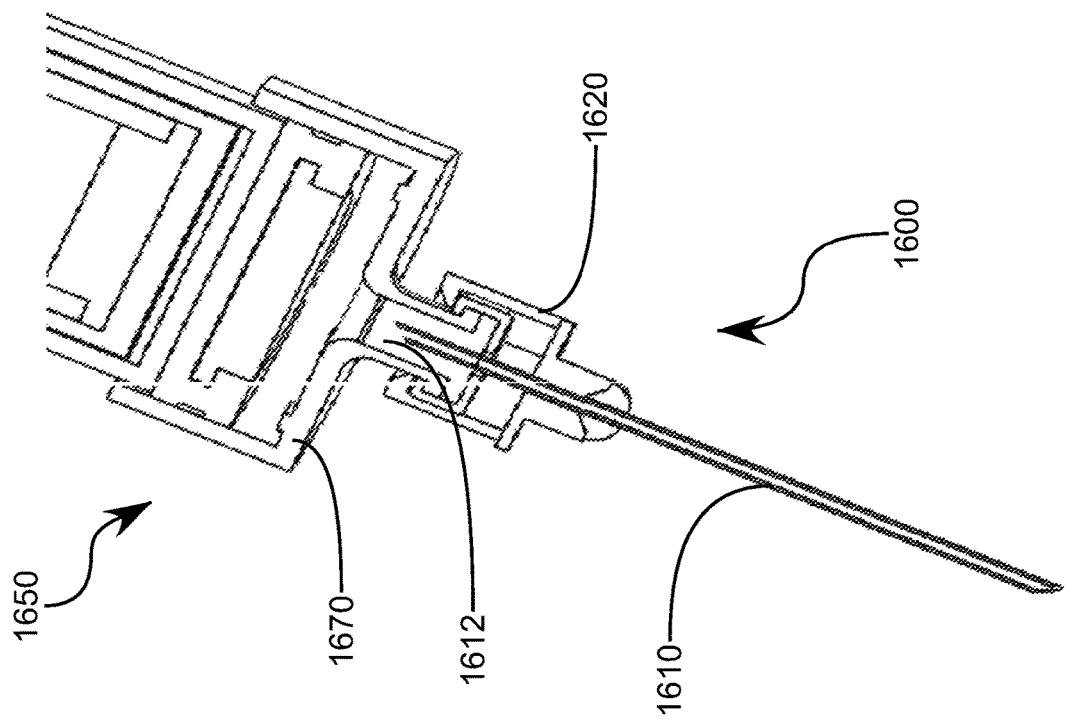

FIGS. 34A-B illustrate an injection or delivery assembly 1600 adaptable for use with any of the auto-injectors discussed above. FIG. 34A illustrates an exemplary mixing assembly 1650, similar to any of the mixing assemblies disclosed herein, the mixing assembly 1650 having an expanded second chamber 1670 containing the mixed drug and liquid component just prior to injection. A septum 1612 is provided between the inlet end of the needle 1610 and separates the interior channel or cannula of the needle from introducing contaminants therethrough into the second chamber 1670 prior to injection. Additionally, septum separates the needle from the interior of the second chamber so as to prevent premature leaking and full mixing of the various components prior to actuation and injection.

It will be appreciated that the needle has both a distal or injection end and a proximal end. The distal end can be configured to enter into a patient at an injection site and the proximal or inlet end being configured to pierce and ultimately penetrate the septum. It will be further appreciated that in FIG. 34A the needle 1610 has still not yet penetrated the septum 1612.

As shown in FIG. 34A, the needle 1610 can be partially embedded into, but not fully penetrated through, the septum 1612 in a stowed state wherein the needle 1610 can penetrate the septum 1612 and open fluid communication out the injection end just prior to injection.

In order to provide penetration of the septum 1612 by the needle 1610, the needle can be carried by a translating needle carrier 1620. The needle carrier 1620 can have a translating body which is allowed to translate axially along the needle axis with respect to the second chamber 1670 and the septum 1612. The degree of translation can be limited or controlled by providing abutting shoulders which interfere with one another at certain points along the relative travel distance between the carrier and the second chamber. In one instance the shoulders can engage to prevent the needle from being released from the system and sliding out of the auto injector entirely, and in another instance the shoulders can engage to provide the axial translation and puncture force of the needle through the septum when pushed down just prior to injection. In the cross-sectional view of FIG. 34A the needle carrier is extended to its maximum distance away from the second chamber.

FIG. 34B illustrates the injection motion of pressing the auto injector up to an injection site. The downward force drives the needle 1610 downward with respect to the needle shield to expose the needle from the interior of the auto injector body. A shoulder or stop can be provided on the interior of the needle shield which engages with the needle carrier and pushes the proximal end of the needle through to fully penetrate through the septum. At this point a fluid pathway is established and fluid communication is provided from the second chamber into the patient's body or other injection site. At this point a second plunger can be pushed into the second chamber thus forcing the mixed drug into the injection site.

Figure 35A:
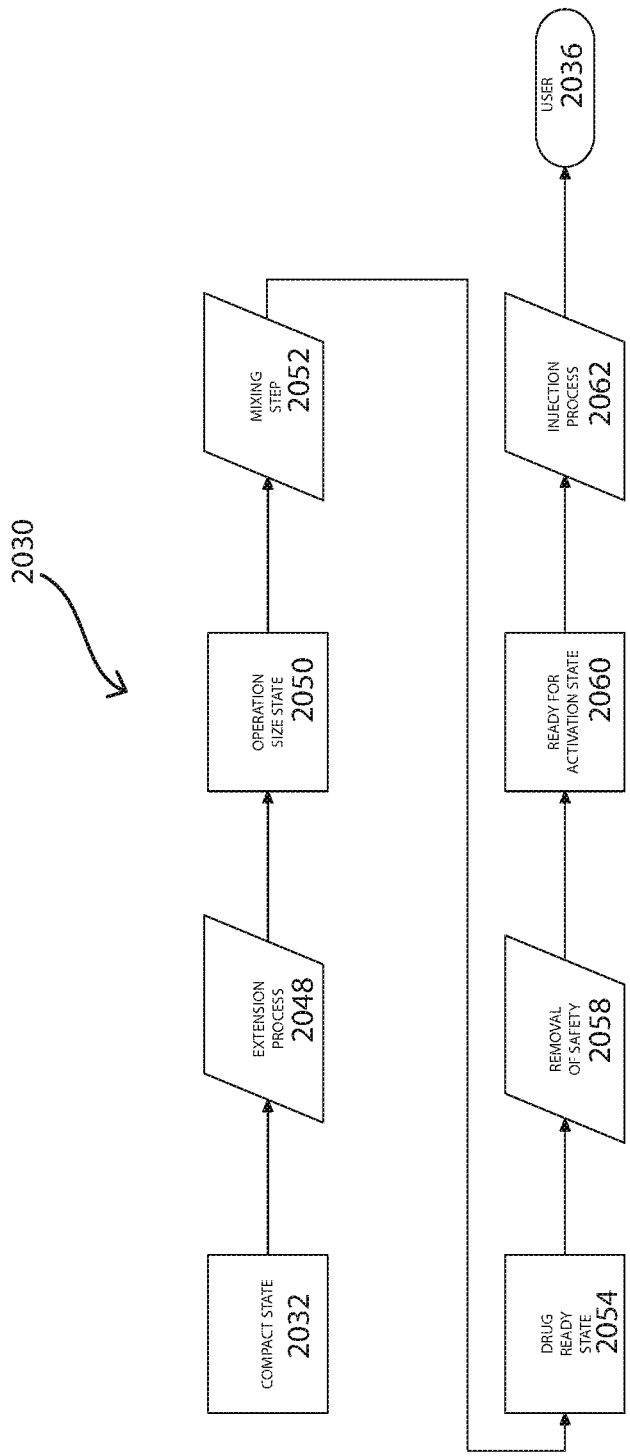
FIG. 35A is a schematic of a method of using a portable auto-injector according to one embodiment.

Referring to FIG. 35A, a schematic of a method of using a portable auto-injector 2030 is shown. The portable auto-injector 2030 is carried by a user in a compact state as represented by block 2032. In the compact state 2032, a dry medicament, which is going to be delivered to a user 2036 (as a wet medicament) is stored separately from wet components, such as a dry medicament 2038 and a wet component 2040 as shown in FIG. 42A. In addition, in the compact state 2032, the portable auto-injector 2030 is in a safe position where the auto-injector 2030 cannot inadvertently stab a user 2036 with a needle 2046 until desired, as seen in FIGS. 40A-41B and 43F.

The auto-injector 2030 is moved from the compact state 2032 by an extension process as represented by a parallelogram 2048. The extension process 2048 can take several forms as explained in further detail below, such as by pulling components relative to each other, rotating components relative to each other, or twisting components relative to each other. With the extension process 2048 completed, the auto-injector 2030 is of a size that it is comfortable for the user to operate, an operation size state 2050.

The housing has a larger dimension in the operation size 2050. In one embodiment, the portable auto-injector 2030 is 3 inches by 1 inch by 0.5 inches in the compact state 2032 and 4½ inches by 1 inch by 0.5 inches in the operation size state 2050.

The mixing of the dry medicament and wet components in some embodiments may occur as part of the extension process 2048 or another mixing step as represented by a parallelogram 2052. The mixing step 2052 causes the wet component 2040 to pass through and combine with the dry medicament 2038 therein forming the wet medicament 2034 which is to be delivered to a user 2036. The wet medicament ready state is represented by a block 2054.

In certain embodiments, the extension process 2048 places the auto-injector 2030 in condition for use. In the alternative and as represented in FIG. 35A, the portable auto-injector requires a separate and distinct step of removal of a safety step/pre-activation step as represented by a parallelogram 2058 to place the auto-injector 2030 in the ready for activation state as represented by a block 2060.

Still referring to FIG. 35A, with the auto-injector 2030 in the ready for activation state 2060, the auto-injector 2030 can be placed in proximity to the user 2036. The injection process step as represented by a parallelogram 2062 can be triggered to deliver the drug to the user 2036.

It is recognized that the operator of the portable auto-injector 2030 and the person receiving the drug 2034 can be two distinct persons. For example, the person receiving the wet medicament 2034 could be a child or someone in a state in which at they could not operate the auto-injector 2030.

Figure 35B:
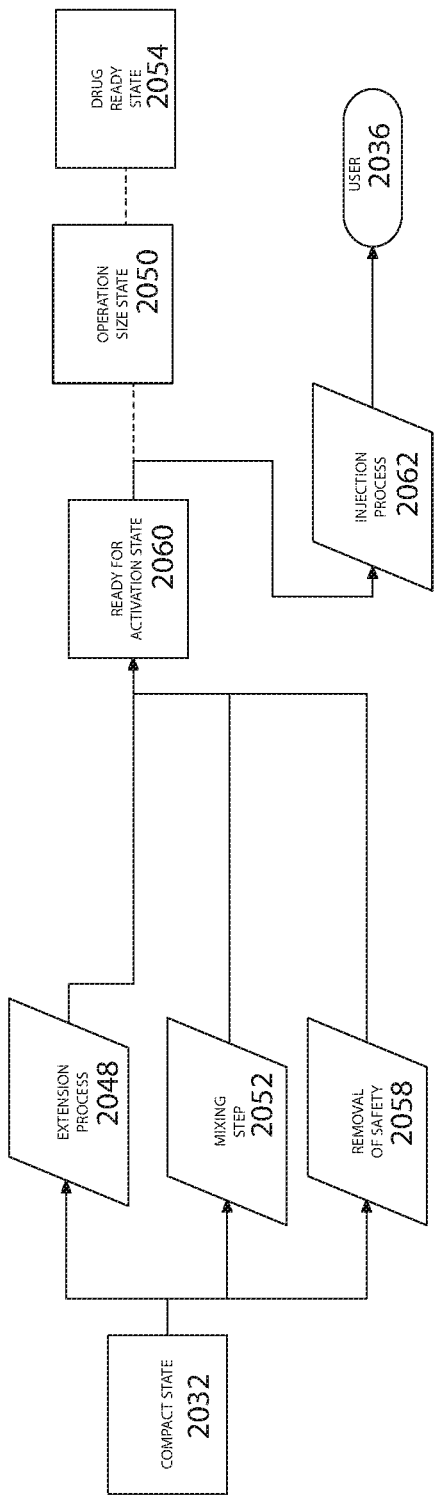
FIG. 35B is a schematic of an alternative embodiment and method of using a portable auto-injector according to one embodiment.

Referring to FIG. 35B, a schematic of an alternative embodiment and method of using a portable auto-injector 2030 is shown. In contrast to the embodiment shown in FIG. 35A, where the extension process 2048, the mixing step 2052, and the removal of the safety 2058 occur at separate and distinct steps, the process of extending the components to the operation size state 2050 accomplish other steps. For example, the extension process 2048 also causes the mixing step 2052. The mixing step 2052 causes the wet component 2040 to pass through and combine with the dry medicament 2038 therein forming the wet medicament 2034 which is going to be delivered to a user 2036.

In addition, the extension process 2048 also results in the removal of the safety 2058 therein placing the auto-injector 2030 in the ready for activation state as represented by a block 2060.

In FIG. 35B, the operation size state block 2050 and the drug ready state block 2054 are shown adjacent to the ready for activation state 2060, the desired state. In certain embodiments, the drugs may be in a ready state in the compact state 2032 (i.e., there is no mixing of a wet component 2040 with a dry medicament 2038 to form the wet medicament 2034 after the portable auto-injector 2030 is shipped to the user in that the wet medicament 2034 is already mixed.) In certain embodiments, the auto-injector 2030 does not have separate components associated with the safety.

Still referring to FIG. 35B, with the auto-injector 2030 in the ready for activation state 2060, the auto-injector 2030 can be placed in proximity to the user 2036. The injection process step as represented by the parallelogram 2062 can be triggered to deliver the drug to the user 2036.

Figure 36C:
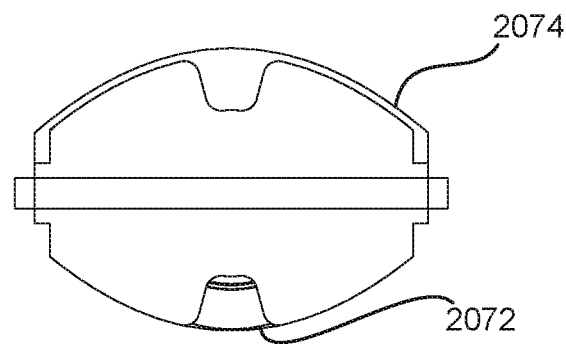
FIG. 36C is a top view of the portable auto-injector 2030 in the compact/storage position.
Figure 36A:
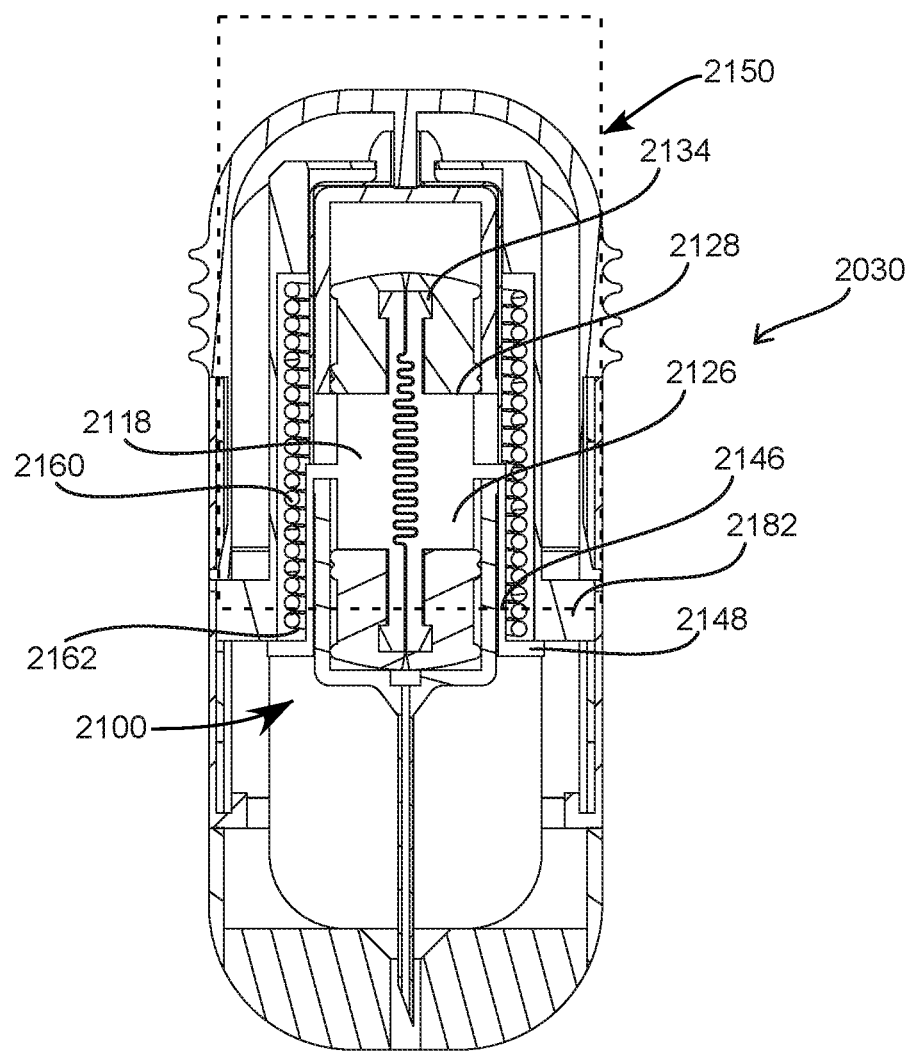
FIG. 36A is a front sectional view of a portable auto-injector 2030 in a compact/storage position 2022.

Referring to FIG. 36A, a front sectional view of a portable auto-injector 2030 in a compact/storage position 2032 is shown. The auto-injector 2030 has a series of components including a housing 2070 having a top shell 2072 and a bottom shell 2074 as best seen in FIG. 36C which shows the top view of the portable auto-injector 2030 in the compact/storage position 2032 and FIG. 36B which shows a side sectional view of the portable auto-injector 2030 in the compact/storage position 2032.

Figure 36B:
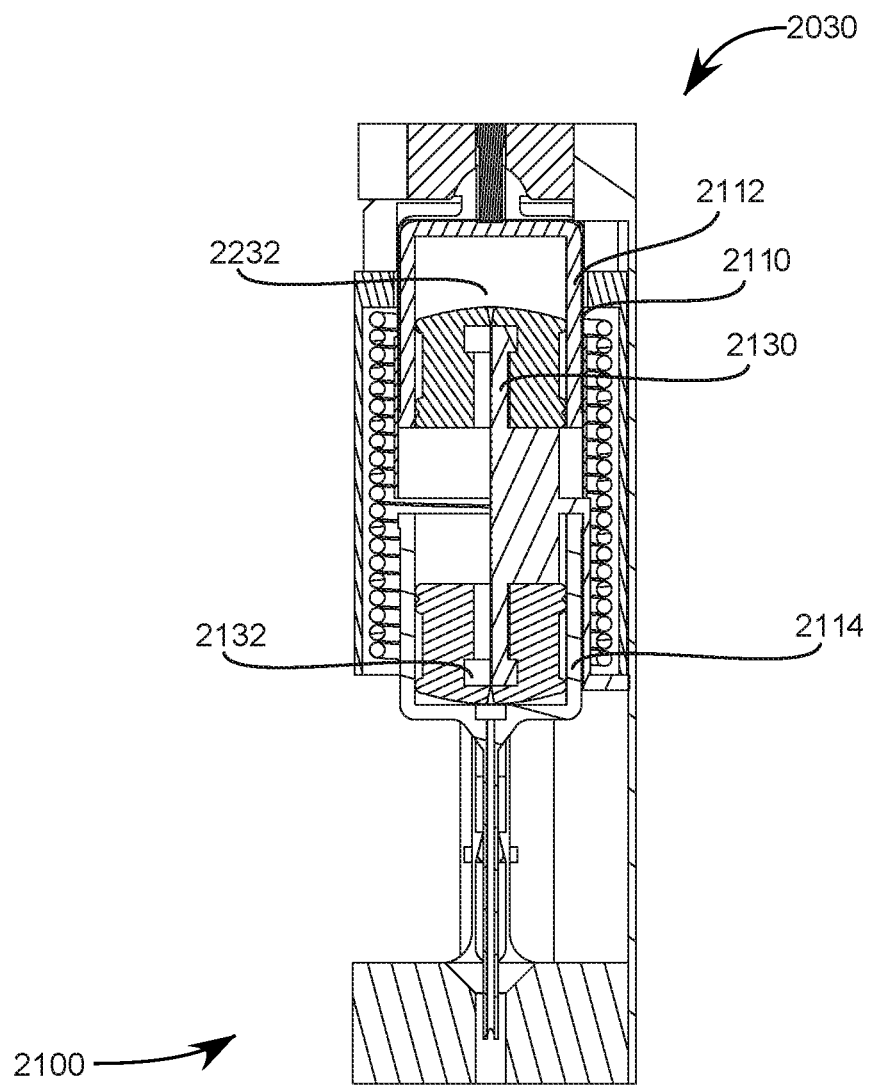
FIG. 36B is a side sectional view of the portable auto-injector 2030 in the compact/storage position 2022 of FIG. 36A.

Illustrated herein is a first actuation device or assembly 2150, the actuation device or assembly 2150 can include an extension component, illustrated herein as an extender slide 2090, which is movable relative to the housing 2070 and configured to cause the effective length of the housing to increase in an axial dimension. The extension component 2090 may be a telescoping component, an unfolding component or re-attachable component. In one embodiment, the extension component, when activated and/or lengthened, allows the first actuation device to cause the movable body to move into the first chamber as illustrated by the load path 2152, shown here as a dotted line extending through various components until acting on the movable body 2118. The housing 2070 has a pair of side walls (not labeled) each having a plurality of grooves that engage components of an extender slide/extension component 2090 for retaining the extender slide 2090 in the compact state 2032 as seen in FIGS. 35A and 35C and the operation state 2050, as seen in FIGS. 36A and 36B. In addition, the housing 2070 has a plurality of detents and stops that interact with components of an injector 2100 for retaining it in the compact state and the operation state. The extender slider/extension component 2090 is held into place by split fingers after an actuation latch member is pulled through the split fingers and the split fingers retain their position while the latch member is supported on the split fingers. In other words, the actuation device 2150 as illustrated translates a manual input from the user into an axial translation of the movable body 2118 into the first chamber 2232 formed by the first vial 2112. This is achieved by transferring a force describing the manual input into the movable body through various mechanical components as described above, but could be achieved through various alternative means as will be recognized by those having skill in the art.

The portable auto-injector 2030 has a wet/dry component combining system 2110. The wet/dry component combining system 2110 has a pair of vials 2112 and 2114. The first vial 2112 has a first sidewall 2113 which defines a chamber configured to hold the wet component 2040 when the auto-injector 2030 is in the compact state 2032. The second vial 2114 has a second sidewall 2115 which is separate and distinct from the first sidewall and defines a chamber being fluidly connected to a needle assembly 2116 that includes the injection needle 2046 and stores the wet medicament 2034 prior to delivery as further described below. The wet/dry component combining system 2110 has a movable body 2118 with a fluidic channel disposed therein and a pair of plungers 2120 and 2122. The first plunger 2120 interacts with the first vial or chamber 2112 and the second plunger 2122 interacts with the second vial or chamber 2114. In another embodiment, first plunger 2120 and second plunger 2122 and movable body 2118 with fluidic channel are all made of one piece of material. In another embodiment, these are separate assemblies. In another embodiment 2118 simply creates a fluid path from vial 2112 to vial 2114.

Figure 42A:
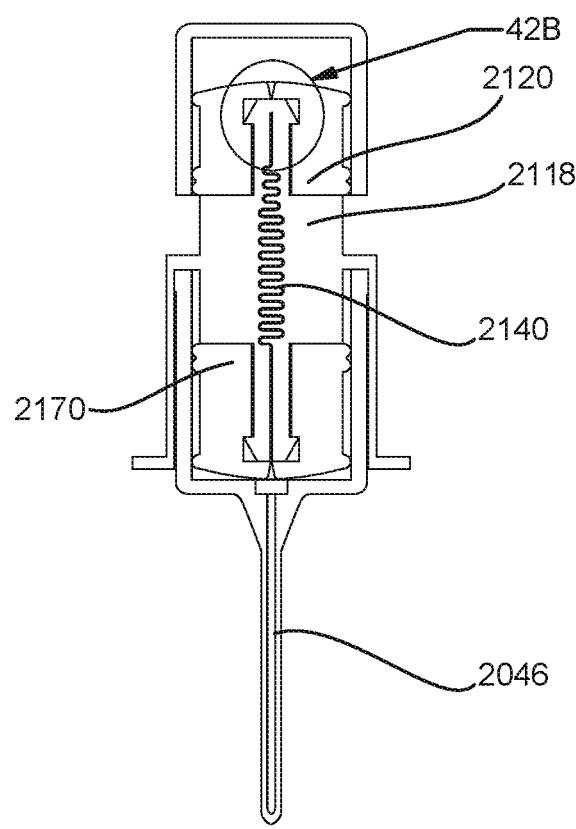
FIG. 42A is an enlarged view of the drug delivery portion of the portable auto-injector.
Figure 42B:
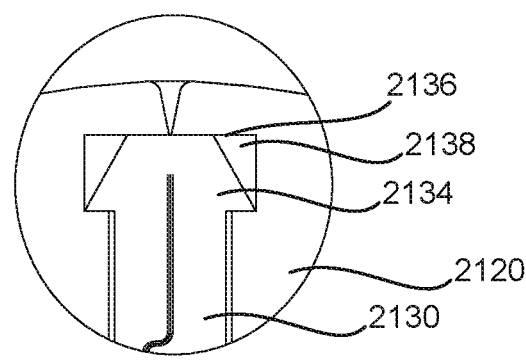
FIG. 42B is an enlarged view of the plunger membrane interface.

The movable body 2118 with a fluidic channel 2140 is interposed between the two vials 2112 and 2114 and the two plungers 2120 and 2122. The movable body 2118 with a fluidic channel has a cylindrical body 2126 and a pair of parallel ends 2128. The movable body 2118 with a fluidic channel 2140 has a pair of posts 2130 and 2132. A post 2130 and 2132 extends from each of the parallel ends 2128. Each post 2130 and 2132 has an enlarged tip 2134 for engaging the walls 2136 of a void 2138 in one of the plungers 2120 and 2122 as best seen in FIG. 42B. The movable body 2118 with a fluidic channel may include a single fluidic channel 2140 that extends from the first post 2130 to the second post 2132. The movable body 2118 has an annular ring 2146 with a lip 2148. The lip 2148 interacts with a first end 2162 of a compression spring 2160.

Figure 36D:
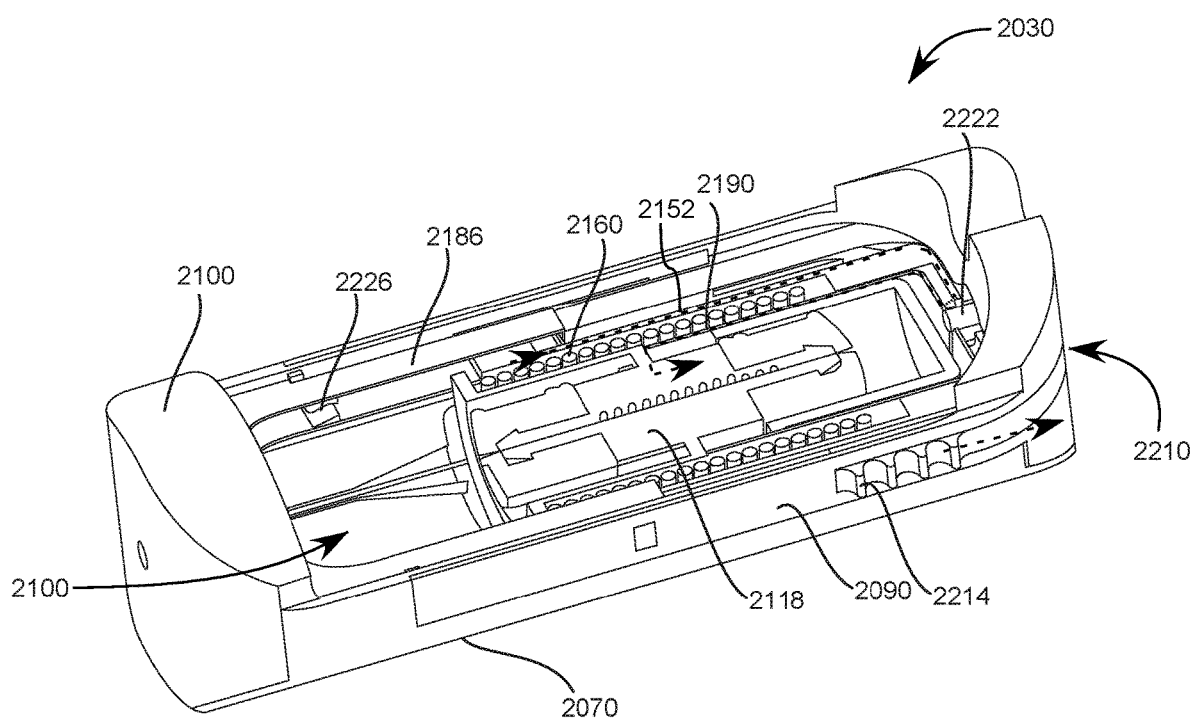
FIG. 36D is a perspective view of the portable auto-injector in the compact/storage position with portions broken away.

The compression spring 2160 has a second end 2164 that interacts with an intra-housing 2170 that has a base 2172 and an annular ring 2174 that encircles the compression spring 2160. The base 2172 of the intra-housing 2170 has an annular lip 2178 that engages the second end 2164 of the compression spring 2160. The base 2172 has a hole 2180. The intra-housing 2170 has a pair of tabs 2182. Each tab 2182 is interposed between a split finger 2186 of the injector 2100 as best seen in FIG. 36D.

The intra-housing 2170 is connected to the extender slide 2090. The two components move together in lateral movement from the compact state 2032 to the operation size state 2050. The extender slides 2090 is the component that a user can grab to move the auto-injector 2030 to the operation size state 2050.

Still referring to FIGS. 36A and 36B, the portable auto-injector 2030 has a drug delivery movement ring 2190. The drug delivery movement ring 2190 has a base 2192 with a stub 2194 that projects through the hole 2180 in the intra-housing 2170. The stub 2194 has a slot 2196 that extends across the stub 2194 which creates a pair of legs that can flex as explained below. The stub has a hole 2198 that extends through the slot 2196. The stub 2194 has a lip 2200 that engages the outer surface of the base of the intra-housing 2170 so the drug delivery movement ring 2190 moves with the intra-housing 2170.

The portable auto-injector has a safety 2210. The safety 2210 has a U-shape with a pair of legs 2212. Each leg 2212 has a series of knurls 2214 to facilitate the user moving the safety 2210 from a safe position as seen in FIGS. 36A-37B, to an activation position as seen in FIGS. 38A-40D and explained below. In addition, each leg 2212 has a detent 2216 that extends through an opening 2218 in the extender slide 2090 to hold the safety 2210 in the safe position. The base 2220 of the U-shaped safety 2210 has a pin 2222. The pin 2222 of the safety 2210 extends into the hole 2198 of the stub 2194 of the drug delivery movement ring 2190.

Figure 38A:
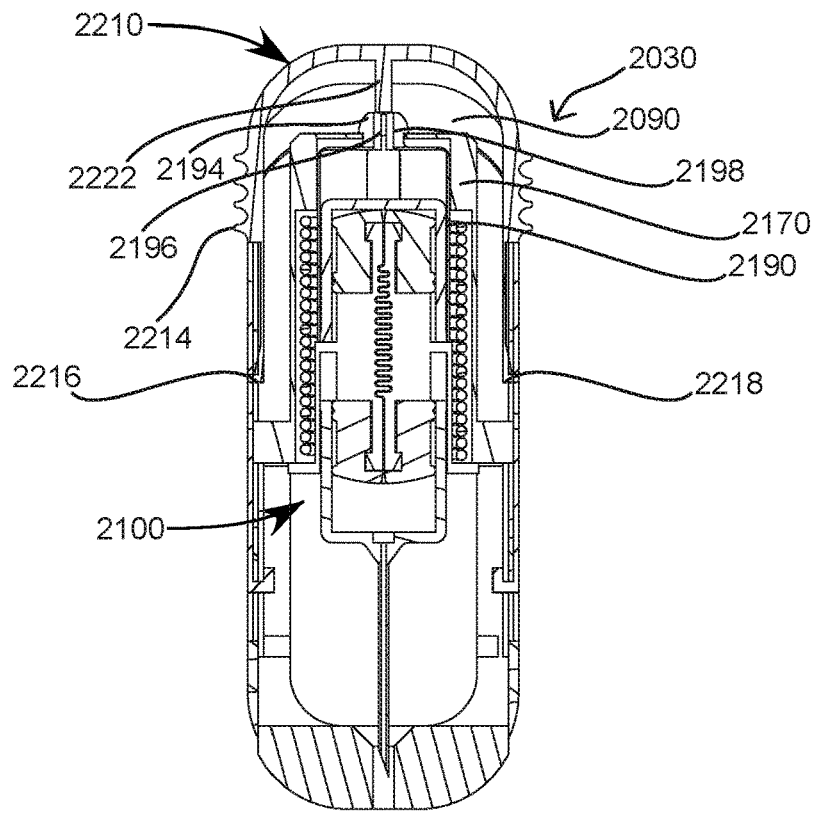
FIG. 38A is a front sectional view of the portable auto-injector 2030 with the safety extracted.
Figure 38B:
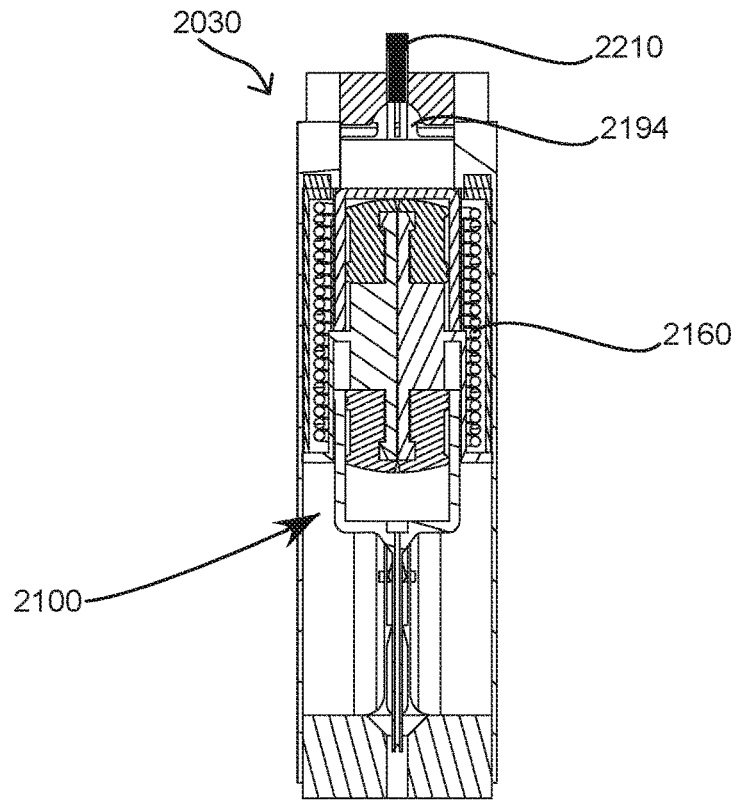
FIG. 38B is a side sectional view of the portable auto-injector 2030 with the safety extracted.

Referring to FIG. 36D, a perspective view of the portable auto-injector 2030 in the compact/storage position 2032 with portions broken away is shown. The safety 2210 is received in a groove within the extender slide 2090. The detent 2216 of the safety 2210 can be seen extending through the opening 2218 in the extender slide 2090 to hold the safety 2210 in the safe position. The series of knurls 2214 project beyond the surface of the adjacent extender slide 2090 to facilitate the user moving the safety 2210 from the safe position as seen in FIG. 36D to the activation position as seen in FIGS. 38A-38B. The pin 2222 of the safety 2210 is shown extending through the hole 2198 of the stub 2194 of the drug delivery movement ring 2190.

The compression spring 2160 is seen extending from the first end 2162 where it engages the lip 2148 of the annular ring 2146 of the movable body 2118 to the second end 2164 where it engages the annular lip 2174 of the base 2172 of the intra-housing 2170. One of the tabs 2182 of the intra-housing 2170 is shown between one of the pair of split fingers 2186 of the injector 2100. In addition, a drive block 2226 is shown on the split finger 2186 of the injector 2100.

The base of the extender slide 2090 can then be provided with a slot to receive a rib on the housing 2070 to maintain alignment.

Figure 37A:
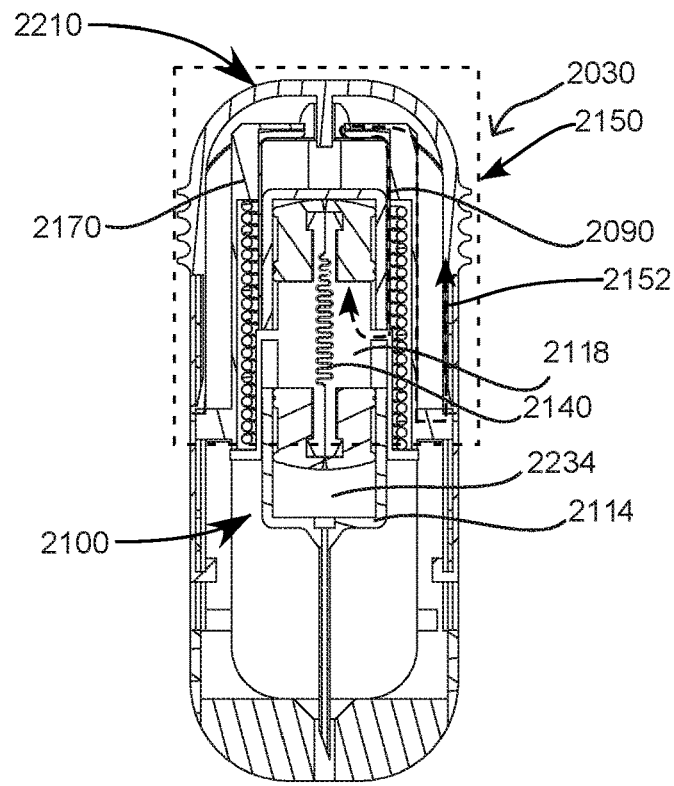
FIG. 37A is a front sectional view of the portable auto-injector 2030 in the extension position.
Figure 37B:
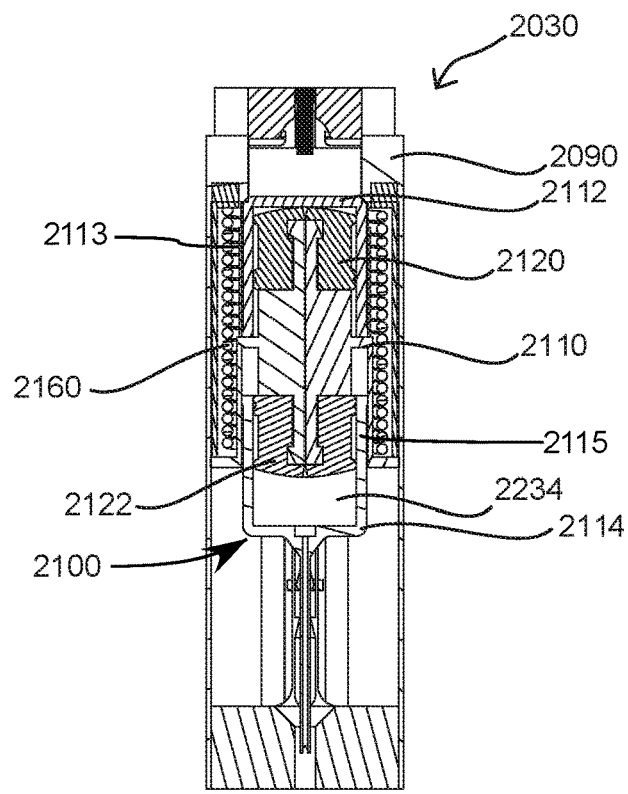
FIG. 37B is a side sectional view of the portable auto-injector 2030 in the extension position.

Referring to FIG. 37A, a front sectional view of the portable auto-injector 2030 in the operation size state 2050 is shown. A side sectional view of the portable auto-injector 2030 in the operation size state 2050 is shown in FIG. 37B. As the extender slide 2090 moves in the extension process 2048 to the operation size state 2050, the intra-housing 2170, the safety 2210, and the drug delivery movement ring 2190 also moves. The movement of the drug delivery movement ring 2190 causes the mixer/movable body 2118 of the drug mixing system 2110 to move upward in response to an extension force applied to the extender slide/extension component 2090, as part of the first actuation device/assembly 2150 as illustrated by load path 2152. This upward movement forces the first plunger 2120 to move upward in the first vial 2112 therein reducing the volume in the first vial 2112; the volume is referred to as a first chamber 2232. This decrease in volume in the first vial 2112 causes the wet component 2040 to be forced through a hollow volume, the micro channel or fluidic channel 2140 in the movable body 2118 that may contain a dry medicament. As the first plunger 2120 moves into the first vial 2112, the second plunger 2122 is moving out of the second vial 2114 therein creating a volume, a second chamber 2234, to receive the wet medicament 2034 created by the mixing of the wet component 2040 with the dry medicament 2038 in the fluidic channel 2140.

In this embodiment, the extension process 2048 and the mixing step 2052 occurs concurrently; this is in contrast to the two distinct steps as described with respect to FIG. 35A. The mixing of the wet component 2040 with the dry medicament 2038 is described with respect to FIGS. 42A and 42B.

Referring to FIG. 38A, a front sectional view of the portable auto-injector 2030 with the safety 2210 extracted is shown. A side sectional view of the portable auto-injector 2030 with the safety 2210 extracted is shown in FIG. 38B. As indicated above, the intra-housing 2170 and the drug delivery movement ring 2190 move with the extender slide 2090. The user engages the knurls 2214 on the safety 2210 moving the safety 2210 to the ready for activation state 2060. The pair of detents 2216 that were held in the openings 2218 of the extender slide 2090 are forced out of the openings 2218 and flex inward by the movement of the safety 2210 upward.

Depression of a bump trigger 2188 forces together stub 2194 into a bump groove, and allows movement of the safety 2210, which then results in the injector 2100 moving downward, which is possible after the safety 2210 (and a pin portion of the safety) is removed. This forcing together of the stub 2194 allows it to fall back through the aperture and releases the stored energy in the compression spring, thus driving the injector out of the housing and into a user or subject. The bump groove may be shaped in a conical or similar shape having an angle(s) that put pressure on the outside of objects and push them inward as the object is forced into the groove. Usually the objects are stubs that won't pass through apertures or holes without pressing the nubs or sides of the stubs allowing them to fit through the aperture or opening.

While the process is referred to as the removal of the safety 2058, the safety 2210 is still connected to the rest of the auto-injector. The movement of the safety 2210 results in the pin 2222 being extracted from the slot 2196 in the stub 2194. With the pin 2222 removed from the stub 2194, the stub 2194 can flex inward into the space occupied by the slot 2198. The lip 2200 of the stub 2194 is no longer engaging the base 2192 of the drug delivery movement ring 2190 so the entire stub 2194 can push through the hole 2180 in the base of the intra-housing 2170 as seen in FIGS. 40A and 40B. However, prior to the movement of the drug delivery movement ring 2190 relative to the intra-housing, the injector 2100, which has been driven downward as described above, needs to be move back up relative to the housing 2070 as described below with respect to FIGS. 39A and 39B.

Figure 39A:
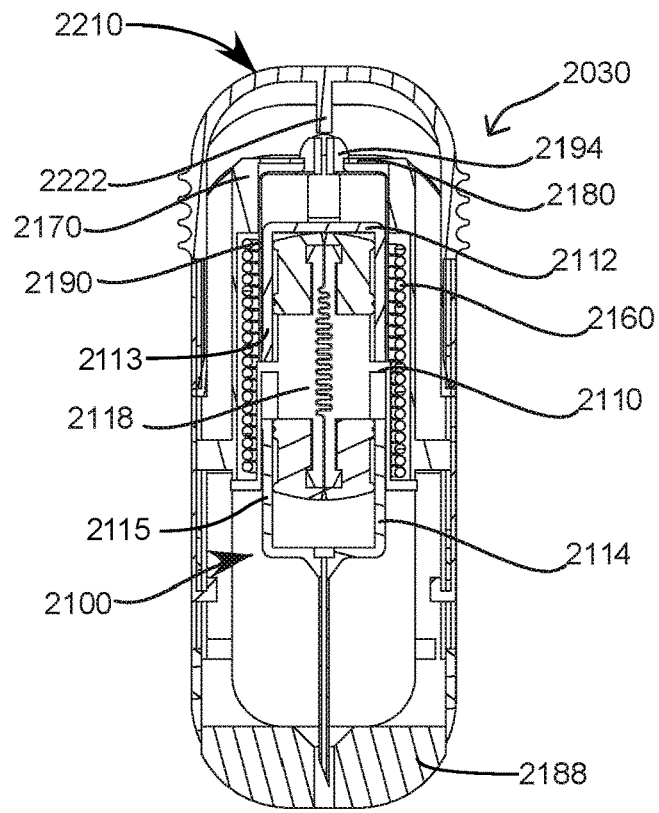
FIG. 39A is a front sectional view of the portable auto-injector 2030 in an injection position with the trigger pushed down.
Figure 39B:
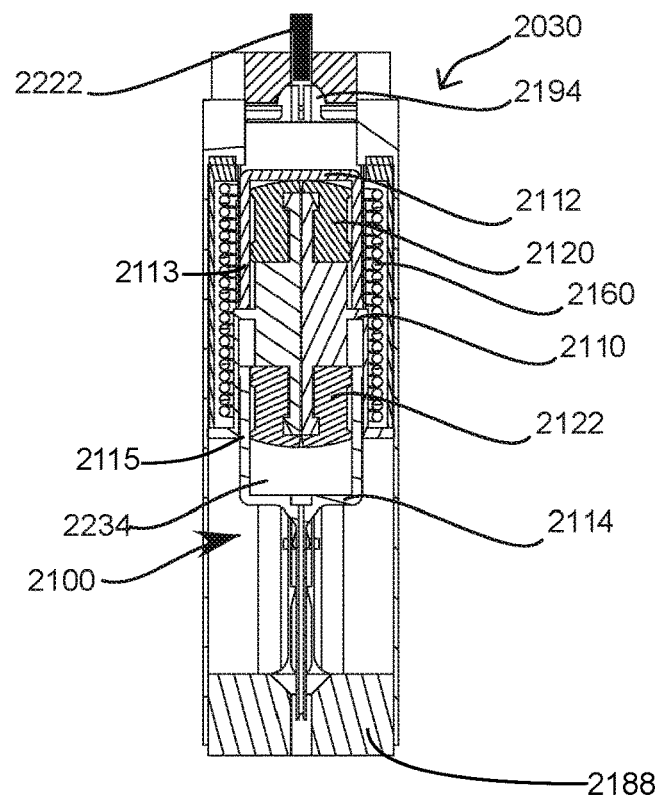
FIG. 39B is a side sectional view of the portable auto-injector 2030 in the injection position with the trigger pushed down.
Figure 40A:
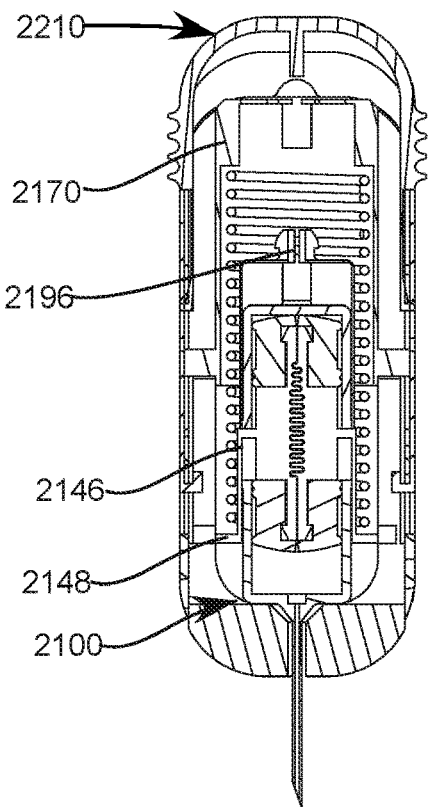
FIG. 40A is a front sectional view of the portable auto-injector 2030 in injecting position.
Figure 40B:
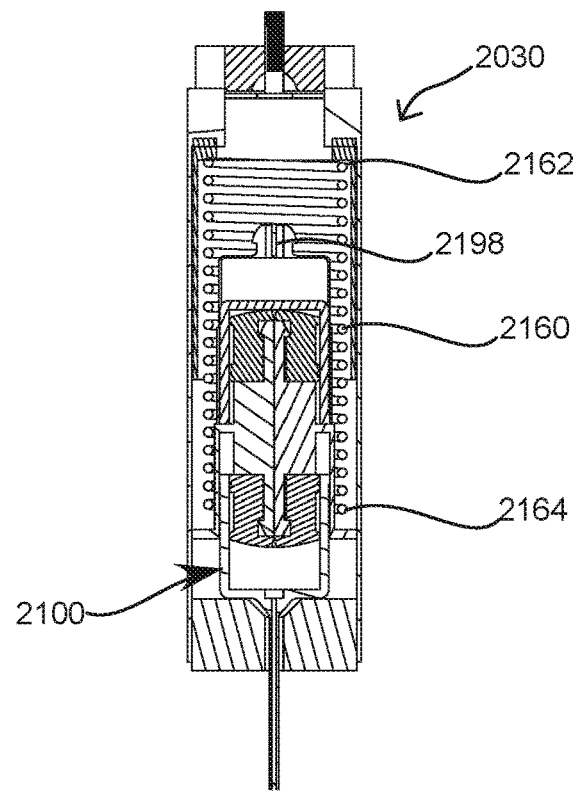
FIG. 40B is a side sectional view of the portable auto-injector 2030 in injecting position.

Referring to FIG. 39A, a front sectional view of the portable auto-injector 2030 in an injection position with the trigger pushed down is shown. A side sectional view of the portable auto-injector 2030 in the injection position with the trigger pushed down is shown in FIG. 39B.

Referring to FIG. 40A, a front sectional view of the portable auto-injector 2030 in the injecting position is shown. A side sectional view of the portable auto-injector 2030 in the injecting position is shown in FIG. 40B. The movement of the injector 2100 upward back into the housing 2070 results in the intra-housing 2170 moving upward relative to the drug delivery movement ring 2190.

In that the pin 2222 of the safety 2240 is no longer in the hole 2198 of the stub 2194, the stub 2194 can flex. The stub 2194 flexes, filling the space of the slot 2196 therein allowing the lip 2200 to pass through the hole 2180 in the base 2172 of the intra-housing 2170. The lip 2148 of the annular ring 2146 of the movable body 2118, which is engaged by the second end 2164 of the compression spring 2160, is forced downward. This force moves the movable body 2118 and the drug delivery movement ring 2190 downward.

The compression spring 2160 continues to push the lip 2148 of the annular ring 2146 of the movable body 2118 with fluidic channel 2140 downward. The needle 2046 is driven downward through an opening in the injector 2100. The needle 2046 is driven until the second vial 2114 engages the injector 2100.

Figure 41A:
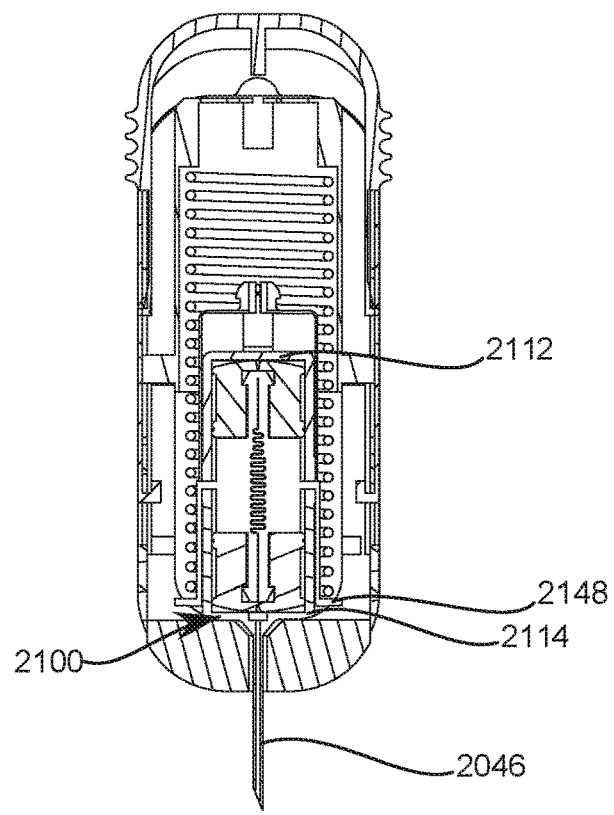
FIG. 41A is a front sectional view of the portable auto-injector 2030 in a drug delivery position.
Figure 41B:
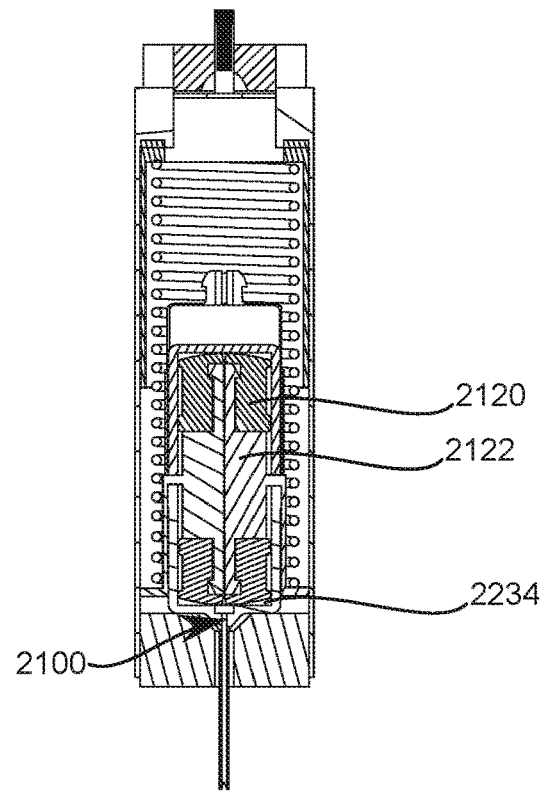
FIG. 41B is a side sectional view of the portable auto-injector 2030 in the drug delivery position of FIG. 41A.

Referring to FIG. 41A, a front sectional view of the portable auto-injector 2030 in a drug delivery position is shown. A side sectional view of the portable auto-injector 2030 in the drug delivery position is shown in FIG. 41B. The compression spring 2160 continues to push the lip 2148 of the annular ring 2146 of the movable body 2118 with fluidic channel 140 downward causing the mixer 2118 and the plungers 2120 and 2122 to move relative to the vials 2112 and 2114 and in particular the second vial 2114 forcing the drug 2034 out of the second chamber 2234 within the second vial 2114 through the needle 2046 into the user 2036.

Referring to FIG. 42A, an enlarged view of the drug mixing system 2110 of the portable auto-injector 2030 is shown. As indicated above, the movement of the movable body 2118 with fluidic channel and the two plungers 2120 and 2122 relative to the vials 2112 and 2114 occurs at different times in the operation. In the embodiment described with respect to FIG. 35A, the mixer 2118 and the two plungers 2120 and 2122 move at a time distinct from the extension process 2048 of the portable auto-injector 2030. In the embodiment described with respect to FIGS. 36A-41B, the movement of the movable body 2118 and the two plungers 2120 and 2122 to combine the wet medicament 2034 occurs with the extension process 2048 into the operation size state 2050. In both cases, the movable body 2118 and the two plungers 2120 and 2122 move again relative to the vials 2112 and 2114 to move the wet medicament 2034 out of the second vial 2114 by reducing the second chamber 2234. The wet medicament 2034 is forced through the needle 2046 which is driven by the compression spring 2160 just prior to the movable 2118 with fluidic channel 2140 and the two plungers 2120 and 2122 move again relative to the vials 2112 and 2114.

Still referring to FIG. 42A, the wet/dry combining system 2110 in one embodiment has first vial 2112 and the second vial 2114 made of glass and/or biocompatible plastic and/or metal and/or any other acceptable material and or other materials acceptable by a regulatory body (such as the FDA) or other approved bodies. The first chamber 2232 of the first vial 2112 is where the liquid solution, the wet component 2040, for dissolving (reconstituting, holding in solution) the dry medicament is stored. In one embodiment the solution may contain water for injection. In one embodiment the solution can be pH optimized with a buffer to enable dissolution. In one embodiment the buffer can be an acid or a base. In one embodiment the buffer can be HCl. In one embodiment, the solution can contain other additives and preservatives, like NaCl, metabisulfite, or others. The first plunger 2120 is inserted into the first vial 2112; the movement of the first plunger 2120 defines the size, the volume, of the first chamber 2232.

The second vial 2114 starts out empty in the embodiments discussed above; the second chamber 2234 essentially has no volume when the auto-injector is in the compact state 2032 as seen in FIGS. 36A-36D. It is recognized that the second vial 2114 may be designed and sized such that the second chamber 2234 has a volume sufficient to contain a liquid such as a pH adjusting solution, which in one embodiment can be water for injection. In another embodiment the pH adjusting solution can contain a buffer. In another embodiment the neutralizing agent may be an acid. In another embodiment the neutralizing agent can be a base. In another embodiment a neutralizing agent could be sodium hydroxide. The second plunger 2122 is inserted in the second vial 2114. Thus, a method of quickly dissolving a dry medicament in a buffer solution, which is later pH adjusted in a second solution in the second chamber and suitable for injecting into a person allows for a quick and compact drug mixing and delivery solution that can have a greater shelf-life and be less susceptible to environmental factors. A neutralizing agent may be used. A buffer may be comprised of an acid and a base.

In the embodiments shown above, the movable body 2118 with fluidic channel 2140 stores the dry medicament 2038. A dry medicament storage assembly (also called the microfluidic assembly) in one embodiment has no microfluidic channels but contains the dry medicament 2038. In another embodiment, it has at least fluidic and/or one microfluidic channel. In another embodiment it has more than one fluidic or microfluidic channel. In another embodiment a dry medicament 2038 is stored inside at least one fluidic and/or microfluidic channel. In another embodiment a dry powder medicament is stored outside the fluidic and/or microfluidic channel while still being contained within the dry medicament storage assembly. In another embodiment a liquid is stored inside the microfluidic or fluidic channel and is forced out by another liquid. In another embodiment different liquid medicaments and/or dry medicaments are stored in a plurality of microfluidic channels inside the microfluidic assembly. In another embodiment, some of the microfluidic channels are in fluid communication with each other. In another embodiment, at least two microfluidic channels are in fluid communication with each other. In another embodiment, none of the microfluidic channels are in fluid communication each other, except for they may all empty into a shared vial or chamber.

Referring to FIG. 42B, in an embodiment one or both of the plungers 2120 and 2122 contain an orifice and/or burst membrane 2244 or sealed structure and/or valve that may break and/or move and/or open and/or create fluid communication between the first vial 2112 and the movable body 2118, the microfluidic assembly, and/or fluid communication between the second vial 2114 and the microfluidic assembly upon the action of extending the device. The placement of the orifice and/or burst membrane 2244 is dependent on the embodiment and the particular medicament and drug.

In the portable auto-injector 2030, the needle assembly 2116 extends from the second vial 2114. In the embodiment shown, the injector 2100 prevents the needle 2046 from premature needle sticks. However, the end of the injector 2100 can be covered to maintain the sterility of the needle 2046. It is recognized that in certain embodiments, the needle assembly 2116 contains a needleless drug delivery mechanism. In one embodiment the needle is covered with a rubber protective barrier which may be used to prevent contamination from entering the needle when the injector is stowed and not in use.

Referring to FIGS. 43A-43F, illustrations of an alternative portable auto-injector in various positions is shown. In this embodiment the auto-injector 2030, the first vial 2112 is narrower and longer than the second vial 2114 therein making the portable auto-injector slightly longer in the stowed compact state and also adding hydraulic assistance to fluid flow from the first vial 2112 into the second vial 2114 which makes the action of extending the injector easier to accomplish. Hydraulic assistance is created by narrowing the vial and making it longer, thus giving extra throw in order to exchange fluid volumes between vials.

Figure 43A:
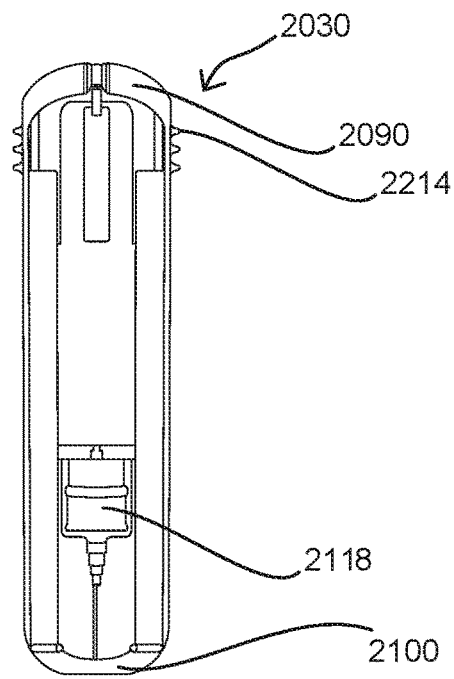
FIGS. 43A-F are illustrations of an alternative portable auto-injector in various positions.

The portable auto-injector 2030 is shown in the compact/storage position in FIG. 43A. It is unable to make an injection in this condition. This is the condition where it may be carried and stored until ready for use.

Figure 43B:
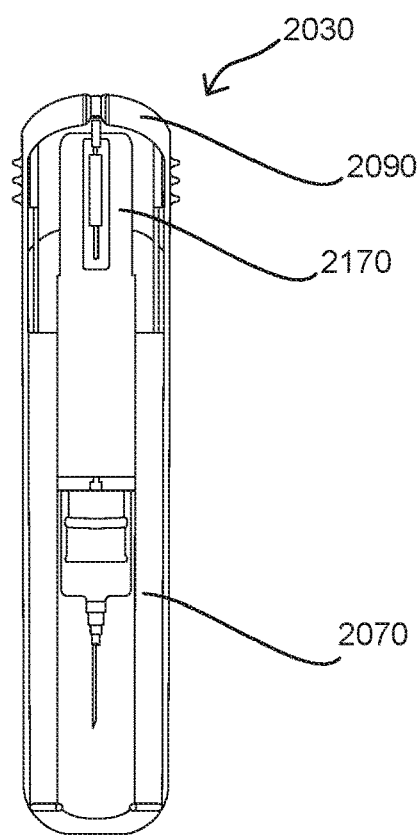

Referring to FIG. 43B, the portable auto-injector in the extended/drug ready position is shown. The moving of the extender, and the extender slide 2090, in an upward direction can then result in the outer pin and the inner pin being extended together; the outer pin is similar to the intra-housing 2170 and the inner pin is similar to the drug delivery movement ring 2190 in the embodiment described with relation to FIGS. 36A-41B. This action causes the first plunger 2120 to move upward into the first vial 2112 in a way that creates a build-up of pressure in the first vial forcing the sealing device 2244, such as an orifice and/or seal and/or or membrane and/or valve, as best seen in FIG. 42B, to move and/or change in some way in order to create fluid communication between the first vial 2112 and the movable body 2118, comprising a dry medicament storage assembly. As the movable body 2118 and the plungers 2120 and 2122 move relative to the vials 2112 and 2114, the volume of the second vial 2114, the second chamber 2234, increases in size. The movable body 2118, the dry medicament storage assembly, is in fluid communication with the second vial 2114. The solution, the wet component 2040, in the first vial 2112 begins to flow into the dry medicament storage assembly, the movable body 2118, dissolving the dry powder into a liquid or wet medicament, the dry medicament 2038, and then flowing into the second vial 2114.

In this state, the extended auto-injector becomes longer making the auto-injector easier to grip. The dissolved liquid medicament and/or partially dissolved medicament is transferred into the second vial 2114 and stored until the next step is initiated.

Figure 43C:
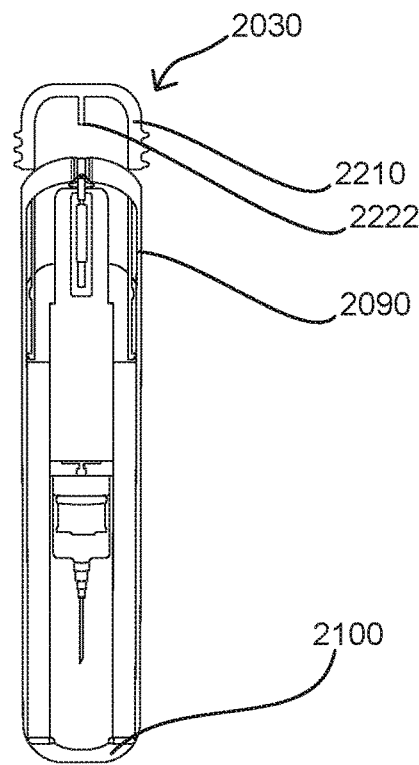

Referring to FIG. 43C, the portable auto-injector 2030 in the ready for activation state with the safety removed is shown. After the inner pin has stopped moving as seen in FIG. 43B, the needle assembly housing is resting on the split fingers and needle assembly housing stops. The safety 2210 can extend further outward and/or be completely removed as shown in FIG. 43C. The outward movement of the safety 2210 results in the safety pin being removed from the stub, which was previously prevent the firing or unloading of the compression spring. A bump switch allows the user or administrator to push on the needle injection side of the injector, which pushes the stub into the bump groove and allows the stub to slide through the hole releasing the stored energy in the compression spring. The released energy forces the needle assembly into the person as well as movable body into the second vial, thus forcing the wet medicament through the needle assembly into the person. While the safety 2210 is shown as slid upward, it is recognized that in some embodiments the safety 2210 can removed entirely from the portable auto-injector 2030. In the same step the trigger extends out from the device on the injection side making the injector ready for injection.

Figure 43D:
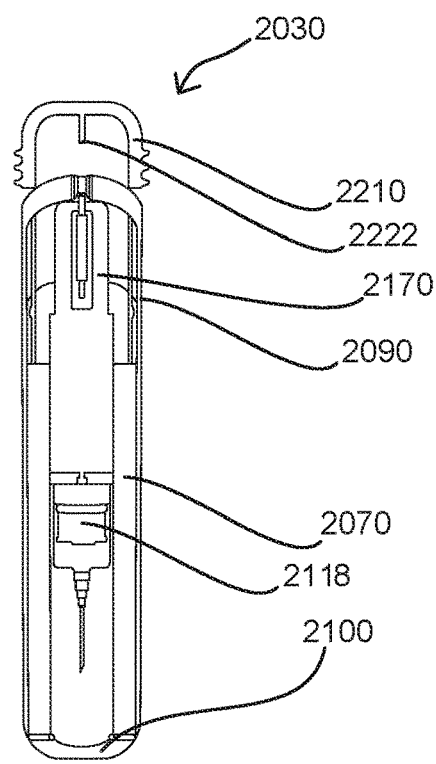
Figure 43E:
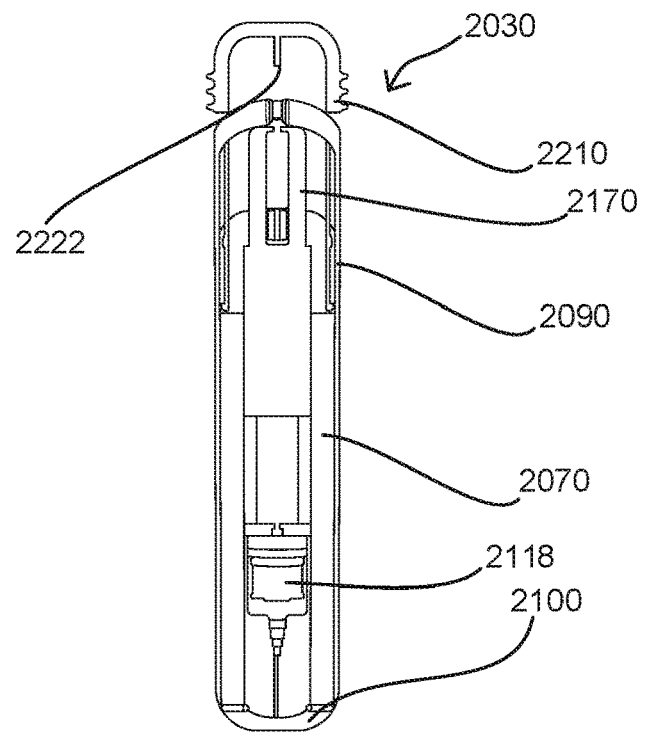
Figure 43F:
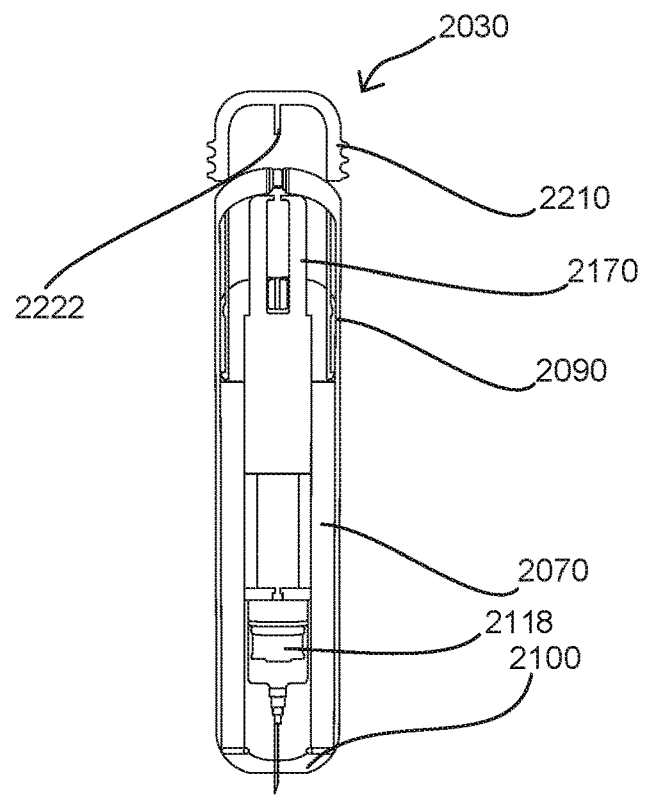

Referring to FIG. 43D, the portable auto-injector 2030 in a pre-trigger position is shown. In this position, the bump trigger 2100 can be pressed causing the needle assembly to rise forcing the bump switch to pinch together. The bump switch becomes smaller allowing it to clear a hole. The needle assembly then ejects, as seen in FIG. 43E under the force of a spring pushing the needle into a human and/or non-human. The spring continues to apply force, which then forces the liquid into the body as seen in FIG. 43F.

Figure 44A:
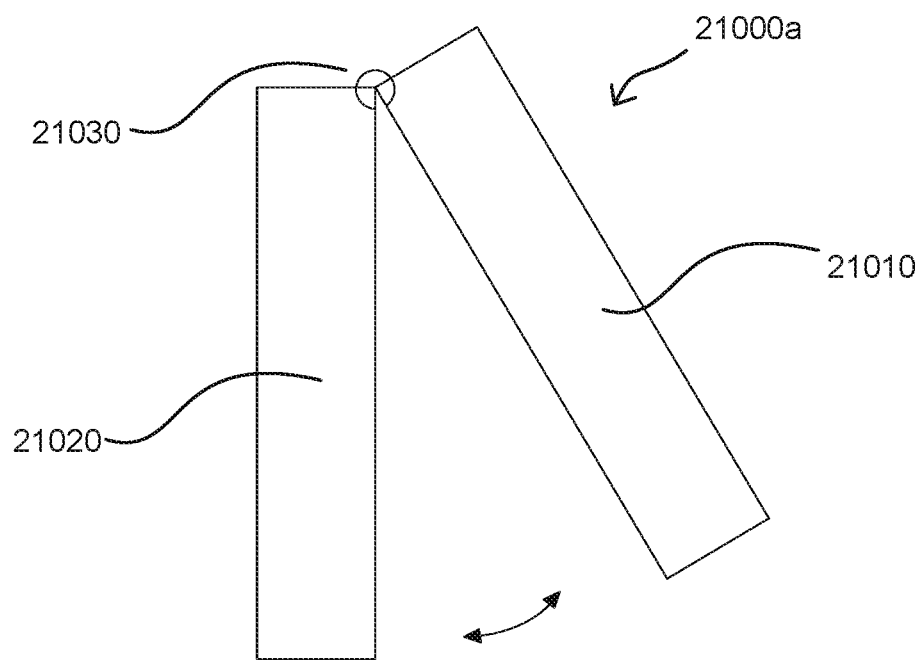
FIG. 44A is a front sectional view of an alternative pivotable portable auto-injector in the compact position.
Figure 44B:
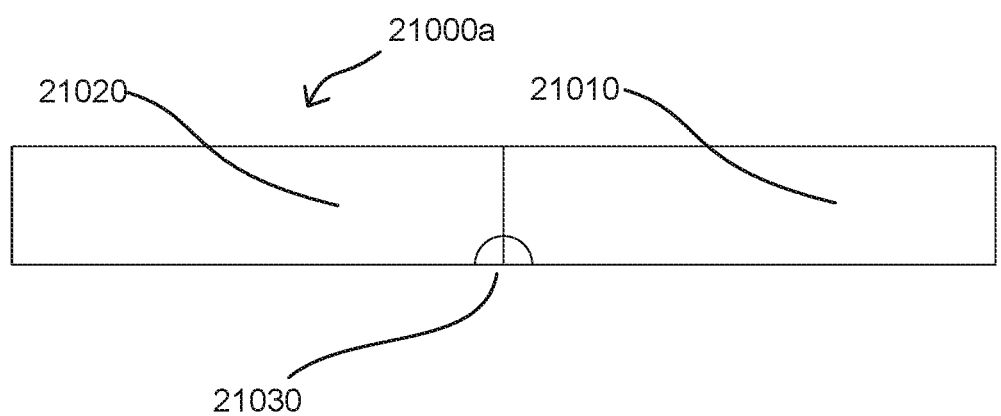
FIG. 44B is a front sectional view of the alternative pivotable portable auto-injector of FIG. 44A in the extended position.

Referring to FIG. 44A, a front sectional view of an alternative pivotable portable auto-injector 21000 in the compact position is shown. Similar to the previous embodiments, the portable auto-injector 2100 has a wet/dry combining system 2110 and an injector 2100. In contrast to the previous embodiments, the auto-injector 21000 does not go from a compact state to the extended state by pulling an extender in a longitudinal direction. In this embodiment, the auto-injector 21000 has a flip design that has an upper housing 21010 that rotates relative to a lower housing 21020 about a hinge point 21030. In this embodiment, the upper housing 21010 contains a drive mechanism that moves the components of the wet/dry combining system 2110 located in the lower hosing. FIG. 10D shows the auto-injector 1000 in the extended state.

Figure 44C:
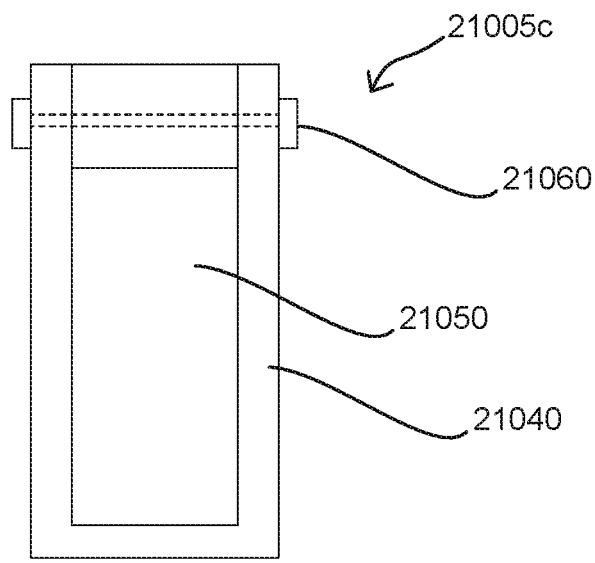
FIG. 44C is a front sectional view of another alternative pivotable portable auto-injector in the compact position.
Figure 44D:
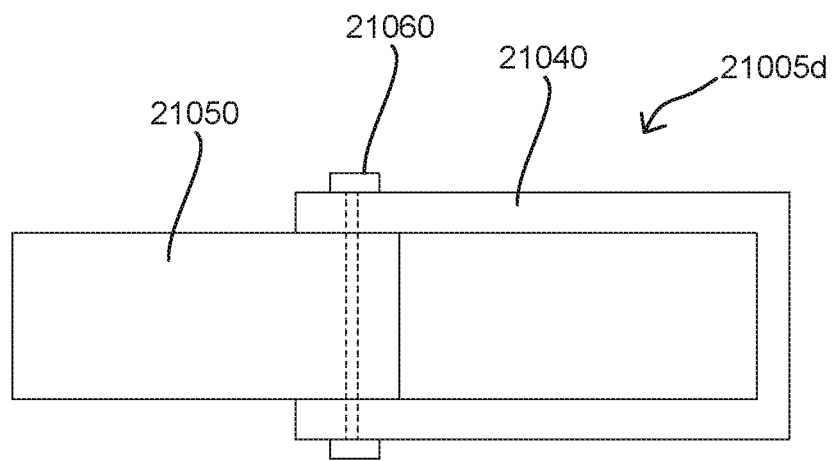
FIG. 44D is a front sectional view of the alternative pivotable portable auto-injector of FIG. 44C in the extended position.

Referring to FIG. 44C, a front sectional view of an alternative pivotable portable auto-injector 21005 in the compact position is shown. Similar to the previous embodiments, the portable auto-injector 2100 has a wet/dry combining system 2110 and an injector 2100. In this embodiment, the auto-injector 21005 has an outer housing 21040 that rotates relative to an inner housing 12050 about a pivot point 21060. FIG. 44D shows the auto-injector 21005 in the extended state.

Figure 45A:
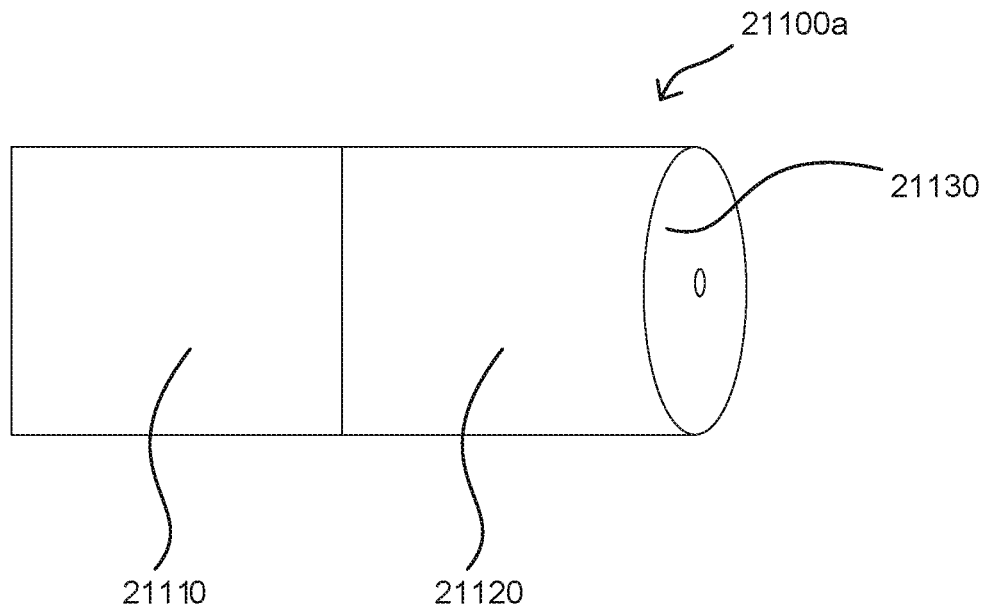
FIG. 45A is a front sectional view of an alternative twist portable auto-injector in the compact position.
Figure 45B:
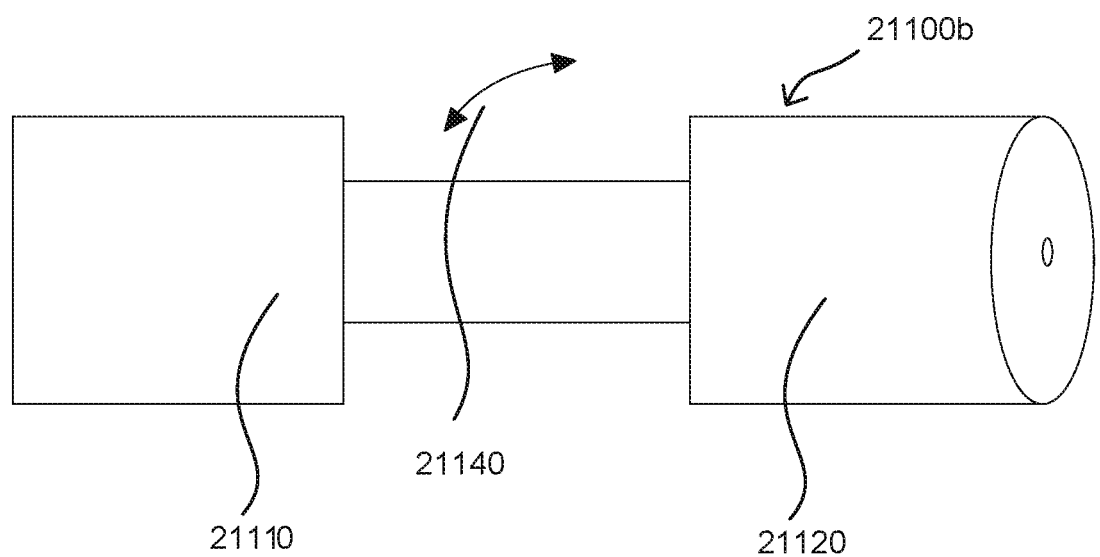
FIG. 45B is a front sectional view of the alternative twist portable auto-injector in the extended position.

Referring to FIG. 45A, a front sectional view of an alternative twist portable auto-injector 21100 in the compact position is shown. In this embodiment, the auto-injector 21100 has an upper housing 21110 and a lower housing 21120. The two housings 21110 and 21120 are rotated relative to each other to allow the housings 21110 and 21120 to move apart through a central telescoping shaft 21140. FIG. 45B shows the twist portable auto-injector 21100 in the extended position. The movable body 2118 in the wet/dry component combining system 2110 is shown with one micro channel 2140 in the embodiment discussed with respect to FIGS. 36A-41B. It is recognized that the wet/dry component combining system 2110 can having multiple conduits or channels and seals. The mixing assembly allows for two different types of medicaments (or two doses of the same) to be mixed and inserted into a person using a single needle or other delivery system. A seal can span the orifices of each storage cavity which are each in fluid communication with a different channel contained within the mixing device.

These channels may vary in length and size enabling a time mixing/release of each medicament. For example, a first wet component is stored in a unique channel(s) that has a pathway shorter than the unique channel(s) in which the second wet component are stored in and are in fluid communication with. The first wet component mixes with the first dry component, homogenizes (in this embodiment, but not all embodiments), enters the needle assembly and is injected into a person, where the second wet component takes longer to mix with the second dry component and follows after the first mixed medicament has entered the needle assembly to be injected into the person. This is useful for two medicaments that are not compatible to be stored in the same portions of the mixing assembly and/or reconstituted or mixed together in the same channel.

Microfluidic devices or systems enable control and manipulation of fluids at very small scales. At sub-centimeter and/or sub-millimeter dimensions, the role of interfaces starts to become dominate and surface tension, fluidic resistance and such begin to control behavior, which may respond differently than macroscopic properties of fluid flow. For example, a main flow channel is machined in glass or polymer with a series of "herringbone" or other type of grooves, which create an environment causing the flow of material through the channel to induce mixing. These structures and features create a series of eddies, vortices, or folds inside the channel, which function to stir or mix and dissolve dry medicaments into a wet component thus forming a solution.

Embodiment may be made of two parts, such as a machined portion where the main channel and grooves have an alternating pattern (these grooves may also be randomized) are all formed therein. A base that is a flat glass or polymer is then attached to machined portion enclosing the main channel.

Alternatively, the flow channel may be constructed to widen and narrow or bulb/bulge along one side, two sides, or around the entire cross-section of the channel. A microchannel that gets wider and smaller may be useful in inducing mixing within the flow channel. For example, the main channel is initially smaller in width and then expands in width to a swell. The swell in other configurations may act as a reservoir or well and have larger amounts of dry component stored therein. Again, the swell may be a larger pocket or open area in which smaller structures may be placed within, the swell and any contained structures therein help cause disruption of flow. Swells or wells may be placed strategically through a micro-channel system to facilitate mixing.

Figure 46:
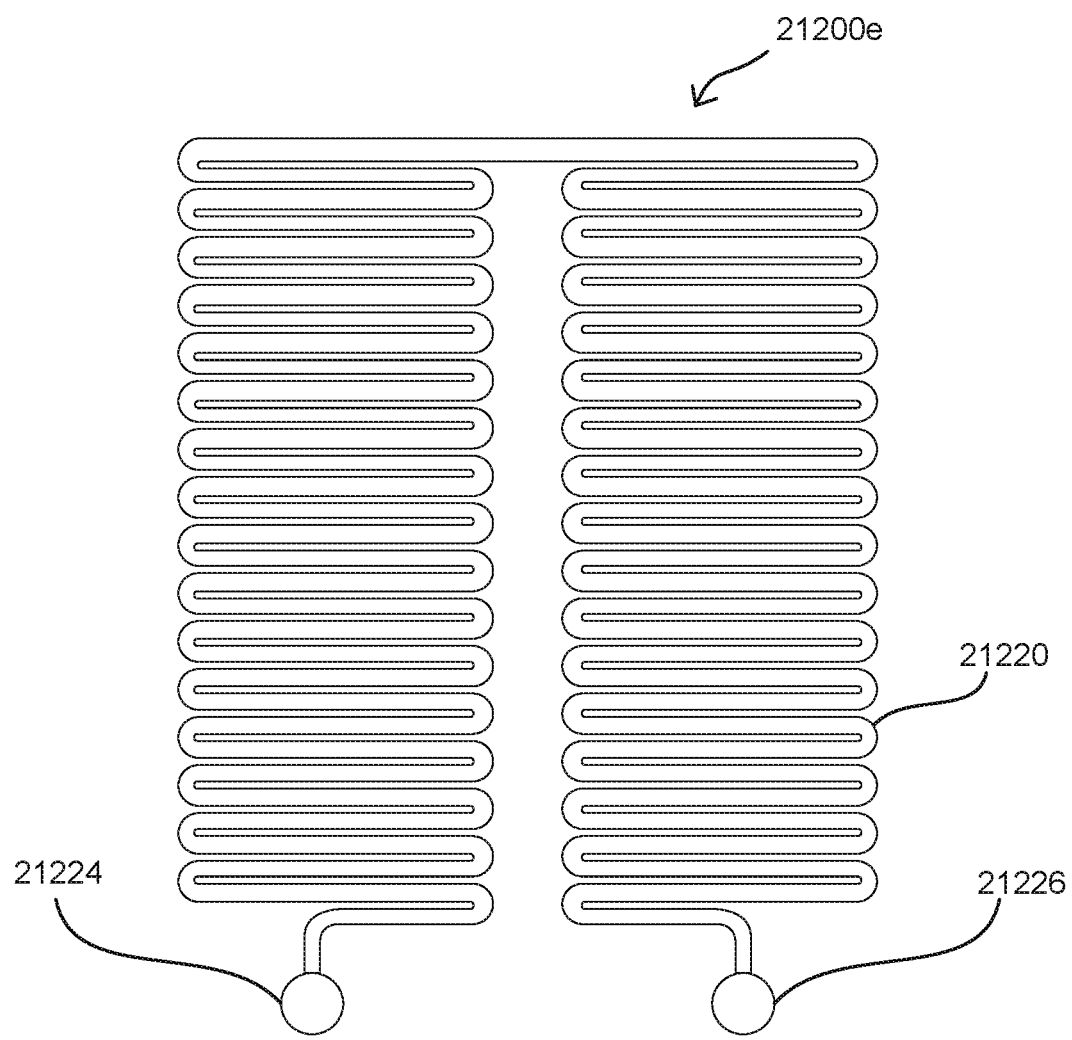
FIGS. 46 and 47 are sectional views of two alternative micro-channels.
Figure 47:
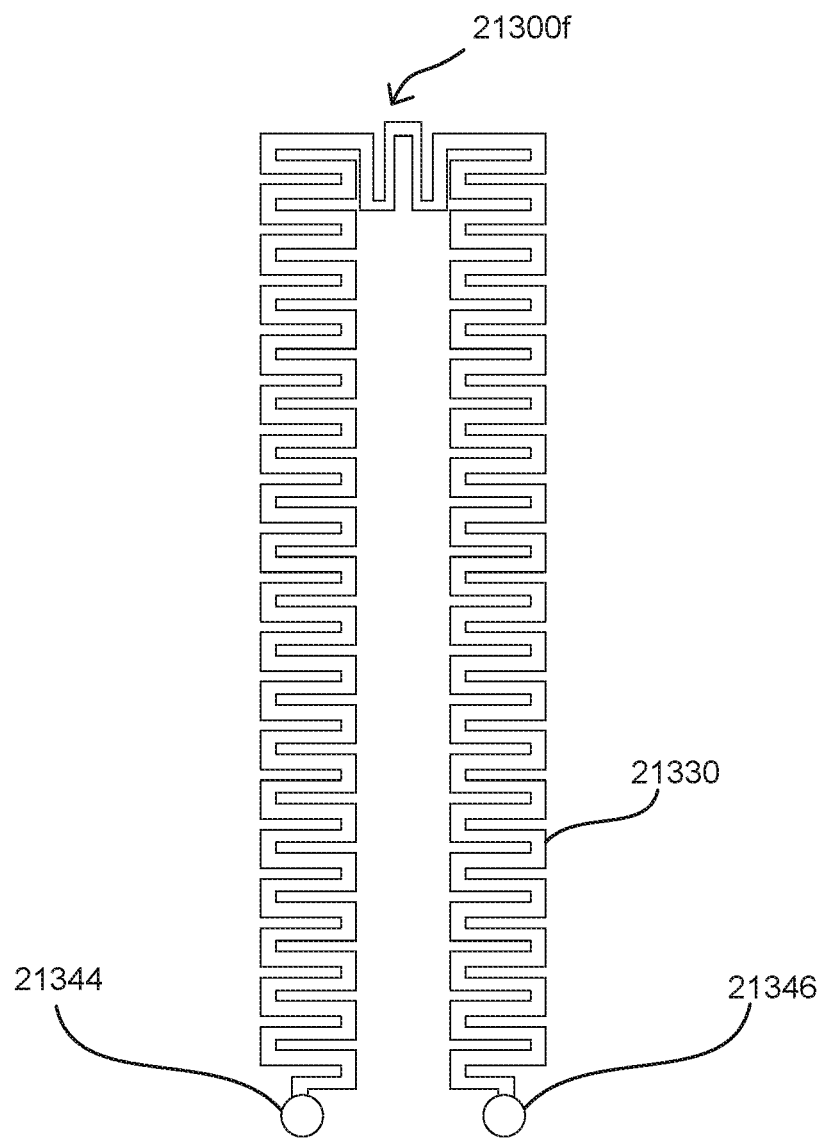

Another way of promoting mixing is to introduce bends or turns into the channels and/or microchannel(s) of the mixing device such as using a serpentine channel shown in FIGS. 46 and 47 rather than a straight channel, varying width, or herringbone design. These serpentines have two functions. First, they enable miniaturization of the plumbing by bending the fluid flow direction so that the channel can double back, thus a longer channel more efficiently utilizes a smaller area. Second, natural flow becomes disrupted every time there is a bend or elbow in the channel, which results in mixing. These serpentine meanders can be designed so there are soft turns 21220 that snake back and forth (shown in embodiment 21200e), or they can be designed with sharp 90-degree bends 21300, which is shown in 21300f. They can even be designed so that the bend exceeds 90 degrees (not shown) that forms a more saw-like tooth pattern. Each embodiment will result in different mixing properties that can enable control over the quantity and quality of mixing. This may be important given that certain drug compounds can be damaged if mixing is too aggressive whereas other compounds may require a more aggressive mixing device. This variability in tuning the mixing conditions allows for a variety of wet/dry components to be used in a compact auto-mixing injector device as control is one key performance attribute of the present application. In each of these microfluidic embodiments 21200e and 21300f each is comprised of a single channel having an opening 21224, 21334 to receive a wet component after the seal has been activated to an open or mixing state and an exit 21226, 21336 configured to be in fluid communication with a needle assembly or an in-between homogenization region.

In another configuration, a straight microfluidic channel configured with parallel walls may be sufficient to mix wet and dry components. Dry components stored inside a portion of the microfluidic channel may act to promote mixing within the channel. When the liquid moves through the channel and begins to push into the dry component contained in a portion therein, the flow front will cause natural turbulence or chaotic flow that focuses the flow towards the center of the channel and then causes the liquid to double back in the reverse direction near the channel wall. In order to make this happen, the channel dimension, which, in one embodiment can be defined by a square cross-section, should be below a certain size. For this embodiment and many of the embodiments described herein, one or both sides of the channel cross-section may have a dimension less than 2 mm, or between 1 mm and 2 mm, or less than 1 mm, or between 500 um and 1 mm, or less than 500 um, or between 250 um and 500 um, or less than 250 um, or between 100 um and 250 um, or less than 100 um, or between 50 um and 100 um, or less than 50 um, or between 10 um and 50 um, or less than 10 um, or between 1 um and 10 um, or less than 1 um. For purposes of this application, channels having a channel with a cross-sectional dimension less than 1 um are considered to be nanofluidic and have their respective set of properties for mixing medicaments.

U.S. patent application Ser. No. 13/529,757 filed on Jun. 21, 2012 and published a published patent application US 2013/0178823 on Jul. 11, 2013 describes additional designs of micro channels and is incorporated herein by reference.

In an embodiment, at least one dimension in the channel is less than 2 millimeters which mixes the dry component 2024 into the wet component 2026 where the Reynolds number in the diluent is less than 2100, relying on chaotic mixing. An example of this could be a series of structures where at least one dimension in the channel is less than 2 millimeters which mixes the dry drug into the diluent where the Reynolds number in the diluent is less than 10, enabling mixing. In some embodiments the dry medicament fully dissolves into the wet component. However, in other embodiments the dry medicament is suspended in the wet component.

It is recognized that the auto-injector 2030 can be replaced by an alternative source of fluid and motive force such as a fluid pump.

In embodiments described above, the actuation force of the auto-injector is supplied by a stored energy source such as the compression spring 2160. It is recognized that the energy may also come from user input. For example, when the user telescopes and/or hinges the device, this mechanical action can simultaneously load the auto-injector with the source of energy and put the device in ready mode. A trigger can then be used to discharge the energy source, pushing the needle into the body and delivering a liquid dose of medicament and/or hydrate a powdered medicament into a liquid dose and deliver this medicament into the body of a patient.

It is recognized that this might be enabled with a tension spring that remains in a coiled state before activation. The action of telescoping the injection device may compress the spring in such a way as to create sufficient potential energy needed to trigger the device during a second actuation step, which can be initiated by pressing the device against an injection step and activate a bump trigger, thus allowing the device to release energy from the spring and inject the medicament into the patient, and thus deliver the medicament. In such an embodiment, the bump trigger can be provided about the injection end of the device and function together with the plungers and spring so as to form a second actuation device or assembly which is actuated so as to enable injection of the mixed medicament components now present in the second vial.

Another embodiment would be to use a compression spring that is in the extended state before activation. The action of telescoping the injection device may compress the spring in such a way to create sufficient potential energy needed to trigger the device, inject the patient, and deliver the medicament.

Most auto-injectors have a pre-stored energy source, for example, a spring or cartridge of compressed gas. If the safety mechanism fails the injector can accidentally fire in an unintended way. Since this device's actuation force is not pre-stored, there is less risk of an accidental discharge and additional degree of safety.

In the embodiments discussed, a blister or burst membrane are described as one method of separating the wet and dry components. It is recognized that for this device another method of sealing is have the seal moved out of the way when the device becomes activated and/or telescoped. For example, like removing a cork from a wine bottle, the sealing structure can be moved out of the way creating fluid communication between the wet and dry components upon telescoping or flipping open the injector.

It is also recognized that while telescoping or flipping the device, after the seal has been removed or moved out of the way, there can be a force that simultaneously draws or pulls fluid into the dry powdered medicament that results in the reconstitution or hydration of the medicament into a liquid dose. This is slightly different from the pushing of liquid into/through the dry powdered medicament.

In one embodiment the dry medicament is epinephrine. In one embodiment the dry medicament is glucagon. In one embodiment the dry medicament is a clotting factor. In one embodiment the dry medicament is diazepam. In one embodiment the dry medicament is Embrel. In one embodiment the dry medicament is Xolair. In one embodiment the dry medicament is a nerve agent antidote, such as butyrylcholinesterase. In one embodiment the dry medicament is sumatriptan. In one embodiment the dry medicament is a pharmaceutical agent. In one embodiment the dry medicament is a biologic. It may also be a small molecule pharmaceutical agent.

Figure 48A:
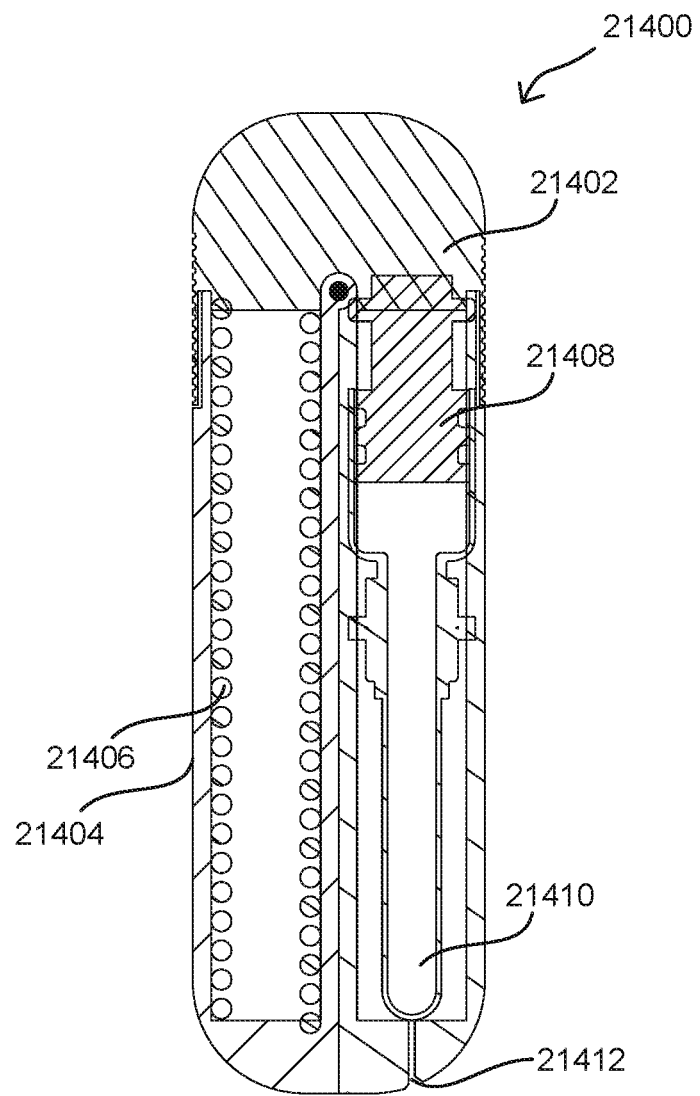
FIGS. 48A-D illustrate an unfolding injector device.
Figure 48B:
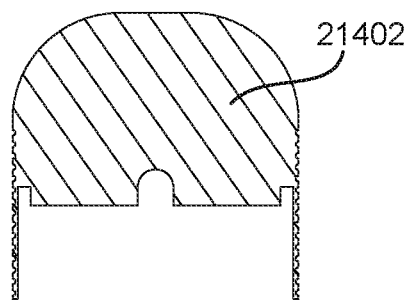
Figure 48C:
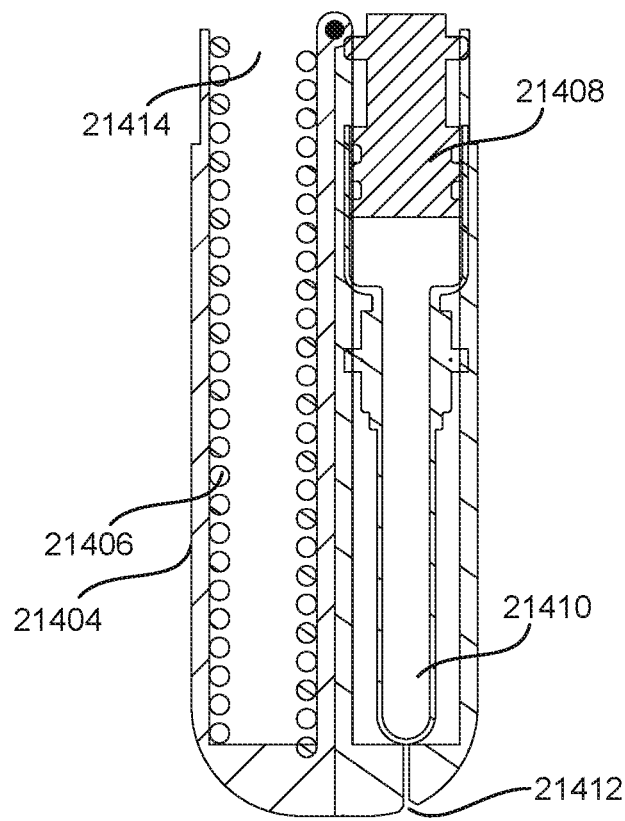
Figure 48D:
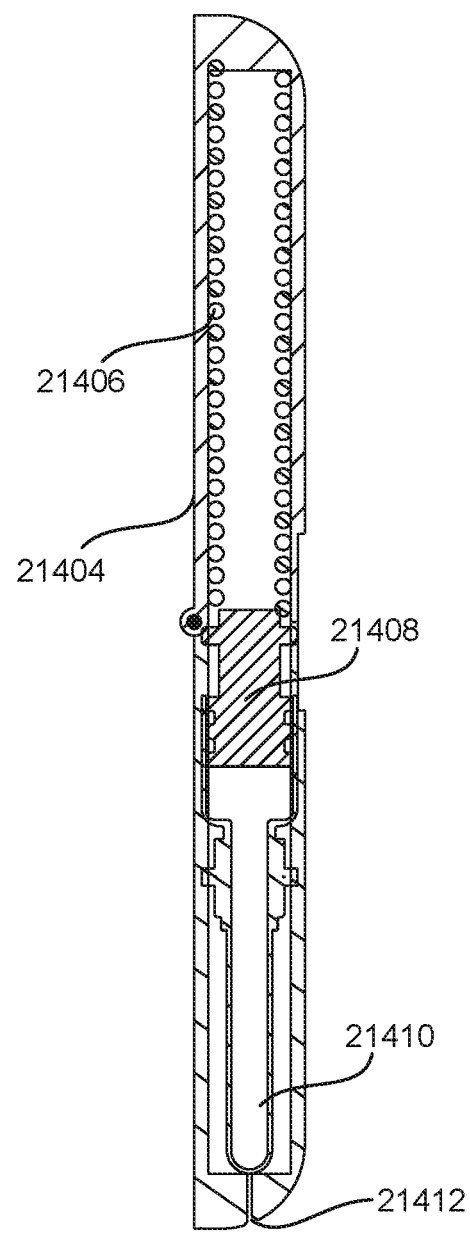

Referring to FIGS. 48A-D illustrate an unfolding injector device. A cross-sectional view of an unfolding mixing and delivery device 21400 is shown. A safety 21402 is positioned one end of 21400 and prevents it from being able to unfold. Upon removal of safety 21402 the housing 21404, which has a preloaded spring 21406 disposed therein, is configured to pivot and elongate the device 21400 as shown in FIG. 48D. Spring 21406 may then engage with a mixing body 21408 that has at least one wet component stored therein and cause it to mix with a dry medicament. For example, as the housing rotates about a hinge the downward pressure on the vial causes the vial to mix with the dry medicament. The mixing assembly is steadied about a ledge prior to downward force of the portion of the housing containing the compressions spring engages the needle and mixing assembly side. The mixing assembly is then actuated as stated as it moves off the ledge and begins combining the wet component from the vial with the dry medicament in the mixing assembly. Similar to the telescoping embodiment above, a bump trigger can be provided at the injection end, which can then act as a second actuation device or assembly, may then cause the preloaded compression spring to engage and cause the needle assembly to protrude from the injection end of the housing. The combined wet medicament may then traverse the needle assembly 21410, which upon a second actuation step causes a needle to protrude through opening 21412 and deliver the wet medicament upon depression against an injection site. As discussed elsewhere, the unfolding device may be comprised of various safety's and release mechanisms that allow for a single or multi-step process of mixing the wet and dry components and delivering such into a subject.

Figure 49B:
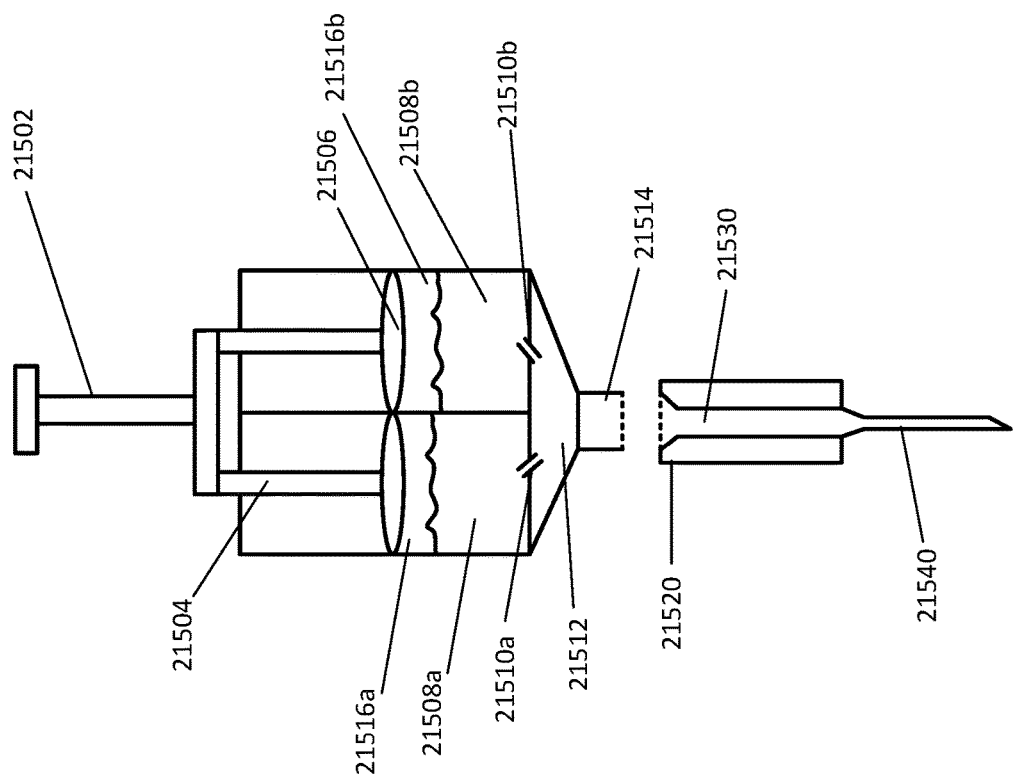
FIGS. 49 A-B illustrate a dual wet chamber injection configured to hold two wet components that combine to aide in dissolving dry medicament in a fluidic channel.
Figure 49A:
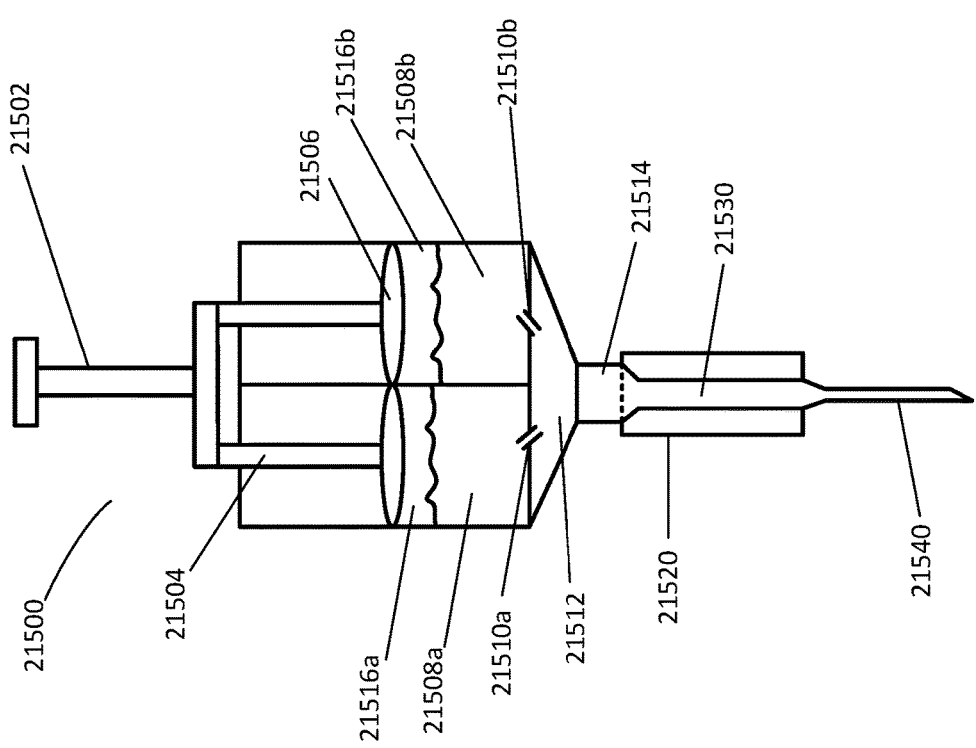

Referring to FIGS. 49A-B, a schematic of alternative embodiment system 21500 having a pair wet component containers 21516a and 21516b that contains a first wet component 21508a and a second wet component 21508b which are mixed together prior to mixing with a dry medicament component. The syringe of the system 21500 has a plunger 21502 with a pair of shafts 21504 that each drive a plunger 21506 in a respective wet component volume. As the respect wet components 21508a and 21508b are pushed through their respective valve 21510a and 21510b, the wet components mix in a wet mixing volume 21512 where a combined wet component is formed.

As the plunger 21502 is continue to push the combined wet component flows through a fluidic channel 21530 of a mixer 21520 that contains the dry medicament component. The combined medicament, which contains the dry medicament within the combined wet component, flows through the needle 21540.

While the two wet component containers 21516a and 21516b are shown the same size, it is recognized that the cross-sectional area can be adjust to tailor the mixing of the two wet components. In certain embodiments that mixer 21520 and needle 21540 component can be separable from the syringe at the syringe output 21514.

Referring to FIGS. 50A-D illustrate a fluidic channel 21610 adjacent to a movable body 21608 disposed between two chambers 21604 and 21606 inside a mixing device 21600. As illustrated a wet component stored initially in chamber 21604 remains until a force moves movable body 1608 into the cavity portion of chamber 21604, which begins forcing the wet component through fluidic channel 21610, which is in a fixed position between chambers 21604 and 21606 and adjacent to movable body 21608. As previously described, the force or pressure created from movable body 21608 entering chamber 21604 is what causes a one-way opening to be forced upon and the wet component to flow through the fluidic channel. A dry medicament may be deposited near the entry, throughout or in pockets of the fluidic channel 21610 and combine with the wet component to form a wet medicament.

Figure 50D:
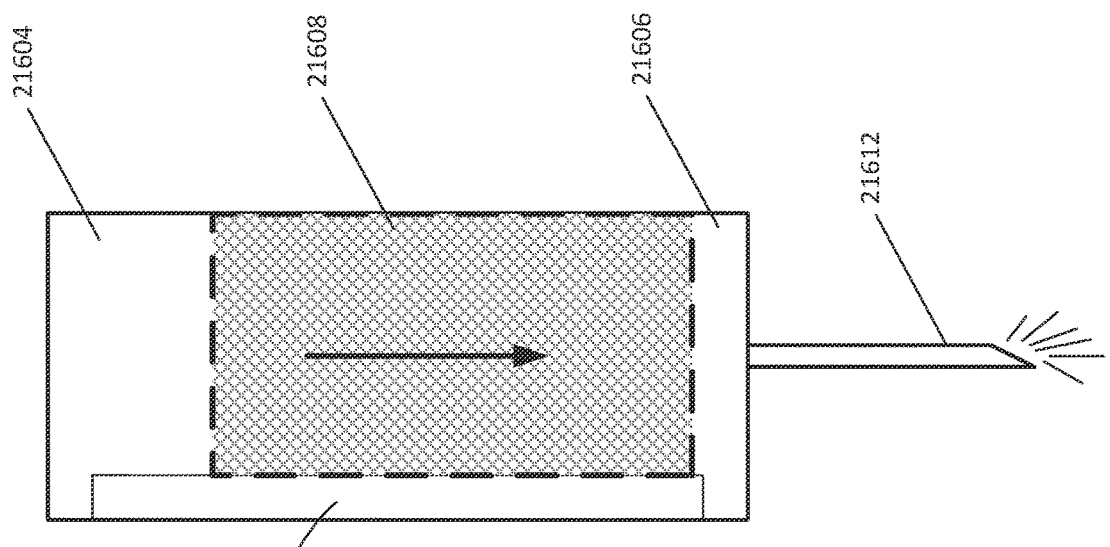
FIGS. 50 A-D illustrate a fluidic channel adjacent a movable body disposed between two chambers.
Figure 50C:
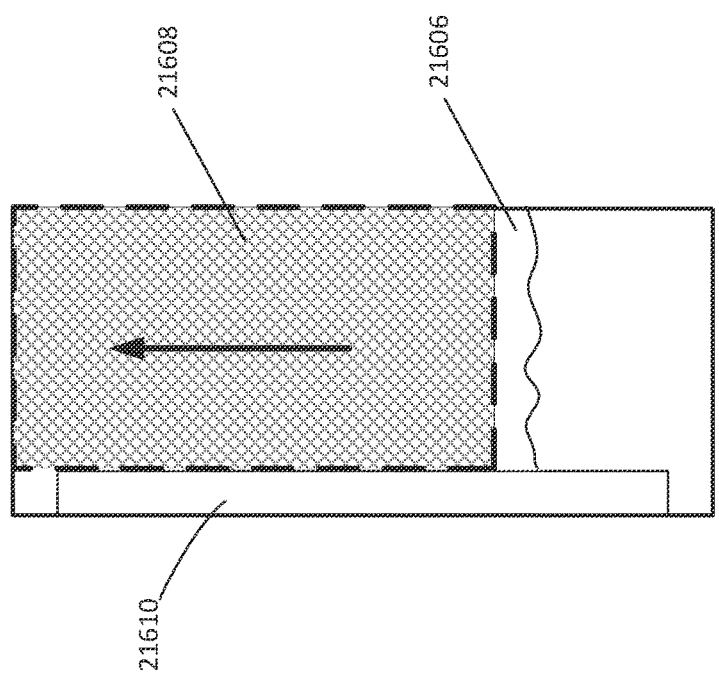

FIG. 50B illustrates the flow from 21604 through 21610 into 21606. Once a majority of the wet component has been forced out of 21604 and combined into chamber 21606, movable body 21608 may again be actuated to force the wet medicament through a needle assembly 21612 into a user or patient. Again, a one way opening between the fluidic channel and 21604 and possibly a second one-way channel between 21606 and 1610 prevents the wet medicament from reentering 21604 and thus forces it through needle assembly 21612 as shown in FIG. 50D.

As used herein, a dry medicament can be of any solid form. In some embodiments, the dry medicament is a powder. In some embodiments, the powdered form of the dry medicament is prepared from lyophilizing a liquid medication. In some embodiments, the powdered form of the dry medicament is prepared from spray-drying, vacuum drying, or chemically precipitating out of a medical solution. In some embodiments, a dry medicament is an amorphous solid. In some embodiments, a dry medicament is a crystalline solid. In some embodiments, a dry medicament can form a porous matrix. In some embodiments, a dry medicament can form a loose assemblage of powder. In some embodiments, a dry medicament can form a loose assemblage of porous matrix.

In some embodiments, a dry medicament can form a loose assemblage of powder with particles (e.g., in the size of about 1 nm to about 1000 μm). In some embodiments, a dry medicament can form a loose assemblage of powder with the particle size ranging from about 1 nm to about 500 μm. In some embodiments, a dry medicament can form a loose assemblage of powder with the particle size ranging from about 1 nm to about 100 μm. In some embodiments, a dry medicament can form a loose assemblage of powder with the particle size ranging from about 1 nm to about 50 μm. In some embodiments, a dry medicament can form a loose assemblage of powder with the particle size ranging from about 1 nm to about 10 μm. In some embodiments, a dry medicament can form a loose assemblage of powder with the particle size ranging from about 1 nm to about 1 μm. In some embodiments, a dry medicament can form a loose assemblage of powder with the particle size ranging from about 1 nm to about 500 nm.

In some embodiments, a dry medicament can form a cake consisting of a porous matrix with particles (e.g., in the size of about 1 nm to about 1000 μm). In some embodiments, a dry medicament can form a cake consisting of a porous matrix with the particle size ranging from about 1 nm to about 500 μm. In some embodiments, a dry medicament can form a cake consisting of a porous matrix with the particle size ranging from about 1 nm to about 100 μm. In some embodiments, a dry medicament can form a cake consisting of a porous matrix with the particle size ranging from about 1 nm to about 50 μm. In some embodiments, a dry medicament can form a cake consisting of a porous matrix with the particle size ranging from about 1 nm to about 10 μm. In some embodiments, a dry medicament can form a cake consisting of a porous matrix with the particle size ranging from about 1 nm to about 1 μm. In some embodiments, a dry medicament can form a cake consisting of a porous matrix with the particle size ranging from about 1 nm to about 500 nm. In some embodiments, a dry medicament can form a cake consisting of a porous matrix with the particle size ranging from about 1 nm to about 100 nm.

As used herein, numerical values of particle size refer to particle diameter as measured using known techniques (e.g., laser diffraction) and instrumentation (e.g., a size range device, for example provided by Malvern). In some embodiments, the size of a particle is representative of a population (e.g., mean, median, or average) of particles (e.g., a dry composition).

In some embodiments, a dry medicament comprises a dry pharmaceutical composition. The dry pharmaceutical composition can be prepared from any suitable method as used in pharmaceutical formulation. For example, a dry pharmaceutical composition may be chemically derived, lyophilized (freeze-dried), spray dried and/or formed using any other technique to put the medicament into a dry form. However, in some embodiments, it is important that the dried drug be easily and rapidly soluble so that the dry composition can be used in an autoinjector that also contains a liquid component that can be mixed with the dry drug to solubilize it upon activation of the autoinjector (e.g., immediately prior to or at the time of injection).

In some embodiments, a dry composition is prepared by drying a solution (e.g., by vacuum drying, freeze drying, lyophilizing, or any suitable drying technique, as aspects of the invention are not limited in this respect). In some embodiments, a dry composition is placed inside an autoinjector as a dry powder. In some embodiments, a dry composition may have any suitable particle size that allows for efficient and rapid dissolution, solubilization, or reconstitution. In some embodiments, the particle size of the dry composition can be controlled by drying a drug solution within a confined volume. For example, in some embodiments, a drug solution is dried within the confines of an autoinjector (e.g., within one or more microfluidic channels of an autoinjector). As a result, the particle size of a dried drug composition may be on the order of the diameter of a microfluidic channel (e.g., from about 1 micron to about 500 microns in diameter). However, smaller or larger particle sizes may be used in some embodiments.

It should be appreciated that the composition can be dried to different extents depending on the conditions used and the nature of the composition (e.g., the drug and other components of the composition). In some embodiments, a dry composition has less than 50% water by weight, less than 40% water by weight, less than 30% water by weight, less than 20% water by weight, less than 10% water by weight, less than 5% water by weight, less than 1% water by weight, less than 0.1% water by weight, less than 0.01% water by weight, or less.

It should be appreciated that a dried drug composition may include the drug alone and/or any other molecules that were present in the drug solution (e.g., one or more salts, stabilizers, anti-oxidants, etc., or any combination thereof).

Accordingly, in some embodiments, the present disclosure provides pharmaceutical compositions comprising a medicament as a dry component. The medicament can be kept out of the liquid phase and stored as a dry medication, for example, as a lyophilized, spray dried, vacuum dried or chemical derived powder. The dry medicament has the advantages of an extended shelf-life, reduced temperature susceptibility, a greater efficacy and potency to endure over a longer period of time and through a wider range of temperature environments.

In some embodiments, a dry medicament and one or more additional dry components (e.g., one or more dry excipients, such as a dry pH adjusting agent) are mixed in solution prior to drying into a powder form. In some embodiments, the dry medicament and one or more additional dry components are dried individually. In some embodiments, the dry medicament and one or more additional dry components are independently processed to achieve a desired particle size ratio using a known technique (e.g., micronization, milling, bashing, grinding).

In some embodiments, the concentration of one or more components (e.g., one or more acids, bases, buffers, salts, excipients, therapeutic agents, medicaments, drugs, or other components described herein) ranges from 1 nM to 1 M, for example from 1 nM to 1 μM, from 1 μm to 1 mM, from 1 mM to 10 mM, from 10 mM to 100 mM, from 100 mM to 500 mM, from 500 mM to 1 M, about 1 mM, about 5 mM, about 10 mM, about 50 mM, about 100 mM, about 500 mM, about 1 M, or higher or lower depending on the component and/or the application (e.g., in the final solution after dissolution).

As described herein, aspects of the application relate to a device that can be charged with wet and dry medicaments which can be combined so as to treat various conditions, such as opioid exposure treatments, e.g. overdose situations, wherein the compounds mixed can include lyophilized or otherwise dried components of the following components: Naloxone; Naloxone Hydrochloride; Nalmefene; Naltrexone. Yet another example of an alternative condition can include pesticide exposure, and treatments, which can include nerve agent exposure, wherein the compounds mixed can include lyophilized or otherwise dried components of the following components: Oximes; Pralidoxime;

Pralidoxime chloride; HI-6; HLö-7; MMB4; Scopolamine; scopolamine hydrobromide; Atropine; atropine hydrobromide; atropine sulfate, etc. In such embodiments the components can also include combination of any oxime powders with scopolamine powders and an atropine-based diluent, which is stable as a liquid, and can thus be utilized as the liquid component.

Accordingly, in some embodiments, a dry medicament as described herein comprises an opioid antagonist, such as nalmefene (e.g., nalmefene hydrochloride), naloxone (e.g., naloxone hydrochloride), naltrexone, or a combination thereof. Specific examples of opioid antagonists that may be used according to the invention include alvimopan, binaltorphimine, buprenorphine, cyclazocine, cyclorphan, cypridime, dinicotinate, beta-funaltrexamine, levallorphan, methylnaltrexone, N-methylnaloxone (naloxone methiodide), N-methylnalmefene, nalbuphine, nalide, nalmefene, nalmexone, nalorphine, nalorphine dinicotinate, naloxone, naloxonazine, naltrendol, naltrexone, naltrindole, oxilorphan, and pentazocine. In some embodiments, the opioid antagonist is nalmefene. In some embodiments, nalmefene refers to a compound of the following IUPAC name: (4R,4aS,7aS,12bS)-3-(cyclopropylmethyl)-7-methylidene-2,4,5,6,7a,13-hexahydro-1H-4,12-methanobenzofuro[3,2-e]isoquinoline-4a,9-diol.

In some embodiments, an opioid antagonist acts on one or more opioid receptors. At least three types of opioid receptors, mu, kappa, and delta opioid receptors, have been reported, and opioid antagonists are generally classified by their effects on the opioid receptors. In some embodiments, an opioid antagonist may antagonize central receptors, peripheral receptors, or both. In some embodiments, an opioid antagonist competitively binds to an opioid receptor with higher affinity than an agonist, but without activating the receptor. This effectively blocks the receptor, preventing the body from responding to opiates and endorphins. In some embodiments, an opioid antagonist can produce relatively weak opioid partial agonist effects, and may therefore not be a pure antagonist. In some embodiments, an opioid antagonist has no partial agonist effects. For example, an opioid antagonist may be a weak inverse agonist at one or more opioid receptors.

In some embodiments, aspects of the invention relate to stabilizing a therapeutic agent (e.g., an opioid antagonist) and making it less susceptible to temperature-induced degradation, by preparing a dry pharmaceutical composition (e.g., a dry salt form) of the therapeutic agent that can be readily reconstituted (e.g., in the context of an autoinjector) for delivery to a patient.

In some embodiments, aspects of the invention relate to a dry composition comprising an opioid antagonist. In some embodiments, a dry composition can be chemically derived, lyophilized, spray dried, vacuum dried, or other method for making a dry composition of matter. In some embodiments, a dry composition comprises an opioid antagonist in the form of a dry free base. In some embodiments, a dry composition comprises an opioid antagonist in the form of a dry salt. In some embodiments, the dry salt is a maleate, malate, fumarate, acid tartrate, bitartrate, hydrogen tartrate, borate, or sulfate salt of the opioid antagonist. In some embodiments, the dry salt is a hydrochloride salt of the opioid antagonist.

In some embodiments, the dry composition comprises an opioid antagonist in a weight of between about 0.1 mg and about 2.0 mg. In some embodiments, the dry composition comprises an opioid antagonist in a weight of between about 0.1 mg and about 1.0 mg. In some embodiments, the dry composition comprises an opioid antagonist in a weight of between about 0.5 mg and about 1.5 mg. In some embodiments, a dry composition comprises nalmefene in a weight of about 0.5 mg (e.g., between about 0.4 mg and about 0.6 mg). In some embodiments, a dry composition comprises nalmefene in a weight of about 1.0 mg (e.g., between about 0.8 mg and about 1.2 mg).

In some embodiments, the dry composition further comprises one or more excipients (e.g., one or more of a dry pH adjusting agent, a salt, an antioxidant, a stabilizing agent). In some embodiments, the one or more excipients include a salt, such as sodium chloride. In some embodiments, a dry composition comprises salt (e.g., sodium chloride) at a concentration of approximately 9.0 mg/mL. In some embodiments, the dry composition comprises salt (e.g., sodium chloride) at a concentration of between about 2.0 and about 20.0 mg/mL (e.g., between about 4.0 mg/mL and about 14.0 mg/mL, between about 6.0 mg/mL and about 12.0 mg/mL, between about 8.0 mg/mL and about 10.0 mg/mL).

In some embodiments, aspects of the invention relate to a sealed container comprising a dry medicament (e.g., a dry opioid antagonist) as described herein. In some embodiments, the sealed container is incorporated into the housing of an injector. In some embodiments, the sealed container is a microfluidic channel in an injector, where the channel is connected to a liquid reservoir. In some embodiments, the dry medicament is placed inside the microfluidic channel. In some embodiments, aspects of the invention relate to an injector comprising a dry medicament composition.

In some embodiments, dry compositions can be prepared and/or delivered in injector devices. In some embodiments, an injector device also contains a liquid reservoir that can be accessed to deliver a fluid to the dry composition in order to solubilize and/or rehydrate and/or dissolve the medicament immediately prior to injection. In some embodiments, the injector is an autoinjector that automatically mixes the dry composition with the fluid when the injector is activated.

In some embodiments the dry medicament is placed within the confines of an autoinjector as a dry powder, for example, the loading of an opioid antagonist in the form of a salt or a free base. In some embodiments the dry medicament is ground using a mortar and pestle to decrease the particle size and improve the dissolution rate.

In some embodiments, aspects of the invention relate to a method of delivering a medicament (e.g., an opioid antagonist) to a subject by dissolving and/or rehydrating and/or mixing a dry composition with a solution sufficient to dissolve the dry medicament (e.g., to dissolve at least 50%, at least 60%, at least 70%, at least 80%, at least 90%, around 95%, or 90-100% of the dry medicament), and delivering the dissolved medicament (and, in some embodiments, some quantity of undissolved medicament) to a subject via injection (e.g., immediately after dissolving the drug). In some embodiments, this can be accomplished by preloading an autoinjector with a dry opioid antagonist and a solution to dissolve the dry opioid antagonist and causing mixing and dissolution of the opioid antagonist by activating the autoinjector. In some embodiments, the solution to dissolve the dry opioid antagonist is pH optimized, where pH optimized means a pH that will result in the dissolution of the various forms of opioid antagonist. In some embodiments, the mixing is performed in an autoinjector prior to injection. In some embodiments, the mixing is performed in a prefilled syringe prior to injection. In some embodiments, the subject is a human subject. In some embodiments, the subject is a non-human subject.

In some embodiments, a liquid component (e.g., the pH optimizing solution) of an injection device has a pH that is capable of dissolving or solubilizing a dry medicament (e.g., a dry opioid antagonist). For example, in some embodiments, the liquid component comprises a pH optimizing agent. As used herein, a pH optimizing agent refers to an agent that has the capacity to optimize the pH of a solution. In some embodiments, a pH optimizing agent facilitates dissolution of the dry medicament. In some embodiments, the pH optimizing agent is an acid as generally described herein. In some embodiments, the pH optimizing agent is a base as generally described herein. In some embodiments, the pH optimizing agent is a buffer.

As used herein, the liquid can be a solvent or a solution. In some embodiments, the liquid is a single solvent. In some embodiments, the liquid is a solution comprising two or more solvents. In some embodiments, the liquid comprises a solvent and a cosolvent. In some embodiments, the liquid comprises water. In some embodiments, the liquid is water. In some embodiments, the liquid is an aqueous solution. In some embodiments, the liquid comprises a non-aqueous solvent, for example, a polar solvent (e.g., dimethyl sulfoxide, ethyl acetate, n-butanol, ethanol, isopropanol, or N-propanol) or a non-polar solvent (e.g., alkane hydrocarbons, such as hexane). In some embodiments, the liquid comprises water and a cosolvent. Examples of cosolvents that can be used with water include PEG 300, propylene glycol, and ethanol. In some embodiments, the liquid is a solution comprising a pH optimizing agent and a single solvent. In some embodiments, the liquid comprises water and a pH optimizing agent. In some embodiments, the pH optimizing agent is an acid as generally defined herein. In some embodiments, the pH optimizing agent is a base as generally defined herein.

In some embodiments, the pH of the liquid is from about 0.1 to about 6.9. In some embodiments, the pH of the liquid is from about 0.5 to about 5.0. In some embodiments, the pH of the liquid is from about 1.0 to about 5.0. In some embodiments, the pH of the liquid is from about 2.0 to about 5.0. In some embodiments, the pH of the liquid is from about 0.1 to about 6.0 (e.g., from about 0.1 to about 5.0, from about 0.1 to about 4.0, from about 0.1 to about 3.0, from about 0.1 to about 2.0, from about 0.1 to about 1.0). In some embodiments, the dry medicament is an opioid antagonist, and the pH of the liquid is from about 0.01 to about 2.2 (e.g., from about 0.25 to about 0.50, from about 0.50 to about 0.75, from about 0.75 to about 1.0, from about 1.0 to about 1.25, from about 1.25 to about 1.5, from about 1.5 to about 1.75, from about 1.75 to about 2.0). In some embodiments, the pH of the liquid is from about 2.0 to about 2.25. In some embodiments, the pH of the liquid is from about 2.25 to about 2.5. In some embodiments, the pH of the liquid is from about 2.5 to about 2.75. In some embodiments, the pH of the liquid is from about 2.75 to about 3.0. In some embodiments, the pH of the liquid is between about 5.0 and about 8.0, between about 6.0 and about 9.0, between about 6.0 and about 8.0, between about 5.5 and about 8.5, between about 6.0 and about 7.0, between about 7.0 and about 8.0, or between about 6.5 and about 7.5. In some embodiments, the pH of the liquid is approximately 7.0. In some embodiments, the pH of the liquid is approximately 7.4.

In some embodiments, the pH of the liquid is between about 2.0 and about 12.0. For example, in some embodiments, the pH of the liquid is between about 2.0 and about 10.0, between about 2.0 and about 8.0, between about 3.0 and about 10.0, between about 4.0 and about 9.0, between about 5.0 and about 9.0, or between about 6.5 and about 8.5.

In some embodiments, the pH of the liquid is above about 7.0. In some embodiments, the pH of the liquid is from about 7.0 to about 13.5. In some embodiments, the pH of the liquid is from about 7.0 to about 12.0. In some embodiments, the pH of the liquid is from about 7.0 to about 10.0. In some embodiments, the pH of the liquid is from about 8.0 to about 13.5. In some embodiments, the pH of the liquid is from about 9.0 to about 13.5. In some embodiments, the pH of the liquid is from about 9.5 to about 13.5.

In some embodiments, the volume of the liquid (e.g., in an autoinjector) is about 100 µL to about 200 µL (e.g., about 100, 125, 150, 175, or about 200 µL). In some embodiments, the volume of the liquid (e.g., in an autoinjector) is about 200 µL to about 300 µL (e.g., about 200, 225, 250, 275, or about 300 µL). In some embodiments, the volume of the liquid (e.g., in an autoinjector) is about 300 µL to about 400 µL (e.g., about 300, 325, 350, 375, or about 400 µL). In some embodiments, the volume of the liquid (e.g., in an autoinjector) is about 400 µL to about 500 µL (e.g., about 400, 425, 450, 475, or about 500 µL). In some embodiments, the volume of the liquid (e.g., in an autoinjector) is about 500 µL to about 600 µL (e.g., about 500, 525, 550, 575, or about 600 µL). In some embodiments, the volume of the liquid (e.g., in an autoinjector) is about 600 µL to about 700 µL (e.g., about 600, 625, 650, 675, or about 700 µL). In some embodiments, the volume of the liquid (e.g., in an autoinjector) is about 700 µL to about 800 µL (e.g., about 700, 725, 750, 775, or about 800 µL). In some embodiments, the volume of the liquid (e.g., in an autoinjector) is about 800 µL to about 1000 µL (e.g., about 800, 850, 900, 950, or about 1000 µL). In some embodiments, the volume of the liquid (e.g., in an autoinjector) is about 1 mL to about 1.5 mL (e.g., about 1, 1.1, 1.2, 1.3, 1.4, or about 1.5 mL). In some embodiments, the liquid is of a volume greater than 1.5 mL.

In some embodiments, a solution formed from reconstitution of a dry composition in a liquid comprises an opioid antagonist at a concentration of approximately 1.0 mg/mL. In some embodiments, the solution comprises the opioid antagonist at a concentration of between about 0.5 mg/mL and about 2.0 mg/mL (e.g., between about 0.5 mg/mL and about 1.5 mg/mL, between about 1.0 mg/mL and about 2.0 mg/mL, between about 1.0 mg/mL and about 1.5 mg/mL). In some embodiments, the solution comprises the opioid antagonist at a concentration of approximately 0.1 mg/mL. In some embodiments, the solution comprises the opioid antagonist at a concentration of between about 0.05 mg/mL and about 0.5 mg/mL (e.g., between about 0.05 mg/mL and about 0.2 mg/mL, between about 0.1 mg/mL and about 0.2 mg/mL, between about 0.05 mg/mL and about 0.1 mg/mL, between about 0.1 mg/mL and about 0.5 mg/mL).

In some embodiments, additional components like metabisulfite, sodium chloride, and/or other materials may also be included in the liquid for dissolving the dry medicament.

In some embodiments, a dry pharmaceutical composition comprises a combination of a dry medicament and one or more dry pH adjusting agents. In some embodiments, a dry pharmaceutical composition can be reconstituted into a solution by mixing with a liquid. In some embodiments, the liquid has a pH that rapidly dissolves the dry medicament. In some embodiments, the dry pH adjusting agent dissolves less rapidly than the dry medicament, resulting in a pH adjustment of the solution after dissolution of the dry medicament. Aspects of the disclosure are useful to promote rapid dissolution of a dry medicament (e.g., an opioid antagonist) at a pH that may not be physiologically acceptable followed by a slower pH change to a physiologically acceptable range. According to the disclosure, this process can be obtained in a single step by mixing a solution with a dry combination of appropriate medicament(s) and pH adjusting agent(s).

In some embodiments, the dry pharmaceutical composition comprises one or more pharmaceutically acceptable carriers. Further provided herein are kits and systems comprising the pharmaceutical compositions as described herein. According to aspects of the invention, the dry pharmaceutical compositions have several advantages over liquid compositions, including increased stability (e.g., a long shelf life, potency and/or chiral stability) over time and upon exposure to changes in temperature.

In some aspects, the disclosure provides a pharmaceutical composition comprising a therapeutically effective amount of a dry medicament and one or more pH adjusting agents (e.g., one or more dry pH adjusting agents). In some embodiments, the pH adjusting agents are solids. In some embodiments, the pharmaceutical composition reaches a first pH after mixing with a liquid. In some embodiments, the first pH is lower than about 7.0. In some embodiments, the first pH is lower than about 6.0. In some embodiments, the first pH is lower than about 5.0. In some embodiments, the first pH is lower than about 4.0. In some embodiments, the first pH is lower than about 3.0. In some embodiments, the first pH is lower than about 2.0. In some embodiments, the first pH is lower than about 2.2. In some embodiments, the first pH is from about 2.2 to about 5.0. In some embodiments, the first pH is lower than about 1.0. In some embodiments, the first pH is over about 7.0. In some embodiments, the first pH is over about 8.0. In some embodiments, the first pH is over about 9.0. In some embodiments, the first pH is over about 10.0. In some embodiments, the first pH is over about 11.0. In some embodiments, the first pH is over about 12.0. In some embodiments, the first pH is over about 13.0. In some embodiments, the dry medicament is more soluble in the liquid than one or more dry pH adjusting agents. In some embodiments, the dry medicament forms a readily solubilized salt upon being mixed with the liquid.

In some embodiments, the solution formed from the pharmaceutical composition or dry medicament and the liquid is further contacted with one or more pH adjusting agents to reach a second pH. In certain embodiments, the second pH is a physiologically acceptable pH. In some embodiments, the second pH is a physiological pH. In some embodiments, the second pH is between about 3.0 and about 10.0 (e.g., between about 3.0 and about 9.0, between about 3.0 and about 8.0, between about 3.0 and about 7.0, between about 4.0 and about 8.0, between about 5.0 and about 9.0, between about 6.0 and about 8.0, between about 4.0 and about 9.0, between about 5.0 and about 9.0, between about 6.0 and about 9.0, between about 7.0 and about 10.0, or between about 8.0 and about 9.0). In some embodiments, the second pH is from about 0.1 to about 4.0 or about 9.5 to about 13.5, and the dry medicament is an opioid antagonist.

In another aspect, the disclosure provides a method of preparing a medical solution comprising mixing a dry pharmaceutical composition as described herein and a liquid. In some embodiments, the pharmaceutical composition is administered (e.g., injected) through a medical device to a subject. In some embodiments, a dry pharmaceutical composition is located in one chamber of a medical device, and the liquid is located in another chamber of the medical device. Before injection, the pharmaceutical composition is mixed with the liquid to dissolve the dry medicament, followed by pH adjustment by one or more dry pH adjusting agents to reach a physiologically acceptable pH. The dissolution and pH adjustment processes are generally completed within less than 5 min. In some embodiments, the dissolution and pH adjustment process are generally completed within less than about 1 min. In some embodiments, the dissolution and pH adjustment process are generally completed within less than about 30 seconds. In some embodiments, the dissolution and pH adjustment process are generally completed within less than about 10 seconds. In some embodiments, the dissolution and pH adjustment process are generally completed within less than about 5 seconds. In some embodiments the dissolution and pH adjustment process are generally completed within less than about 1 second. In certain embodiments, the medical device is an autoinjector.

In some embodiments, the pH adjusting agent is completely separate from the dry medicament. In certain embodiments, the pH adjusting agent is of particles different from the particles of the dry medicament. In certain embodiments, the pH adjusting agent is of particles associated with the particles of the dry medicament. In certain embodiments, the pH adjusting agent is of particles within the particles of the dry medicament. In certain embodiments, the pH adjusting agent is of particles embedded in the particles of the dry medicament. In certain embodiments, the sizes of the particles of pH adjusting agent and the dry medicament are different. In certain embodiments, the sizes of the particles of pH adjusting agent and the dry medicament are similar. In certain embodiments, the pH adjusting agent dissolves slower than the dry medicament.

Figure 51:
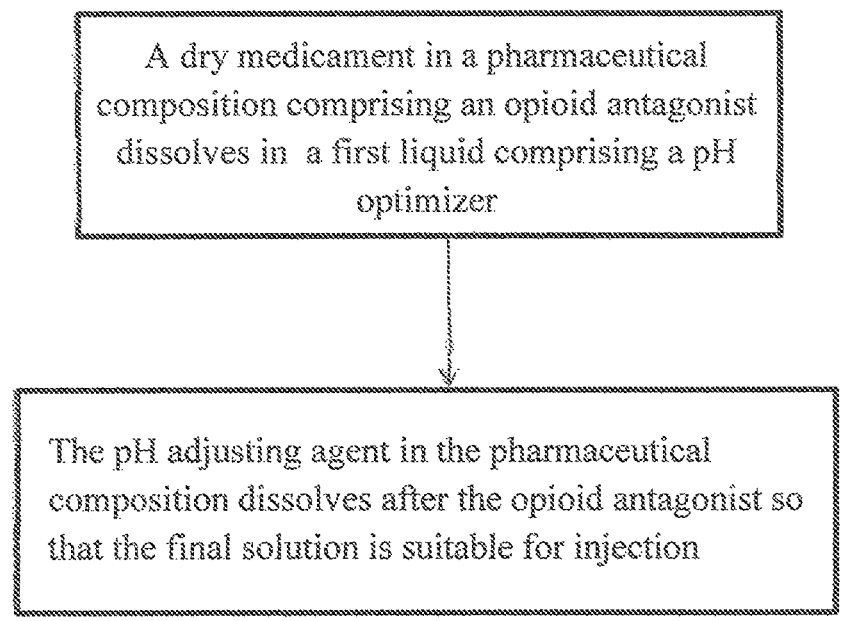
FIG. 51 illustrates a non-limiting method for a single-stage mixing and injection process.

In some aspects, the disclosure provides useful pharmaceutical compositions to store a medicament in a solid form and thus prevents its degradation. The disclosure further provides methods of preparing a medical solution from the pharmaceutical compositions as described herein. In some embodiments, a single stage mixing occurs prior to injection as illustrated by the scheme in FIG. 51. In some embodiments, upon mixing the pharmaceutical composition and the liquid, the dry medicament dissolves faster than (e.g., before) the one or more pH adjusting agents. In some embodiments, the pH adjusting agent acts to adjust the pH value of the mixture from the favorable first pH for dissolving the dry medicament to the second pH proper for injection to a subject.

In some embodiments, the dry medicament is not associated with the one or more pH adjusting agents. In some embodiments, the dry medicament and the one or more pH adjusting agents are in different particles. In some embodiments, the dry medicament is in particles that are smaller than the one or more pH adjusting agents. In some embodiments, the dry medicament particles have a size greater than 1 nm. In some embodiments, the dry medicament particles have a size greater than 5 nm. In some embodiments, the dry medicament particles have a size greater than 10 nm. In some embodiments, the dry medicament particles have a size greater than 50 nm. In some embodiments, the dry medicament particles have a size greater than 100 nm. In some embodiments, the dry medicament particles have a size greater than 500 nm. In some embodiments, the dry medicament particles have a size greater than 1 µm. In some embodiments, the dry medicament particles have a size greater than 5 µm. In some embodiments, the dry medicament particles have a size greater than 10 µm. In some embodiments, the dry medicament particles have a size of about 20 µm to about 40 µm (e.g., about 20, 22.5, 25, 27.5, 30, 32.5, 35, or about 40 µm). In some embodiments, the dry medicament particles have a size greater than 50 µm. In some embodiments, the dry medicament particles have a size greater than 100 µm. In some embodiments, the dry medicament particles have a size greater than 500 µm. In some embodiments, the one or more pH adjusting agent particles have a size greater than 1 nm. In some embodiments, the one or more pH adjusting agent particles have a size greater than 5 nm. In some embodiments, the one or more pH adjusting agent particles have a size greater than 10 nm. In some embodiments, the one or more pH adjusting agent particles have a size greater than 50 nm. In some embodiments, the one or more pH adjusting agent particles have a size of about 40 µm to about 60 µm (e.g., about 40, 45, 47.5, 50, 52.5, 55, 57.5, or about 60 µm). In some embodiments, the one or more pH adjusting agent particles have a size greater than 100 nm. In some embodiments, the one or more pH adjusting agent particles have a size greater than 500 nm. In some embodiments, the one or more pH adjusting agent particles have a size greater than 1 µm. In some embodiments, the one or more pH adjusting agent particles have a size greater than 5 µm. In some embodiments, the one or more pH adjusting agent particles have a size greater than 10 µm. In some embodiments, the one or more pH adjusting agent particles have a size greater than 50 µm. In some embodiments, the one or more pH adjusting agent particles have a size greater than 100 µm. In some embodiments, the one or more pH adjusting agent particles have a size greater than 500 µm.

In some embodiments, the dry medicament is in particles that are dissolved before the one or more pH adjusting agents. In some embodiments, the dry medicament particles dissolve faster than the one or more pH adjusting agent particles. In some embodiments, the dry medicament is in particles that are bigger than the one or more pH adjusting agents. In some embodiments, the dry medicament is in particles that are of similar size as the one or more pH adjusting agents. As it is to be understood, different formulations (e.g., coating, caging, etc.) of the dry medicament and the pH adjusting agents can alter the inherent solubility of these substances to achieve different dissolution rates.

In some embodiments, the pH adjusting agent is coated with one or more layers of a pharmaceutically acceptable carrier. In some embodiments, the pharmaceutically acceptable carrier is a solid. A pharmaceutically acceptable carrier includes any and all diluents, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

In some embodiments, the pH adjusting agent is coated with one or more layers of a pharmaceutically acceptable polymer. In some embodiments, the pH adjusting agent is released after dissolution of the dry medicament after being mixed with the first liquid.

Figure 52A:
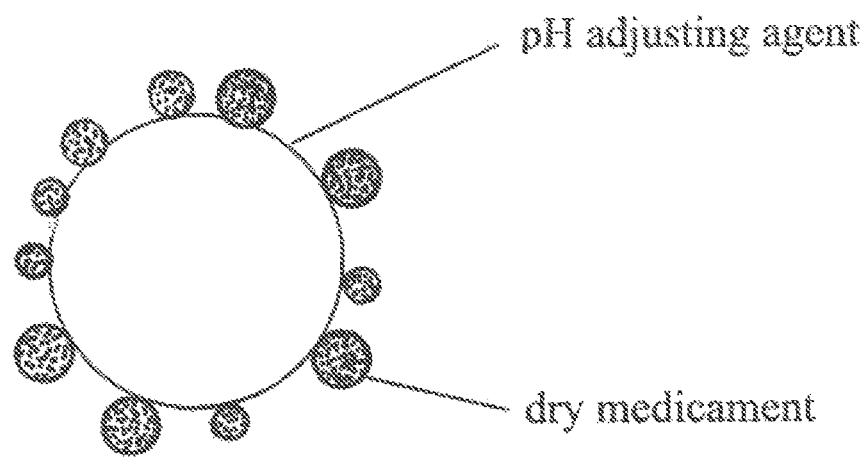
FIGS. 52A-52B show non-limiting coatings of a pH adjusting agent with a dry medicament.
Figure 52B:
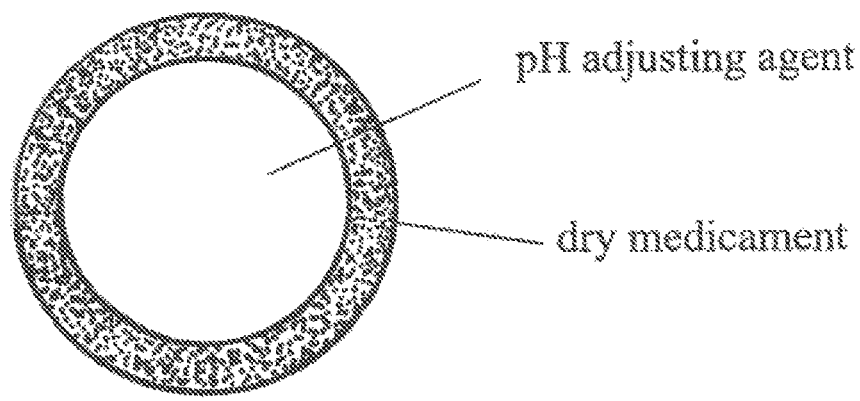

In some embodiments, the dry medicament is associated with the pH adjusting agent (e.g., FIG. 52A). In some embodiments, the pH adjusting agent is coated with one or more layers of the dry medicament (e.g., FIG. 52B). In some embodiments, a dry buffer is coated with one more layers of an opioid antagonist.

Figure 53A:
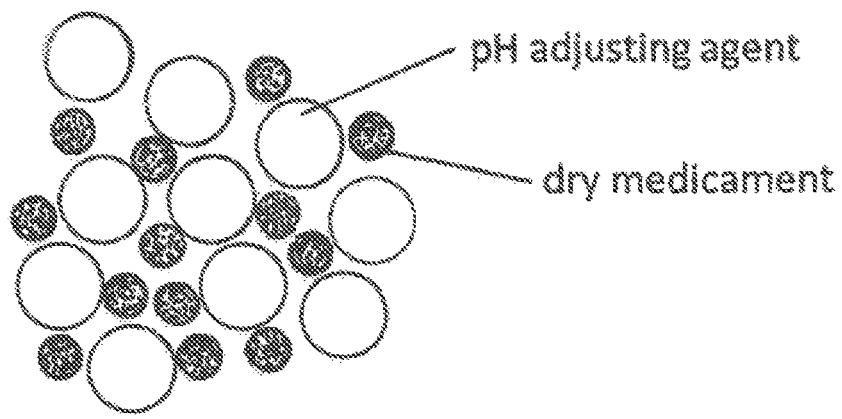
FIGS. 53A-53B show non-limiting examples of mixtures comprising a dry medicament and a dry pH adjusting agent
Figure 53B:
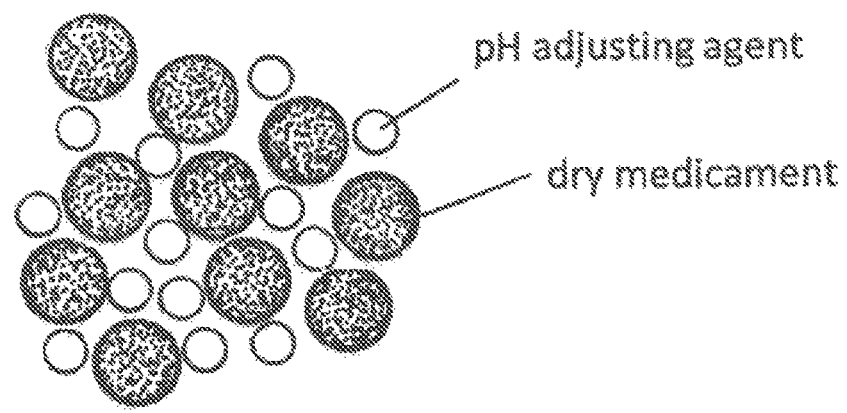

In some embodiments, the different dissolution rates of a dry medicament and a pH adjusting agent is achieved by different particle size. In some embodiments, the particle size of the dry medicament is smaller relative to the particle size of the pH adjusting agent so that the smaller medicament particle dissolves first and/or more quickly (e.g., FIG. 53A). In some embodiments, the particle size of the dry medicament is larger relative to the particle size of the pH adjusting agent (e.g., FIG. 53B). For example, in some embodiments, the different dissolution rates of the dry medicament and the pH adjusting agent can be achieved by including a slow release coating on the pH adjusting agent. The properties of certain slow release coatings could be such that a smaller particle size provides a favorable rate of dissolution of the pH adjusting agent.

As used herein, a pH adjusting agent is an agent that can change the pH value of a solution. In some embodiments, the pH adjusting agent adjusts the pH of the solution to a physiologically acceptable pH suitable for administration. In some embodiments, the pH adjusting agent is an acid as generally described herein. In some embodiments, the pH adjusting agent is a base as generally described herein. In some embodiments, the pH adjusting agent is a buffer as generally described herein. In some embodiments, the pH adjusting agent is a salt.

In some embodiments, upon mixing a dry composition and a liquid, the dry medicament dissolves faster than the one or more pH adjusting agents. In some embodiments, the pH adjusting agent acts to adjust the pH value of the mixture from the favorable pH for dissolving the dry medicament to the pH proper for injection in a subject. In some embodiments, the pH of the final solution is a physiologically acceptable pH.

In some embodiments, the pharmaceutical composition comprising an opioid antagonist is placed inside a chamber of a device (e.g., an autoinjector). A first liquid comprising a pH optimizing agent (e.g., an acid such as HCl) is placed in another chamber. In some embodiments, the HCl solution is of 1 M or higher. In some embodiments, the HCl solution is of 0.1 M or higher. In some embodiments, the HCl solution is of 0.01 M or higher. In some embodiments, the HCl solution is of 0.001 M or higher. In some embodiments, the HCl solution is of 0.0001 M or higher. In some embodiments, the HCl solution is of 0.00001 M or higher. In some embodiments, the HCl solution is of 0.000001 M or higher.

In some embodiments, the opioid antagonist is dissolved into a first liquid comprising a pH optimizing agent so the pH of the dissolved material is below a pH of 6, is below a pH of 5, is below a pH of 4, is below a pH of 3, is below a pH of 2, is between a pH of 2-5. In some embodiments, the dissolved opioid antagonist solution is secondly adjusted with a pH adjusting agent so the final pH is physiologically acceptable for administration.

In some embodiments, the dry medicament dissolves in the first solution faster than the dry pH adjusting agent. However, as the pH adjusting agent dissolves, it adjusts the pH of the resulting solution, for example to a pH range that is more physiologically acceptable than the pH of the first solution. In some embodiments, the dry pH adjusting agent is an acid. In some embodiments, the dry pH adjusting agent is a base. In some embodiments, the dry pH adjusting agent is a buffer. In some embodiments, the buffer comprises a salt of a weak acid or a salt of a weak base, for example sodium acetate, (e.g., in dry powder form). In some embodiments, the buffer may comprise a mixture of a weak acid and its conjugate base, or a weak base and its conjugate acid (e.g., in dry powder form). In some embodiments, the buffer may comprise a mixture of citric acid and its conjugate base (e.g., in dry powder form). In some embodiments, the buffer may comprise a mixture of acetic acid and its conjugate base (e.g., in dry powder form). In some embodiments, the buffer may comprise a mixture of tartaric acid and its conjugate base (e.g., in dry powder form). In some embodiments, a buffer (e.g., in a dry powder form) for adjusting the pH of the dissolved medicament solution is already mixed with the dry medicament as described herein. However, in some embodiments, buffer (e.g., in a dry powder form) is contained inside a reservoir to receive the dissolved solution. In some embodiments, the buffer may be useful to increase the pH of the dissolved solution above a pH of 2 if a pH upon dissolution drops below a pH of 2. In some embodiments, a pH adjusting dry agent is a base. In some embodiments, the pH adjusting dry agent is sodium hydroxide. In some embodiments, the adjustment of the pH of the solution by the pH adjusting agent makes the resulting solution suitable for injection. It should be appreciated that, in some embodiments, a feature is that a medicament is being provided in an acid or a base to facilitate dissolution of the medicament and a buffer adjusts the mixture to a pH suitable for injection.

In some embodiments, one or more pH adjusting agents (e.g., in a dry form) are present in a dry composition containing a medicament and form a buffering system. In certain embodiments, a pH adjusting agent is a buffer. In certain embodiments, a pH adjusting agent is buffering agent. In certain embodiments, the buffering agent is a sodium or potassium buffering agent. In certain embodiments, the buffering agent is sodium citrate or sodium acetate. In certain embodiments, the buffer system comprises trisodium citrate and citric acid.

In some embodiments, the methods provided herein allow quick dissolution of a dry composition inside a medical device (e.g., an autoinjector or prefilled syringe) by using a liquid (e.g., a pH optimized solution) to dissolve an opioid antagonist, followed by pH adjustment due to the slower dissolution of a pH adjusting agent (e.g., a buffer) to reach a final pH range between about 4.0 to about 10.0 for injection.

In certain embodiments, provided herein is a medical device that stores a dry medicament in a first chamber and a liquid in a second chamber. The dry powdered medicament can quickly dissolve within the liquid followed by pH adjustment to a pH suitable for injection due to the slower dissolution of a pH adjusting agent (e.g., that is provided mixed with the medicament in a dry composition). In some embodiments, the benefits of the thermal stability of the powdered medication along with the ability to rapidly dissolve the powdered medication into a liquid dose just prior to delivery provide patients with a medicament that has much lesser storage requirements and a longer shelf life. In certain embodiments, the medical device is an autoinjector. In certain embodiments, the powdered form of an opioid antagonist is located in the first chamber of the autoinjector and an aqueous solution comprising an acid is located in the second chamber of the autoinjector. In some embodiments, the powdered form of an opioid antagonist is mixed with a powdered form of a pH adjusting agent (e.g., a buffer in a dry form).

In some embodiments, a dry composition comprising a dry opioid antagonist and a dry pH adjusting agent (e.g., citrate, acetate, or other pH adjusting agent) is provided (e.g., in an autoinjector) in a weight from about 25 mg to about 50 mg (e.g., about 25, 27.5, 30, 32.5, 35, 37.5, 40, 42.5, 45, 47.5, or about 50 mg). In some embodiments, the dry composition comprising a dry opioid antagonist and a dry pH adjusting agent (e.g., citrate, acetate, or other pH adjusting agent) is provided (e.g., in an autoinjector) in a weight from about 15 to about 25 mg (e.g., about 15, 16, 17, 18, 19, 20, 21, 22, 23, 24, or about 25 mg). In some embodiments, the dry composition comprising a dry opioid antagonist and a dry pH adjusting agent (e.g., citrate, acetate, or other pH adjusting agent) is provided (e.g., in an autoinjector) in a weight from about 5 to about 15 mg (e.g., about 5, 6, 7, 8, 9, 10, 11, 12, 13, 14, or about 15 mg). In some embodiments, the dry composition comprising a dry opioid antagonist and a dry pH adjusting agent (e.g., citrate, acetate, or other pH adjusting agent) is provided (e.g., in an autoinjector) in a weight from about 3 to about 5 mg (e.g., about 3, 3.25, 3.5, 3.75, 4, 4.1, 4.2, 4.3, 4.4, 4.5, 4.75, or about 5 mg). In some embodiments, the dry composition comprising a dry opioid antagonist and a dry pH adjusting agent (e.g., citrate, acetate, or other pH adjusting agent) is provided (e.g., in an autoinjector) in a weight from about 1 mg to about 3 mg (e.g., about 1, 1.25, 1.5, 1.75, 2, 2.1, 2.15, 2.17, 2.2, 2.3, 2.4, 2.5, 2.75, or about 3 mg). In some embodiments, the dry composition comprising a dry opioid antagonist and a dry pH adjusting agent (e.g., citrate, acetate, or other pH adjusting agent) is provided (e.g., in an autoinjector) in a weight from about 0.1 mg to about 1 mg (e.g., about 0.1, 0.2, 0.3, 0.4, 0.5, 0.6, 0.7, 0.8, 0.9, or about 1 mg).

In certain embodiments, provided herein is a medical device comprising a dry composition. In some embodiments, the dry composition comprises a dry medicament. In some embodiments, the dry composition comprises a dry opioid antagonist and a dry pH adjusting agent (e.g., citrate, acetate, or other pH adjusting agent). In some embodiments, the dry composition comprises about 1% of the dry medicament by weight and about 99% of the dry pH adjusting agent by weight. In some embodiments, the dry composition comprises about 2% of the dry medicament by weight and about 98% of the dry pH adjusting agent by weight. In some embodiments, the dry composition comprises about 3% of the dry medicament by weight and about 97% of the dry pH adjusting agent by weight. In some embodiments, the dry composition comprises about 4% of the dry medicament by weight and about 96% of the dry pH adjusting agent by weight. In some embodiments, the dry composition comprises about 5% of the dry medicament by weight and about 95% of the dry pH adjusting agent by weight. In some embodiments, the dry composition comprises about 6% of the dry medicament by weight and about 94% of the dry pH adjusting agent by weight. In some embodiments, the dry composition comprises about 7% of the dry medicament by weight and about 93% of the dry pH adjusting agent by weight. In some embodiments, the dry composition comprises about 8% of the dry medicament by weight and about 92% of the dry pH adjusting agent by weight. In some embodiments, the dry composition comprises about 9% of the dry medicament by weight and about 91% of the dry pH adjusting agent by weight. In some embodiments, the dry composition comprises about 10% of the dry medicament by weight and about 90% of the dry pH adjusting agent by weight. In some embodiments, the dry composition comprises between about 10% to about 15% of the dry medicament by weight and between about 85% to about 90% of the dry pH adjusting agent by weight. For example, about 10%, 11%, 12%, 13%, 14%, or about 15% of the dry medicament by weight and about 85%, 86%, 87%, 88%, 89%, or about 90% of the dry pH adjusting agent by weight. In some embodiments, the dry composition comprises between about 15% to about 20% of the dry medicament by weight and between about 80% to about 85% of the dry pH adjusting agent by weight. For example, about 15%, 16%, 17%, 18%, 19%, or about 20% of the dry medicament by weight and about 80%, 81%, 82%, 83%, 84%, or about 85% of the dry pH adjusting agent by weight. In some embodiments, the dry composition comprises between about 20% to about 25% of the dry medicament by weight and between about 75% to about 80% of the dry pH adjusting agent by weight. For example, about 20%, 21%, 22%, 23%, 24%, or about 25% of the dry medicament by weight and about 75%, 76%, 77%, 78%, 79%, or about 80% of the dry pH adjusting agent by weight. In some embodiments, the dry composition comprises between about 25% to about 40% of the dry medicament by weight and between about 60% to about 75% of the dry pH adjusting agent by weight. For example, about 25%, 27.5%, 30%, 32.5%, 35%, 37.5% or about 40% of the dry medicament by weight and about 60%, 62.5%, 65%, 67.5%, 70%, 72.5%, or about 80% of the dry pH adjusting agent by weight. In some embodiments, the dry composition comprises between about 40% to about 55% of the dry medicament by weight and between about 45% to about 60% of the dry pH adjusting agent by weight. For example, about 40%, 42.5%, 45%, 47.5%, 50%, 52.5% or about 55% of the dry medicament by weight and about 45%, 47.5%, 50%, 52.5%, 55%, 57.5%, or about 60% of the dry pH adjusting agent by weight. In some embodiments, the dry composition comprises between about 55% to about 70% of the dry medicament by weight and between about 30% to about 45% of the dry pH adjusting agent by weight. For example, about 55%, 57.5%, 60%, 62.5%, 65%, 67.5% or about 70% of the dry medicament by weight and about 30%, 32.5%, 35%, 37.5%, 40%, 42.5%, or about 45% of the dry pH adjusting agent by weight. In some embodiments, the dry composition comprises between about 70% to about 85% of the dry medicament by weight and between about 15% to about 30% of the dry pH adjusting agent by weight. For example, about 70%, 72.5%, 75%, 77.5%, 80%, 82.5% or about 85% of the dry medicament by weight and about 15%, 17.5%, 20%, 22.5%, 25%, 27.5%, or about 30% of the dry pH adjusting agent by weight. In some embodiments, the dry composition comprises between about 85% to about 99% of the dry medicament by weight and between about 1% to about 15% of the dry pH adjusting agent by weight. For example, about 85%, 87.5%, 90%, 92.5%, 95%, 97.5% or about 99% of the dry medicament by weight and about 1%, 2.5%, 5%, 7.5%, 10%, 12.5%, or about 15% of the dry pH adjusting agent by weight.

Before administration, the liquid in a first chamber of a device is contacted with the pharmaceutical composition in a second chamber to generate a solution for injection. In certain embodiments, the contact is carried out in the first chamber. In certain embodiments, the contact is carried out in a second chamber. In certain embodiments, the contact is carried out in a third chamber. In certain embodiments, the pharmaceutical composition and the first fluid mix partially. In certain embodiments, the pharmaceutical composition and the first fluid completely mix to generate a solution. In certain embodiments, an opioid antagonist is located in the second chamber and contacted with a liquid from the first chamber. In certain embodiments, the dissolution of the opioid antagonist in the first liquid is followed by a release of a pH adjusting agent to bring the final pH of the opioid antagonist solution to within a physiologically acceptable range.

In some embodiments, the different dissolution rates of the opioid antagonist and the pH adjusting agent is achieved by different particle size. In some embodiments, the particle size of the opioid antagonist is smaller relative to the particle size of the pH adjusting agent so that the smaller opioid antagonist particle is more likely to dissolve first, and/or more quickly, while the pH is initially lower than 2.2, and the pH adjusting agent, with the larger particle size, dissolves more slowly causing the pH of the combined solution to then increase into a target range of about 2.2 to about 5.0.

As generally defined herein, an acid is a chemical substance that dissociates in aqueous solution to give H+. In certain embodiments, the acid is an organic acid. In certain embodiments, the acid is an inorganic acid. Examples of acids include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, propionic acid, pyroglutamic acid, salicylic acid, sebacic acid, stearic acid, succinic acid, sulfuric acid, tartaric acid, thiocyanic acid, toluenesulfonic acid, and undecylenic acid. In some embodiments, the acid is sulfuric acid, hydrochloric acid, hydrobromic acid, nitric acid, phosphoric acid, perchloric acid, formic acid, acetic acid, propionic acid, oxalic acid, maleic acid, citric acid, succinic acid, malonic acid, tartaric acid, or a combination thereof. In certain embodiments, the acid is hydrochloric acid, nitric acid, sulfuric acid, phosphoric acid, tartaric acid, malic acid, malonic acid, maleic acid, fumaric acid, succinic acid, or formic acid.

As generally defined herein, a base is a chemical substance that dissociates in aqueous solution to give OH—. In certain embodiments, the base is an organic base. In certain embodiments, the base is an inorganic base. In certain embodiments, the base is an alkaline base. Examples of the bases include, but are not limited to, sodium citrate, sodium acetate, sodium hydroxide, potassium hydroxide, lithium hydroxide, ammonium hydroxide, calcium hydroxide, magnesium hydroxide, iron hydroxide, zinc hydroxide, copper hydroxide, manganese hydroxide, aluminum hydroxide, isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, or combinations thereof. In some embodiments, the base is sodium hydroxide or potassium hydroxide.

As used herein, the term "buffer" refers to either a buffering agent or a buffering solution comprising one or more buffering agents. As generally defined herein, a buffering agent is a weak acid or base used to maintain the pH of a solution near a chosen value after the addition of another acid or base. The function of a buffering agent is to prevent a rapid change in pH when acids or bases are added to the solution. Exemplary buffering agents include but are not limited to citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof. In certain embodiments, the buffer is a sodium salt, a calcium salt, a potassium salt, or an ammonium salt. In certain embodiments, the buffer is a citrate, acetate, phosphate, sulfate, nitrate, tartrate, succinate, malate, or maleate. In certain embodiments, the buffer is sodium citrate, sodium acetate, potassium hydroxide, potassium citrate, potassium acetate, sodium succinate, or potassium succinate.

The pharmaceutical composition provided herein can be administered by a parenteral, intravenous, intradermal, intramuscular, or subcutaneous administration. In certain embodiments, the route of administration is subcutaneous. In certain embodiments, the route of administrate is intravenous.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Also encompassed by the disclosure are kits (e.g., pharmaceutical packs). The inventive kits may be useful for preventing and/or treating a disease or condition (e.g., an opioid overdose). The kits provided may comprise an inventive pharmaceutical composition and a container (e.g., a vial, ampule, bottle, syringe, and/or dispenser package, or other suitable container). The kits provided may comprise an inventive pharmaceutical composition in a medical device (e.g., an autoinjector). In certain embodiments, the kits further include instructions for administering the composition.

Pharmaceutically acceptable excipients include any and all diluents, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

In some embodiments, the amount of a therapeutic agent in the medical solution is an effective amount sufficient to elicit the desired biological response, i.e., treat the condition. In some embodiments, the amount of a therapeutic agent in the medical solution is a therapeutically effective amount sufficient to provide a therapeutic benefit in the treatment of a condition or to delay or minimize one or more symptoms associated with the condition. The term "therapeutically effective amount" can encompass an amount that improves overall therapy, reduces or avoids symptoms or causes of the condition, or enhances the therapeutic efficacy of another therapeutic agent. In some embodiments, the effective amount is a prophylactically effective amount sufficient to prevent a condition, or one or more symptoms associated with the condition or prevent its recurrence. In some embodiments, a subject is treated in accordance with the application by reducing, reversing, or preventing the development of one or more symptoms associated with opioid exposure (e.g., an opioid overdose). Examples of symptoms associated with an opioid overdose include, without limitation, loss of consciousness, unresponsiveness to outside stimuli, slurred speech or inability to speak while conscious, abnormal breathing (e.g., slow, shallow, erratic, or stoppage of breathing), change in skin or fingernail coloring, vomiting, and abnormal (e.g., slow, erratic, or absent) pulse or heartbeat.

As used herein, the effective amount of a therapeutic agent will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

In some embodiments, the medical solution is administered to a human subject. In some embodiments, the medical solution is administered to a non-human subject.

In certain embodiments, the dry medicaments or pharmaceutical compositions as described herein are stable upon changes of temperature. In some embodiments, a dry composition described herein and/or exemplified in the Examples retains greater than 90% potency, greater than 95% potency, between 90% and 100% potency, or between 90% and 115% potency when subjected to the following temperature exposure of less than −30° C., or between −30° C. and −25° C., or less than −25° C., or between −25° C. and −20° C., or less than −20° C., or between −20° C. and −15° C., or less than −15° C., or between −15° C. and −10° C., or less than −10° C., or between −10° C. and −5° C., or less than −5° C., or between −5° C. and 0° C., or less than 0° C., or between 0° C. and 5° C., or less than 5° C., or between 5° C. and 10° C., or less than 10° C., or between 10° C. and 15° C., or less than 15° C., or between 15° C. and 20° C. or less than 20° C. or between 20° C. and 25° C. or greater than 25° C., or between 25° C. and 30° C., or greater than 30° C. or between 30° C. and 35° C., or greater than 35° C., or between 35° C. and 40° C., or greater than 40° C., or between 40° C. and 45° C., or greater than 45° C., or between 45° C. and 50° C., or greater than 50° C., or between 50° C. and 55° C. or greater than 55° C., or between 55° C. and 60° C., or greater than 60° C. for up to 1 year, 2 years, 3 years, 5 years, 7 years, for up to 10 years or for greater than 10 years.

In some embodiments, after the opioid antagonist powder has been dissolved in an injector device, the resulting solution retains a potency greater than 90% potency, greater than 95% potency, between 90% and 100% potency, or between 90% and 115% potency even when the dry opioid antagonist has been previously subject to a temperature exposure of less than −30° C., or between −30° C. and −25° C., or less than −25° C., or between −25° C. and −20° C., or less than −20° C., or between −20° C. and −15° C., or less than −15° C., or between −15° C. and −10° C., or less than −10° C., or between −10° C. and −5° C., or less than −5° C., or between −5° C. and 0° C., or less than 0° C., or between 0° C. and 5° C., or less than 5° C., or between 5° C. and 10° C., or less than 10° C., or between 10° C. and 15° C., or less than 15° C., or between 15° C. and 20° C. or less than 20° C. or between 20° C. and 25° C. or greater than 25° C., or between 25° C. and 30° C., or greater than 30° C. or between 30° C. and 35° C., or greater than 35° C., or between 35° C. and 40° C., or greater than 40° C., or between 40° C. and 45° C., or greater than 45° C., or between 45° C. and 50° C., or greater than 50° C., or between 50° C. and 55° C. or greater than 55° C., or between 55° C. and 60° C., or greater than 60° C. for up to 1 year, 2 years, 3 years, 5 years, 7 years, for up to 10 years or for greater than 10 years.

In certain embodiments, the dry medicaments or pharmaceutical compositions as described herein comprise a chiral therapeutic agent. In certain embodiments, the dry medicaments or pharmaceutical compositions as described herein comprise a chiral opioid antagonist. In some embodiments, a dry pharmaceutical composition described herein retains a chiral purity greater than 60%, greater than 70%, greater than 75%, greater than 80%, greater than 85%, greater than 90%, greater than 95%, 95% to 100%, opioid antagonist when subject to a temperature exposure of less than −30° C., or between −30° C. and −25° C., or less than −25° C., or between −25° C. and −20° C., or less than −20° C., or between −20° C. and −15° C., or less than −15° C., or between −15° C. and −10° C., or less than −10° C., or between −10° C. and −5° C., or less than −5° C., or between −5° C. and 0° C., or less than 0° C., or between 0° C. and 5° C., or less than 5° C., or between 5° C. and 10° C., or less than 10° C., or between 10° C. and 15° C., or less than 15° C., or between 15° C. and 20° C. or less than 20° C. or between 20° C. and 25° C. or greater than 25° C., or between 25° C. and 30° C., or greater than 30° C. or between 30° C. and 35° C., or greater than 35° C., or between 35° C. and 40° C., or greater than 40° C., or between 40° C. and 45° C., or greater than 45° C., or between 45° C. and 50° C., or greater than 50° C., or between 50° C. and 55° C. or greater than 55° C., or between 55° C. and 60° C., or greater than 60° C. for up to 1 year, 2 years, 3 years, 5 years, 7 years, for up to 10 years or for greater than 10 years.

In some embodiments, after the opioid antagonist powder has been dissolved in an injector device, the resulting solution retains a chiral purity greater than 60%, greater than 70%, greater than 75%, greater than 80%, greater than 85%, greater than 90%, greater than 95%, 95% to 100%, even when the dry opioid antagonist has been previously subject to a temperature exposure of less than −30° C., or between −30° C. and −25° C., or less than −25° C., or between −25° C. and −20° C., or less than −20° C., or between −20° C. and −15° C., or less than −15° C., or between −15° C. and −10° C., or less than −10° C., or between −10° C. and −5° C., or less than −5° C., or between −5° C. and 0° C., or less than 0° C., or between 0° C. and 5° C., or less than 5° C., or between 5° C. and 10° C., or less than 10° C., or between 10° C. and 15° C., or less than 15° C., or between 15° C. and 20° C. or less than 20° C. or between 20° C. and 25° C. or greater than 25° C., or between 25° C. and 30° C., or greater than 30° C. or between 30° C. and 35° C., or greater than 35° C., or between 35° C. and 40° C., or greater than 40° C., or between 40° C. and 45° C., or greater than 45° C., or between 45° C. and 50° C., or greater than 50° C., or between 50° C. and 55° C. or greater than 55° C., or between 55° C. and 60° C., or greater than 60° C. for up to 1 year, 2 years, 3 years, 5 years, 7 years, for up to 10 years or for greater than 10 years.

It should be understood that there are several movable components from the various embodiments that allow for the various mixing devices that are activated or actuated by a user, which can include the removable cap, which can be axially or rotatably removed from the housing, the frame, which can be rotated and cause the valve to move to an open position and the plunger shaft protrusion to drop into a channel thus releasing a portion of energy from a channel in an inner vial sleeve, the inner vial sleeve, which can rotate and also cause the valve to align, the plunger shaft, which can drive the displacement mechanism within the first chamber, the movable body, which can be directly mechanically coupled to the energy source and driven into the first or second chamber, and the intermediate support, which can be rotated with respect to the inner vial sleeve. Each of these movable components can be actuated, driven, rotated, translate, and can also actuate, drive, rotate and translate other components. In some embodiments a single movable component can be identified to cause multiple actions or steps.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

The invention claimed is:
1. A dual chamber drug mixing system comprising:
 a housing;
 a first chamber and a second chamber disposed at least partially within the housing, the first chamber axially aligned with the second chamber, wherein the first chamber has an outlet, the outlet of the first chamber offset from a central longitudinal axis of the housing, and the second chamber has an inlet and wherein the first chamber and the second chamber are not in communication during a closed state;

a first medicament component provided in the first chamber;

a second medicament component provided outside the first chamber, the second medicament component including an opioid antagonist compound in the amount of 1 mg/kg to 25 mg/kg based on a recipient's weight;

a user operable mixing system having a first displacement mechanism, wherein when the user operable mixing system is activated, fluidic communication occurs between the outlet of the first chamber and the inlet of the second chamber and the first displacement mechanism within the first chamber drives the first medicament component into the second chamber; and a valve disposed between the outlet of the first chamber and the inlet of the second chamber, wherein the valve is configured to open or close a fluidic pathway between the first chamber and the second chamber, wherein the first chamber and the second chamber are configured to move within the housing independently with respect to each other, as the first chamber has a first sidewall and the second chamber has a second sidewall separate and distinct from the first sidewall.

2. The dual chamber drug mixing system of claim 1, further comprising a needle assembly in fluid communication with an outlet of the second chamber.

3. The dual chamber drug mixing system of claim 1, wherein the first displacement mechanism is mechanically coupled to the valve.

4. The dual chamber drug mixing system of claim 1, wherein the first displacement mechanism causes the valve to align the outlet of the first chamber with the inlet of the second chamber.

5. The dual chamber drug mixing system of claim 1, wherein the first displacement mechanism is rotatable.

6. The dual chamber drug mixing system of claim 1, wherein the first displacement mechanism can be axially translated.

7. The dual chamber drug mixing system of claim 1, wherein the second chamber is configured to axially move and expand a volume of the second chamber formed therein.

8. The dual chamber drug mixing system of claim 1, wherein a volume of the second chamber is configured to expand as the second chamber moves axially during a mixing phase and contract as the second chamber moves axially during a delivery phase.

9. The dual chamber drug mixing system of claim 1, wherein the second chamber is a cartridge having a seal disposed between the second chamber and a needle assembly.

10. The dual chamber drug mixing system of claim 1, wherein the second chamber is a syringe component having a staked needle on one end, and wherein the staked needle forms an outlet to the second chamber.

11. The dual chamber drug mixing system of claim 1, wherein the opioid antagonist is naltrexone.

12. A dual chamber medication mixing device comprising:

a housing containing a first chamber with an outlet offset from a central longitudinal axis and a second chamber having an inlet;

a first medicament component provided in the first chamber, wherein the first medicament component being provided in liquid form;

a second medicament component provided in the second chamber, the second medicament component being dry and including an opioid antagonist compound in the amount of 1 mg/kg to 25 mg/kg based on a recipient's weight;

a valve assembly being disposed between the first chamber and the second chamber, the valve assembly being configured to selectively allow fluid communication between the first chamber and the second chamber;

a user operable mixing system having a fluidic channel, the user operable mixing system configured to rotate about the central longitudinal axis to selectively align the fluidic channel with the valve assembly; and a first displacement mechanism, the first displacement mechanism being configured to cause movement of the first medicament component from the first chamber into the second chamber, thus causing the first medicament component and the second medicament component to mix thus resulting in a mixed medicament compound;

wherein the opioid antagonist compound is naltrexone; and a bump switch configured to activate a second actuation mechanism to drive the mixed medicament compound in the second chamber through a delivery assembly.

13. The dual chamber medication mixing device of claim 12, wherein the delivery assembly includes a needle assembly in fluid communication with an outlet of the second chamber.

14. The dual chamber medication mixing device of claim 12, wherein the first displacement mechanism is rotatable.

15. The dual chamber medication mixing device of claim 12, wherein the first displacement mechanism can be axially translated.

16. The dual chamber medication mixing device of claim 12, wherein the second chamber is configured to axially move and expand a volume of the second chamber formed therein.

17. The dual chamber medication mixing device of claim 12, wherein a volume of the second chamber is configured to expand as the second chamber moves axially during a mixing phase and contract as the second chamber moves axially during a delivery phase.

* * * * *